(12) United States Patent
Remaut et al.

(10) Patent No.: US 12,084,477 B2
(45) Date of Patent: *Sep. 10, 2024

(54) PROTEIN PORES

(71) Applicants: VIB VZW, Ghent (BE); Vrije Universiteit Brussel, Brussels (BE); Oxford Nanopore Technologies PLC, Oxford (GB)

(72) Inventors: Han Remaut, Ghent (BE); Sander Egbert Van Der Verren, Serskamp (BE); Nani Van Gerven, Huizingen (BE); Lakmal Nishantha Jayasinghe, Oxford (GB); Elizabeth Jayne Wallace, Oxford (GB); Pratik Raj Singh, Oxford (GB); Richard George Hambley, Oxford (GB); Michael Robert Jordan, Oxford (GB); John Joseph Kilgour, Oxford (GB)

(73) Assignees: VIB VZW, Ghent (BE); Vrije Universiteit Brussel, Brussels (BE); Oxford Nanopore Technologies PLC, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/933,061

(22) Filed: Sep. 16, 2022

(65) Prior Publication Data

US 2023/0079731 A1    Mar. 16, 2023

Related U.S. Application Data

(63) Continuation of application No. 16/624,341, filed as application No. PCT/GB2018/051858 on Jul. 2, 2018, now Pat. No. 11,572,387.

(30) Foreign Application Priority Data

Jun. 30, 2017  (EP) .................................... 17179099

(51) Int. Cl.
A61K 38/00   (2006.01)
B82Y 15/00   (2011.01)
C07K 14/00   (2006.01)

(52) U.S. Cl.
CPC .............. *C07K 14/00* (2013.01); *B82Y 15/00* (2013.01)

(58) Field of Classification Search
None
See application file for complete search history.

(56) References Cited

U.S. PATENT DOCUMENTS

| | | |
|---|---|---|
| 5,795,782 A | 8/1998 | Church et al. |
| 6,015,714 A | 1/2000 | Baldarelli et al. |
| 6,114,121 A | 9/2000 | Fujiwara et al. |
| 6,150,112 A | 11/2000 | Weissman et al. |
| 6,362,002 B1 | 3/2002 | Denison et al. |
| 6,426,231 B1 | 7/2002 | Bayley et al. |
| 6,627,067 B1 | 9/2003 | Branton et al. |
| 6,824,659 B2 | 11/2004 | Bayley et al. |
| 6,863,833 B1 | 3/2005 | Bloom et al. |
| 6,916,665 B2 | 7/2005 | Bayley et al. |
| 6,927,070 B1 | 8/2005 | Bayley et al. |
| 7,189,503 B2 | 3/2007 | Akeson et al. |
| 8,105,846 B2 | 1/2012 | Bayley et al. |
| 8,785,211 B2 | 7/2014 | Bayley et al. |
| 8,822,160 B2 | 9/2014 | Bayley et al. |
| 8,828,208 B2 | 9/2014 | Canas et al. |
| 9,073,990 B2 | 7/2015 | Paas et al. |
| 9,127,313 B2 | 9/2015 | Brown et al. |
| 9,222,082 B2 | 12/2015 | Jayasinghe et al. |
| 9,447,152 B2 | 9/2016 | Clarke et al. |
| 9,562,887 B2 | 2/2017 | Maglia et al. |
| 9,580,480 B2 | 2/2017 | Lu et al. |
| 9,588,079 B2 | 3/2017 | Gundlach et al. |
| 9,732,381 B2 | 8/2017 | Stoddart et al. |
| 9,751,915 B2 | 9/2017 | Clarke et al. |
| 9,777,049 B2 | 10/2017 | Bruce et al. |
| 10,006,905 B2 | 6/2018 | Maglia et al. |
| 10,167,503 B2 | 1/2019 | Clarke et al. |

(Continued)

FOREIGN PATENT DOCUMENTS

| | | |
|---|---|---|
| CA | 2381139 A1 | 3/2001 |
| CN | 102116783 A | 7/2011 |

(Continued)

OTHER PUBLICATIONS

Taylor et al. New insight into the molecular control of bacterial functional amyloid. Front Cell Infect Microbiol. 2015; 5: 33 (Year: 2015).*
International Search Report and Written Opinion for Application No. PCT/GB2018/051858, mailed Sep. 11, 2018.
International Preliminary Report on Patentability for Application No. PCT/GB2018/051858, mailed Jan. 9, 2020.
[No Author Listed] EBI Accession No. GSP:AXX09397. May 13, 2010.
[No Author Listed] EBI Accession No. A0A085GH19. Oct. 29, 2014.
[No Author Listed] EBI Accession No. A0A0DILDB9. Apr. 29, 2015.
[No Author Listed] EBI Accession No. EMBLCDS:ABV05494. Sep. 11, 2007.

(Continued)

*Primary Examiner* — Aradhana Sasan
*Assistant Examiner* — Mercy H Sabila
(74) *Attorney, Agent, or Firm* — Wolf, Greenfield & Sacks, P.C.

(57) ABSTRACT

The present invention relates to novel protein pores and their uses in analyte detection and characterisation. The invention particularly relates to an isolated pore complex formed by a CsgG-like pore and a modified CsgF peptide, or a homologue or mutant thereof, thereby incorporating an additional channel constriction or reader head in the nanopore. The invention further relates to a transmembrane pore complex and methods for production of the pore complex and for use in molecular sensing and nucleic acid sequencing applications.

28 Claims, 34 Drawing Sheets

Specification includes a Sequence Listing.

(56) References Cited

U.S. PATENT DOCUMENTS

| | | |
|---|---|---|
| 10,266,885 B2 | 4/2019 | Jayasinghe et al. |
| 10,385,389 B2 | 8/2019 | Heron et al. |
| 10,400,014 B2 | 9/2019 | Howorka et al. |
| 10,443,097 B2 | 10/2019 | Jayasinghe et al. |
| 10,472,673 B2 | 11/2019 | Maglia et al. |
| 10,514,378 B2 | 12/2019 | Maglia et al. |
| 10,669,581 B2 | 6/2020 | Stoddart et al. |
| 10,802,015 B2 | 10/2020 | Maglia et al. |
| 10,844,432 B2 | 11/2020 | Jayasinghe et al. |
| 10,882,889 B2 | 1/2021 | Bruce et al. |
| 10,975,428 B2 | 4/2021 | Jayasinghe et al. |
| 10,976,300 B2 | 4/2021 | Maglia et al. |
| 10,976,311 B2 | 4/2021 | Maglia et al. |
| 10,995,372 B2 | 5/2021 | Jayasinghe et al. |
| 11,021,747 B2 | 6/2021 | Garalde et al. |
| 11,034,734 B2 | 6/2021 | Howorka et al. |
| 11,104,709 B2 | 8/2021 | Maglia et al. |
| 11,169,138 B2 | 11/2021 | Maglia et al. |
| 11,186,868 B2 | 11/2021 | Jayasinghe et al. |
| 11,307,192 B2 | 4/2022 | Jayasinghe et al. |
| 11,572,387 B2 | 2/2023 | Remaut et al. |
| 11,597,970 B2 | 3/2023 | Jayasinghe et al. |
| 11,685,949 B2 | 6/2023 | Jayasinghe et al. |
| 11,725,235 B2 | 8/2023 | Heron et al. |
| 11,739,377 B2 | 8/2023 | Jayasinghe et al. |
| 11,761,956 B2 | 9/2023 | Maglia et al. |
| 11,845,780 B2 | 12/2023 | Bruce et al. |
| 2001/0044137 A1 | 11/2001 | Heyman et al. |
| 2002/0028458 A1 | 3/2002 | Lexow |
| 2002/0094526 A1 | 7/2002 | Bayley et al. |
| 2002/0197614 A1 | 12/2002 | Mosaic |
| 2003/0044816 A1 | 3/2003 | Denison et al. |
| 2003/0099951 A1 | 5/2003 | Akeson et al. |
| 2003/0165936 A1 | 9/2003 | Rabbani et al. |
| 2003/0211502 A1 | 11/2003 | Sauer et al. |
| 2003/0215881 A1 | 11/2003 | Bayley et al. |
| 2004/0209299 A1 | 10/2004 | Pinter et al. |
| 2004/0214177 A1 | 10/2004 | Bension |
| 2005/0053961 A1 | 3/2005 | Akeson et al. |
| 2006/0063171 A1 | 3/2006 | Akeson et al. |
| 2006/0105461 A1 | 5/2006 | Tom-Moy et al. |
| 2007/0218471 A1 | 9/2007 | Kim et al. |
| 2008/0121534 A1 | 5/2008 | White et al. |
| 2008/0311582 A1 | 12/2008 | Bayley et al. |
| 2009/0111115 A1 | 4/2009 | Drmanac et al. |
| 2009/0256116 A1 | 10/2009 | Shumaker-Parry et al. |
| 2009/0283412 A1 | 11/2009 | Sansinena et al. |
| 2009/0298075 A1 | 12/2009 | Travers et al. |
| 2009/0298188 A1 | 12/2009 | Peti-Peterdi |
| 2010/0120098 A1 | 5/2010 | Grunenwald et al. |
| 2010/0196203 A1 | 8/2010 | Sanghera et al. |
| 2010/0297638 A1 | 11/2010 | Bayley et al. |
| 2011/0120871 A1 | 5/2011 | Reid et al. |
| 2011/0121840 A1 | 5/2011 | Sanghera et al. |
| 2011/0177498 A1 | 7/2011 | Clarke et al. |
| 2011/0229877 A1 | 9/2011 | Jayasinghe et al. |
| 2011/0311965 A1 | 12/2011 | Maglia et al. |
| 2012/0058468 A1 | 3/2012 | Mckeown |
| 2012/0064599 A1 | 3/2012 | Jayasinghe et al. |
| 2012/0100530 A1 | 4/2012 | Moysey et al. |
| 2012/0107802 A1 | 5/2012 | Stoddart et al. |
| 2012/0322679 A1 | 12/2012 | Brown et al. |
| 2014/0051069 A1 | 2/2014 | Jayasinghe et al. |
| 2014/0186823 A1 | 7/2014 | Clarke et al. |
| 2014/0194324 A1 | 7/2014 | Gormley et al. |
| 2014/0262784 A1 | 9/2014 | Clarke et al. |
| 2014/0296083 A1 | 10/2014 | Brown et al. |
| 2015/0008126 A1 | 1/2015 | Maglia et al. |
| 2015/0031020 A1 | 1/2015 | Jayasinghe et al. |
| 2015/0068904 A1 | 3/2015 | Bruce et al. |
| 2015/0152495 A1 | 6/2015 | Stava et al. |
| 2015/0175663 A1 | 6/2015 | Yokoi et al. |
| 2015/0177237 A1 | 6/2015 | Turner et al. |
| 2015/0191709 A1 | 7/2015 | Heron et al. |
| 2015/0218629 A1 | 8/2015 | Heron et al. |
| 2015/0346149 A1 | 12/2015 | Brown et al. |
| 2016/0010147 A1 | 1/2016 | Heron et al. |
| 2016/0053300 A1 | 2/2016 | Maglia et al. |
| 2016/0370358 A1 | 12/2016 | Maglia et al. |
| 2017/0058337 A1 | 3/2017 | Clarke et al. |
| 2017/0058338 A1 | 3/2017 | Jayasinghe et al. |
| 2017/0107569 A1 | 4/2017 | Heron et al. |
| 2017/0233803 A1 | 8/2017 | Stoddart et al. |
| 2017/0306398 A1 | 10/2017 | Jayasinghe et al. |
| 2018/0030526 A1 | 2/2018 | Brown et al. |
| 2018/0095066 A1 | 4/2018 | Jayasinghe et al. |
| 2018/0148481 A2 | 5/2018 | Howorka et al. |
| 2018/0208632 A1 | 7/2018 | Bruce et al. |
| 2018/0209952 A1 | 7/2018 | Maglia et al. |
| 2018/0334707 A1 | 11/2018 | Stoddart et al. |
| 2018/0335425 A1 | 11/2018 | Maglia et al. |
| 2018/0364214 A1 | 12/2018 | Maglia et al. |
| 2019/0071721 A1 | 3/2019 | Jayasinghe et al. |
| 2019/0202876 A1 | 7/2019 | Jayasinghe et al. |
| 2019/0300582 A1 | 10/2019 | Jayasinghe et al. |
| 2019/0330282 A1 | 10/2019 | Jayasinghe et al. |
| 2019/0346431 A1 | 11/2019 | Maglia et al. |
| 2020/0017556 A1* | 1/2020 | Howorka ............ G01N 27/447 |
| 2020/0072824 A1 | 3/2020 | Maglia et al. |
| 2020/0087724 A1 | 3/2020 | Heron et al. |
| 2020/0224262 A1 | 7/2020 | Jayasinghe et al. |
| 2020/0299336 A9 | 9/2020 | Jayasinghe et al. |
| 2020/0299337 A9 | 9/2020 | Jayasinghe et al. |
| 2020/0407785 A1 | 12/2020 | Stoddart et al. |
| 2021/0139972 A1 | 5/2021 | Jayasinghe et al. |
| 2021/0147486 A1 | 5/2021 | Remaut et al. |
| 2021/0147490 A1 | 5/2021 | Remaut et al. |
| 2021/0269872 A1 | 9/2021 | Jayasinghe et al. |
| 2021/0284696 A1 | 9/2021 | Remaut et al. |
| 2021/0292376 A1 | 9/2021 | Howorka et al. |
| 2021/0317520 A1 | 10/2021 | Jayasinghe et al. |
| 2021/0324020 A1 | 10/2021 | Bruce et al. |
| 2021/0395811 A1 | 12/2021 | Garalde et al. |
| 2021/0405039 A1 | 12/2021 | Maglia et al. |
| 2022/0024985 A9* | 1/2022 | Remaut ............. G01N 33/6872 |
| 2022/0056517 A1 | 2/2022 | Remaut et al. |
| 2022/0064230 A1 | 3/2022 | Jayasinghe et al. |
| 2022/0091096 A1 | 3/2022 | Maglia et al. |
| 2022/0119879 A1 | 4/2022 | Jayasinghe et al. |
| 2022/0154269 A9 | 5/2022 | Jayasinghe et al. |
| 2022/0162264 A9 | 5/2022 | Remaut et al. |
| 2022/0283141 A1 | 9/2022 | Jayasinghe et al. |
| 2023/0295715 A1* | 9/2023 | Jayasinghe ........... C12Q 1/6869 435/6.1 |
| 2024/0026441 A1 | 1/2024 | Heron et al. |
| 2024/0044881 A1 | 2/2024 | Maglia et al. |
| 2024/0060126 A1 | 2/2024 | Jayasinghe et al. |

FOREIGN PATENT DOCUMENTS

| | | | |
|---|---|---|---|
| CN | 102174554 A | 9/2011 | |
| CN | 102317310 A | 1/2012 | |
| CN | 103460040 A | 12/2013 | |
| EP | 2194123 B1 | 8/2012 | |
| EP | 2682460 | 1/2014 | |
| GB | 2453377 | 4/2009 | |
| GB | 1314695.6 | 8/2013 | |
| JP | H10-146190 | 6/1998 | |
| JP | 2005-253427 | 9/2005 | |
| JP | 2015-514128 A | 5/2015 | |
| WO | WO 1999/005167 | 2/1999 | |
| WO | WO 2000/028312 A1 | 5/2000 | |
| WO | WO 2001/042782 | 6/2001 | |
| WO | WO 2001/059453 | 8/2001 | |
| WO | WO 2002/042496 | 5/2002 | |
| WO | WO 2003/095669 | 11/2003 | |
| WO | WO 2005/013666 A2 | 2/2005 | |
| WO | WO-2005076010 A2 * | 8/2005 | ............ G01N 33/53 |
| WO | WO 2006/028508 | 3/2006 | |
| WO | WO 2006/100484 | 9/2006 | |
| WO | WO 2007/057668 | 5/2007 | |
| WO | WO 2007/075987 | 7/2007 | |
| WO | WO 2007/084103 | 7/2007 | |
| WO | WO 2008/102120 | 8/2008 | |

(56) References Cited

FOREIGN PATENT DOCUMENTS

| WO | WO 2008/102121 | | 8/2008 |
|----|----|----|----|
| WO | WO 2008/124107 | | 10/2008 |
| WO | WO 2009/020682 | A2 | 2/2009 |
| WO | WO 2009/024775 | A1 | 2/2009 |
| WO | WO 2009/035647 | | 3/2009 |
| WO | WO 2009/044170 | A1 | 4/2009 |
| WO | WO 2009/077734 | A2 | 6/2009 |
| WO | WO 2009/143425 | A1 | 11/2009 |
| WO | WO 2010/004265 | A1 | 1/2010 |
| WO | WO 2010/004273 | A1 | 1/2010 |
| WO | WO 2010/034018 | | 3/2010 |
| WO | WO 2010/055307 | A1 | 5/2010 |
| WO | WO 2010/086602 | A1 | 8/2010 |
| WO | WO 2010/086603 | A1 | 8/2010 |
| WO | WO 2010/086622 | A1 | 8/2010 |
| WO | WO 2010/122293 | A1 | 10/2010 |
| WO | WO 2010/148126 | A1 | 12/2010 |
| WO | WO 2011/067559 | A1 | 6/2011 |
| WO | WO 2012/005857 | A1 | 1/2012 |
| WO | WO 2012/042226 | A1 | 4/2012 |
| WO | WO 2012/107778 | A2 | 8/2012 |
| WO | WO 2012/164270 | A1 | 12/2012 |
| WO | WO 2013/014451 | A1 | 1/2013 |
| WO | WO 2013/041878 | A1 | 3/2013 |
| WO | WO 2013/057495 | A1 | 4/2013 |
| WO | WO 2013/098561 | A1 | 7/2013 |
| WO | WO 2013/098562 | A1 | 7/2013 |
| WO | WO 2013/109970 | A1 | 7/2013 |
| WO | WO 2013/153359 | A1 | 10/2013 |
| WO | WO 2014/013259 | A1 | 1/2014 |
| WO | WO 2014/013260 | A1 | 1/2014 |
| WO | WO 2014/013262 | A1 | 1/2014 |
| WO | WO 2014/064443 | A1 | 5/2014 |
| WO | WO 2014/064444 | A1 | 5/2014 |
| WO | WO 2014/122654 | A2 | 8/2014 |
| WO | WO 2014/135838 | A1 | 9/2014 |
| WO | WO 2014/142850 | A1 | 9/2014 |
| WO | WO 2014/153047 | A1 | 9/2014 |
| WO | WO 2014/153625 | A1 | 10/2014 |
| WO | WO 2014/187924 | A1 | 11/2014 |
| WO | WO 2015/022544 | A1 | 2/2015 |
| WO | WO 2015/051378 | A1 | 4/2015 |
| WO | WO 2015/055981 | A1 | 4/2015 |
| WO | WO 2015/097289 | A1 | 7/2015 |
| WO | WO 2015/110777 | A1 | 7/2015 |
| WO | WO 2015/124935 | A1 | 8/2015 |
| WO | WO 2015/150786 | A1 | 10/2015 |
| WO | WO 2015/150787 | A1 | 10/2015 |
| WO | WO 2015/166275 | A1 | 11/2015 |
| WO | WO 2015/166276 | A1 | 11/2015 |
| WO | WO-2016034591 | A2 * | 3/2016 ........... C07K 14/245 |
| WO | WO 2016/055778 | A1 | 4/2016 |
| WO | WO 2016/166232 | A1 | 10/2016 |
| WO | WO 2017/149316 | A1 | 9/2017 |
| WO | WO 2017/149317 | A1 | 9/2017 |
| WO | WO 2017/149318 | A1 | 9/2017 |
| WO | WO 2018/146491 | A1 | 8/2018 |
| WO | WO 2018/211241 | A1 | 11/2018 |
| WO | WO 2019/002893 | A1 | 1/2019 |

OTHER PUBLICATIONS

[No Author Listed] Enterobacteria phage vB_EcoM-ACG-C40, complete genome. Genbank Acc. No. NC 019399.1. 2 pages. [97 pages in 70046US02].

[No Author Listed] NCBI Genbank Accession No. ABV05494. Jan. 31, 2014, 1 page.

[No Author Listed] Helicos BioSciences Corporation, "Helicos Genetic Analysis System," Specification Sheet retrieved online at: www.helicosbio.com/Portals/0/Documents/Helicos_SalesSpec.pdf, 4 pages (2008).

[No Author Listed] Nextera™ DNA Sample Preparation Kits (Illumina) Oct. 2011. (2 pages).

[No Author Listed] Oxford Nanopore "Product" brochure (2020) https://nanoporetech.com/sites/default/files/s3/literature/product-brochure.Pdf (36 pages).

[No Author Listed] Protein Databank entries of AlphaFold structure prediction for POAE98 and POA202, 2 pages.

[No Author Listed] Uniprot Accession No. A0A081NL13. Oct. 29, 2014. 4 pages.

[No Author Listed] Uniprot Accession No. A0A0P7DN88. Jan. 20, 2016. 3 pages.

[No Author Listed] Uniprot Accession No. POAE98 and POA202 search results, last accessed Mar. 29, 2022. 4 pages.

[No Author Listed] Uniprot Accession No. Q8Z727. Oct. 24, 2003. 4 pages.

[No Author Listed] UniProt, "SubName: Full=Curli production assembly/transport component {ECO:0000313:EMBL:CTR43957.1};", XP002783536, retrieved from EBI accession No. UNIPROT:A0A0K3UZP3, Nov. 11, 2015.

[No Author Listed] UniprotKB Accession No. N2DXI0, Jun. 26, 2013, 1 page.

[No Author Listed], *Escherichia coli* HS curli production assembly/transport subunit. Accession No. ABV05494. Sep. 11, 2007. 2 pages.

Afonine et al., Real-space refinement in PHENIX for cryo-EM and crystallography. Acta Crystallogr D Struct Biol. 2018;74(Pt 6):531-544. doi: 10.1107/S2059798318006551.

Ahern, Biochemical, reagents kits offer scientists good return on investment. The Scientist. Jul. 24, 1995;9(15):20.

Akeson et al., Microsecond time-scale discrimination among polycytidylic acid, polyadenylic acid, and polyuridylic acid as homopolymers or as segments within single RNA molecules. Biophys J. Dec. 1999;77(6):3227-33.

Altschul et al. Basic local alignment search tool. J Mol Biol. Oct. 5, 1990;215(3):403-10. doi: 10.1016/S0022-2836(05)80360-2.

Altschul, A protein alignment scoring system sensitive at all evolutionary distances. J Mol Evol. Mar. 1993;36(3):290-300. doi: 10.1007/BF00160485.

Aoki et al., Single channel properties of lysenin measured in artificial lipid bilayers and their applications to biomolecule detection. Proc Jpn Acad Ser B Phys Biol Sci. 2010;86(9):920-5.

Aravind et al., The DNA-Repair Protein AlkB, EGL-9, and Leprecan Define New Families of 2-oxoglutarate-andIron-Dependent Dioxygenases. Genome Biology. 2001;2:1-8.

Ashkenasy et al., Recognizing a single base in an individual DNA strand: a step toward DNA sequencing in nanopores. Angew Chem Int Ed Engl. Feb. 18, 2005;44(9):1401-4.

Ashkenasy et al., Single Nucleobase Sensitivity of a-Hemolysin (a-HL) Transmembrane Protein Pore: Toward Single DNA Sequencing. ACS National Meeting. 2005;45(13), Abstract No. 74.

Ashton et al., MinION Nanopore Sequencing Identifies the Position and Structure of a Bacterial antibiotic Resistance Island. Nat Biotechnol. Mar. 2015;33(3):296-302.

Astier et al., Stochastic detection of motor protein-RNA complexes by single-channel current recording. Chemphyschem. Oct. 22, 2007;8(15):2189-94.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Atkins et al., Structure-function relationships of a novel bacterial toxin, hemolysin E. The role of alpha G. J Biol Chem. Dec. 29, 2000;275(52):41150-5.

Avrameas, Coupling of enzymes to proteins with glutaraldehyde. Use of the conjugates for the detection of antigens and antibodies. Immunochemistry. Jan. 1969;6(1):43-52.

Ayub et al., Engineered transmembrane pores. Curr Opin Chem Biol. 2016;34:117-126. doi: 10.1016/j.cbpa.2016.08.005. Author Manuscript, 16 pages.

Bayley et al., Stochastic sensors inspired by biology. Nature. Sep. 13, 2001;413(6852):226-30.

Bayley et al., Wrestling with native chemical ligation. ACS Chem Biol. Dec. 18, 2009;4(12):983-5. doi: 10.1021/cb900304p.

(56) References Cited

OTHER PUBLICATIONS

Bayley, Membrane-protein structure: Piercing insights. Nature. Jun. 4, 2009;459(7247):651-2. doi: 10.1038/459651a.

Bayley, Nanopore Sequencing: From Imagination to Reality. Clin Chem. 2015;61(1):25-31.

Bayley, Sequencing single molecules of DNA. Curr Opin Chem Biol. Dec. 2006; 10(6):628-37. Epub Nov. 20, 2006.

Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.

Bezrukov et al., Counting Polymers Moving Through a Single Ion Channel. Nature. Jul. 28, 1994;370:279-81.

Bianco et al., Helicase unwinding: active or merely perfect? J Mol Biol. Jul. 13, 2012;420(3):139-40. doi: 10.1016/j.jmb.2012.04.030. Epub May 2, 2012.

Bleijlevens et al., Changes in Protein Dynamics of the DNA Repair Dioxygenase AlkB Upon Binding of FE2+ and 2-Oxoglutarate. Biochemistry. Mar. 26, 2012;51:3334-41.

Bleijlevens et al., Dynamic States of the DNA Repair Enzyme AlkB regulate Product Release. Eur Mol Biol Org. Jul. 11, 2008;9(9):872-77.

Boersma et al., Continuous stochastic detection of amino acid enantiomers with a protein nanopore. Angew Chem Int Ed Engl. Sep. 17, 2012;51(38):9606-9. doi: 10.1002/anie.201205687. Epub Aug. 29, 2012.

Bourdon et al., Molecular cloning and sequence analysis of a chondroitin sulfate proteoglycan cDNA. Proc Natl Acad Sci U S A. Mar. 1985;82(5):1321-5.

Braha et al., Carriers versus adapters in stochastic sensing. Chemphyschem. May 2005;6(5):889-92.

Braha et al., Designed protein pores as components for biosensors. Chem Biol. Jul. 1997;4(7):497-505.

Branton et al., The potential and challenges of nanopore sequencing. Nat Biotechnol. Oct. 2008;26(10):1146-53. doi:10.1038/nbt.1495.

Braslavsky et al., Sequence information can be obtained from single DNA molecules. Proc Natl Acad Sci U S A. Apr. 1, 2003;100(7):3960-4. Epub Mar. 21, 2003.

Brown et al., Tools for macromolecular model building and refinement into electron cryo-microscopy reconstructions. Acta Crystallogr D Biol Crystallogr. 2015;71(Pt 1):136-153. doi:10.1107/S1399004714021683.

Burton et al., ClpX-mediated remodeling of mu transpososomes: selective unfolding of subunits destabilizes the entire complex. Mol Cell. Aug. 2001;8(2):449-54. doi: 10.1016/s1097-2765(01)00307-0.

Butler et al., Determination of RNA orientation during translocation through a biological nanopore. Biophys J. Jan. 1, 2006;90(1):190-9. Epub Oct. 7, 2005.

Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.

Byrd et al., Dda helicase tightly couples translocation on singlestranded DNA to unwinding of duplex DNA: Dda is an optimally active helicase. J Mol Biol. Jul. 13, 2012;420(3):141-54. doi: 10.1016/j.jmb.2012.04.007. Epub Apr. 11, 2012.

Cao et al., Structure of the nonameric bacterial amyloid secretion channel. Proc Natl Acad Sci USA. Dec. 16, 2014;111(50):E5439-44. doi: 10.1073/pnas.1411942111. Epub Dec. 1, 2014.

Caruccio, Preparation of next-generation sequencing libraries using Nextera™ technology: simultaneous DNA fragmentation and adaptor tagging by in vitro transposition. Methods Mol Biol. 2011;733:241-55. doi: 10.1007/978-1-61779-089-8_17.

Chan, Advances in sequencing technology. Mutat Res. Jun. 3, 2005;573(1-2):13-40.

Chapman et al., Role of *Escherichia coli* curli operons in directing amyloid fiber formation. Science. 2002;295(5556):851-855. doi: 10.1126/science.1067484. Author Manuscript, 9 pages.

Cheley et al., A functional protein pore with a "retro" transmembrane domain. Protein Sci. Jun. 1999;8(6):1257-67.

Cheley et al., A genetically encoded pore for the stochastic detection of a protein kinase. Chembiochem. Dec. 2006;7(12):1923-7.

Cheley et al., Spontaneous oligomerization of a staphylococcal alpha-hemolysin conformationally constrained by removal of residues that form the transmembrane beta-barrel. Protein Eng. Dec. 1997;10(12):1433-43.

Chen et al., Atomic Layer Deposition to Fine-Tune the Surface Properties and Diameters of Fabricated Nanopores. Nano Lett. Jun. 25, 2004;4(7):1333-1337.

Chen et al., Outer membrane protein G: Engineering a quiet pore for biosensing. Proc Natl Acad Sci U S A. Apr. 29, 2008;105(17):6272-7. doi: 10.1073/pnas.0711561105. Epub Apr. 28, 2008.

Cheng et al., Design and testing of aptamer-based electrochemical biosensors for proteins and small molecules. Bioelectrochemistry. Nov. 2009;77(1):1-12. doi: 10.1016/j.bioelechem.2009.04.007. Epub May 5, 2009.

Chin et al., Addition of a photocrosslinking amino acid to the genetic code of Escherichiacoli. Proc Natl Acad Sci U S A. Aug. 20, 2002;99(17):11020-4. doi: 10.1073/pnas.172226299. Epub Aug. 1, 2002.

Chin et al., The Metabolite alpha-Ketoglutarate Extends Lifespan by Inhibiting ATP Synthase and TOR. Nature. Jul. 19, 2014;510:397-401.

Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.

Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.

Comai et al., Protein engineering modulates the transport properties and ion selectivity of the pores formed by staphylococcal gammahaemolysins in lipid membranes. Mol Microbiol. Jun. 2002;44(5):1251-67.

Dani et al., MspA Porin-Gold Nanoparticle Assemblies: Enhanced Binding through a Controlled Cysteine Mutation. Nano Lett. Apr. 2008;8(4):1229-36. doi: 10.1021/nl072658h. Epub Mar. 5, 2008.

De Vlaminck et al., Mechanism of homology recognition in DNA recombination from dual-molecule experiments. Mol Cell. Jun. 8, 2012;46(5):616-24. doi: 10.1016/j.molcel.2012.03.029. Epub May 3, 2012.

Deamer et al., Characterization of nucleic acids by nanopore analysis. Acc Chem Res. Oct. 2002;35(10):817-25.

Deamer et al., Nanopores and nucleic acids: prospects for ultrarapid sequencing. Trends Biotechnol. Apr. 2000;18(4):147-51.

Derrington et al., A Novel DNA Sensing Technique Using Nanopore MSPA. 54th Annual Meeting of the Biophysical Society, Poster 2182-Plat, 2 pages (2010).

Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.

Devereux et al., A comprehensive set of sequence analysis programs for the VAX. Nucleic Acids Res. Jan. 11, 1984;12(1 Pt 1):387-95. doi: 10.1093/nar/12.1part1.387.

Dorre et al., Techniques for single molecule sequencing. Bioimaging, vol. 5:139-152 (1997).

Eid et al., Real-time DNA sequencing from single polymerase molecules. Science. Jan. 2, 2009;323(5910):133-8. doi:10.1126/science.1162986. Epub Nov. 20, 2008.

Eifler et al., Cytotoxin ClyA from *Escherichia coli* assembles to a 13-meric pore independent of its redox-state. EMBO J. Jun. 7, 2006;25(11):2652-61. doi: 10.1038/sj.emboj.7601130. Epub May 11, 2006.

Eliseev et al., Aminocyclodextrins as Selective Hosts with Several Binding Sites for Nucleotides. Angew. Chem. Int. Ed. Engl., vol. 32(9):1331-1333 (1993).

Eliseev et al., Molecular Recognition of Nucleotides, Nucleosides, and Sugars by Aminocyclodextrins. J. Am. Chem. Soc., vol. 116:6081-6088 (1994).

Engelhardt et al., A tetrameric porin limits the cell wall permeability of *Mycobacterium smegmatis*. J Biol Chem. Oct. 4, 2002;277(40):37567-72. Epub Jul. 18, 2002.

(56) References Cited

OTHER PUBLICATIONS

Epstein, Assembly, Spatial Distribution, and Secretion Activity of the Curlin Secretion Lipoprotein, CsgG. Dissertation. The University of Michigan. 2008. 167 pages.
Ergel et al., Protein Dynamics Control the Progression and Efficiency of the Catalytic Reaction Cycle of the *Escherichia coli* DNA-Repair Enzyme AlkB. J Biol Chem. Oct. 24, 2014;289(43):29584-601.
Fahie et al., Resolved Single-Molecule Detection of Individual Species Within a Mixture of Anti-Biotin Antibodies Using an Engineered Monometric Nanopore. Am Chem Soc. Jan. 9, 2015;9(2):1089-98.
Fiume et al., Savant: genome browser for high-throughput sequencing data. Bioinformatics. Aug. 15, 2010;26(16):1938-44. doi: 10.1093/bioinformatics/btq332. Epub Jun. 20, 2010.
Flomenbom et al., Single stranded DNA translocation through a nanopore: a master equation approach. Phys Rev E Stat Nonlin Soft Matter Phys. Oct. 2003;68(4 Pt 1):041910. Epub Oct. 14, 2003.
Flusberg et al., Direct detection of DNA methylation during single-molecule, real-time sequencing. Nat Methods. Jun. 2010;7(6):461-5. doi: 10.1038/nmeth.1459. Epub May 9, 2010.
Fologea et al., Potential analytical applications of lysenin channels for detection of multivalent ions. Anal Bioanal Chem. Oct. 2011;401(6):1871-9. doi:10.1007/s00216-011-5277-8. Epub Aug. 5, 2011.
Franceschini et al., A nanopore machine promotes the vectorial transport of DNA across membranes. Sep. 2013; Nat Commun. 2013;4:2415. doi: 10.1038/ncomms3415.
Franceschini et al., DNA Translocation through Nanopores at Physiological Ionic Strengths Requires Precise Nanoscale Engineering. ACS Nano. Sep. 27, 2016;10(9):8394-402. doi: 10.1021/acsnano.6b03159. Epub Aug. 15, 2016.
Freedman et al., Single Molecule Unfolding and Stretching of Protein Domains Inside a Solid-State Nanopore by Electric Field. Scientific Reports. Apr. 10, 2013;3(1638):1-8.
Galenkamp et al., Direct electrical quantification of glucose and asparagine from bodily fluids using nanopores. Nat Commun. 2018;9(1):4085. Published Oct. 5, 2018. doi:10.1038/s41467-018-06534-1.
Genschel et al., Interaction of *E. coli* single-stranded DNA binding protein (SSB) with exonuclease I. The carboxy-terminus of SSB is the recognition site for the nuclease. Biol Chem. Mar. 2000;381(3):183-92.
Gershow et al., Recapturing and trapping single molecules with a solid-state nanopore. Nat Nanotechnol. Dec. 2007;2(12):775-9. doi:10.1038/nnano.2007.381. Epub Dec. 2, 2007.
Ghosal, Electrokinetic-flow-induced viscous drag on a tethered DNA inside a nanopore. Phys Rev E Stat Nonlin Soft Matter Phys. Dec. 2007;76(6 Pt 1): 061916. Epub Dec. 26, 2007.
Gibson et al., AgfC and AgfE facilitate extracellular thin aggregative fimbriae synthesis in *Salmonella enteritidis*. Microbiology. Apr. 2007;153(Pt 4):1131-1140. doi: 10.1099/mic.0.2006/000935-0.
Gilbert et al., Two Structural Transitions in Membrane Pore Formation by Pneumolysin, the Pore-Forming Toxin of *Streptococcus pneumoniae*. Cell. May 28, 1999;97:647-655.
Goedhart et al., Quantitative co-expression of proteins at the single cell level—application to a multimeric FRET sensor. PLoS One. 2011;6(11):e27321. doi: 10.1371/journal.pone.0027321. Epub Nov. 17, 2011.
Goryshin et al., Tn5 in vitro transposition. J Biol Chem. Mar. 27, 1998;273(13):7367-74. doi: 10.1074/jbc.273.13.7367.
Gouridis et al., Conformational Dynamics in Substrate-Binding Domains Influences Transport in the ABC Importer GinPQ. Nat Stuct Mol Biol. Dec. 8, 2014;22(1):57-66.
Goyal et al., Crystallization and preliminary X-ray crystallographic analysis of the curli transporter CsgG. Acta Crystallographica Section F: Structural Biology and Crystallization Communications. Dec. 1, 2013;69(12):1349-53.

Goyal et al., Structural and mechanistic insights into the bacterial amyloid secretion channel CsgG. Nature. Dec. 11, 2014;516(7530):250-3 with Supplemental Information. doi: 10.1038/nature13768. Epub Sep. 14, 2014.
Gu et al., Capture of a single molecule in a nanocavity. Science. Jan. 26, 2001;291(5504):636-40.
Gu et al., Electroosmotic enhancement of the binding of a neutral molecule to a transmembrane pore. Proc Natl Acad Sci U S A. Dec. 23, 2003;100(26): 15498-503. Epub Dec. 15, 2003.
Gu et al., Interaction of the noncovalent molecular adapter, beta-cyclodextrin, with the staphylococcal alpha-hemolysin pore. Biophys J. Oct. 2000; 79(4):1967-75.
Gu et al., Prolonged residence time of a noncovalent molecular adapter, beta-cyclodextrin, within the lumen of mutant alpha-hemolysin pores. J Gen Physiol. Nov. 2001;118(5):481-94.
Gu et al., Reversal of charge selectivity in transmembrane protein pores by using noncovalent molecular adapters. Proc Natl Acad Sci U S A. Apr. 11, 2000;97(8):3959-64.
Gu et al., Stochastic sensing of organic analytes by a pore-forming protein containing a molecular adapter. Nature. Apr. 22, 1999;398(6729):686-90.
Guan et al., Stochastic sensing of TNT with a genetically engineered pore. Chembiochem. Oct. 2005;6(10):1875-81.
Guasch et al., Detailed architecture of a DNA translocating machine: the high-resolution structure of the bacteriophage phi29 connector particle. J Mol Biol. Jan. 25, 2002;315(4):663-76.
Guo et al., Nanopore sensor for copper ion detection using a polyamine decorated β-cyclodextrin as the recognition element. RSC Adv. 2017;7:15315. doi: 10.1039/c7ra00454k. 6 pages.
Hall et al., Hybrid pore formation by directed insertion of α-haemolysin into solid-state nanopores. Nat Nanotechnol. Dec. 2010;5(12):874-7. doi: 10.1038/nnano.2010.237. Epub Nov. 28, 2010.
Hammar et al., Expression of two csg operons is required for production of fibronectin- and congo red-binding curli polymers in *Escherichia coli* K-12. Mol Microbiol. Nov. 1995;18(4):661-70. doi: 10.1111/j.1365-2958.1995.mmi_18040661.x.
Han et al., Characterization and optimization of an entropic trap for DNA separation. Anal Chem. Jan. 15, 2002;74(2):394-401.
Han et al., RecJ exonuclease: substrates, products and interaction with SSB. Nucleic Acids Res. Feb. 18, 2006;34(4):1084-91. Print 2006.
Haque et al., DNA-associated click chemistry. Science China Chemistry. Feb. 2014;57(2):215-231. doi:10.1007/s11426-013-5035-1.
Haque et al., Solid-State and Biological Nanopore for Real-Time Sensing of Single Chemical and Sequencing of DNA. Nano Today. Feb. 2013;8(1):56-74.
He et al. 2012; The T4 phage SF1 B helicase dda is structurally optimized to perform DNA strand separation. Structure. 20:1189-1200.
Heng et al., Sizing DNA using a nanometer-diameter pore. Biophys J. Oct. 2004;87(4):2905-11. doi: 10.1529/biophysj.104.041814. Epub Aug. 23, 2004.
Henrickson et al., Driven DNA transport into an asymmetric nanometer-scale pore. Phys Rev Lett. Oct. 2, 2000;85(14):3057-60.
Heron et al., Direct detection of membrane channels from gels using water-in-oil droplet bilayers. J Am Chem Soc. Dec. 26, 2007;129(51):16042-7. Epub Dec. 1, 2007.
Higgins et al., DNA-joining enzymes: a review. Methods Enzymol. 1979;68:50-71. doi: 10.1016/0076-6879(79)68006-0.
Holden et al., Direct introduction of single protein channels and pores into lipid bilayers. J Am Chem Soc. May 11, 2005;127(18):6502-3.
Holden et al., Functional bionetworks from nanoliter water droplets. J Am Chem Soc. Jul. 11, 2007;129(27):8650-5. Epub Jun. 16, 2007.
Hornblower et al., Single-molecule analysis of DNA-protein complexes using nanopores. Nat Methods. Apr. 2007;4(4):315-7. Epub Mar. 4, 2007.
Howorka et al., DNA Duplex Formation of Individual DNA Strands within a Single Protein Pore. Biophysical Journal, vol. 82{1, pt. 2):508a, No. 2482-Plat (2002).
Howorka et al., Kinetics of duplex formation for individual DNA strands within a single protein nanopore. Proc Natl Acad Sci U S A. Nov. 6, 2001;98(23):12996-3001. Epub Oct. 23, 2001.

(56) References Cited

OTHER PUBLICATIONS

Howorka et al., Nanopore Analytics: Sensing of Single Molecules. The Royal Society of Chemistry. Jun. 15, 2009;38:2360-84.
Howorka et al., Nanopores as protein sensors. Nat Biotechnol. Jun. 7, 2012;30(6):506-7. doi: 10.1038/nbt.2264.
Howorka et al., Probing distance and electrical potential within a protein pore with tethered DNA. Biophys J. Dec. 2002;83(6):3202-10.
Howorka et al., Sequence-specific detection of individual DNA strands using engineered nanopores. Nat Biotechnol. Jul. 2001;19(7):636-9.
Hu et al., Theory of DNA translocation through narrow ion channels and nanopores with charged walls. Phys Rev E Stat Nonlin Soft Matter Phys. Sep. 2008;78(3 Pt 1):032901. Epub Sep. 10, 2008.
Huff et al., Functions of the periplasmic loop of the porin MspA from *Mycobacterium smegmatis*. J Biol Chem. Apr. 10, 2009;284(15):10223-31. doi: 10.1074/jbc.M808599200. Epub Feb. 10, 2009.
Hwang et al., Electrical behavior of droplet interface bilayer networks: experimental analysis and modeling. J Am Chem Soc. Sep. 26, 2007;129(38):11854-64. Epub Sep. 1, 2007.
Iacovache et al., Structure and assembly of pore-forming proteins. Curr Opin Struct Biol. Apr. 2010;20(2):241-6. doi:10.1016/j.sbi.2010.01.013. Epub Feb. 19, 2010.
Ide et al., Lysenin forms a voltage-dependent channel in artificial lipid bilayer membranes. Biochem Biophys Res Commun. Jul. 21, 2006;346(1):288-92. Epub May 26, 2006.
Ivanov et al., DNA tunneling detector embedded in a nanopore. Nano Lett. Jan. 12, 2011;11(1):279-85. doi: 10.1021/nl103873a. Epub Dec. 6, 2010.
Jain et al., The Oxford Nanopore MinION: delivery of nanopore sequencing to the genomics community. Genome Biol. Nov. 25, 2016;17(1):239. doi: 10.1186/s13059-016-1103-0. Erratum in: Genome Biol. Dec. 13, 2016;17(1):256.
Jayasinghe et al., The leukocidin pore: evidence for an octamer with four LukF subunits and four LukS subunits alternating around a central axis. Protein Sci. Oct. 2005;14(10):2550-61.
Johnston et al., Coexpression of proteins in bacteria using T7-based expression plasmids: expression of heteromeric cell-cycle and transcriptional regulatory complexes. Protein Expr Purif. Dec. 2000;20(3):435-43.
Juncker et al., Prediction of lipoprotein signal peptides in Gram-negative bacteria. Protein Sci. 2003;12(8):1652-1662. doi:10.1110/ps.0303703.
Jung et al., The internal cavity of the staphylococcal alpha-hemolysin pore accommodates approximately 175 exogenous amino acid residues. Biochemistry. Jun. 28, 2005;44(25):8919-29.
Kalli et al., Conformational changes in talin on binding to anionic phospholipid membranes facilitate signaling by integrin transmembrane helices. PLoS Comput Biol. Oct. 2013;9(10):e1003316. doi:10.1371/journal.pcbi.1003316.
Kanaan et al., UPF1-like helicase grip on nucleic acids dictates processivity. Nat Commun. Sep. 14, 2018;9(1):3752. doi: 10.1038/s41467-018-06313-y.
Kang et al., Single protein pores containing molecular adapters at high temperatures. Angew Chem Int Ed Engl. Feb. 25, 2005;44(10):1495-9.
Kasianowicz et al., Characterization of individual polynucleotide molecules using a membrane channel. Proc Natl Acad Sci U S A. Nov. 26, 1996;93(24):13770-3.
Khulbe et al., DNA translocation through a-hemolysin nanopores with potential application to macromolecular data storage. Journal Applied Physics, vol. 97(104317):1-7 (2005).
Kimanius et al., Accelerated cryo-EM structure determination with parallelisation using GPUs in RELION-2. Elife. 2016;5:e18722. Published Nov. 15, 2016. doi: 10.7554/eLife.18722. 21 pages.
Klenchin et al., Phosphate coordination and movement of DNA in the Tn5 synaptic complex: role of the (R)YREK motif. Nucleic Acids Res. Oct. 2008;36(18):5855-62. doi: 10.1093/nar/gkn577. Epub Sep. 12, 2008.

Kobayashi et al., Comparative Physiology and Biochemistry, 2005, vol. 22, No. 3-4, pp. 139-148.
Kolinko et al., Single-cell genomics reveals potential for magnetite and greigite biomineralization in an uncultivated multicellular magnetotactic prokaryote. Environ Microbiol Rep. Oct. 2014;6(5):524-31. doi: 10.1111/1758-2229.12198. Epub Aug. 28, 2014. Abstract Only.
Krylova et al., DNA aptamers for as analytical tools for the quantitative analysis of DNA-dealkylating enzymes. Anal Biochem. 2011;414(2):261-265. doi:10.1016/j.ab.2011.03.010.
Kumar et al., PEG-labeled nucleotides and nanopore detection for single molecule DNA sequencing by synthesis. Sci Rep. 2012;2:684. Epub Sep. 21, 2012.
Langecker et al., Synthetic lipid membrane channels formed by designed DNA nanostructures. Science. Nov. 16, 2012;338(6109):932-6. doi: 10.1126/science.1225624.
Le et al., Thermostable DNA ligase-mediated PCR production of circular plasmid (PPCP) and its application in directed evolution via in situ error-prone PCR. DNA Res. Aug. 2013;20(4):375-82. doi: 10.1093/dnares/dst016. Epub Apr. 30, 2013.
Li et al., ChIA-PET tool for comprehensive chromatin interaction analysis with paired-end tag sequencing. Genome Biol. 2010;11(2):R22. doi: 10.1186/GB-2010-11-2-r22. Epub Feb. 25, 2010.
Li et al., Different Anomeric Sugar Bound States of Maltose Binding Protein Resolved by a Cytolysin A Nanopore Tweezer. ACS Nano. 2020;14(2):1727-1737. doi:10.1021/acsnano.9b07385.
Li et al., DNA molecules and configurations in a solid-state nanopore microscope. Nat Mater. Sep. 2003;2(9):611-5. Epub Aug. 24, 2003.
Li, Minimap2: pairwise alignment for nucleotide sequences. Bioinformatics. 2018;34(18):3094-3100. doi: 10.1093/bioinformatics/bty191.
Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.
Loferer et al., Availability of the fibre subunit CsgA and the nucleator protein CsgB during assembly of fibronectin-binding curli is limited by the intracellular concentration of the novel lipoprotein CsgG. Mol Microbiol. 1997;26(1):11-23. doi:10.1046/j.1365-2958.1997.5231883.x.
Lovett, The DNA Exonucleases of *Escherichia coli*. EcoSal Plus. Dec. 2011;4(2):10.1128/ecosalplus.4.4.7. doi: 10.1128/ecosalplus.4.4.7. Author Manuscript, 45 pages.
Lu et al., Expression, purification and structural analysis of csgF gene of curli systems from *Escherichia coli* CFT073. Microbiol China. 2016, 43(9):2063-2071. doi:10.13344/j.microbiol.china.150752.
Lu et al., Protein Motion and Configurations in a Form-Fitting Nanopore: Avidin in ClyA. Biophys J. Sep. 4, 2018; 115(5):801-808. Epub Aug. 4, 2018. doi: 10.1016/j.bpj.2018.07.024.
Luchian et al., Single-Molecule Covalent Chemistry with Spatially Separated Reactants. Angew. Chem. Int. Ed. 2003;42:3766-771.
Ludtke, Single-Particle Refinement and Variability Analysis in EMAN2.1. Methods Enzymol. 2016;579:159-89. doi: 10.1016/bs.mie.2016.05.001. Epub Jul. 1, 2016.
Ludwig et al., Analysis of the SlyA-Controlled Expression, Subcellular Localization and Pore-Forming Activity of a 34 kDa Haemolysin (ClyA) from *Escherichia coli* K-12. Mol Microbiol. 1999;31(2):557-67.
Luo et al., Influence of polymer-pore interactions on translocation. Phys Rev Lett. Oct. 5, 2007;99(14):148102. Epub Oct. 1, 2007.
Maglia et al., DNA strands from denatured duplexes are translocated through engineered protein nanopores at alkaline pH. Nano Lett. Nov. 2009;9(11):3831-6. doi: 10.1021/nl9020232.
Maglia et al., Engineering a Biomimetic Biological Nanopore to Selectively Capture Folded Target Proteins. Biophysical J. Feb. 5, 2013;104(2):518a.
Maglia et al., Enhanced translocation of single DNA molecules through alpha-hemolysin nanopores by manipulation of internal charge. Proc Natl Acad Sci U S A. Dec. 16, 2008;105(50):19720-5. doi: 10.1073/pnas.0808296105. Epub Dec. 5, 2008.
Makaram et al., Trends in Nanomaterial-Based Non-Invasive Diabetes Sensing Technologies. Diagnostics. Apr. 21, 2014;4:27-46.

(56) References Cited

OTHER PUBLICATIONS

Manrao et al., Nucleotide Discrimination with DNA Immobilized in the MspA Nanopore. PLoS One, vol. 6(10):e25723, 7 pages (2011).
Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.
Manrao et al., Single Nucleotide Discrimination in Single Stranded DNA Immobilized within Biological Nanopore MSPA. 54th Annual Meeting of the Biophysical Society, 3 pages (2010).
Martin et al., Nanoscale protein pores modified with PAMAM dendrimers. J Am Chem Soc. Aug. 8, 2007;129(31):9640-9. Epub Jul. 18, 2007.
Marziali et al., New DNA sequencing methods. Annu Rev Biomed Eng. 2001;3:195-223.
Mathé et al., Orientation discrimination of single-stranded DNA inside the alpha-hemolysin membrane channel. Proc Natl Acad Sci U S A. Aug. 30, 2005;102(35):12377-82. Epub Aug. 19, 2005.
Matsuura et al., Real-time observation of a single DNA digestion by lambda exonuclease under a fluorescence microscope field. Nucleic Acids Res. Aug. 15, 2001;29(16):E79.
Meller et al., Rapid nanopore discrimination between single polynucleotide molecules. Proc Natl Acad Sci U S A. Feb. 1, 2000;97(3):1079-84.
Meller et al., Single molecule measurements of DNA transport through a nanopore. Electrophoresis. Aug. 2002;23(16):2583-91.
Meller, Dynamics of polynucleotide transport through nanometre-scale pores. Journal Physics: Condensed Matter, vol. 15:R581-R607 (2003).
Merzlyak et al., Conductance and ion selectivity of a mesoscopic protein nanopore probed with cysteine scanning mutagenesis. Biophys J. Nov. 2005;89(5):3059-70. Epub Aug. 5, 2005.
Mikheyev et al., A First Look at the Oxford Nanopore MinION Sequencer. Mol Ecol Res. 2014;14:1097-1102.
Miles et al., The Staphylococcal Leukocidin Bicomponent Toxin Forms Large Ionic Channels. Biochemistry. Jun. 28, 2001;40:8514-522.
Mitchell et al., Chemical tags facilitate the sensing of individual DNA strands with nanopores. Angew Chem Int Ed Engl. 2008;47(30):5565-8. doi: 10.1002/anie.200800183.
Miyazaki et al., MEGAWHOP Cloning: A Method of Creating Random Mutagenesis Libraries via Megaprimer PCR of Whole Plasmids. Methods in Enzymology. 2011;498:399-406.
Mohammad et al., Controlling a single protein in a nanopore through electrostatic traps. J Am Chem Soc. Mar. 26, 2008;130(12):4081-8. doi: 10.1021/ja710787a. Epub Mar. 6, 2008.
Moreau et al., Coupling ion channels to receptors for biomolecule sensing. Nat Nanotechnol. Oct. 2008;3(10):620-5. doi: 10.1038/nnano.2008.242. Epub Sep. 7, 2008.
Movileanu et al., Detecting protein analytes that modulate transmembrane movement of a polymer chain within a single protein pore. Nat Biotechnol. Oct. 2000;18(10):1091-5.
Movileanu et al., Location of a constriction in the lumen of a transmembrane pore by targeted covalent attachment of polymer molecules. J Gen Physiol. Mar. 2001;117(3):239-52.
Moyer et al., Correlation Between Sweat Glucose and Blood Glucose in Subjects with Diabetes. Diabetes Technol Ther. 2012;14(5):398-402.
Mueller et al., RCSB Protein Data Bank No. 2WCD. Mar. 11, 2009. doi: 10.2210/pdb2WCD/pdb. 5 pages.
Mueller et al., The Structure of Cytolytic alpha-Helical Toxin Pore Reveals its Assembly Mechanism. Nature. Jun. 4, 2009;459:726-731.
Mueller et al., The Structure of Cytolytic alpha-Helical Toxin Pore Reveals its Assembly Mechanism. Nature. Jun. 4, 2009;459: Supplemental Information.
Muller et al., DNA-directed assembly of artificial multienzyme complexes. Biochem Biophys Res Commun. Dec. 5, 2008;377(1):62-7. doi: 10.1016/j.bbrc.2008.09.078. Epub Sep. 25, 2008.
Mund et al., LEGO-NMR spectroscopy: a method to visualize individual subunits in large heteromeric complexes. Angew Chem Int Ed Engl. Oct. 18, 2013;52(43):11401-5. doi: 10.1002/anie.201304914. Epub Aug. 14, 2013.
Nakane et al., A nanosensor for transmembrane capture and identification of single nucleic Acid molecules. Biophys J. Jul. 2004;87(1):615-21. Erratum in: Biophys J. Nov. 2004;87(5):3618.
Nakane et al., Nanopore sensors for nucleic acid analysis. J. Phys.: Condens. Matter, vol. 15: R 1365- R1393 (2003).
Niedzwiecki et al., Inspection of the Engineered FhuA deltaC/delta4L Protein Nanopore by Polymer Exclusion. Biophys J. Nov. 2012;103:2115-124.
Nikolaidou et al., alpha-Ketoglutarate: Biological Effects of a Novel Biomarker of Heart Failure. Heart. Sep. 2010;96(17). 2 pages.
Nivala et al., Unfoldase-mediated protein translocation through an α-hemolysin nanopore. Nat Biotechnol. Mar. 2013;31(3):247-50. doi: 10.1038/nbt.2503. Epub Feb. 3, 2013. Author Manuscript, 10 pages.
Notice of Opposition for European Patent No. EP3097210 dated Aug. 12, 2019.
Ogasawara et al., Determination of Reduced Nicotinamide Adenine Dinucleotid Phosphate Concentration Using High-Performance Liquid Chromatography with Fluorescence Detection: Ratio of the Reduced Form as a Biomarker of Oxidative Stress. Biol Pharm Bull. Nov. 2009;32(11):1819-18223.
Oukhaled et al., Dynamics of Completely Unfolded and Native Proteins through Solid-State Nanopores as a Function of Electric Driving Force. Am Chem Soc. 2011 Arp 8;5(5):3628-38.
Pavlenok et al., Hetero-oligomeric MspA pores in Mycobacterium smegmatis. FEMS Microbiol Lett. Apr. 2016;363(7). pii: fnw046. doi:10.1093/femsle/fnw046. Epub Feb. 23, 2016.
Pavlenok et al., MspA nanopores from subunit dimers. PLoS One. 2012;7(6):e38726. doi: 10.1371/journal.pone.0038726. Epub Jun. 18, 2012.
Peabody et al., Type II protein secretion and its relationship to bacterial type IV pili and archaeal flagella. Microbiology. Nov. 2003;149(Pt 11):3051-3072. doi: 10.1099/mic.0.26364-0.
Pfeiffer et al., Bivalent cholesterol-based coupling of oligonucleotides to lipid membrane assemblies. J Am Chem Soc. Aug. 25, 2004;126(33):10224-5.
Plesa et al., Fast Translocation of Proteins through Solid State Nanopores. Nano Lett. Jan. 23, 2013:13:658-663.
Pud et al., Mechanical Trapping of DNA in a Double-Nanopore System. Nano Lett. 2016;16(12):8021-8028. doi:10.1021/acs.nanolett. 6b04642. Author Manuscript, 17 pages.
Purnell et al., Nucleotide identification and orientation discrimination of DNA homopolymers immobilized in a protein nanopore. Nano Lett. Sep. 2008;8(9):3029-34. doi: 10.1021/nl802312f. Epub Aug. 13, 2008.
Quick et al., A reference Bacterial Genome Dataset Generated on the MinION Portable Single-Molecule Nanopore Sequencer. GigaScience. 2014;3(22):1-6.
Rajagopalan et al., Interaction of Dihydrofolate Reductase with Methotrexate: Ensemble and Single-Molecule Kinetics. PNAS. Oct. 15, 2002:99(21):13481-6.
Rasko et al., The pangenome structure of *Escherichia coli:* comparative genomic analysis of *E. coli* commensal and pathogenic isolates. J Bacteriol. Oct. 2008;190(20):6881-93. doi:10.1128/JB. 00619-08. Epub Aug. 1, 2008.
Reznikoff, Tn5 as a model for understanding DNA transposition. Mol Microbiol. Mar. 2003;47(5):1199-206. doi: 10.1046/j.1365-2958.2003.03382.x.
Rhee et al., Comprehensive genome-wide protein-DNA interactions detected at single- nucleotide resolution. Cell. Dec. 9, 2011;147(6):1408-19. doi: 10.1016/j.cell.2011.11.013.
Rhee et al., Nanopore sequencing technology: research trends and applications. Trends Biotechnol. Dec. 2006;24(12):580-6. Epub Oct. 19, 2006.
Robinson et al., Secretion of curli fibre subunits is mediated by the outer membrane-localized CsgG protein. Mol Microbiol. Feb. 2006;59(3):870-81. doi: 10.1111/j.1365-2958.2005.04997.x.
Rodriguez-Gallego et al., Mapping of the Circulating Metabolome Reveals alpha-Ketoglutarate as a Predictor of Morbid Obesity-Associated Non-Alcoholic Fatty Liver Disease. Int J of Obesity. 2015;39:279-287.

(56) References Cited

OTHER PUBLICATIONS

Rohou et al., CTFFIND4: Fast and accurate defocus estimation from electron micrographs. J Struct Biol. Nov. 2015;192(2):216-21. doi: 10.1016/j.jsb.2015.08.008. Epub Aug. 13, 2015.
Rotem et al., Protein detection by nanopores equipped with aptamers. J Am Chem Soc. Feb. 8, 2012;134(5):2781-7. doi:10.1021/ja2105653. Epub Jan. 26, 2012.
Rucker et al., Recombinant ferritin: modulation of subunit stoichiometry in bacterial expression systems. Protein Eng. 1997;10(8):967-973. doi: 10.1093/protein/10.8.967.
Russo et al., Reversible permeabilization of plasma membranes with an engineered switchable pore. Nat Biotechnol. Mar. 1997;15(3):278-82.
Saariaho et al., Characteristics of MuA transposase-catalyzed processing of model transposon end DNA hairpin substrates. Nucleic Acids Res. Jun. 6, 2006;34(10):3139-49.
Sanchez-Quesada et al., Cyclic Peptides as Molecular Adapters for a Pore-Forming Protein. Journal American Chemical Society, vol. 122(48):11757-11766 (2000).
Sanchez-Quesada et al., Single DNA rotaxanes of a transmembrane pore protein. Angew Chem Int Ed Engl. Jun. 7, 2004;43(23):3063-7.
Sanderson, Personal genomes: Standard and pores. Nature. Nov. 6, 2008;456(7218):23-5. doi: 10.1038/456023a.
Sauer-Budge et al., Unzipping kinetics of double-stranded DNA in a nanopore. Phys Rev Lett. Jun. 13, 2003;90(23):238101. Epub Jun. 9, 2003.
Scheres, Relion: implementation of a Bayesian approach to cryo-EM structure determination. J Struct Biol. Dec. 2012;180(3):519-30. doi: 10.1016/j.jsb.2012.09.006. Epub Sep. 19, 2012.
Shelbourne et al., Fast copper-free click DNA ligation by the ring-strain promoted alkyne-azide cycloaddition reaction. Chem Commun (Camb). Jun. 14, 2011;47(22):6257-9. doi: 10.1039/c1cc10743g. Epub May 6, 2011.
Sivanathan et al., Generating extracellular amyloid aggregates using E. coli cells. Genes Dev. Dec. 1, 2012;26(23):2659-67. doi: 10.1101/gad.205310.112. Epub Nov. 19, 2012.
Skocaj et al., The sensing of membrane microdomains based on pore-forming toxins. Curr Med Chem. 2013;20(4):491-501.
Smeets et al., Salt dependence of ion transport and DNA translocation through solid-state nanopores. Nano Lett. Jan. 2006;6(1):89-95.
Soni et al., Synchronous optical and electrical detection of biomolecules traversing through solid-state nanopores. Rev Sci Instrum. Jan. 2010;81(1):014301. doi: 10.1063/1.3277116.
Soskine et al., An engineered ClyA nanopore detects folded target proteins by selective external association and pore entry. Nano Lett. Sep. 12, 2012;12(9):4895-900. doi:10.1021/nl3024438. Epub Aug. 6, 2012. Author Manuscript, 13 pages.
Soskine et al., Single-Molecule Analyte Recognition with ClyA Nanopores Equipped with Internal Protein Adaptors. J Am Chem Soc. 2015;137:5793-97.
Soskine et al., Tuning the size and properties of ClyA nanopores assisted by directed evolution. J Am Chem Soc. Sep. 11, 2013;135(36):13456-63. doi: 10.1021/ja4053398. Epub Aug. 27, 2013.
Sternberg et al., DNA interrogation by the CRISPR RNA-guided endonuclease Cas9. Nature. Mar. 6, 2014;507(7490):62-7. doi: 10.1038/nature13011. Epub Jan. 29, 2014. Author Manuscript, 16 pages.
Stoddart et al., Multiple base-recognition sites in a biological nanopore: two heads are better than one. Angew Chem Int Ed Engl. 2010;49(3):556-9. doi: 10.1002/anie.200905483.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Sutherland et al., An analysis of mismatched duplex DNA unzipping through a bacterial nanopore. Biochem Cell Biol. Jun. 2004;82(3):407-12.
Taylor et al., Atomic resolution insights into curli fiber biogenesis. Structure. Sep. 7, 2011;19(9):1307-16. doi: 10.1016/j.str.2011.05.015.
Taylor et al., New insight into the molecular control of bacterial functional amyloids. Front Cell Infect Microbiol. Apr. 8, 2015;5:33. doi: 10.3389/fcimb.2015.00033.
Third Party Observation for Application No. EP 15759438.3, mailed Oct. 20, 2022. 11 pages.
Third Party Observation for Application No. EP 15759438.3, mailed Sep. 17, 2021. 21 pages.
Third Party Observation for Application No. EP 18734933.7, mailed Apr. 11, 2022. 14 pages.
Third Party Observation for European Application No. EP18734933.7, mailed Sep. 27, 2021.
Trewick et al., Oxidative Demethylation by Escherichia coli AlkB Directly Reverts DNA Base Damage. Nature. Sep. 12, 2002:419:174-78.
Tuteja et al., Helicases as molecular motors: An insight. Physica A. Dec. 1, 2006;372(1):70-83. doi: 10.1016/j.physa.2006.05.014. Epub Jun. 5, 2006.
Van De Goor, Nanopore Detection: Threading DNA Through a Tiny Hole. PharmaGenomics, vol. 4 (3):28-30 (2004).
Van Der Verren et al., A dual-constriction biological nanopore resolves homonucleotide sequences with high fidelity. Nat Biotechnol. Dec. 2020;38(12):1415-1420. doi: 10.1038/s41587-020-0570-8. Epub Jul. 6, 2020. Author Manuscript, 25 pages.
Van Gerven et al., Bacterial amyloid formation: structural insights into curli biogenesis. Trends Microbiol. Nov. 2015; 23(11):693-706. EPub Oct. 1, 2015. doi: 10.1016/j.tim.2015.07.010. Author Manuscript, 24 pages.
Van Gerven et al., Secretion and functional display of fusion proteins through the curlibiogenesis pathway. Mol Microbiol. Mar. 2014;91(5):1022-35. doi:10.1111/mmi.12515. Epub Feb. 12, 2014.
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f. Author Manuscript, 16 pages.
Van Meervelt et al., Detection of Two Isomeric Binding Configurations in a Protein-Aptamer Complex with a Biological Nanopore. Am Chem Soc. Dec. 10, 2014;8(12):12826-35.
Van Meervelt et al., Real-Time Conformational Changes and Controlled Orientation of Native Proteins Inside a Protein Nanoreactor. J Am Chem Soc. Dec. 27, 2017;139(51):18640-18646. EPub Dec. 5, 2017. doi: 10.1021/jacs.7b10106.
Walker et al., Key residues for membrane binding, oligomerization, and pore forming activity of staphylococcal alpha-hemolysin identified by cysteine scanning mutagenesis and targeted chemical modification. J Biol Chem. Sep. 29, 1995;270(39):23065-71.
Wallace et al., E. coli hemolysin E (HlyE, ClyA, SheA): X-ray crystal structure of the toxin and observation of membrane pores by electron microscopy. Cell. Jan. 21, 2000;100(2):265-76.
Wang et al., Engineering of protein nanopores for sequencing, chemical or protein sensing and disease diagnosis. Curr Opin Biotechnol. Jun. 2018;51:80-89. doi: 10.1016/j.copbio.2017.11.006. Epub Dec. 10, 2017.
Wang et al., Measuring and modeling the kinetics of individual DNA-DNA polymerase complexes on a nanopore. ACS Nano. May 28, 2013;7(5):3876-86. doi: 10.1021/nn401180j. Epub Apr. 16, 2013.
Wang et al., Nanopores with a spark for single-molecule detection. Nat Biotechnol. Jul. 2001;19(7):622-3.
Wang et al., Protein engineering with non-natural amino acids. InTechOpen; Feb. 24, 2012. DOI: 10.5772/28719.
Wanunu et al., DNA translocation governed by interactions with solid-state nanopores. Biophys J. Nov. 15, 2008;95(10):4716-25. doi: 10.1529/biophysj.108.140475. Epub Aug. 15, 2008.
Wanunu, Nanopores: A journey towards DNA sequencing. Phys Life Rev. Jun. 2012;9(2):125- 58. doi: 10.1016/j.plrev.2012.05.010. Epub May 18, 2012.
Welford et al., The Selectivity and Inhibition of AlkB. J. Biol. Chem. Mar. 21, 2003;278(12):10157-161.

(56) References Cited

OTHER PUBLICATIONS

Wendell et al., Translocation of double-stranded DNA through membrane-adapted phi29 motor protein nanopores. Nat Nanotechnol. 2009;4(11):765-772. doi: 10.1038/nnano.2009.259.

White et al., Single Ion-Channel Recordings Using Glass Nanopore Membranes. J Am Chem Soc. 2007;129:11766-775.

Wiedmann et al., Ligase chain reaction (LCR)—overview and applications. PCR Methods Appl. Feb. 1994;3(4):S51-64. doi: 10.1101/gr.3.4.s51.

Wilkinson et al., Bacterial DNA ligases. Mol Microbiol. Jun. 2001;40(6):1241-8. doi: 10.1046/j.1365-2958.2001.02479.x.

Wolfe et al., Catalyzing the translocation of polypeptides through attractive interactions. J Am Chem Soc. Nov. 14, 2007;129(45):14034-41. Epub Oct. 19, 2007.

Wong et al., Polymer capture by electro-osmotic flow of oppositely charged nanopores. J Chem Phys. Apr. 28, 2007;126(16):164903.

Wu et al., Protein nanopores with covalently attached molecular adapters. J Am Chem Soc. Dec. 26, 2007;129(51):16142-8. Epub Nov. 30, 2007.

Wu et al., Sequence-specific capture of protein-DNA complexes for mass spectrometric protein identification. PLoS One. 2011;6(10):e26217. doi: 10.1371/journal.pone.0026217. Epub Oct. 20, 2011.

Wu et al., Single-molecule detection of nitrogen mustards by covalent reaction within a protein nanopore. J Am Chem Soc. May 20, 2008;130(21):6813-9. doi: 10.1021/ja8004607. Epub Apr. 30, 2008.

Yen et al., SWR-C and INO80 chromatin remodelers recognize nucleosome-free regions near +1 nucleosomes. Cell. Sep. 12, 2013;154(6):1246-56. doi: 10.1016/j.cell.2013.08.043.

Yoo et al., Glucose Biosensors: An Overview of Use in Clinical Practice. Sensors. May 4, 2010;10:4558-4576.

Zernia et al., Current Blockades of Proteins inside Nanopores for Real-Time Metabolome Analysis. ACS Nano. Feb. 25, 2020; 14(2):2296-2307. EPub Jan. 31, 2020. doi: 10.1021/acsnano.9b09434.

Zernia et al., Current Blockades of Proteins inside Nanopores for Real-Time Metabolome Analysis. ACS Nano. Feb. 25, 2020; 14(Supplemental Information). EPub Jan. 31, 2020. doi: 10.1021/acsnano.9b09434. 19 pages.

Zheng et al., MotionCor2: anisotropic correction of beam-induced motion for improved cryo-electron microscopy. Nat Methods. Apr. 2017;14(4):331-332. doi: 10.1038/nmeth.4193. Epub Feb. 27, 2017.

Zhou et al., Ion Channel Probes for Scanning Ion Conductance Microscopy. Langmuir. Nov. 25, 2014;30:15351-355.

Devos et al., Practical limits of function prediction. Proteins. Oct. 1, 2000;41(1):98-107.

Fleckenstein et al., "UPI0002CA1AFE" Uniprot Accession No., https://www.uniprot.org/uniparc/UPI0002CA1AFE, Jun. 26, 2013 (Jun. 26, 2013).

Kisselev, Polypeptide release factors in prokaryotes and eukaryotes: same function, different structure. Structure. Jan. 2002;10(1):8-9. doi: 10.1016/s0969-2126(01)00703-1.

Whisstock et al., Prediction of protein function from protein sequence and structure. Q Rev Biophys. Aug. 2003;36(3):307-40. doi: 10.1017/s0033583503003901.

Witkowski et al., Conversion of a beta-ketoacyl synthase to a malonyl decarboxylase by replacement of the active-site cysteine with glutamine. Biochemistry. Sep. 7, 1999;38(36):11643-50. doi: 10.1021/bi990993h.

U.S. Appl. No. 18/363,859, filed Aug. 2, 2023, Maglia et al.
U.S. Appl. No. 18/340,823, filed Jun. 23, 2023, Heron et al.
U.S. Appl. No. 18/341,906, filed Jun. 27, 2023, Jayasinghe et al.
U.S. Appl. No. 18/159,718, filed Jan. 26, 2023, Jayasinghe et al.
U.S. Appl. No. 18/313,079, filed May 5, 2023, Jayasinghe et al.

Cao et al., Mapping the sensing spots of aerolysin for single oligonucleotides analysis. Nat Commun. Jul. 19, 2018;9(1):2823. doi: 10.1038/s41467-018-05108-5. 9 pages.

Colas et al., Microscopical investigations of nisin-loaded nanoliposomes prepared by Mozafari method and their bacterial targeting. Micron. 2007;38(8):841-7. doi: 10.1016/j.micron.2007.06.013. Epub Jul. 3, 2007.

González-Pérez et al., Biomimetic triblock copolymer membrane arrays: a stable template for functional membrane proteins. Langmuir. Sep. 15, 2009;25(18):10447-50. doi: 10.1021/la902417m.

Ho et al., Engineering a nanopore with co-chaperonin function. Sci Adv. Dec. 11, 2015;1(11):e1500905. doi: 10.1126/sciadv.1500905. 9 pages.

Montal et al., Formation of bimolecular membranes from lipid monolayers and a study of their electrical properties. Proc Natl Acad Sci U S A. Dec. 1972;69(12):3561-6. doi: 10.1073/pnas.69.12.3561.

Willems et al., Single-molecule nanopore enzymology. Philos Trans R Soc Lond B Biol Sci. Aug. 5, 2017;372(1726):20160230. doi: 10.1098/rstb.2016.0230. 11 pages.

Extended European Search Report dated Dec. 15, 2023 in connection with European Application No. 23172407.1.

Dong et al., Oroxylin A inhibits hemolysis via hindering the self-assembly of α-hemolysin heptameric transmembrane pore. PLoS Comput Biol. 2013;9(1):e1002869. doi: 10.1371/journal.pcbi.1002869. Epub Jan. 17, 2013.

Fiaschi et al., Auto-Assembling Detoxified Staphylococcus aureus Alpha-Hemolysin Mimicking the Wild-Type Cytolytic Toxin. Clin Vaccine Immunol. Jun. 6, 2016;23(6):442-50. doi: 10.1128/CVI.00091-16.

Ghanem et al., Chimeric mutants of staphylococcal hemolysin, which act as both one-component and two-component hemolysin, created by grafting the stem domain. FEBS J. Jun. 2022;289(12):3505-3520. doi: 10.1111/febs.16354. Epub Feb. 16, 2022.

Walker et al., Assembly of the oligomeric membrane pore formed by Staphylococcal alpha-hemolysin examined by truncation mutagenesis. J Biol Chem. Oct. 25, 1992;267(30):21782-6.

\* cited by examiner

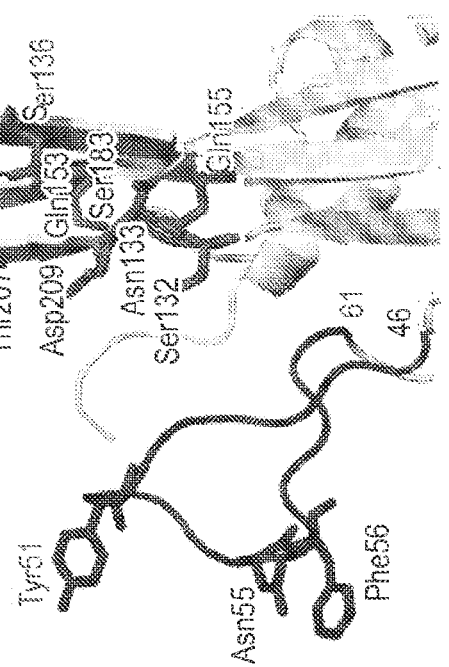
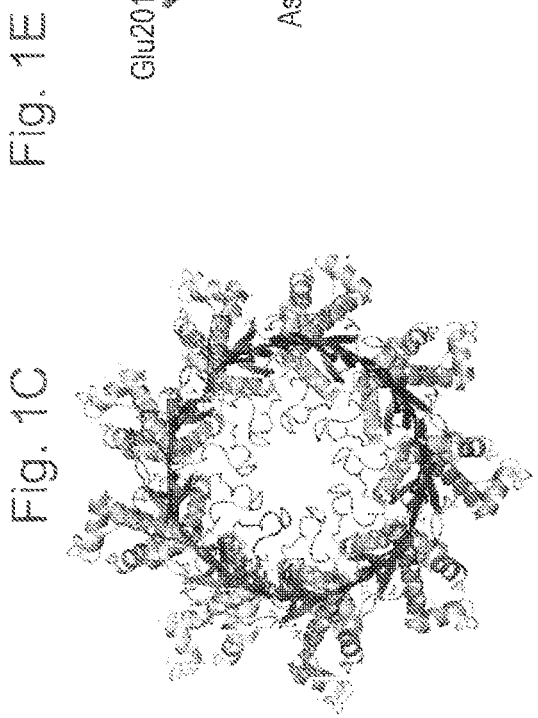
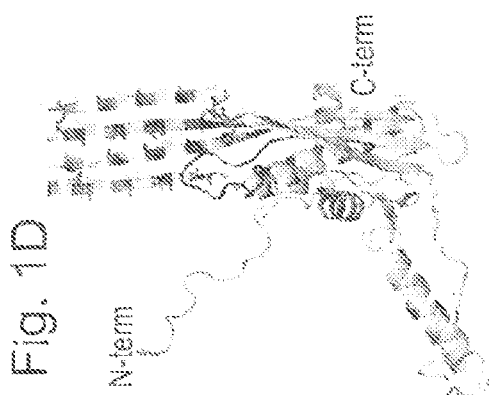
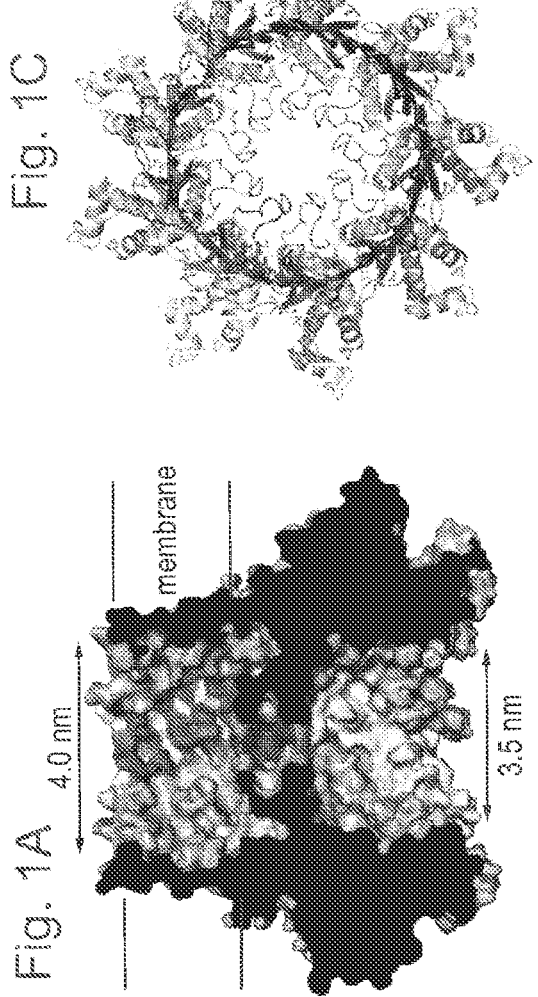
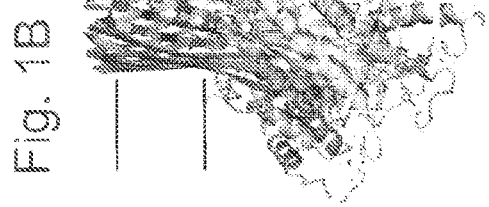

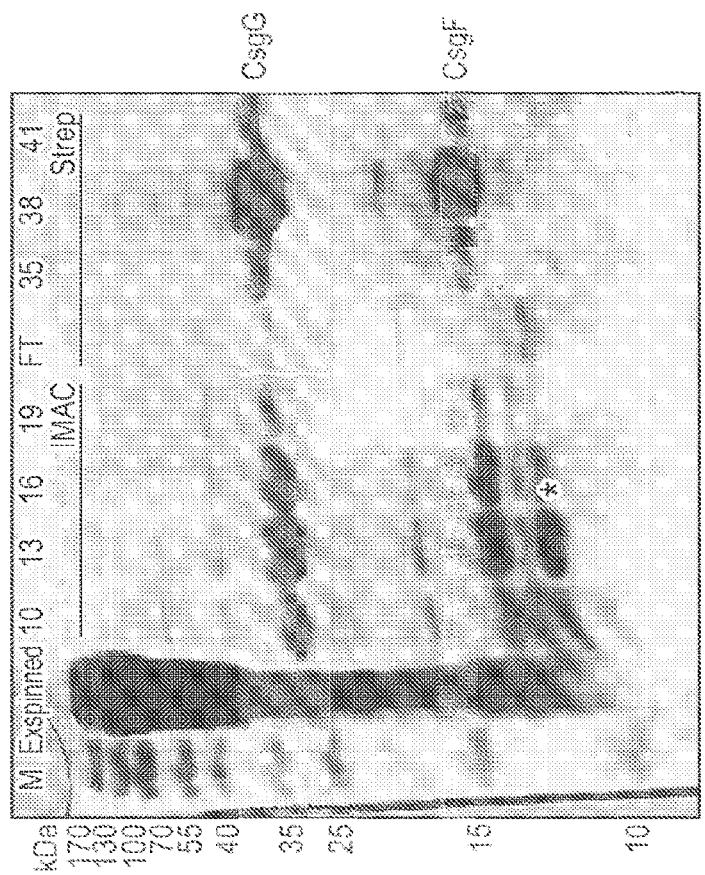
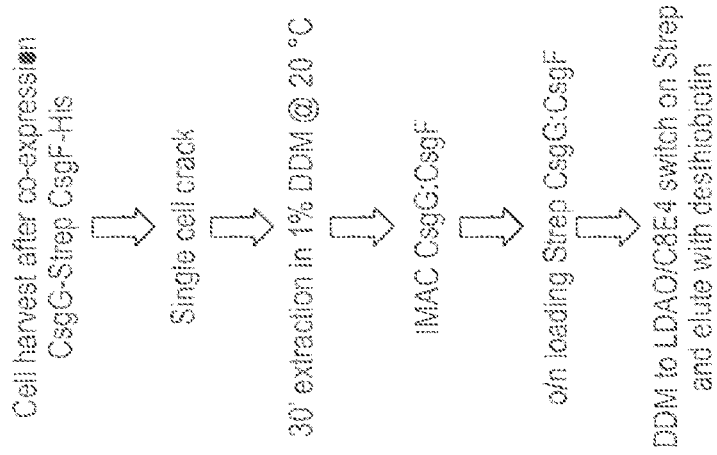

(a) (CsgG)₉

(b) (CsgG)₁₈

Fig. 8

Fig. 9A
CsgF 1-27: GTMTFQFR (SEQ ID NO: 37)
CsgF 1-38: GTMTFQFRNPNFGGNPNNG (SEQ ID NO: 38)
CsgF 1-48: GTMTFQFRNPNFGGNPNNGAFLLNSAQAQ (SEQ ID NO: 39)
CsgF 1-64: GTMTFQFRNPNFGGNPNNGAFLLNSAQAQNSYKDPSYNDDFGIET (SEQ ID NO: 40)
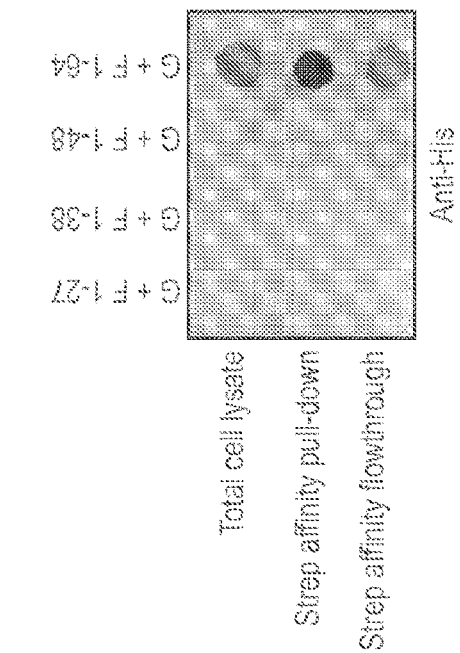
Fig. 9C
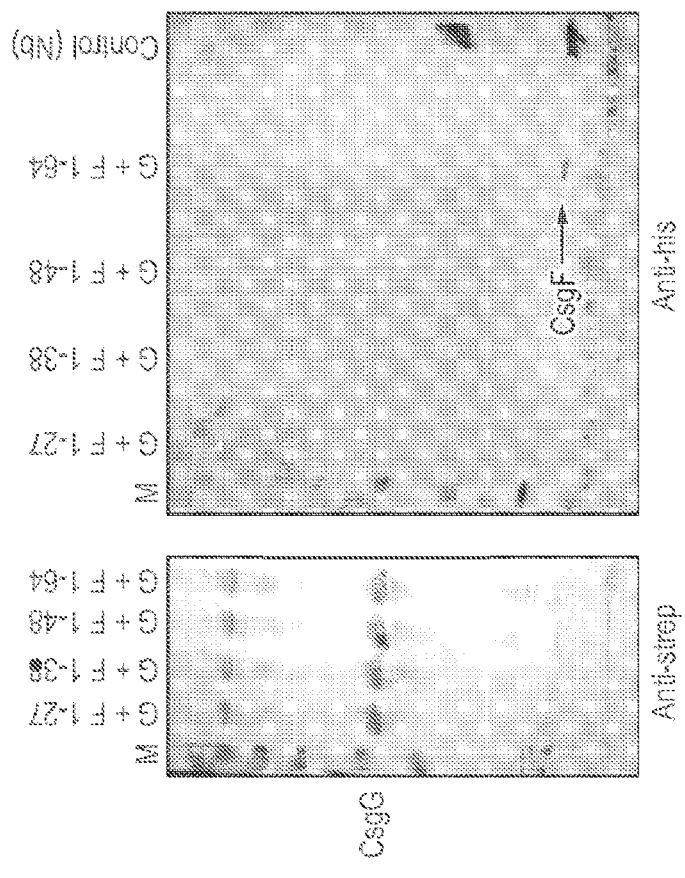
Fig. 9B

CsF "FCP"

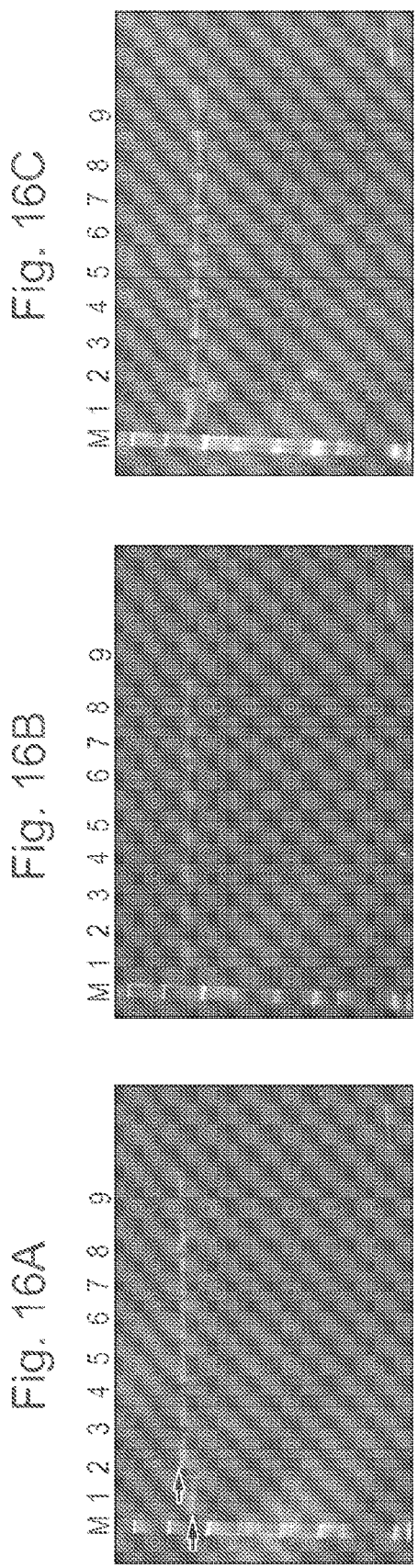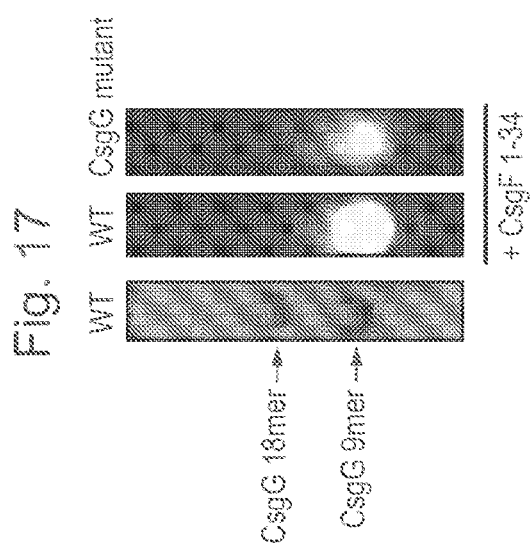

| CsgG res# | CsgF res# |
|---|---|
| Q153C | G1C |
| N133 | T4 |
| S136 | F5 |
| Q187 | R8 |
| E203 | R8 |
| E203 | N9 |
| R142 | N11 |
| E201 | N11 |
| D149 | F12 |
| E203 | F12 |
| F191 | A26 |
| F144 | Q29 |

MS analysis of the S-S complex (SEQ ID NO: 291) Seq: YFGIGADTQYCLDQIAVNLR-CTMTFQFE    Score: 6.86e-005

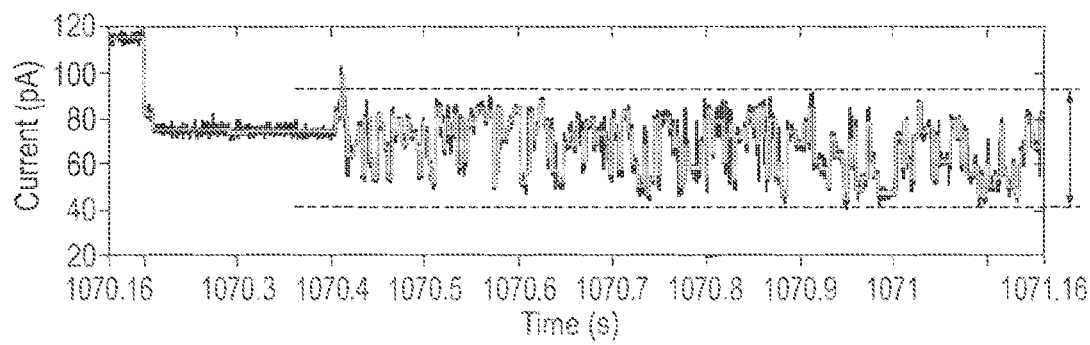
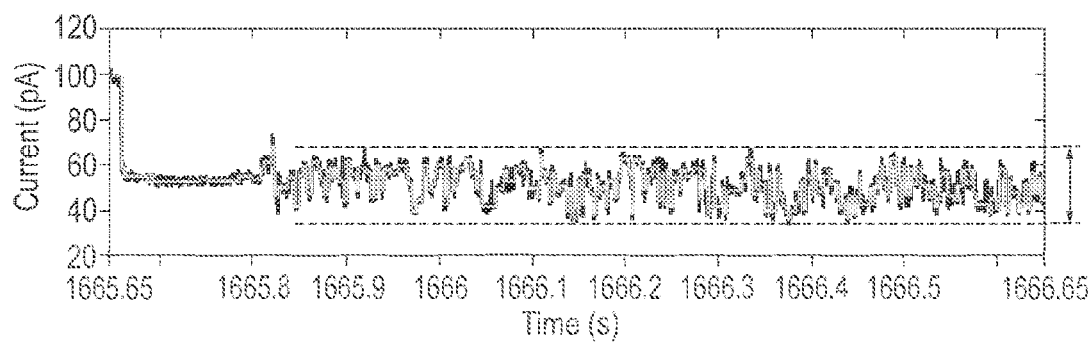
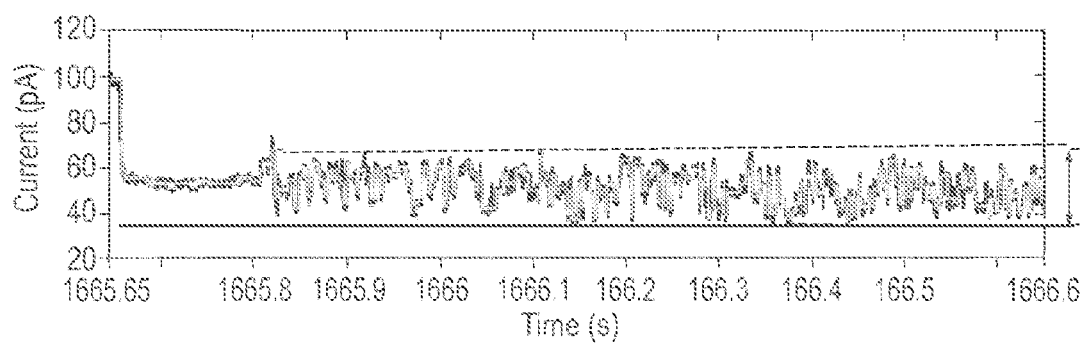

approx. 5 bases dominate the current signal mixed sequence

10xT   10xT   10xT homopolymer sequence

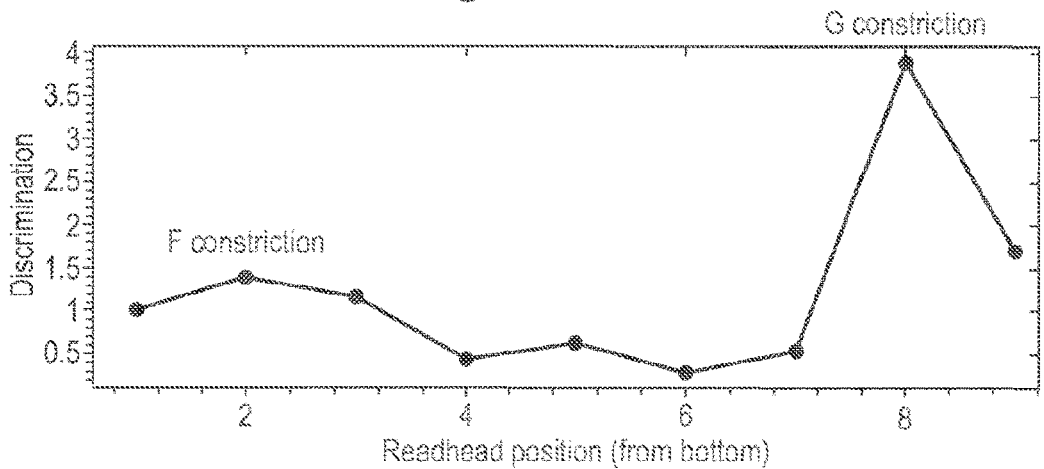

| SEQ ID NOs: | Name | Sequence | C3 location |
|---|---|---|---|
| 292 | SS20 | AAAAAAAAAAAAAAAAAAAAAAAAAAAAAAAAAAAAAAAAA/3Bio/ | 0 |
| 293 | SS21 | AAAAAAAAAAAAAAAAAAAAAAAAAAAAAAAAAAAAAAAA/iSpC3/A/3Bio/ | 2 |
| 294 | SS22 | AAAAAAAAAAAAAAAAAAAAAAAAAAAAAAAAAAAAAAA/iSpC3/AA/3Bio/ | 3 |
| 295 | SS23 | AAAAAAAAAAAAAAAAAAAAAAAAAAAAAAAAAAAAAA/iSpC3/AAA/3Bio/ | 4 |
| 296 | SS24 | AAAAAAAAAAAAAAAAAAAAAAAAAAAAAAAAAAAAA/iSpC3/AAAA/3Bio/ | 5 |
| 297 | SS25 | AAAAAAAAAAAAAAAAAAAAAAAAAAAAAAAAAAAA/iSpC3/AAAAA/3Bio/ | 6 |
| 298 | SS26 | AAAAAAAAAAAAAAAAAAAAAAAAAAAAAAAAAAA/iSpC3/AAAAAA/3Bio/ | 7 |
| 299 | SS27 | AAAAAAAAAAAAAAAAAAAAAAAAAAAAAAAAAA/iSpC3/AAAAAAA/3Bio/ | 8 |
| 300 | SS28 | AAAAAAAAAAAAAAAAAAAAAAAAAAAAAAAAA/iSpC3/AAAAAAAA/3Bio/ | 9 |
| 301 | SS29 | AAAAAAAAAAAAAAAAAAAAAAAAAAAAAAAA/iSpC3/AAAAAAAAA/3Bio/ | 10 |
| 302 | SS30 | AAAAAAAAAAAAAAAAAAAAAAAAAAAAAAA/iSpC3/AAAAAAAAAA/3Bio/ | 11 |
| 303 | SS31 | AAAAAAAAAAAAAAAAAAAAAAAAAAAAAA/iSpC3/AAAAAAAAAAA/3Bio/ | 12 |
| 304 | SS32 | AAAAAAAAAAAAAAAAAAAAAAAAAAAAA/iSpC3/AAAAAAAAAAAA/3Bio/ | 13 |
| 305 | SS33 | AAAAAAAAAAAAAAAAAAAAAAAAAAAAA/iSpC3/AAAAAAAAAAAAA/3Bio/ | 14 |
| 306 | SS34 | AAAAAAAAAAAAAAAAAAAAAAAAAAA/iSpC3/AAAAAAAAAAAAAA/3Bio/ | 15 |
| 307 | SS35 | AAAAAAAAAAAAAAAAAAAAAAAAAA/iSpC3/AAAAAAAAAAAAAAA/3Bio/ | 16 |
| 308 | SS36 | AAAAAAAAAAAAAAAAAAAAAAAAA/iSpC3/AAAAAAAAAAAAAAAA/3Bio/ | 17 |
| 309 | SS37 | AAAAAAAAAAAAAAAAAAAAAAAA/iSpC3/AAAAAAAAAAAAAAAAA/3Bio/ | 18 |
| 310 | SS38 | AAAAAAAAAAAAAAAAAAAAAAA/iSpC3/AAAAAAAAAAAAAAAAAA/3Bio/ | 19 |

Multiple points of
contribution
CsgG:CsgF

TTTTT
(SEQ ID NO: 311) CAGTCGCATCGGTTTTTACTGCGGGCTG

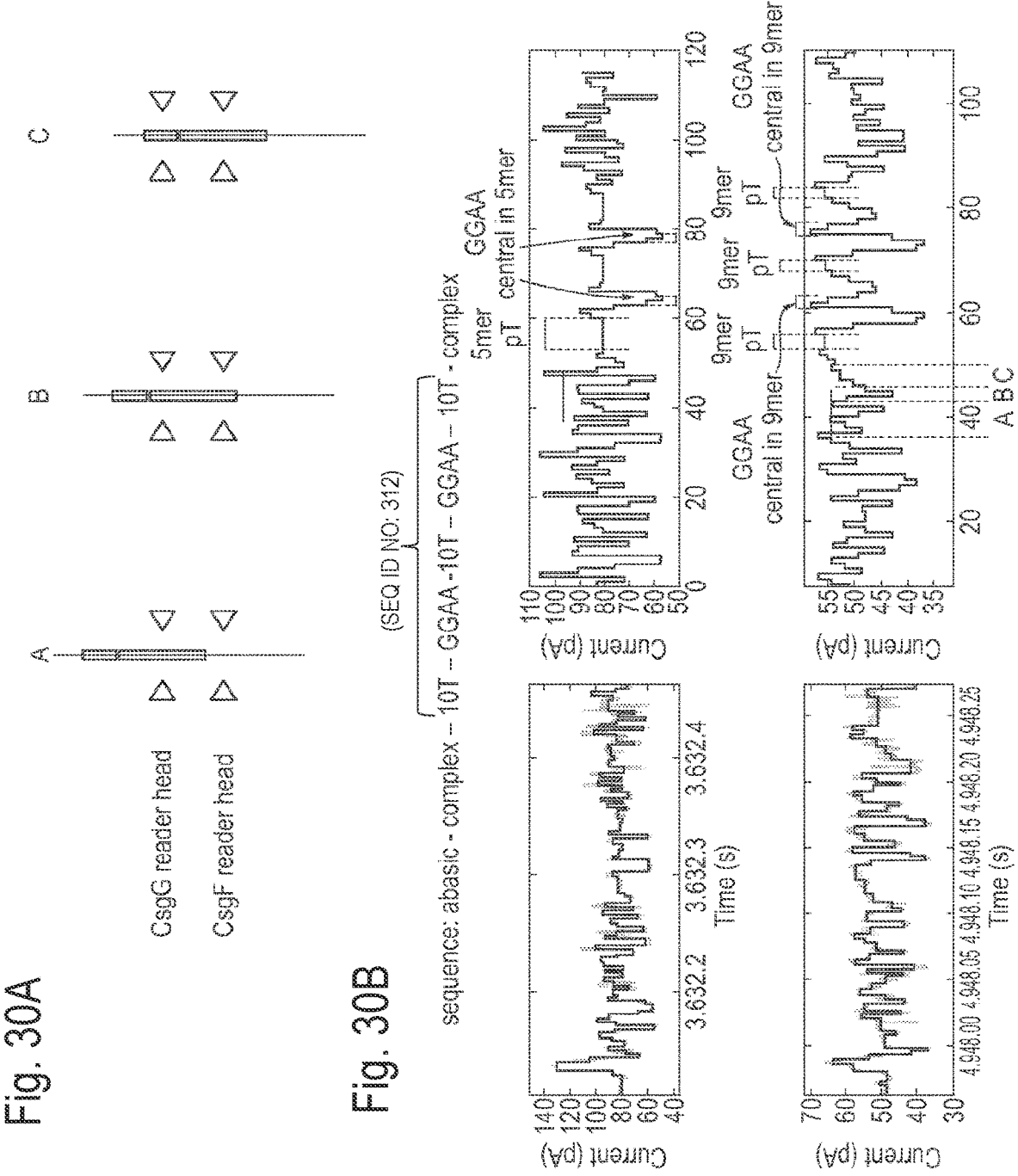

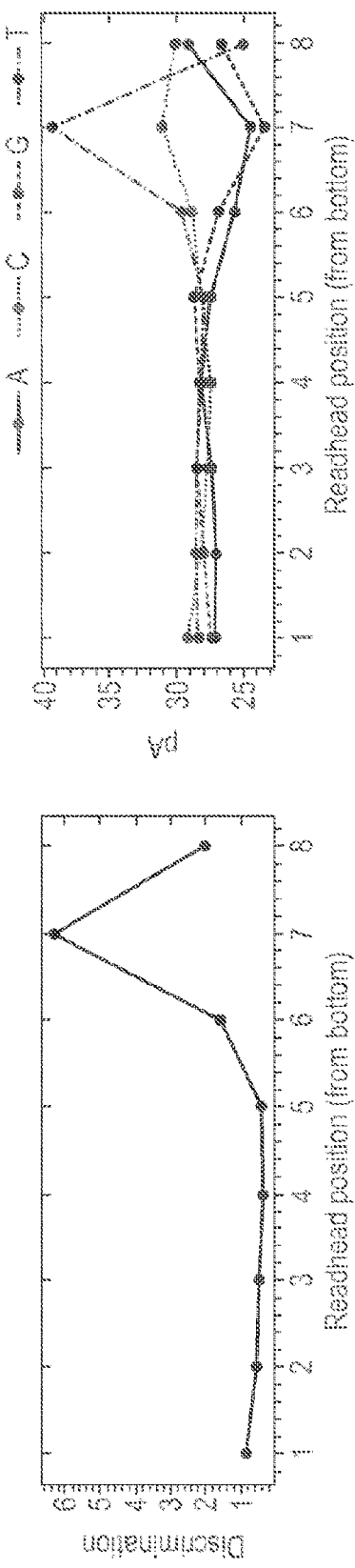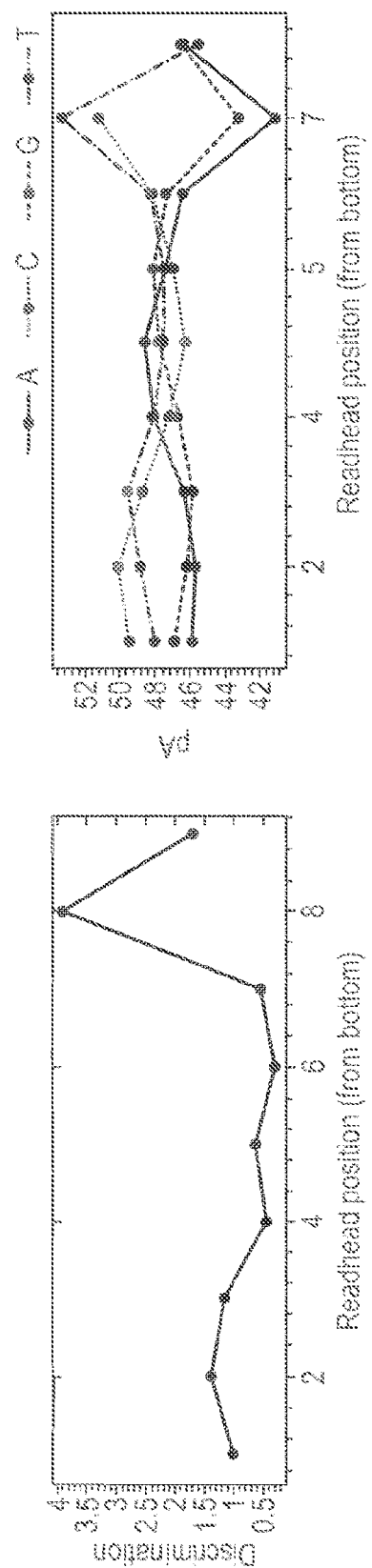

SEQUENCE LISTING

```
Sequence total quantity: 333
SEQ ID NO: 1            moltype = DNA  length = 834
FEATURE                 Location/Qualifiers
source                  1..834
                        mol_type = genomic DNA
                        organism = Escherichia coli
SEQUENCE: 1
atgcagcgct tatttctttt ggttgccgtc atgttactga gcggatgctt aaccgccccg    60
cctaaagaag ccgccagacc gacattaatg cctcgtgctc agagctacaa agatttgacc   120
catctgccag cgccgacggg taaaatcttt gtttcggtat acaacattca ggacgaaacc   180
gggcaattta aaccctaccc ggcaagtaac ttctccactg ctgttccgca aagcgccacg   240
gcaatgctgg tcacggcact gaaagattct cgctggttta taccgctgga gcgccagggc   300
ttacaaaacc tgcttaacga gcgcaagatt attcgtgcgg cacaagaaaa cggcacggtt   360
gccattaata accgaatccc gctgcaatct ttaacggcgg caaatatcat ggttgaaggt   420
tcgattatcg gttatgaaag caacgtcaaa tctggcgggg ttggggcaag atattttggc   480
atcggtgccg acacgcaata ccagctcgat cagattgccg tgaacctgcg cgtcgtcaat   540
gtgagtaccg gcgagatcct ttcttcggtg aacaccagta agacgatact ttcctatgaa   600
gttcaggccg gggttttccg ctttattgac taccagcgct tgcttgaagg ggaagtgggt   660
tacacctcga acgaacctgt tatgctgtgc ctgatgtcgg ctatcgaaac aggggtcatt   720
ttcctgatta atgatggtat cgaccgtggt ctgtgggatt tgcaaaataa agcagaacgg   780
cagaatgaca ttctggtgaa ataccgccat atgtcggttc caccggaatc ctga          834

SEQ ID NO: 2            moltype = AA  length = 277
FEATURE                 Location/Qualifiers
source                  1..277
                        mol_type = protein
                        organism = Escherichia coli
SEQUENCE: 2
MQRLFLLVAV MLLSGCLTAP PKEAARPTLM PRAQSYKDLT HLPAPTGKIF VSVYNIQDET    60
GQFKPYPASN FSTAVPQSAT AMLVTALKDS RWFIPLERQG LQNLLNERKI IRAAQENGTV   120
AINNRIPLQS LTAANIMVEG SIIGYESNVK SGGVGARYFG IGADTQYQLD QIAVNLRVVN   180
VSTGEILSSV NTSKTILSYE VQAGVFRFID YQRLLEGEVG YTSNEPVMLC LMSAIETGVI   240
FLINDGIDRG LWDLQNKAER QNDILVKYRH MSVPPES                            277

SEQ ID NO: 3            moltype = AA  length = 262
FEATURE                 Location/Qualifiers
source                  1..262
                        mol_type = protein
                        organism = Escherichia coli
SEQUENCE: 3
CLTAPPKEAA RPTLMPRAQS YKDLTHLPAP TGKIFVSVYN IQDETGQFKP YPASNFSTAV    60
PQSATAMLVT ALKDSRWFIP LERQGLQNLL NERKIIRAAQ ENGTVAINNR IPLQSLTAAN   120
IMVEGSIIGY ESNVKSGGVG ARYFGIGADT QYQLDQIAVN LRVVNVSTGE ILSSVNTSKT   180
ILSYEVQAGV FRFIDYQRLL EGEVGYTSNE PVMLCLMSAI ETGVIFLIND GIDRGLWDLQ   240
NKAERQNDIL VKYRHMSVPP ES                                            262

SEQ ID NO: 4            moltype = AA  length = 414
FEATURE                 Location/Qualifiers
source                  1..414
                        mol_type = protein
                        organism = Escherichia coli
SEQUENCE: 4
ATGCGTGTCA AACATGCAGT AGTTCTACTC ATGCTTATTT CGCCATTAAG TTGGGCTGGA    60
ACCATGACTT TCCAGTTCCG TAATCCAAAC TTTGGTGGTA ACCCAAATAA TGGCGCTTTT   120
TTATTAAATA GCGCTCAGGC CCAAAACTCT TATAAAGATC CGAGCTATAA CGATGACTTT   180
GGTATTGAAA CACCCTCAGC GTTAGATAAC TTTACTCAGG CCATCCAGTC ACAAATTTTA   240
GGTGGGCTAC TGTCGAATAT TAATACCGGT AAACCGGGCG GCATGGTGAC CAACGATTAT   300
ATTGTCGATA TTGCCAACCG CGATGGTCAA TTGCAGTTGA ACGTGACAGA TCGTAAAACC   360
GGACAAACCT CGACCATCCA GGTTTCGGGT TTACAAAATA ACTCAACCGA TTTT         414
```

```
SEQ ID NO: 5              moltype = AA   length = 138
FEATURE                   Location/Qualifiers
source                    1..138
                          mol_type = protein
                          organism = Escherichia coli
SEQUENCE: 5
MRVKHAVVLL MLISPLSWAG TMTFQFRNPN FGGNPNNGAF LLNSAQAQNS YKDPSYNDDF   60
GIETPSALDN FTQAIQSQIL GGLLSNINTG KPGRMVTNDY IVDIANRDGQ LQLNVTDRKT  120
GQTSTIQVSG LQNNSTDF                                                138

SEQ ID NO: 6              moltype = AA   length = 119
FEATURE                   Location/Qualifiers
source                    1..119
                          mol_type = protein
                          organism = Escherichia coli
SEQUENCE: 6
GTMTFQFRNP NFGGNPNNGA FLLNSAQAQN SYKDPSYNDD FGIETPSALD NFTQAIQSQI   60
LGGLLSNINT GKPGRMVTND YIVDIANRDG QLQLNVTDRK TGQTSTIQVS GLQNNSTDF   119

SEQ ID NO: 7              moltype = DNA   length = 106
FEATURE                   Location/Qualifiers
misc_feature              1..106
                          note = fragment of wild-type E. coli CsgF encoding amino
                            acids 1 to 27and a C-terminal 6 His tag
source                    1..106
                          mol_type = other DNA
                          organism = synthetic construct
SEQUENCE: 7
atgcgtgtca aacatgcagt agttctactc atgcttattt cgccattaag ttgggctgga   60
accatgactt ccagttccg tcatcaccat caccatcact aagccc                  106

SEQ ID NO: 8              moltype = AA   length = 33
FEATURE                   Location/Qualifiers
REGION                    1..33
                          note = fragment of wild-type E. coli CsgF encompassing
                            amino acids 1 to27 and a C-terminal 6 His tag
source                    1..33
                          mol_type = protein
                          organism = synthetic construct
SEQUENCE: 8
MRVKHAVVLL MLISPLSWAG TMTFQFRHHH HHH                                33

SEQ ID NO: 9              moltype = DNA   length = 139
FEATURE                   Location/Qualifiers
misc_feature              1..139
                          note = fragment of wild-type E. coli CsgF encoding amino
                            acids 1 to 38and a C-terminal 6 His tag
source                    1..139
                          mol_type = other DNA
                          organism = synthetic construct
SEQUENCE: 9
atgcgtgtca aacatgcagt agttctactc atgcttattt cgccattaag ttgggctgga   60
accatgactt ccagttccg taatccaaac tttggtggta acccaaataa tggccatcac  120
catcaccatc actaagccc                                               139

SEQ ID NO: 10             moltype = AA   length = 44
FEATURE                   Location/Qualifiers
REGION                    1..44
                          note = fragment of wild-type E. coli CsgF encompassing
                            amino acids 1 to38 and a C-terminal 6 His tag
source                    1..44
                          mol_type = protein
                          organism = synthetic construct
SEQUENCE: 10
MRVKHAVVLL MLISPLSWAG TMTFQFRNPN FGGNPNNGHH HHHH                    44

SEQ ID NO: 11             moltype = DNA   length = 169
FEATURE                   Location/Qualifiers
misc_feature              1..169
                          note = fragment of wild-type E. coli CsgF encoding amino
                            acids 1 to 48and a C-terminal 6 His tag
source                    1..169
                          mol_type = other DNA
                          organism = synthetic construct
SEQUENCE: 11
atgcgtgtca aacatgcagt agttctactc atgcttattt cgccattaag ttgggctgga   60
accatgactt ccagttccg taatccaaac tttggtggta acccaaataa tggcgctttt  120
ttattaaata gcgctcaggc ccaacatcac catcaccatc actaagccc              169
```

```
SEQ ID NO: 12            moltype = AA  length = 54
FEATURE                  Location/Qualifiers
REGION                   1..54
                         note = fragment of wild-type E. coli CsgF encompassing
                          amino acids 1 to48 and a C-terminal 6 His tag
source                   1..54
                         mol_type = protein
                         organism = synthetic construct
SEQUENCE: 12
MRVKHAVVLL MLISPLSWAG TMTFQFRNPN FGGNPNNGAF LLNSAQAQHH HHHH           54

SEQ ID NO: 13            moltype = DNA  length = 217
FEATURE                  Location/Qualifiers
misc_feature             1..217
                         note = fragment of wild-type E. coli CsgF encoding amino
                          acids 1 to 64and a C-terminal 6 His tag
source                   1..217
                         mol_type = other DNA
                         organism = synthetic construct
SEQUENCE: 13
atgcgtgtca aacatgcagt agttctactc atgcttattt cgccattaag ttgggctgga    60
accatgactt tccagttccg taatccaaac tttggtggta acccaaataa tggcgctttt   120
ttattaaata gcgctcaggc ccaaaactct tataaagatc cgagctataa cgatgacttt   180
ggtattgaaa cacatcacca tcaccatcac taagccc                            217

SEQ ID NO: 14            moltype = AA  length = 70
FEATURE                  Location/Qualifiers
REGION                   1..70
                         note = fragment of wild-type E. coli CsgF encompassing
                          amino acids 1 to64 and a C-terminal 6 His tag
source                   1..70
                         mol_type = protein
                         organism = synthetic construct
SEQUENCE: 14
MRVKHAVVLL MLISPLSWAG TMTFQFRNPN FGGNPNNGAF LLNSAQAQNS YKDPSYNDDF    60
GIETHHHHHH                                                           70

SEQ ID NO: 15            moltype = AA  length = 34
FEATURE                  Location/Qualifiers
REGION                   1..34
                         note = residues 20 to 53 of E. coli CsgF
source                   1..34
                         mol_type = protein
                         organism = synthetic construct
SEQUENCE: 15
GTMTFQFRNP NFGGNPNNGA FLLNSAQAQN SYKD                                34

SEQ ID NO: 16            moltype = AA  length = 25
FEATURE                  Location/Qualifiers
REGION                   1..25
                         note = residues 20 to 42 of E. coli CsgF, including KD at
                          its C-terminus
source                   1..25
                         mol_type = protein
                         organism = synthetic construct
SEQUENCE: 16
GTMTFQFRNP NFGGNPNNGA FLLKD                                          25

SEQ ID NO: 17            moltype = AA  length = 32
FEATURE                  Location/Qualifiers
REGION                   1..32
                         note = residues 23 to 55 of CsgF homologue Q88H88
source                   1..32
                         mol_type = protein
                         organism = synthetic construct
SEQUENCE: 17
TELVYTPVNP AFGGNPLNGT WLLNNAQAQN DY                                  32

SEQ ID NO: 18            moltype = AA  length = 32
FEATURE                  Location/Qualifiers
REGION                   1..32
                         note = residues 25 to 57 of CsgF homologue A0A143HJA0
source                   1..32
                         mol_type = protein
                         organism = synthetic construct
SEQUENCE: 18
TELIYEPVNP NFGGNPLNGS YLLNNAQAQD RH                                  32
```

-continued

| | | |
|---|---|---|
| SEQ ID NO: 19<br>FEATURE<br>REGION<br><br>source | moltype = AA length = 32<br>Location/Qualifiers<br>1..32<br>note = residues 21 to 53 of CsgF homologue Q5E245<br>1..32<br>mol_type = protein<br>organism = synthetic construct | |
| SEQUENCE: 19<br>SELVYTPVNP NFGGNPLNTS HLFGGANAIN DY | | 32 |
| SEQ ID NO: 20<br>FEATURE<br>REGION<br><br>source | moltype = AA length = 32<br>Location/Qualifiers<br>1..32<br>note = residues 19 to 51 of CsgF homologue Q084E5<br>1..32<br>mol_type = protein<br>organism = synthetic construct | |
| SEQUENCE: 20<br>TQLVYTPVNP AFGGSYLNGS YLLANASAQN EH | | 32 |
| SEQ ID NO: 21<br>FEATURE<br>REGION<br><br>source | moltype = AA length = 32<br>Location/Qualifiers<br>1..32<br>note = residues 15 to 47 of CsgF homologue F0LZU2<br>1..32<br>mol_type = protein<br>organism = synthetic construct | |
| SEQUENCE: 21<br>SSLVYEPVNP TFGGNPLNTT HLFSRAEAIN DY | | 32 |
| SEQ ID NO: 22<br>FEATURE<br>REGION<br><br>source | moltype = AA length = 32<br>Location/Qualifiers<br>1..32<br>note = residues 26 to 58 of CsgF homologue A0A136HQR0<br>1..32<br>mol_type = protein<br>organism = synthetic construct | |
| SEQUENCE: 22<br>TELVYEPINP SFGGNPLNGS FLLSKANSQN AH | | 32 |
| SEQ ID NO: 23<br>FEATURE<br>REGION<br><br>source | moltype = AA length = 32<br>Location/Qualifiers<br>1..32<br>note = residues 21 to 53 of CsgF homologue A0A0W1SRL3<br>1..32<br>mol_type = protein<br>organism = synthetic construct | |
| SEQUENCE: 23<br>TEIVYQPINP SFGGNPMNGS FLLQKAQSQN AH | | 32 |
| SEQ ID NO: 24<br>FEATURE<br>REGION<br><br>source | moltype = AA length = 33<br>Location/Qualifiers<br>1..33<br>note = residues 26 to 59 of CsgF homologue B0UH01<br>1..33<br>mol_type = protein<br>organism = synthetic construct | |
| SEQUENCE: 24<br>SSLVYQPVNP AFGGPQLNGS WLQAEANAQN IPQ | | 33 |
| SEQ ID NO: 25<br>FEATURE<br>REGION<br><br>source | moltype = AA length = 31<br>Location/Qualifiers<br>1..31<br>note = residues 22 to 53 of CsgF homologue Q6NAU5<br>1..31<br>mol_type = protein<br>organism = synthetic construct | |
| SEQUENCE: 25<br>GSLVYTPTNP AFGGSPLNGS WQMQQATAGN H | | 31 |
| SEQ ID NO: 26<br>FEATURE<br>REGION<br><br>source | moltype = AA length = 32<br>Location/Qualifiers<br>1..32<br>note = residues 7 to 38 of CsgF homologue G8PUY5<br>1..32<br>mol_type = protein<br>organism = synthetic construct | |
| SEQUENCE: 26<br>QQLIYQPTNP SFGGYAANTT HLFATANAQK TA | | 32 |

```
SEQ ID NO: 27           moltype = AA  length = 32
FEATURE                 Location/Qualifiers
REGION                  1..32
                        note = residues 25 to 57 of CsgF homologue A0A0S2ETP7
source                  1..32
                        mol_type = protein
                        organism = synthetic construct
SEQUENCE: 27
GDLVYTPVNP SFGGSPLNSA HLLSIAGAQK NA                                  32

SEQ ID NO: 28           moltype = AA  length = 32
FEATURE                 Location/Qualifiers
REGION                  1..32
                        note = residues 19 to 51 of CsgF homologue E3I1Z1
source                  1..32
                        mol_type = protein
                        organism = synthetic construct
SEQUENCE: 28
AELGYTPVNP SFGGSPLNGS TLLSEASAQK PN                                  32

SEQ ID NO: 29           moltype = AA  length = 31
FEATURE                 Location/Qualifiers
REGION                  1..31
                        note = residues 24 to 55 of CsgF homologue F3Z094
source                  1..31
                        mol_type = protein
                        organism = synthetic construct
SEQUENCE: 29
TELVFSFTNP SFGGDPMIGN FLLNKADSQK R                                   31

SEQ ID NO: 30           moltype = AA  length = 32
FEATURE                 Location/Qualifiers
REGION                  1..32
                        note = residues 21 to 53 of CsgF homologue A0A176T7M2
source                  1..32
                        mol_type = protein
                        organism = synthetic construct
SEQUENCE: 30
QQLVYKSINP FFGGGDSFAY QQLLASANAQ ND                                  32

SEQ ID NO: 31           moltype = AA  length = 31
FEATURE                 Location/Qualifiers
REGION                  1..31
                        note = residues 14 to 45 of CsgF homologue D2QPP8
source                  1..31
                        mol_type = protein
                        organism = synthetic construct
SEQUENCE: 31
QALVYHPNNP AFGGNTFNYQ WMLSSAQAQD R                                   31

SEQ ID NO: 32           moltype = AA  length = 32
FEATURE                 Location/Qualifiers
REGION                  1..32
                        note = residues 28 to 58 of CsgF homologue N2IYT1
source                  1..32
                        mol_type = protein
                        organism = synthetic construct
SEQUENCE: 32
TELVYTPKNP AFGGSPLNGS YLLGNAQAQN DY                                  32

SEQ ID NO: 33           moltype = AA  length = 32
FEATURE                 Location/Qualifiers
REGION                  1..32
                        note = residues 26 to 58 of CsgF homologue W7QHV5
source                  1..32
                        mol_type = protein
                        organism = synthetic construct
SEQUENCE: 33
GQLIYQPINP SFGGDPLLGN HLLNKAQAQD TK                                  32

SEQ ID NO: 34           moltype = AA  length = 32
FEATURE                 Location/Qualifiers
REGION                  1..32
                        note = residues 23 to 55 of CsgF homologue D4ZLW2
source                  1..32
                        mol_type = protein
                        organism = synthetic construct
```

```
SEQUENCE: 34
TQLIYTPVNP NFGGSYLNGS YLLANASVQN DH                              32

SEQ ID NO: 35           moltype = AA  length = 32
FEATURE                 Location/Qualifiers
REGION                  1..32
                        note = residues 21 to 53 of CsgF homologue D2QT92
source                  1..32
                        mol_type = protein
                        organism = synthetic construct
SEQUENCE: 35
QAFVYHPNNP NFGGNTFNYS WMLSSAQAQD RT                              32

SEQ ID NO: 36           moltype = AA  length = 31
FEATURE                 Location/Qualifiers
REGION                  1..31
                        note = residues 20 to 51 of CsgF homologue A0A167UJA2
source                  1..31
                        mol_type = protein
                        organism = synthetic construct
SEQUENCE: 36
QGLIYKPKNP AFGGDTFNYQ WLASSAESQN K                               31

SEQ ID NO: 37           moltype = AA  length = 8
FEATURE                 Location/Qualifiers
REGION                  1..8
                        note = residues 20 to 27 of wild-type E. coli CsgF
source                  1..8
                        mol_type = protein
                        organism = synthetic construct
SEQUENCE: 37
GTMTFQFR                                                         8

SEQ ID NO: 38           moltype = AA  length = 19
FEATURE                 Location/Qualifiers
REGION                  1..19
                        note = residues 20 to 38 of wild-type E. coli CsgF
source                  1..19
                        mol_type = protein
                        organism = synthetic construct
SEQUENCE: 38
GTMTFQFRNP NFGGNPNNG                                             19

SEQ ID NO: 39           moltype = AA  length = 29
FEATURE                 Location/Qualifiers
REGION                  1..29
                        note = residues 20 to 48 of wild-type E. coli CsgF
source                  1..29
                        mol_type = protein
                        organism = synthetic construct
SEQUENCE: 39
GTMTFQFRNP NFGGNPNNGA FLLNSAQAQ                                  29

SEQ ID NO: 40           moltype = AA  length = 45
FEATURE                 Location/Qualifiers
REGION                  1..45
                        note = residues 20 to 64 of wild-type E. coli CsgF
source                  1..45
                        mol_type = protein
                        organism = synthetic construct
SEQUENCE: 40
GTMTFQFRNP NFGGNPNNGA FLLNSAQAQN SYKDPSYNDD FGIET                45

SEQ ID NO: 41           moltype = DNA  length = 24
FEATURE                 Location/Qualifiers
misc_feature            1..24
                        note = primer CsgF_d27_end
source                  1..24
                        mol_type = other DNA
                        organism = synthetic construct
SEQUENCE: 41
acggaactgg aaagtcatgg ttcc                                       24

SEQ ID NO: 42           moltype = DNA  length = 30
FEATURE                 Location/Qualifiers
misc_feature            1..30
                        note = primer CsgF_d38_end
```

```
source                    1..30
                          mol_type = other DNA
                          organism = synthetic construct
SEQUENCE: 42
gccattattt gggttaccac caaagtttgg                                           30

SEQ ID NO: 43             moltype = DNA   length = 30
FEATURE                   Location/Qualifiers
misc_feature              1..30
                          note = primer CsgF_d48_end
source                    1..30
                          mol_type = other DNA
                          organism = synthetic construct
SEQUENCE: 43
ttgggcctga gcgctattta ataaaaaagc                                           30

SEQ ID NO: 44             moltype = DNA   length = 33
FEATURE                   Location/Qualifiers
misc_feature              1..33
                          note = primer CsgF_d64_end
source                    1..33
                          mol_type = other DNA
                          organism = synthetic construct
SEQUENCE: 44
tgtttcaata ccaaagtcat cgttatagct cgg                                       33

SEQ ID NO: 45             moltype = DNA   length = 25
FEATURE                   Location/Qualifiers
misc_feature              1..25
                          note = primer pNa62_CsgF_histag_Fw
source                    1..25
                          mol_type = other DNA
                          organism = synthetic construct
SEQUENCE: 45
catcaccatc accatcacta agccc                                                25

SEQ ID NO: 46             moltype = DNA   length = 32
FEATURE                   Location/Qualifiers
misc_feature              1..32
                          note = primer CsgF-His_pET22b_FW
source                    1..32
                          mol_type = other DNA
                          organism = synthetic construct
SEQUENCE: 46
cccccatatg ggaaccatga ctttccagtt cc                                        32

SEQ ID NO: 47             moltype = DNA   length = 55
FEATURE                   Location/Qualifiers
misc_feature              1..55
                          note = primer CsgF-His_pET22b_Rev
source                    1..55
                          mol_type = other DNA
                          organism = synthetic construct
SEQUENCE: 47
ccccgaattc ctaatggtga tggtgatggt ggtaaaaatc ggttgagtta ttttg               55

SEQ ID NO: 48             moltype = DNA   length = 58
FEATURE                   Location/Qualifiers
misc_feature              1..58
                          note = primer csgEFG_pDONR221_FW
source                    1..58
                          mol_type = other DNA
                          organism = synthetic construct
SEQUENCE: 48
ggggacaagt ttgtacaaaa aagcaggcta cctcaggcga taaagccatg aaacgtta            58

SEQ ID NO: 49             moltype = DNA   length = 72
FEATURE                   Location/Qualifiers
misc_feature              1..72
                          note = primer csgEFG_pDONR221_Rev
source                    1..72
                          mol_type = other DNA
                          organism = synthetic construct
SEQUENCE: 49
ggggaccact ttgtacaaga aagctgggtg tttaaactca ttttcgaac tgcgggtggc           60
tccaagcgct gg                                                              72

SEQ ID NO: 50             moltype = DNA   length = 59
FEATURE                   Location/Qualifiers
```

```
misc_feature              1..59
                          note = primer Mut_csgF_His_FW
source                    1..59
                          mol_type = other DNA
                          organism = synthetic construct
SEQUENCE: 50
caaaataact caaccgattt tcatcaccat caccatcact aagccccagc ttcataagg      59

SEQ ID NO: 51             moltype = DNA  length = 59
FEATURE                   Location/Qualifiers
misc_feature              1..59
                          note = primer Mut_csgF_His_Rev
source                    1..59
                          mol_type = other DNA
                          organism = synthetic construct
SEQUENCE: 51
ccttatgaag ctgggcctta gtgatggtga tggtgatgaa atcggttga gttattttg       59

SEQ ID NO: 52             moltype = DNA  length = 21
FEATURE                   Location/Qualifiers
misc_feature              1..21
                          note = primer DelCsgE_Rev
source                    1..21
                          mol_type = other DNA
                          organism = synthetic construct
SEQUENCE: 52
agcctgcttt tttgtacaaa c                                               21

SEQ ID NO: 53             moltype = DNA  length = 23
FEATURE                   Location/Qualifiers
misc_feature              1..23
                          note = primer DelCsgE FW
source                    1..23
                          mol_type = other DNA
                          organism = synthetic construct
SEQUENCE: 53
ataaaaaatt gttcggaggc tgc                                             23

SEQ ID NO: 54             moltype = AA  length = 30
FEATURE                   Location/Qualifiers
REGION                    1..30
                          note = residues 1 to 29 of mature E. coli CsgF
source                    1..30
                          mol_type = protein
                          organism = synthetic construct
SEQUENCE: 54
GTMTFQFRNP NFGGNPNNGA FLLNSAQAQN                                      30

SEQ ID NO: 55             moltype = AA  length = 35
FEATURE                   Location/Qualifiers
REGION                    1..35
                          note = residues 1 to 45 of mature E. coli CsgF
source                    1..35
                          mol_type = protein
                          organism = synthetic construct
SEQUENCE: 55
GTMTFQFRNP NFGGNPNNGA FLLNSAQAQN SYKDP                                35

SEQ ID NO: 56             moltype = AA  length = 155
FEATURE                   Location/Qualifiers
REGION                    1..155
                          note = a mutated (T4C/N17S) CsgF sequence with a signal
                           sequence, and aTEV protease cleavage site (ENLYFQS)
                           inserted between residues 35and 36 of sequence of the
                           mature protein
source                    1..155
                          mol_type = protein
                          organism = synthetic construct
SEQUENCE: 56
MRVKHAVVLL MLISPLSWAG TMCFQFRNPN FGGNPSNGAF LLNSAQAQNS YKDPENLYFQ     60
SSYNDDFGIE TPSALDNFTQ AIQSQILGGL LSNINTGKPG RMVTNDYIVD IANRDGQLQL    120
NVTDRKTGQT STIQVSGLQN NSTDFSAWSH PQFEK                               155

SEQ ID NO: 57             moltype = AA  length = 155
FEATURE                   Location/Qualifiers
REGION                    1..155
                          note = a mutated (N17S-Del) CsgF sequence with a signal
                           sequence, and aTEV protease cleavage site (ENLYFQS)
```

-continued

```
                              inserted between residues 35and 36 of sequence of the
                              mature protein
source                        1..155
                              mol_type = protein
                              organism = synthetic construct
SEQUENCE: 57
MRVKHAVVLL MLISPLSWAG TMTFQFRNPN FGGNPSNGAF LLNSAQAQNS YKDPENLYFQ    60
SSYNDDFGIE TPSALDNFTQ AIQSQILGGL LSNINTGKPG RMVTNDYIVD IANRDGQLQL   120
NVTDRKTGQT STIQVSGLQN NSTDFSAWSH PQFEK                              155

SEQ ID NO: 58                 moltype = AA  length = 155
FEATURE                       Location/Qualifiers
REGION                        1..155
                              note = a mutated (G1C/N17S) CsgF sequence with a signal
                                sequence, and aTEV protease cleavage site (ENLYFQS)
                                inserted between residues 35and 36 of sequence of the
                                mature protein
source                        1..155
                              mol_type = protein
                              organism = synthetic construct
SEQUENCE: 58
MRVKHAVVLL MLISPLSWAC TMTFQFRNPN FGGNPSNGAF LLNSAQAQNS YKDPENLYFQ    60
SSYNDDFGIE TPSALDNFTQ AIQSQILGGL LSNINTGKPG RMVTNDYIVD IANRDGQLQL   120
NVTDRKTGQT STIQVSGLQN NSTDFSAWSH PQFEK                              155

SEQ ID NO: 59                 moltype = AA  length = 155
FEATURE                       Location/Qualifiers
REGION                        1..155
                              note = a mutated (G1C) CsgF sequence with a signal
                                sequence, and a TEVprotease cleavage site (ENLYFQS)
                                inserted between residues 35 and36 of sequence of the
                                mature protein
source                        1..155
                              mol_type = protein
                              organism = synthetic construct
SEQUENCE: 59
MRVKHAVVLL MLISPLSWAC TMTFQFRNPN FGGNPNNGAF LLNSAQAQNS YKDPENLYFQ    60
SSYNDDFGIE TPSALDNFTQ AIQSQILGGL LSNINTGKPG RMVTNDYIVD IANRDGQLQL   120
NVTDRKTGQT STIQVSGLQN NSTDFSAWSH PQFEK                              155

SEQ ID NO: 60                 moltype = AA  length = 155
FEATURE                       Location/Qualifiers
REGION                        1..155
                              note = a CsgF sequence with a signal sequence, a TEV
                                protease cleavagesite (ENLYFQS) inserted between residues
                                45 and 46 of sequence ofthe mature protein, and a His10
                                tag at the C-terminus
source                        1..155
                              mol_type = protein
                              organism = synthetic construct
SEQUENCE: 60
MRVKHAVVLL MLISPLSWAG TMTFQFRNPN FGGNPNNGAF LLNSAQAQNS YKDPSYNDDF    60
GIETENLYFQ SPSALDNFTQ AIQSQILGGL LSNINTGKPG RMVTNDYIVD IANRDGQLQL   120
NVTDRKTGQT STIQVSGLQN NSTDFHHHHH HHHHH                              155

SEQ ID NO: 61                 moltype = AA  length = 155
FEATURE                       Location/Qualifiers
REGION                        1..155
                              note = a CsgF sequence with a signal sequence, a TEV
                                protease cleavagesite (ENLYFQS) inserted between residues
                                35 and 36 of sequence ofthe mature protein, and a His10
                                tag at the C-terminus
source                        1..155
                              mol_type = protein
                              organism = synthetic construct
SEQUENCE: 61
MRVKHAVVLL MLISPLSWAG TMTFQFRNPN FGGNPNNGAF LLNSAQAQNS YKDPENLYFQ    60
SSYNDDFGIE TPSALDNFTQ AIQSQILGGL LSNINTGKPG RMVTNDYIVD IANRDGQLQL   120
NVTDRKTGQT STIQVSGLQN NSTDFHHHHH HHHHH                              155

SEQ ID NO: 62                 moltype = AA  length = 155
FEATURE                       Location/Qualifiers
REGION                        1..155
                              note = a CsgF sequence with a signal sequence, a TEV
                                protease cleavagesite (ENLYFQS) inserted between residues
                                30 and 31 of sequence ofthe mature protein, and a His10
                                tag at the C-terminus.
```

```
source                   1..155
                         mol_type = protein
                         organism = synthetic construct
SEQUENCE: 62
MRVKHAVVLL MLISPLSWAG TMTFQFRNPN FGGNPNNGAF LLNSAQAQNE NLYFQSSYKD    60
PSYNDDFGIE TPSALDNFTQ AIQSQILGGL LSNINTGKPG RMVTNDYIVD IANRDGQLQL   120
NVTDRKTGQT STIQVSGLQN NSTDFHHHHH HHHHH                              155

SEQ ID NO: 63            moltype = AA   length = 149
FEATURE                  Location/Qualifiers
REGION                   1..149
                         note = a CsgF sequence with a signal sequence, a TEV
                          protease cleavagesite (ENLYFQS) inserted between residues
                          45 and 51 of sequence ofthe mature protein, and a His10
                          tag at the C-terminus
source                   1..149
                         mol_type = protein
                         organism = synthetic construct
SEQUENCE: 63
MRVKHAVVLL MLISPLSWAG TMTFQFRNPN FGGNPNNGAF LLNSAQAQNS YKDPSYNDDF    60
GIETENLYFQ SFTQAIQSQI LGGLLSNINT GKPGRMVTND YIVDIANRDG QLQLNVTDRK   120
TGQTSTIQVS GLQNNSTDFH HHHHHHHHH                                     149

SEQ ID NO: 64            moltype = AA   length = 149
FEATURE                  Location/Qualifiers
REGION                   1..149
                         note = a CsgF sequence with a signal sequence, a TEV
                          protease cleavagesite (ENLYFQS) inserted between residues
                          30 and 37 of sequence ofthe mature protein, and a His10
                          tag at the C-terminus
source                   1..149
                         mol_type = protein
                         organism = synthetic construct
SEQUENCE: 64
MRVKHAVVLL MLISPLSWAG TMTFQFRNPN FGGNPNNGAF LLNSAQAQNE NLYFQSYNDD    60
FGIETPSALD NFTQAIQSQI LGGLLSNINT GKPGRMVTND YIVDIANRDG QLQLNVTDRK   120
TGQTSTIQVS GLQNNSTDFH HHHHHHHHH                                     149

SEQ ID NO: 65            moltype = AA   length = 155
FEATURE                  Location/Qualifiers
REGION                   1..155
                         note = a CsgF sequence with a signal sequence, a HCV C3
                          proteasecleavage site (LEVLFQGP) inserted between residues
                          34 and 36 ofsequence of the mature protein, and a His10
                          tag at the C-terminus
source                   1..155
                         mol_type = protein
                         organism = synthetic construct
SEQUENCE: 65
MRVKHAVVLL MLISPLSWAC TMTFQFRNPN FGGNPNNGAF LLNSAQAQNS YKDLEVLFQG    60
PSYNDDFGIE TPSALDNFTQ AIQSQILGGL LSNINTGKPG RMVTNDYIVD IANRDGQLQL   120
NVTDRKTGQT STIQVSGLQN NSTDFSAWSH PQFEK                              155

SEQ ID NO: 66            moltype = AA   length = 156
FEATURE                  Location/Qualifiers
REGION                   1..156
                         note = a CsgF sequence with a signal sequence, a HCV C3
                          proteasecleavage site (LEVLFQGP) inserted between residues
                          42 and 43 ofsequence of the mature protein, and a His10
                          tag at the C-terminus
source                   1..156
                         mol_type = protein
                         organism = synthetic construct
SEQUENCE: 66
MRVKHAVVLL MLISPLSWAC TMTFQFRNPN FGGNPNNGAF LLNSAQAQNS YKDPSYNDDF    60
GILEVLFQGP ETPSALDNFT QAIQSQILGG LLSNINTGKP GRMVTNDYIV DIANRDGQLQ   120
LNVTDRKTGQ TSTIQVSGLQ NNSTDFSAWS HPQFEK                             156

SEQ ID NO: 67            moltype = AA   length = 148
FEATURE                  Location/Qualifiers
REGION                   1..148
                         note = a CsgF sequence with a signal sequence, a HCV C3
                          proteasecleavage site (LEVLFQGP) inserted between residues
                          38 and 47 ofsequence of the mature protein, and a His10
                          tag at the C-terminus
source                   1..148
                         mol_type = protein
                         organism = synthetic construct
```

```
SEQUENCE: 67
MRVKHAVVLL MLISPLSWAC TMTFQFRNPN FGGNPNNGAF LLNSAQAQNS YKDPSYNLEV    60
LFQGPSALDN FTQAIQSQIL GGLLSNINTG KPGRMVTNDY IVDIANRDGQ LQLNVTDRKT   120
GQTSTIQVSG LQNNSTDFSA WSHPQFEK                                     148

SEQ ID NO: 68              moltype = AA  length = 248
FEATURE                    Location/Qualifiers
source                     1..248
                           mol_type = protein
                           organism = Citrobacter koseri
SEQUENCE: 68
MPRAQSYKDL THLPMPTGKI FVSVYNIQDE TGQFKPYPAS NFSTAVPQSA TAMLVTALKD    60
SRWFIPLERQ GLQNLLNERK IIRAAQENGT VAINNRIPLQ SLTAANIMVE GSIIGYESNV   120
KSGGVGARYF GIGADTQYQL DQIAVNLRVV NVSTGEILSS VNTSKTILSY EVQAGVFRFI   180
DYQRLLEGEI GYTSNEPVML CLMSAIETGV IFLINDGIDR GLWDLQNKAE RQNDILVKYR   240
HMSVPPES                                                           248

SEQ ID NO: 69              moltype = AA  length = 223
FEATURE                    Location/Qualifiers
source                     1..223
                           mol_type = protein
                           organism = Salmonella enterica
SEQUENCE: 69
CLTAPPKQAA KPTLMPRAQS YKDLTHLPAP TGKIFVSVYN IQDETGQFKP YPASNFSTAV    60
PQSATAMLVT ALKDSRWFIP LERQGLQNLL NERKIIRAAQ ENGTVAMNNR IPLQSLTAAN   120
IMVEGSIIGY ESNVKSGGVG ARYFGIGADT QYQLDQIAVN LRVVNVSTGE ILSSVNTSKT   180
ILSYEVQAGV FRFIDYQRLL EGEIGYTSNE PVMLCLMSAI ETG                    223

SEQ ID NO: 70              moltype = AA  length = 262
FEATURE                    Location/Qualifiers
source                     1..262
                           mol_type = protein
                           organism = Citrobacter amalonaticus
SEQUENCE: 70
CLTAPPKEAA KPTLMPRAQS YKDLTHLPIP TGKIFVSVYN IQDETGQFKP YPASNFSTAV    60
PQSATAMLVT ALKDSRWFVP LERQGLQNLL NERKIIRAAQ ENGTVAINNR IPLQSLTAAN   120
IMVEGSIIGY ESNVKSGGVG ARYFGIGADT QYQLDQIAVN LRVVNVSTGE ILSSVNTSKT   180
ILSYEVQAGV FRFIDYQRLL EGEIGYTSNE PVMLCLMSAI ETGVIFLIND GIDRGLWDLQ   240
NKADRQNDIL VKYRHMSVPP ES                                           262

SEQ ID NO: 71              moltype = AA  length = 262
FEATURE                    Location/Qualifiers
source                     1..262
                           mol_type = protein
                           organism = Citrobacter rodentium
SEQUENCE: 71
CLTTPPKEAA KPTLMPRAQS YKDLTHLPVP TGKIFVSVYN IQDETGQFKP YPASNFSTAV    60
PQSATAMLVT ALKDSRWFIP LERQGLQNLL NERKIIRAAQ ENGTVAINNR IPLPSLTAAN   120
IMVEGSIIGY ESNVKSGGAG ARYFGIGADT QYQLDQIAVN LRVVNVSTGE ILSSVNTSKT   180
ILSYEVQAGV FRFIDYQRLL EGEIGYTSNE PVMLCLMSAI ETGVIFLIND GIDRGLWDLQ   240
NKADRQNDIL VKYRQMSVPP ES                                           262

SEQ ID NO: 72              moltype = AA  length = 262
FEATURE                    Location/Qualifiers
source                     1..262
                           mol_type = protein
                           organism = Enterobacter asburiae
SEQUENCE: 72
CLTAPPKEAA KPTLMPRAQS YRDLTHLPAP TGKIFVSVYN IQDETGQFKP YPASNFSTAV    60
PQSATAMLVT ALKDSHWFIP LERQGLQNLL NERKIIRAAQ ENGTVANNNR MPLQSLAAAN   120
VMIEGSIIGY ESNVKSGGVG ARYFGIGADT QYQLDQIAVN LRVVNVSTGE VLSSVNTSKT   180
ILSYEVQAGV FRFIDYQRLL EGEIGYTSNE PVMMCLMSAI ETGVIFLIND GIDRGLWDLQ   240
NKADAQNPVL VKYRDMSVPP ES                                           262

SEQ ID NO: 73              moltype = AA  length = 262
FEATURE                    Location/Qualifiers
source                     1..262
                           mol_type = protein
                           organism = Yokenella regensburgei
SEQUENCE: 73
CLTAPPKEAA KPTLMPRAQS YRDLTHLPLP SGKVFVSVYN IQDETGQFKP YPASNFSTAV    60
PQSATAMLVT ALKDSRWFVP LERQGLQNLL NERKIIRAAQ ENGTVADNNR IPLQSLTAAN   120
VMIEGSIIGY ESNVKSGGVG ARYFGIGADT QYQLDQIAVN LRVVNVSTGE VLSSVNTSKT   180
ILSYEVQAGV FRFVDYQRLL EGEIGYTSNE PVMLCLMSAI ETGVIYLIND GIERGLWDLQ   240
QKADVDNPIL ARYRNMSAPP ES                                           262

SEQ ID NO: 74              moltype = AA  length = 262
FEATURE                    Location/Qualifiers
source                     1..262
```

```
                            mol_type = protein
                            note = Cronobacter pulveris
                            organism = unidentified
SEQUENCE: 74
CLTAAPPKEAA KPTLMPRAQS YRDLTNLPDP KGKLFVSVYN IQDETGQFKP YPASNFSTAV    60
PQSATSMLVT ALKDSRWFIP LERQGLQNLL NERKIIRAAQ ENGTVAENNR MPLQSLVAAN   120
VMIEGSIIGY ESNVKSGGVG ARYFGIGGDT QYQLDQIAVN LRVVNVSTGE VLSSVNTSKT   180
ILSYEVQAGV FRFIDYQRLL EGEIGYTANE PVMLCLMSAI ETGVIHLIND GINRGLWELK   240
NKGDAKNTIL AKYRSMAVPP ES                                            262

SEQ ID NO: 75               moltype = AA   length = 262
FEATURE                     Location/Qualifiers
source                      1..262
                            mol_type = protein
                            organism = Rahnella aquatilis
SEQUENCE: 75
CLTAAPKEAA RPTLLPRAPS YTDLTHLPSP QGRIFVSVYN IQDETGQFKP YPACNFSTAV    60
PQSATAMLVS ALKDSKWFIP LERQGLQNLL NERKIIRAAQ ENGSVAINNQ RPLSSLVAAN   120
ILIEGSIIGY ESNVKSGGVG ARYFGIGAST QYQLDQIAVN LRAVDVNTGE VLSSVNTSKT   180
ILSYEVQAGV FRFIDYQRLL EGELGYTTNE PVMLCLMSAI ESGVIYLVND GIERNLWQLQ   240
NPSEINSPIL QRYKNNIVPA ES                                            262

SEQ ID NO: 76               moltype = AA   length = 259
FEATURE                     Location/Qualifiers
source                      1..259
                            mol_type = protein
                            organism = Kluyvera ascorbata
SEQUENCE: 76
CITSPPKQAA KPTLLPRSQS YQDLTHLPEP QGRLFVSVYN ISDETGQFKP YPASNFSTSV    60
PQSATAMLVS ALKDSNWFIP LERQGLQNLL NERKIIRAAQ ENGTVAVNNR TQLPSLVAAN   120
ILIEGSIIGY ESNVKSGGAG ARYFGIGAST QYQLDQIAVN LRVVNVSTGE VLSSVNTSKT   180
ILSYEFQAGV FRYIDYQRLL EGEVGYTVNE PVMLCLMSAI ETGVIYLVND GISRNLWQLK   240
NASDINSPVL EKYKSIIVP                                                259

SEQ ID NO: 77               moltype = AA   length = 259
FEATURE                     Location/Qualifiers
source                      1..259
                            mol_type = protein
                            organism = Hafnia alvei
SEQUENCE: 77
CLTAPPKQAA KPTLMPRAQS YQDLTHLPEP AGKLFVSVYN IQDETGQFKP YPASNFSTAV    60
PQSATAMLVS ALKDSGWFIP LERQGLQNLL NERKIIRAAQ ENGTAAVNNQ HQLSSLVAAN   120
VLVEGSIIGY ESNVKSGGAG ARFFGIGAST QYQLDQIAVN LRVVDVNTGQ VLSSVNTSKT   180
ILSYEVQAGV FRYIDYQRLL EGEIGYTTNE PVMLCVMSAI ETGVIYLVND GINRNLWTLK   240
NPQDAKSSVL ERYKSTIVP                                                259

SEQ ID NO: 78               moltype = AA   length = 255
FEATURE                     Location/Qualifiers
source                      1..255
                            mol_type = protein
                            note = Enterobacteriaceae bacterium
                            organism = unidentified
SEQUENCE: 78
CITTPPQEAA KPTLLPRDAT YKDLVSLPQP RGKIYVAVYN IQDETGQFQP YPASNFSTSV    60
PQSATAMLVS SLKDSRWFVP LERQGLNNLL NERKIIRAAQ QNGTVGDNNA SPLPSLYSAN   120
VIVEGSIIGY ASNVKTGGFG ARYFGIGGST QYQLDQVAVN LRIVNVHTGE VLSSVNTSKT   180
ILSYEIQAGV FRFIDYQRLL EGEAGFTTNE PVMTCLMSAI EEGVIHLIND GINKKLWALS   240
NAADINSEVL TRYRK                                                    255

SEQ ID NO: 79               moltype = AA   length = 258
FEATURE                     Location/Qualifiers
source                      1..258
                            mol_type = protein
                            organism = Plesiomonas shigelloides
SEQUENCE: 79
ITEVPKEAAK PTLMPRASTY KDLVALPKPN GKIIVSVYSV QDETGQFKPL PASNFSTAVP    60
QSGNAMLTSA LKDSGWFVPL EREGLQNLLN ERKIIRAAQE NGTVAANNQQ PLPSLLSANV   120
VIEGAIIGYD SDIKTGGAGA RYFGIGADGK YRVDQVAVNL RAVDVRTGEV LLSVNTSKTI   180
LSSELSAGVF RFIEYQRLLE LEAGYTTNEP VMMCMMSALE AGVAHLIVEG IRQNLWSLQN   240
PSDINNPIIQ RYMKEDVP                                                 258

SEQ ID NO: 80               moltype = AA   length = 248
FEATURE                     Location/Qualifiers
source                      1..248
                            mol_type = protein
                            note = Vibrio fischeri
                            organism = unidentified
```

```
SEQUENCE: 80
PETSESPTLM QRGANYIDLI SLPKPQGKIF VSVYDFRDQT GQYKPQPNSN FSTAVPQGGT    60
ALLTMALLDS EWFYPLERQG LQNLLTERKI IRAAQKKQES ISNHGSTLPS LLSANVMIEG   120
GIVAYDSNIK TGGAGARYLG IGGSGQYRAD QVTVNIRAVD VRSGKILTSV TTSKTILSYE   180
VSAGAFRFVD YKELLEVELG YTNNEPVNIA LMSAIDSAVI HLIVKGVQQG LWRPANLDTR   240
NNPIFKKY                                                           248

SEQ ID NO: 81           moltype = AA  length = 248
FEATURE                 Location/Qualifiers
source                  1..248
                        mol_type = protein
                        organism = Aliivibrio logei
SEQUENCE: 81
PDASESPTLM QRGATYLDLI SLPKPQGKIY VSVYDFRDQT GQYKPQPNSN FSTAVPQGGT    60
ALLTMALLDS EWFYPLERQG LQNLLTERKI IRAAQKKQES ISNHGSTLPS LLSANVMIEG   120
GIVAYDSNIK TGGAGARYLG IGGSGQYRAD QVTVNIRAVD VRSGKILTSV TTSKTILSYE   180
LSAGAFRFVD YKELLEVELG YTNNEPVNIA LMSAIDSAVI HLIVKGIEEG LWRPENQNGK   240
ENPIFRKY                                                           248

SEQ ID NO: 82           moltype = AA  length = 254
FEATURE                 Location/Qualifiers
source                  1..254
                        mol_type = protein
                        organism = Photobacterium sp.
SEQUENCE: 82
PETSKEPTLM ARGTAYQDLV SLPLPKGKVY VSVYDFRDQT GQYKPQPNSN FSTAVPQGGA    60
ALLTTALLDS RWFMPLEREG LQNLLTERKI IRAAQKKDEI PTNHGVHLPS LASANIMVEG   120
GIVAYDTNIQ TGGAGARYLG VGASGQYRTD QVTVNIRAVD VRTGRILLSV TTSKTILSKE   180
LQTGVFKFVD YKDLLEAELG YTTNEPVNLA VMSAIDAAVV HVIVDGIKTG LWEPLRGEDL   240
QHPIIQEYMN RSKP                                                    254

SEQ ID NO: 83           moltype = AA  length = 261
FEATURE                 Location/Qualifiers
source                  1..261
                        mol_type = protein
                        organism = Aeromonas veronii
SEQUENCE: 83
CATHIGSPVA DEKATLMPRS VSYKELISLP KPKGKIVAAV YDFRDQTGQY LPAPASNFST    60
AVTQGGVAML STALWDSQWF VPLEREGLQN LLTERKIVRA AQNKPNVPGN NANQLPSLVA   120
ANILIEGGIV AYDSNVRTGG AGAKYFGIGA SGEYRVDQVT VNLRAVDIRS GRILNSVTTS   180
KTVMSQQVQA GVFRFVEYKR LLEAEAGFST NEPVQMCVMS AIESGVIRLI ANGVRDNLWQ   240
LADQRDIDNP ILQEYLQDNA P                                            261

SEQ ID NO: 84           moltype = AA  length = 239
FEATURE                 Location/Qualifiers
source                  1..239
                        mol_type = protein
                        organism = Shewanella sp.
SEQUENCE: 84
ASSSLMPKGE SYYDLINLPA PQGVMLAAVY DFRDQTGQYK PIPSSNFSTA VPQSGTAFLA    60
QALNDSSWFI PVEREGLQNL LTERKIVRAG LKGDANKLPQ LNSAQILMEG GIVAYDTNVR   120
TGGAGARYLG IGAATQFRVD TVTVNLRAVD IRTGRLLSSV TTTKSILSKE ITAGVFKFID   180
AQELLESELG YTSNEPVSLC VASAIESAVV HMIADGIWKG AWNLADQASG LRSPVLQKY    239

SEQ ID NO: 85           moltype = AA  length = 233
FEATURE                 Location/Qualifiers
source                  1..233
                        mol_type = protein
                        organism = Pseudomonas putida
SEQUENCE: 85
QDSETPTLTP RASTYYDLIN MPRPKGRLMA VVYGFRDQTG QYKPTPASSF STSVTQGAAS    60
MLMDALSASG WFVVLEREGL QNLLTERKII RASQKKPDVA ENIMGELPPL QAANLMEGG   120
IIAYDTNVRS GGEGARYLGI DISREYRVDQ VTVNLRAVDV RTGQVLANVM TSKTIYSVGR   180
SAGVFKFIEF KKLLEAEVGY TTNEPAQLCV LSAIESAVGH LLAQGIEQRL WQV          233

SEQ ID NO: 86           moltype = AA  length = 234
FEATURE                 Location/Qualifiers
source                  1..234
                        mol_type = protein
                        organism = Shewanella violacea
SEQUENCE: 86
MPKSDTYYDL IGLPHPQGSM LAAVYDFRDQ TGQYKAIPSS NFSTAVPQSG TAFLAQALND    60
SSWFVPVERE GLQNLLTERK IVRAGLKGEA NQLPQLSSAQ ILMEGGIVAY DTNIKTGGAG   120
ARYLGIGVNS KFRVDTVTVN LRAVDIRTGR LLSSVTTTKS ILSKEVSAGV FKFIDAQDLL   180
ESELGYTSNE PVSLCVAQAI ESAVVHMIAD GIWKRAWNLA DTASGLNNPV LQKY         234

SEQ ID NO: 87           moltype = AA  length = 245
FEATURE                 Location/Qualifiers
source                  1..245
```

```
                        mol_type = protein
                        organism = Marinobacterium jannaschii
SEQUENCE: 87
LTRRMSTYQD LIDMPAPRGK IVTAVYSFRD QSGQYKPAPS SSFSTAVTQG AAAMLVNVLN      60
DSGWFIPLER EGLQNILTER KIIRAALKKD NVPVNNSAGL PSLLAANIML EGGIVGYDSN     120
IHTGGAGARY FGIGASEKYR VDEVTVNLRA IDIRTGRILH SVLTSKKILS REIRSDVYRF    180
IEFKHLLEME AGITTNDPAQ LCVLSAIESA VAHLIVDGVI KKSWSLADPN ELNSPVIQAY    240
QQQRI                                                                245

SEQ ID NO: 88           moltype = AA  length = 234
FEATURE                 Location/Qualifiers
source                  1..234
                        mol_type = protein
                        organism = Chryseobacterium oranimense
SEQUENCE: 88
PSDPERSTMG ELTPSTAELR NLPLPNEKIV IGVYKFRDQT GQYKPSENGN NWSTAVPQGT      60
TTILIKALED SRWFIPIERE NIANLLNERQ IIRSTRQEYM KDADKNSQSL PPLLYAGILL     120
EGGVISYDSN TMTGGFGARY FGIGASTQYR QDRITIYLRA VSTLNGEILK TVYTSKTILS    180
TSVNGSFFRY IDTERLLEAE VGLTQNEPVQ LAVTEAIEKA VRSLIIEGTR DKIW           234

SEQ ID NO: 89           moltype = AA  length = 45
FEATURE                 Location/Qualifiers
REGION                  1..45
                        note = CsgF peptide
source                  1..45
                        mol_type = protein
                        organism = synthetic construct
SEQUENCE: 89
CTMTFQFRNP NFGGNPNNGA FLLNSAQAQN SYKDPSYNDD FGIET                      45

SEQ ID NO: 90           moltype = AA  length = 29
FEATURE                 Location/Qualifiers
REGION                  1..29
                        note = CsgF peptide
source                  1..29
                        mol_type = protein
                        organism = synthetic construct
SEQUENCE: 90
CTMTFQFRNP NFGGNPNNGA FLLNSAQAQ                                        29

SEQ ID NO: 91           moltype = AA  length = 35
FEATURE                 Location/Qualifiers
REGION                  1..35
                        note = CsgF peptide
source                  1..35
                        mol_type = protein
                        organism = synthetic construct
SEQUENCE: 91
CTMTFQFRNP NFGGNPNNGA FLLNSAQAQN SYKDP                                 35

SEQ ID NO: 92           moltype = AA  length = 35
FEATURE                 Location/Qualifiers
REGION                  1..35
                        note = CsgF peptide
source                  1..35
                        mol_type = protein
                        organism = synthetic construct
SEQUENCE: 92
GTMTFQFRNP NFGGNPSNGA FLLNSAQAQN SYKDP                                 35

SEQ ID NO: 93           moltype = AA  length = 35
FEATURE                 Location/Qualifiers
REGION                  1..35
                        note = CsgF peptide
source                  1..35
                        mol_type = protein
                        organism = synthetic construct
SEQUENCE: 93
CTMTFQFRNP NFGGNPNNGA FLLNSAQAQN SYKYP                                 35

SEQ ID NO: 94           moltype = AA  length = 45
FEATURE                 Location/Qualifiers
REGION                  1..45
                        note = CsgF peptide
source                  1..45
                        mol_type = protein
                        organism = synthetic construct
SEQUENCE: 94
GTMTFQFRNP NFGGNPSNGA FLLNSAQAQN SYKDPSYNDD FGIET                      45
```

```
SEQ ID NO: 95          moltype = AA  length = 35
FEATURE                Location/Qualifiers
REGION                 1..35
                       note = CsgF peptide
source                 1..35
                       mol_type = protein
                       organism = synthetic construct
SEQUENCE: 95
CTMTFQFRNP NFGGNPSNGA FLLNSAQAQN SYKYP                                 35

SEQ ID NO: 96          moltype = AA  length = 39
FEATURE                Location/Qualifiers
REGION                 1..39
                       note = CsgF peptide
source                 1..39
                       mol_type = protein
                       organism = synthetic construct
SEQUENCE: 96
CTMTFQFRNP NFGGNPNNGA FLLNSAQAQH HHHHHHHHH                             39

SEQ ID NO: 97          moltype = AA  length = 45
FEATURE                Location/Qualifiers
REGION                 1..45
                       note = CsgF peptide
source                 1..45
                       mol_type = protein
                       organism = synthetic construct
SEQUENCE: 97
CTMTFQFRNP NFGGNPNNGA FLLNSAQAQN SYKDPHHHHH HHHHH                      45

SEQ ID NO: 98          moltype = AA  length = 35
FEATURE                Location/Qualifiers
REGION                 1..35
                       note = CsgF peptide
source                 1..35
                       mol_type = protein
                       organism = synthetic construct
SEQUENCE: 98
GTMTFQFRNP NFGGNPSNGA FLLNSAQAQN SYKYP                                 35

SEQ ID NO: 99          moltype = AA  length = 35
FEATURE                Location/Qualifiers
REGION                 1..35
                       note = CsgF peptide
source                 1..35
                       mol_type = protein
                       organism = synthetic construct
SEQUENCE: 99
GTMTFQFRNP NFGGNPSNGA FLLNSAQAQN SYKNP                                 35

SEQ ID NO: 100         moltype = AA  length = 35
FEATURE                Location/Qualifiers
REGION                 1..35
                       note = CsgF peptide
source                 1..35
                       mol_type = protein
                       organism = synthetic construct
SEQUENCE: 100
GTMCFQFRNP NFGGNPSNGA FLLNSAQAQN SYKDP                                 35

SEQ ID NO: 101         moltype = AA  length = 35
FEATURE                Location/Qualifiers
REGION                 1..35
                       note = CsgF peptide
source                 1..35
                       mol_type = protein
                       organism = synthetic construct
SEQUENCE: 101
GTMCFQFRNP NFGGNPSNGA FLLNSAQAQN SYKYP                                 35

SEQ ID NO: 102         moltype = AA  length = 35
FEATURE                Location/Qualifiers
REGION                 1..35
                       note = CsgF peptide
source                 1..35
                       mol_type = protein
                       organism = synthetic construct
```

```
SEQUENCE: 102
GTMCFQFRNP NFGGNPSNGA FLLNSAQAQN SYKNP                               35

SEQ ID NO: 103          moltype = AA   length = 35
FEATURE                 Location/Qualifiers
REGION                  1..35
                        note = CsgF peptide
source                  1..35
                        mol_type = protein
                        organism = synthetic construct
SEQUENCE: 103
CTMCFQFRNP NFGGNPSNGA FLLNSAQAQN SYKDP                               35

SEQ ID NO: 104          moltype = AA   length = 35
FEATURE                 Location/Qualifiers
REGION                  1..35
                        note = CsgF peptide
source                  1..35
                        mol_type = protein
                        organism = synthetic construct
SEQUENCE: 104
CTMCFQFRNP NFGGNPSNGA FLLNSAQAQN SYKNP                               35

SEQ ID NO: 105          moltype = AA   length = 35
FEATURE                 Location/Qualifiers
REGION                  1..35
                        note = CsgF peptide
source                  1..35
                        mol_type = protein
                        organism = synthetic construct
SEQUENCE: 105
CTMCFQFRNP NFGGNPSNGA FLLNSAQAQN SYKYP                               35

SEQ ID NO: 106          moltype = AA   length = 35
FEATURE                 Location/Qualifiers
REGION                  1..35
                        note = CsgF peptide
source                  1..35
                        mol_type = protein
                        organism = synthetic construct
SEQUENCE: 106
GTMTFQFRNP NFGGNPVNGA FLLNSAQAQN SYKDP                               35

SEQ ID NO: 107          moltype = AA   length = 35
FEATURE                 Location/Qualifiers
REGION                  1..35
                        note = CsgF peptide
source                  1..35
                        mol_type = protein
                        organism = synthetic construct
SEQUENCE: 107
GTMTFQFRNP NFGGNPANGA FLLNSAQAQN SYKDP                               35

SEQ ID NO: 108          moltype = AA   length = 35
FEATURE                 Location/Qualifiers
REGION                  1..35
                        note = CsgF peptide
source                  1..35
                        mol_type = protein
                        organism = synthetic construct
SEQUENCE: 108
GTMTFQFRNP NFGGNPFNGA FLLNSAQAQN SYKDP                               35

SEQ ID NO: 109          moltype = AA   length = 30
FEATURE                 Location/Qualifiers
REGION                  1..30
                        note = CsgF peptide
source                  1..30
                        mol_type = protein
                        organism = synthetic construct
SEQUENCE: 109
GTMTFQFRNP NFGGNPSNGA FLLNSAQAQN                                     30

SEQ ID NO: 110          moltype = AA   length = 30
FEATURE                 Location/Qualifiers
REGION                  1..30
                        note = CsgF peptide
```

```
source                  1..30
                        mol_type = protein
                        organism = synthetic construct
SEQUENCE: 110
GTMTFQFRNP NFGGNPVNGA FLLNSAQAQN                                       30

SEQ ID NO: 111          moltype = AA   length = 30
FEATURE                 Location/Qualifiers
REGION                  1..30
                        note = CsgF peptide
source                  1..30
                        mol_type = protein
                        organism = synthetic construct
SEQUENCE: 111
GTMTFQFRNP NFGGNPANGA FLLNSAQAQN                                       30

SEQ ID NO: 112          moltype = AA   length = 30
FEATURE                 Location/Qualifiers
REGION                  1..30
                        note = CsgF peptide
source                  1..30
                        mol_type = protein
                        organism = synthetic construct
SEQUENCE: 112
GTMTFQFRNP NFGGNPFNGA FLLNSAQAQN                                       30

SEQ ID NO: 113          moltype = AA   length = 35
FEATURE                 Location/Qualifiers
REGION                  1..35
                        note = CsgF peptide
source                  1..35
                        mol_type = protein
                        organism = synthetic construct
SEQUENCE: 113
GTMTFQFRNP NFGGNPVNGA FLLNSAQAQN SYKYP                                 35

SEQ ID NO: 114          moltype = AA   length = 35
FEATURE                 Location/Qualifiers
REGION                  1..35
                        note = CsgF peptide
source                  1..35
                        mol_type = protein
                        organism = synthetic construct
SEQUENCE: 114
GTMTFQFRNP NFGGNPANGA FLLNSAQAQN SYKYP                                 35

SEQ ID NO: 115          moltype = AA   length = 35
FEATURE                 Location/Qualifiers
REGION                  1..35
                        note = CsgF peptide
source                  1..35
                        mol_type = protein
                        organism = synthetic construct
SEQUENCE: 115
GTMTFQFRNP NFGGNPFNGA FLLNSAQAQN SYKYP                                 35

SEQ ID NO: 116          moltype = AA   length = 35
FEATURE                 Location/Qualifiers
REGION                  1..35
                        note = CsgF peptide
source                  1..35
                        mol_type = protein
                        organism = synthetic construct
SEQUENCE: 116
GTMTFQFRNP NFGGNPSNGQ FLLNSAQAQN SYKDP                                 35

SEQ ID NO: 117          moltype = AA   length = 14
FEATURE                 Location/Qualifiers
REGION                  1..14
                        note = CsgF peptide
source                  1..14
                        mol_type = protein
                        organism = synthetic construct
SEQUENCE: 117
GTMTFQFRHH HHHH                                                        14
```

```
SEQ ID NO: 118          moltype = AA  length = 25
FEATURE                 Location/Qualifiers
REGION                  1..25
                        note = CsgF peptide
source                  1..25
                        mol_type = protein
                        organism = synthetic construct
SEQUENCE: 118
GTMTFQFRNP NFGGNPNNGH HHHHH                                           25

SEQ ID NO: 119          moltype = AA  length = 35
FEATURE                 Location/Qualifiers
REGION                  1..35
                        note = CsgF peptide
source                  1..35
                        mol_type = protein
                        organism = synthetic construct
SEQUENCE: 119
GTMTFQFRNP NFGGNPNNGA FLLNSAQAQH HHHHH                                35

SEQ ID NO: 120          moltype = AA  length = 51
FEATURE                 Location/Qualifiers
REGION                  1..51
                        note = CsgF peptide
source                  1..51
                        mol_type = protein
                        organism = synthetic construct
SEQUENCE: 120
GTMTFQFRNP NFGGNPNNGA FLLNSAQAQN SYKDPSYNDD FGIETHHHHH H              51

SEQ ID NO: 121          moltype = AA  length = 35
FEATURE                 Location/Qualifiers
source                  1..35
                        mol_type = protein
                        organism = synthetic construct
SEQUENCE: 121
GQMTFQFRNP NFGGNPNNGA FLLNSAQAQN SYKDP                                35

SEQ ID NO: 122          moltype = AA  length = 35
FEATURE                 Location/Qualifiers
source                  1..35
                        mol_type = protein
                        organism = synthetic construct
SEQUENCE: 122
GNMTFQFRNP NFGGNPNNGS FLLNSAQAQN SYKDP                                35

SEQ ID NO: 123          moltype = AA  length = 35
FEATURE                 Location/Qualifiers
source                  1..35
                        mol_type = protein
                        organism = synthetic construct
SEQUENCE: 123
GNMTFQFRNP NFGGNPNNGA FLLNSAQAQN SYKDP                                35

SEQ ID NO: 124          moltype = AA  length = 35
FEATURE                 Location/Qualifiers
source                  1..35
                        mol_type = protein
                        organism = synthetic construct
SEQUENCE: 124
GNMTFQFRNP NFGGNPNNGA FLLNEAQAQN SYKDP                                35

SEQ ID NO: 125          moltype = AA  length = 35
FEATURE                 Location/Qualifiers
source                  1..35
                        mol_type = protein
                        organism = synthetic construct
SEQUENCE: 125
ANMTFQFRNP NFGGNPNNGA FLLNSAQAQN SYKDP                                35

SEQ ID NO: 126          moltype = AA  length = 35
FEATURE                 Location/Qualifiers
source                  1..35
                        mol_type = protein
                        organism = synthetic construct
SEQUENCE: 126
GSMTFQFRNP NFGGNPNNGA FMLNEAQAQN SYKDP                                35
```

```
SEQ ID NO: 127          moltype = AA   length = 35
FEATURE                 Location/Qualifiers
source                  1..35
                        mol_type = protein
                        organism = synthetic construct
SEQUENCE: 127
GTMTFQFRNP NFGGNPNNGA FLLNSAQAQN SYTDP                                   35

SEQ ID NO: 128          moltype = AA   length = 35
FEATURE                 Location/Qualifiers
source                  1..35
                        mol_type = protein
                        organism = synthetic construct
SEQUENCE: 128
GNMVFQFRDP SFGGNPNNGS FLLNNAQAQN SYKDP                                   35

SEQ ID NO: 129          moltype = AA   length = 35
FEATURE                 Location/Qualifiers
source                  1..35
                        mol_type = protein
                        organism = synthetic construct
SEQUENCE: 129
GNMVFQFVNP NFGGNPNNGA YLLNSAQAQN SYKDP                                   35

SEQ ID NO: 130          moltype = AA   length = 35
FEATURE                 Location/Qualifiers
source                  1..35
                        mol_type = protein
                        organism = synthetic construct
SEQUENCE: 130
GNMVFQFVNP NFGGNPNNGS YLLNSAQAQN SYKDP                                   35

SEQ ID NO: 131          moltype = AA   length = 35
FEATURE                 Location/Qualifiers
source                  1..35
                        mol_type = protein
                        organism = synthetic construct
SEQUENCE: 131
GNMVYQFINP NFGGNPNNGT YLLNGAQAQN SYKDP                                   35

SEQ ID NO: 132          moltype = AA   length = 35
FEATURE                 Location/Qualifiers
source                  1..35
                        mol_type = protein
                        organism = synthetic construct
SEQUENCE: 132
GNMVFQFINP NFGGNPNNGA FLLNEAQAQN SYKDP                                   35

SEQ ID NO: 133          moltype = AA   length = 35
FEATURE                 Location/Qualifiers
source                  1..35
                        mol_type = protein
                        organism = synthetic construct
SEQUENCE: 133
GNMVFQFINP NFGGNPNNGS FLLNEAMAQN SYKDP                                   35

SEQ ID NO: 134          moltype = AA   length = 35
FEATURE                 Location/Qualifiers
source                  1..35
                        mol_type = protein
                        organism = synthetic construct
SEQUENCE: 134
GNMVFQFVNP NFGGNPNNGS FLLNEAMAQN SYKDP                                   35

SEQ ID NO: 135          moltype = AA   length = 35
FEATURE                 Location/Qualifiers
source                  1..35
                        mol_type = protein
                        organism = synthetic construct
SEQUENCE: 135
GNLVFQFVNP NFGGNPNNGS YLLSQAMAQN SYKDP                                   35

SEQ ID NO: 136          moltype = AA   length = 35
FEATURE                 Location/Qualifiers
source                  1..35
                        mol_type = protein
                        organism = synthetic construct
SEQUENCE: 136
GNLTFQFVNP NFGGNPNNGA FLLSQANAQN SYKDP                                   35
```

| | | |
|---|---|---|
| SEQ ID NO: 137 | moltype = AA length = 35 | |
| FEATURE | Location/Qualifiers | |
| source | 1..35 | |
| | mol_type = protein | |
| | organism = synthetic construct | |
| SEQUENCE: 137 | | |
| SPLIYQPVNP NFGGNPLNGS YLMSNAQAQN SYKDP | | 35 |
| | | |
| SEQ ID NO: 138 | moltype = AA length = 35 | |
| FEATURE | Location/Qualifiers | |
| source | 1..35 | |
| | mol_type = protein | |
| | organism = synthetic construct | |
| SEQUENCE: 138 | | |
| SELVYQPVNP NFGGNPLNGN YLLGNAQAQN DYKDP | | 35 |
| | | |
| SEQ ID NO: 139 | moltype = AA length = 35 | |
| FEATURE | Location/Qualifiers | |
| source | 1..35 | |
| | mol_type = protein | |
| | organism = synthetic construct | |
| SEQUENCE: 139 | | |
| TELVYAPVNP SFGGNPLNGT YLLNNATAQD RHKDP | | 35 |
| | | |
| SEQ ID NO: 140 | moltype = AA length = 35 | |
| FEATURE | Location/Qualifiers | |
| source | 1..35 | |
| | mol_type = protein | |
| | organism = synthetic construct | |
| SEQUENCE: 140 | | |
| TELIYEPVNP NFGGNPLNGS YLLNNAQAQD RHKDP | | 35 |
| | | |
| SEQ ID NO: 141 | moltype = AA length = 35 | |
| FEATURE | Location/Qualifiers | |
| source | 1..35 | |
| | mol_type = protein | |
| | organism = synthetic construct | |
| SEQUENCE: 141 | | |
| TELVYQPVNP NFGGNPLNGT FLLNNAQAQD TNDDP | | 35 |
| | | |
| SEQ ID NO: 142 | moltype = AA length = 35 | |
| FEATURE | Location/Qualifiers | |
| source | 1..35 | |
| | mol_type = protein | |
| | organism = synthetic construct | |
| SEQUENCE: 142 | | |
| TELVYTPVNP AFGGNPLNGT WLLNNAQAQN DYDDP | | 35 |
| | | |
| SEQ ID NO: 143 | moltype = AA length = 35 | |
| FEATURE | Location/Qualifiers | |
| source | 1..35 | |
| | mol_type = protein | |
| | organism = synthetic construct | |
| SEQUENCE: 143 | | |
| TELVYTPVNP AFGGNPLNGT WLLNNAQAQN DHDDP | | 35 |
| | | |
| SEQ ID NO: 144 | moltype = AA length = 35 | |
| FEATURE | Location/Qualifiers | |
| source | 1..35 | |
| | mol_type = protein | |
| | organism = synthetic construct | |
| SEQUENCE: 144 | | |
| TELVYTPINP AFGGNPLNGT WLLNNAQAQN DHEDP | | 35 |
| | | |
| SEQ ID NO: 145 | moltype = AA length = 35 | |
| FEATURE | Location/Qualifiers | |
| source | 1..35 | |
| | mol_type = protein | |
| | organism = synthetic construct | |
| SEQUENCE: 145 | | |
| TELVYTPVNP SFGGNPLNGT WLLNNAQAQN DHEDP | | 35 |
| | | |
| SEQ ID NO: 146 | moltype = AA length = 35 | |
| FEATURE | Location/Qualifiers | |
| source | 1..35 | |
| | mol_type = protein | |
| | organism = synthetic construct | |

```
SEQUENCE: 146
TELVYAPVNP SFGGNPLNGT WLLNNAQAQN DKKDP                               35

SEQ ID NO: 147          moltype = AA   length = 35
FEATURE                 Location/Qualifiers
source                  1..35
                        mol_type = protein
                        organism = synthetic construct
SEQUENCE: 147
TELVYTPVNP RFGGNPLNGA WLLANAQAQN NEKDP                               35

SEQ ID NO: 148          moltype = AA   length = 35
FEATURE                 Location/Qualifiers
source                  1..35
                        mol_type = protein
                        organism = synthetic construct
SEQUENCE: 148
TELVYTPVNP SFGGSPLNGA WLLGNAQAQN DTTDP                               35

SEQ ID NO: 149          moltype = AA   length = 35
FEATURE                 Location/Qualifiers
source                  1..35
                        mol_type = protein
                        organism = synthetic construct
SEQUENCE: 149
TELVYTPVNP SFGGSPLNGA WLLGNAQAQN NKKDP                               35

SEQ ID NO: 150          moltype = AA   length = 35
FEATURE                 Location/Qualifiers
source                  1..35
                        mol_type = protein
                        organism = synthetic construct
SEQUENCE: 150
SELVYTPINP SFGGNPLNGG WLLGNAQAQN DHSAP                               35

SEQ ID NO: 151          moltype = AA   length = 35
FEATURE                 Location/Qualifiers
source                  1..35
                        mol_type = protein
                        organism = synthetic construct
SEQUENCE: 151
TELVYTPKNP AFGGSPLNGS YLLGNAQAQN DYDDP                               35

SEQ ID NO: 152          moltype = AA   length = 35
FEATURE                 Location/Qualifiers
source                  1..35
                        mol_type = protein
                        organism = synthetic construct
SEQUENCE: 152
TELVYVPVNP AFGGSPLNGS YLLNSAQAQN RHKDP                               35

SEQ ID NO: 153          moltype = AA   length = 35
FEATURE                 Location/Qualifiers
source                  1..35
                        mol_type = protein
                        organism = synthetic construct
SEQUENCE: 153
TELVYTPVNP AFGGSPLNGS YLLNAAQAQN KTKDP                               35

SEQ ID NO: 154          moltype = AA   length = 35
FEATURE                 Location/Qualifiers
source                  1..35
                        mol_type = protein
                        organism = synthetic construct
SEQUENCE: 154
TELIYTPVNP NFGGSPLNGQ WLLNSAQVTN KHTDP                               35

SEQ ID NO: 155          moltype = AA   length = 35
FEATURE                 Location/Qualifiers
source                  1..35
                        mol_type = protein
                        organism = synthetic construct
SEQUENCE: 155
SELIYTPTNP AFGGNPINGN YLLSNAQAQD TYKNP                               35
```

```
SEQ ID NO: 156          moltype = AA  length = 35
FEATURE                 Location/Qualifiers
source                  1..35
                        mol_type = protein
                        organism = synthetic construct
SEQUENCE: 156
WELVYVPVNP NFGGNPINGS ALLGNAQSQD KYKDP                                  35

SEQ ID NO: 157          moltype = AA  length = 35
FEATURE                 Location/Qualifiers
source                  1..35
                        mol_type = protein
                        organism = synthetic construct
SEQUENCE: 157
SELVYSPVNP SFGGNPINGT YLLGNAQSQN KHTSG                                  35

SEQ ID NO: 158          moltype = AA  length = 35
FEATURE                 Location/Qualifiers
source                  1..35
                        mol_type = protein
                        organism = synthetic construct
SEQUENCE: 158
TEIIYTPINP SFGGNPLNAN MLLSKAQAQN KHKAP                                  35

SEQ ID NO: 159          moltype = AA  length = 35
FEATURE                 Location/Qualifiers
source                  1..35
                        mol_type = protein
                        organism = synthetic construct
SEQUENCE: 159
TELIYTPINP SFGGNPLNAN MLLSKAQAQN KHKAP                                  35

SEQ ID NO: 160          moltype = AA  length = 35
FEATURE                 Location/Qualifiers
source                  1..35
                        mol_type = protein
                        organism = synthetic construct
SEQUENCE: 160
TELVYTPINP SFGGSPLNAN MLLNKAQSQN KHKAP                                  35

SEQ ID NO: 161          moltype = AA  length = 35
FEATURE                 Location/Qualifiers
source                  1..35
                        mol_type = protein
                        organism = synthetic construct
SEQUENCE: 161
TELVYKPINP SFGGNPLNAN MLLSKAQAQN KHRAP                                  35

SEQ ID NO: 162          moltype = AA  length = 35
FEATURE                 Location/Qualifiers
source                  1..35
                        mol_type = protein
                        organism = synthetic construct
SEQUENCE: 162
TELVYKPINP SFGGNPLNAN MLLNKAQAQN KHRAP                                  35

SEQ ID NO: 163          moltype = AA  length = 35
FEATURE                 Location/Qualifiers
source                  1..35
                        mol_type = protein
                        organism = synthetic construct
SEQUENCE: 163
TELVYKPINP AFGGNPLNAN MLLSKAQSQN KHRAP                                  35

SEQ ID NO: 164          moltype = AA  length = 35
FEATURE                 Location/Qualifiers
source                  1..35
                        mol_type = protein
                        organism = synthetic construct
SEQUENCE: 164
TEIVYKPINP SFGGNPLNAS MLLNKAMAQN KHRAP                                  35

SEQ ID NO: 165          moltype = AA  length = 35
FEATURE                 Location/Qualifiers
source                  1..35
                        mol_type = protein
                        organism = synthetic construct
```

```
SEQUENCE: 165
SELVYTPINP SFGGSPLNGS HLLNKAQAQN KHKAP                              35

SEQ ID NO: 166          moltype = AA   length = 35
FEATURE                 Location/Qualifiers
source                  1..35
                        mol_type = protein
                        organism = synthetic construct
SEQUENCE: 166
TELVYTPINP SFGGSPLNGA MLLNKAQSQN KHRAP                              35

SEQ ID NO: 167          moltype = AA   length = 35
FEATURE                 Location/Qualifiers
source                  1..35
                        mol_type = protein
                        organism = synthetic construct
SEQUENCE: 167
SELVYTPINP SFGGSPLNAS MLLNKAQSQN KHKAH                              35

SEQ ID NO: 168          moltype = AA   length = 35
FEATURE                 Location/Qualifiers
source                  1..35
                        mol_type = protein
                        organism = synthetic construct
SEQUENCE: 168
TELVYEPINP SFGGNPLNGS FLLSKANSQN AHTAP                              35

SEQ ID NO: 169          moltype = AA   length = 35
FEATURE                 Location/Qualifiers
source                  1..35
                        mol_type = protein
                        organism = synthetic construct
SEQUENCE: 169
TELVYEPINP SFGGNPLNGS FLLSKANSQN AHSAP                              35

SEQ ID NO: 170          moltype = AA   length = 35
FEATURE                 Location/Qualifiers
source                  1..35
                        mol_type = protein
                        organism = synthetic construct
SEQUENCE: 170
TELVYTPINP SFGGNPLNGS FLLSKAQSQN DHTAP                              35

SEQ ID NO: 171          moltype = AA   length = 35
FEATURE                 Location/Qualifiers
source                  1..35
                        mol_type = protein
                        organism = synthetic construct
SEQUENCE: 171
TEIVYQPINP SFGGNPLNGN FLLQKAQTQN AHSAP                              35

SEQ ID NO: 172          moltype = AA   length = 35
FEATURE                 Location/Qualifiers
source                  1..35
                        mol_type = protein
                        organism = synthetic construct
SEQUENCE: 172
TEIVYQPINP SFGGNPMNGS FLLQKAQSQN AHTAP                              35

SEQ ID NO: 173          moltype = AA   length = 35
FEATURE                 Location/Qualifiers
source                  1..35
                        mol_type = protein
                        organism = synthetic construct
SEQUENCE: 173
TELVYTPINP SFGGNPLNGN FLLQKAQSQN DYSAE                              35

SEQ ID NO: 174          moltype = AA   length = 35
FEATURE                 Location/Qualifiers
source                  1..35
                        mol_type = protein
                        organism = synthetic construct
SEQUENCE: 174
TELVYTPINP SFGGNPLNGN FLLQKAQSQN SHKAD                              35
```

```
SEQ ID NO: 175          moltype = AA  length = 35
FEATURE                 Location/Qualifiers
source                  1..35
                        mol_type = protein
                        organism = synthetic construct
SEQUENCE: 175
TELVYTPINP SFGGNPLNGN FLLQKAQSQN AHTAA                                35

SEQ ID NO: 176          moltype = AA  length = 35
FEATURE                 Location/Qualifiers
source                  1..35
                        mol_type = protein
                        organism = synthetic construct
SEQUENCE: 176
TELVYEPINP SFGGSPLNGS YLLSKANAQN THSAS                                35

SEQ ID NO: 177          moltype = AA  length = 35
FEATURE                 Location/Qualifiers
source                  1..35
                        mol_type = protein
                        organism = synthetic construct
SEQUENCE: 177
TELVYTPINP SFGGSPLNGS YLLNKANAQN DHSEG                                35

SEQ ID NO: 178          moltype = AA  length = 35
FEATURE                 Location/Qualifiers
source                  1..35
                        mol_type = protein
                        organism = synthetic construct
SEQUENCE: 178
TELVYTPINP SFGGSPLNGS YLLNKANIQN DHTAE                                35

SEQ ID NO: 179          moltype = AA  length = 35
FEATURE                 Location/Qualifiers
source                  1..35
                        mol_type = protein
                        organism = synthetic construct
SEQUENCE: 179
TELVYTPINP SFGGSALNGS FLLSKAQGQN KHKAE                                35

SEQ ID NO: 180          moltype = AA  length = 35
FEATURE                 Location/Qualifiers
source                  1..35
                        mol_type = protein
                        organism = synthetic construct
SEQUENCE: 180
TELIYTPVNP SFGGNPLNGT FLLNKAQAQN DNQAT                                35

SEQ ID NO: 181          moltype = AA  length = 35
FEATURE                 Location/Qualifiers
source                  1..35
                        mol_type = protein
                        organism = synthetic construct
SEQUENCE: 181
TELVYTPINP SFGGSPLNGS FLLNKAQSQN DNQSP                                35

SEQ ID NO: 182          moltype = AA  length = 35
FEATURE                 Location/Qualifiers
source                  1..35
                        mol_type = protein
                        organism = synthetic construct
SEQUENCE: 182
TELVYTPVNP SFGGSALNGS FLLNKAQAQN DNART                                35

SEQ ID NO: 183          moltype = AA  length = 35
FEATURE                 Location/Qualifiers
source                  1..35
                        mol_type = protein
                        organism = synthetic construct
SEQUENCE: 183
GQLVYVPVNP SFGGNPLNGS YLLQSAQAQK RYPYP                                35

SEQ ID NO: 184          moltype = AA  length = 35
FEATURE                 Location/Qualifiers
source                  1..35
                        mol_type = protein
                        organism = synthetic construct
```

```
SEQUENCE: 184
GELIYQPINP SFGGNPLNGS YLLGKAQAQD THEDP                                35

SEQ ID NO: 185          moltype = AA   length = 35
FEATURE                 Location/Qualifiers
source                  1..35
                        mol_type = protein
                        organism = synthetic construct
SEQUENCE: 185
GELIYRPINP SFGGDPFNGS YLLGKAQAQD THKDP                                35

SEQ ID NO: 186          moltype = AA   length = 35
FEATURE                 Location/Qualifiers
source                  1..35
                        mol_type = protein
                        organism = synthetic construct
SEQUENCE: 186
GELVYRPINP SFGGDPLNGN YLLNKAQAQD DNKDP                                35

SEQ ID NO: 187          moltype = AA   length = 35
FEATURE                 Location/Qualifiers
source                  1..35
                        mol_type = protein
                        organism = synthetic construct
SEQUENCE: 187
GNLIYQPINP SFGGDPFVGS YLLGKAQAQD TTTDP                                35

SEQ ID NO: 188          moltype = AA   length = 35
FEATURE                 Location/Qualifiers
source                  1..35
                        mol_type = protein
                        organism = synthetic construct
SEQUENCE: 188
GDLIYKPINP SFGGDPFTGS YLLGKAQSQD TNTDP                                35

SEQ ID NO: 189          moltype = AA   length = 35
FEATURE                 Location/Qualifiers
source                  1..35
                        mol_type = protein
                        organism = synthetic construct
SEQUENCE: 189
GELIYRPLNP SFGGDPFMGS YLLGKAQSQD TNTDP                                35

SEQ ID NO: 190          moltype = AA   length = 35
FEATURE                 Location/Qualifiers
source                  1..35
                        mol_type = protein
                        organism = synthetic construct
SEQUENCE: 190
GQLIYQPINP SFGGDPLLGN HLLNKAQAQD TKRDP                                35

SEQ ID NO: 191          moltype = AA   length = 35
FEATURE                 Location/Qualifiers
source                  1..35
                        mol_type = protein
                        organism = synthetic construct
SEQUENCE: 191
SPLVYEPVNP TFGGNPLNGA VLMDQANAQN KHTDP                                35

SEQ ID NO: 192          moltype = AA   length = 35
FEATURE                 Location/Qualifiers
source                  1..35
                        mol_type = protein
                        organism = synthetic construct
SEQUENCE: 192
STLVYQPNNP NFGGNPANGP NLLNEANAQN KHTDP                                35

SEQ ID NO: 193          moltype = AA   length = 35
FEATURE                 Location/Qualifiers
source                  1..35
                        mol_type = protein
                        organism = synthetic construct
SEQUENCE: 193
SELVYTPNNP SFGGNPLNGP VLLMQAAAQN KFKES                                35
```

```
SEQ ID NO: 194          moltype = AA   length = 35
FEATURE                 Location/Qualifiers
source                  1..35
                        mol_type = protein
                        organism = synthetic construct
SEQUENCE: 194
SELVYVPNNP SFGGNPLNGP VLLNQATAQN KFTEK                                35

SEQ ID NO: 195          moltype = AA   length = 35
FEATURE                 Location/Qualifiers
source                  1..35
                        mol_type = protein
                        organism = synthetic construct
SEQUENCE: 195
SELVYTPVNP SFGGNPLNGS YLMNQATAQN KFKES                                35

SEQ ID NO: 196          moltype = AA   length = 35
FEATURE                 Location/Qualifiers
source                  1..35
                        mol_type = protein
                        organism = synthetic construct
SEQUENCE: 196
SELVYTPVNP NFGGNPLNTS HLFGGANAIN DYKGP                                35

SEQ ID NO: 197          moltype = AA   length = 35
FEATURE                 Location/Qualifiers
source                  1..35
                        mol_type = protein
                        organism = synthetic construct
SEQUENCE: 197
TELVYTPINP SFGGNPLNSN HLLGIANAIN DHKAP                                35

SEQ ID NO: 198          moltype = AA   length = 35
FEATURE                 Location/Qualifiers
source                  1..35
                        mol_type = protein
                        organism = synthetic construct
SEQUENCE: 198
TELIYTPVNP SFGGNALNSS HLFGVANAIN DYQAP                                35

SEQ ID NO: 199          moltype = AA   length = 35
FEATURE                 Location/Qualifiers
source                  1..35
                        mol_type = protein
                        organism = synthetic construct
SEQUENCE: 199
TELIYTPVNP NFGGSPLNGS YLLAGANAIN DYKPP                                35

SEQ ID NO: 200          moltype = AA   length = 35
FEATURE                 Location/Qualifiers
source                  1..35
                        mol_type = protein
                        organism = synthetic construct
SEQUENCE: 200
SELVYTPVNP TFGGNPLNST ILINHANAIN DYQDP                                35

SEQ ID NO: 201          moltype = AA   length = 35
FEATURE                 Location/Qualifiers
source                  1..35
                        mol_type = protein
                        organism = synthetic construct
SEQUENCE: 201
SELVYTPINP SFGGNPLNST ILINHANAIN DYSDP                                35

SEQ ID NO: 202          moltype = AA   length = 35
FEATURE                 Location/Qualifiers
source                  1..35
                        mol_type = protein
                        organism = synthetic construct
SEQUENCE: 202
TELIYTPINP SFGGNPLNST ILINHANAIN DYTDP                                35

SEQ ID NO: 203          moltype = AA   length = 35
FEATURE                 Location/Qualifiers
source                  1..35
                        mol_type = protein
                        organism = synthetic construct
```

```
SEQUENCE: 203
TELVYVPVNP SFGGNPNNGI VLLNAANAIN KHKDP                        35

SEQ ID NO: 204         moltype = AA  length = 33
FEATURE                Location/Qualifiers
source                 1..33
                       mol_type = protein
                       organism = synthetic construct
SEQUENCE: 204
LVYEPVNPTF GGNPLNTTHL FNRAEAINDY EAD                          33

SEQ ID NO: 205         moltype = AA  length = 35
FEATURE                Location/Qualifiers
source                 1..35
                       mol_type = protein
                       organism = synthetic construct
SEQUENCE: 205
SSLVYEPVNP TFGGNPLNTT HLFSRAEAIN DYEGS                        35

SEQ ID NO: 206         moltype = AA  length = 34
FEATURE                Location/Qualifiers
source                 1..34
                       mol_type = protein
                       organism = synthetic construct
SEQUENCE: 206
TQLIYTPVNP NFGGSYLNGS YLLANASAQN DHKG                         34

SEQ ID NO: 207         moltype = AA  length = 34
FEATURE                Location/Qualifiers
source                 1..34
                       mol_type = protein
                       organism = synthetic construct
SEQUENCE: 207
TQLIYTPVNP NFGGSYLNGS YLLANASVQN DHKT                         34

SEQ ID NO: 208         moltype = AA  length = 34
FEATURE                Location/Qualifiers
source                 1..34
                       mol_type = protein
                       organism = synthetic construct
SEQUENCE: 208
TQLVYTPVNP AFGGSYLNGS YLLANASAQN EHQG                         34

SEQ ID NO: 209         moltype = AA  length = 34
FEATURE                Location/Qualifiers
source                 1..34
                       mol_type = protein
                       organism = synthetic construct
SEQUENCE: 209
TQLTYTPVNP NFGGSYLNGS YLLSNASAQN KHSG                         34

SEQ ID NO: 210         moltype = AA  length = 34
FEATURE                Location/Qualifiers
source                 1..34
                       mol_type = protein
                       organism = synthetic construct
SEQUENCE: 210
TQLIYQPVNP AFGGSYLNGS YLLANAAAQN DHQS                         34

SEQ ID NO: 211         moltype = AA  length = 35
FEATURE                Location/Qualifiers
source                 1..35
                       mol_type = protein
                       organism = synthetic construct
SEQUENCE: 211
AELGYTPVNP SFGGSPLNGS TLLSEASAQK PNAPT                        35

SEQ ID NO: 212         moltype = AA  length = 35
FEATURE                Location/Qualifiers
source                 1..35
                       mol_type = protein
                       organism = synthetic construct
SEQUENCE: 212
GDLVYTPVNP SFGGSPLNSA HLLSIAGAQK NATAS                        35
```

| | | |
|---|---|---|
| SEQ ID NO: 213 | moltype = AA length = 35 | |
| FEATURE | Location/Qualifiers | |
| source | 1..35 | |
| | mol_type = protein | |
| | organism = synthetic construct | |
| SEQUENCE: 213 | | |
| QDLVYTPVNP SFGGNPLNSN HLLSIANAQR EATAR | | 35 |
| | | |
| SEQ ID NO: 214 | moltype = AA length = 35 | |
| FEATURE | Location/Qualifiers | |
| source | 1..35 | |
| | mol_type = protein | |
| | organism = synthetic construct | |
| SEQUENCE: 214 | | |
| GDLVYTPVNP SFGGNPLNSS HLFAIANAQR DATAS | | 35 |
| | | |
| SEQ ID NO: 215 | moltype = AA length = 35 | |
| FEATURE | Location/Qualifiers | |
| source | 1..35 | |
| | mol_type = protein | |
| | organism = synthetic construct | |
| SEQUENCE: 215 | | |
| QDIVHEPISP TFGGNPFNSN HILGIANAQN KTKDP | | 35 |
| | | |
| SEQ ID NO: 216 | moltype = AA length = 35 | |
| FEATURE | Location/Qualifiers | |
| source | 1..35 | |
| | mol_type = protein | |
| | organism = synthetic construct | |
| SEQUENCE: 216 | | |
| QDLVHQPISP TFGGNPFNSN HVLGVANANN DTRDP | | 35 |
| | | |
| SEQ ID NO: 217 | moltype = AA length = 35 | |
| FEATURE | Location/Qualifiers | |
| source | 1..35 | |
| | mol_type = protein | |
| | organism = synthetic construct | |
| SEQUENCE: 217 | | |
| QDLVHQPISP TFGGNPFNSA HILGTANAQN DTTNP | | 35 |
| | | |
| SEQ ID NO: 218 | moltype = AA length = 35 | |
| FEATURE | Location/Qualifiers | |
| source | 1..35 | |
| | mol_type = protein | |
| | organism = synthetic construct | |
| SEQUENCE: 218 | | |
| QDLVHSPISP TFGGNPFNSA HILGTANAQN DYRDP | | 35 |
| | | |
| SEQ ID NO: 219 | moltype = AA length = 35 | |
| FEATURE | Location/Qualifiers | |
| source | 1..35 | |
| | mol_type = protein | |
| | organism = synthetic construct | |
| SEQUENCE: 219 | | |
| QDIVYQPTDP TFGGNPFNSA HLLGIANAQN TYKDP | | 35 |
| | | |
| SEQ ID NO: 220 | moltype = AA length = 35 | |
| FEATURE | Location/Qualifiers | |
| source | 1..35 | |
| | mol_type = protein | |
| | organism = synthetic construct | |
| SEQUENCE: 220 | | |
| QDIVYEPVDP SFGGNAFNSA HLLGIANSQN DYRDP | | 35 |
| | | |
| SEQ ID NO: 221 | moltype = AA length = 35 | |
| FEATURE | Location/Qualifiers | |
| source | 1..35 | |
| | mol_type = protein | |
| | organism = synthetic construct | |
| SEQUENCE: 221 | | |
| QDIVYQPINP SFGGNPFNSN HLLGIANAQN DFTNP | | 35 |
| | | |
| SEQ ID NO: 222 | moltype = AA length = 35 | |
| FEATURE | Location/Qualifiers | |
| source | 1..35 | |
| | mol_type = protein | |
| | organism = synthetic construct | |

```
SEQUENCE: 222
QDLTYKPINP TFGGNSFNSN HLLGVANAQN DYRDK                                    35

SEQ ID NO: 223          moltype = AA   length = 35
FEATURE                 Location/Qualifiers
source                  1..35
                        mol_type = protein
                        organism = synthetic construct
SEQUENCE: 223
QELVYTPVNP SFGGNPFNSA HLLAVANAQD KTEAP                                    35

SEQ ID NO: 224          moltype = AA   length = 35
FEATURE                 Location/Qualifiers
source                  1..35
                        mol_type = protein
                        organism = synthetic construct
SEQUENCE: 224
SDIVYTPINP SFGGSPFNSA HLLGIASAQN KYKDP                                    35

SEQ ID NO: 225          moltype = AA   length = 35
FEATURE                 Location/Qualifiers
source                  1..35
                        mol_type = protein
                        organism = synthetic construct
SEQUENCE: 225
QDIVYTPVNP SFGGNPFNSA HLLGIASAQN KYKDP                                    35

SEQ ID NO: 226          moltype = AA   length = 35
FEATURE                 Location/Qualifiers
source                  1..35
                        mol_type = protein
                        organism = synthetic construct
SEQUENCE: 226
SELVYTPINP SFGGNPFNSA HLLGVATAQS KYKDP                                    35

SEQ ID NO: 227          moltype = AA   length = 35
FEATURE                 Location/Qualifiers
source                  1..35
                        mol_type = protein
                        organism = synthetic construct
SEQUENCE: 227
SDLVYTPNNP SFGGNPFNSA HLLGVANAIN KYKDP                                    35

SEQ ID NO: 228          moltype = AA   length = 35
FEATURE                 Location/Qualifiers
source                  1..35
                        mol_type = protein
                        organism = synthetic construct
SEQUENCE: 228
GQLTYRPINP SFGGDPFNSA HLLGIANAND RYKDP                                    35

SEQ ID NO: 229          moltype = AA   length = 35
FEATURE                 Location/Qualifiers
source                  1..35
                        mol_type = protein
                        organism = synthetic construct
SEQUENCE: 229
SDLVFEFTNP SFGGNPFNSA HLLAVANAQN NTTDP                                    35

SEQ ID NO: 230          moltype = AA   length = 35
FEATURE                 Location/Qualifiers
source                  1..35
                        mol_type = protein
                        organism = synthetic construct
SEQUENCE: 230
QQLVYTPINP AFGGNPFNSS QLLAIANAQN QFLPK                                    35

SEQ ID NO: 231          moltype = AA   length = 35
FEATURE                 Location/Qualifiers
source                  1..35
                        mol_type = protein
                        organism = synthetic construct
SEQUENCE: 231
SDYVYRPNNP SFGGDAFNSA HLIGLAERQN KHKET                                    35
```

```
SEQ ID NO: 232           moltype = AA  length = 34
FEATURE                  Location/Qualifiers
source                   1..34
                         mol_type = protein
                         organism = synthetic construct
SEQUENCE: 232
TELVYQAVNP AFGGYPANGQ HLLAVASATN KHGD                                 34

SEQ ID NO: 233           moltype = AA  length = 35
FEATURE                  Location/Qualifiers
source                   1..35
                         mol_type = protein
                         organism = synthetic construct
SEQUENCE: 233
TELVYLPVNP SFGGYPANGA GLLATATATS KHTEN                                35

SEQ ID NO: 234           moltype = AA  length = 35
FEATURE                  Location/Qualifiers
source                   1..35
                         mol_type = protein
                         organism = synthetic construct
SEQUENCE: 234
GNLIYQPVNP AFGGSPLNGA WLQSEASAQN IPQAR                                35

SEQ ID NO: 235           moltype = AA  length = 35
FEATURE                  Location/Qualifiers
source                   1..35
                         mol_type = protein
                         organism = synthetic construct
SEQUENCE: 235
SSLVYQPVNP AFGGPQLNGS WLQAEANAQN IPQAA                                35

SEQ ID NO: 236           moltype = AA  length = 35
FEATURE                  Location/Qualifiers
source                   1..35
                         mol_type = protein
                         organism = synthetic construct
SEQUENCE: 236
SQLVYRATNP SFGGDPLNGN WLLSQASAQG EGASS                                35

SEQ ID NO: 237           moltype = AA  length = 34
FEATURE                  Location/Qualifiers
source                   1..34
                         mol_type = protein
                         organism = synthetic construct
SEQUENCE: 237
TELVFSFTNP SFGGDPMIGN FLLNKADSQK RFAE                                 34

SEQ ID NO: 238           moltype = AA  length = 34
FEATURE                  Location/Qualifiers
source                   1..34
                         mol_type = protein
                         organism = synthetic construct
SEQUENCE: 238
TELIFQFTNP AFGGNPLYGS YYLQSAQMQN IFKE                                 34

SEQ ID NO: 239           moltype = AA  length = 34
FEATURE                  Location/Qualifiers
source                   1..34
                         mol_type = protein
                         organism = synthetic construct
SEQUENCE: 239
SNLTFYFTNP SFGGNPMYGD FLLREAEMQN SFKE                                 34

SEQ ID NO: 240           moltype = AA  length = 34
FEATURE                  Location/Qualifiers
source                   1..34
                         mol_type = protein
                         organism = synthetic construct
SEQUENCE: 240
QQLVYTPKNP NFGGSSFNYA WLQSSADAQN SFTD                                 34

SEQ ID NO: 241           moltype = AA  length = 34
FEATURE                  Location/Qualifiers
source                   1..34
                         mol_type = protein
                         organism = synthetic construct
```

```
SEQUENCE: 241
QALVYTPKNP NFGGNSYNYQ WLLSSADAQN SFED                                  34

SEQ ID NO: 242          moltype = AA  length = 34
FEATURE                 Location/Qualifiers
source                  1..34
                        mol_type = protein
                        organism = synthetic construct
SEQUENCE: 242
QQLVYTPKNP NFGGNTFNYQ WLLSSATAQN SFTE                                  34

SEQ ID NO: 243          moltype = AA  length = 34
FEATURE                 Location/Qualifiers
source                  1..34
                        mol_type = protein
                        organism = synthetic construct
SEQUENCE: 243
QQLTYQPKNP NFGGETFNYQ WLLSSANAQN SFKD                                  34

SEQ ID NO: 244          moltype = AA  length = 34
FEATURE                 Location/Qualifiers
source                  1..34
                        mol_type = protein
                        organism = synthetic construct
SEQUENCE: 244
QQLVYTPKNP AFGGETFNYQ WLQSSAQAQN SFKA                                  34

SEQ ID NO: 245          moltype = AA  length = 35
FEATURE                 Location/Qualifiers
source                  1..35
                        mol_type = protein
                        organism = synthetic construct
SEQUENCE: 245
QRFVYTPVNP AFGGNTFNYS WLQASATAQN TTVDP                                 35

SEQ ID NO: 246          moltype = AA  length = 36
FEATURE                 Location/Qualifiers
source                  1..36
                        mol_type = protein
                        organism = synthetic construct
SEQUENCE: 246
QRFVYEPINP AFGGSGTFNY SWLQASATAQ NRIQDP                                36

SEQ ID NO: 247          moltype = AA  length = 35
FEATURE                 Location/Qualifiers
source                  1..35
                        mol_type = protein
                        organism = synthetic construct
SEQUENCE: 247
QQLVYKSINP FFGGGDSFAY QQLLASANAQ NDFVE                                 35

SEQ ID NO: 248          moltype = AA  length = 34
FEATURE                 Location/Qualifiers
source                  1..34
                        mol_type = protein
                        organism = synthetic construct
SEQUENCE: 248
QNLVYKPINP FFGGDTFNYQ QLLAAANAQN DFEE                                  34

SEQ ID NO: 249          moltype = AA  length = 34
FEATURE                 Location/Qualifiers
source                  1..34
                        mol_type = protein
                        organism = synthetic construct
SEQUENCE: 249
QDLVYTPISP FFGGSTFNYQ QILASYSAQN SFTE                                  34

SEQ ID NO: 250          moltype = AA  length = 34
FEATURE                 Location/Qualifiers
source                  1..34
                        mol_type = protein
                        organism = synthetic construct
SEQUENCE: 250
QQFSYKPISP FFGGDTFNYQ QIITSYTLQN SLSE                                  34
```

```
SEQ ID NO: 251          moltype = AA  length = 34
FEATURE                 Location/Qualifiers
source                  1..34
                        mol_type = protein
                        organism = synthetic construct
SEQUENCE: 251
QQFVYKPVNP AFGGDTFNYQ WLLSSANAQN QFDD                                34

SEQ ID NO: 252          moltype = AA  length = 35
FEATURE                 Location/Qualifiers
source                  1..35
                        mol_type = protein
                        organism = synthetic construct
SEQUENCE: 252
QQLVYKPINP AFGGDTFNYQ WLLSSANAQN QFDDG                               35

SEQ ID NO: 253          moltype = AA  length = 34
FEATURE                 Location/Qualifiers
source                  1..34
                        mol_type = protein
                        organism = synthetic construct
SEQUENCE: 253
QQLVYKPINP AFGGDTFNYQ WLLSSANAQN QFDQ                                34

SEQ ID NO: 254          moltype = AA  length = 34
FEATURE                 Location/Qualifiers
source                  1..34
                        mol_type = protein
                        organism = synthetic construct
SEQUENCE: 254
QQLVYKPINP AFGGDTFNYQ WLLSSASAQN QFDN                                34

SEQ ID NO: 255          moltype = AA  length = 34
FEATURE                 Location/Qualifiers
source                  1..34
                        mol_type = protein
                        organism = synthetic construct
SEQUENCE: 255
QQFVYKPINP AFGGDTFNYQ WLLSSASAQN QFDN                                34

SEQ ID NO: 256          moltype = AA  length = 34
FEATURE                 Location/Qualifiers
source                  1..34
                        mol_type = protein
                        organism = synthetic construct
SEQUENCE: 256
QQLVYKPVNP AFGGETFNYQ WLLSSASAQN SIED                                34

SEQ ID NO: 257          moltype = AA  length = 34
FEATURE                 Location/Qualifiers
source                  1..34
                        mol_type = protein
                        organism = synthetic construct
SEQUENCE: 257
QQFSYTPINP AFGGNTFNYQ WLIQSAEAQN KFTD                                34

SEQ ID NO: 258          moltype = AA  length = 34
FEATURE                 Location/Qualifiers
source                  1..34
                        mol_type = protein
                        organism = synthetic construct
SEQUENCE: 258
QQFTYKPINP AFGGDTFNYQ WLIQSAEAQN KFTD                                34

SEQ ID NO: 259          moltype = AA  length = 34
FEATURE                 Location/Qualifiers
source                  1..34
                        mol_type = protein
                        organism = synthetic construct
SEQUENCE: 259
QQLVYRPINP AFGGDTFNYQ WLYQSAELQN KFTD                                34

SEQ ID NO: 260          moltype = AA  length = 34
FEATURE                 Location/Qualifiers
source                  1..34
                        mol_type = protein
                        organism = synthetic construct
```

```
SEQUENCE: 260
QQFSYKPLNP AFGGDTFNYN WLLSSATSQN SFTA                                              34

SEQ ID NO: 261         moltype = AA  length = 34
FEATURE                Location/Qualifiers
source                 1..34
                       mol_type = protein
                       organism = synthetic construct
SEQUENCE: 261
QQFSYKPLNP AFGGDTFNYN WLLSSANAQN GFTQ                                              34

SEQ ID NO: 262         moltype = AA  length = 34
FEATURE                Location/Qualifiers
source                 1..34
                       mol_type = protein
                       organism = synthetic construct
SEQUENCE: 262
QDLAYKPINP AFGGDTFNYN WLLSSAQAQN DYKE                                              34

SEQ ID NO: 263         moltype = AA  length = 35
FEATURE                Location/Qualifiers
source                 1..35
                       mol_type = protein
                       organism = synthetic construct
SEQUENCE: 263
QDLVYKPVNP AFGGDSFNYQ WLLSSAQEQN DFKEK                                             35

SEQ ID NO: 264         moltype = AA  length = 34
FEATURE                Location/Qualifiers
source                 1..34
                       mol_type = protein
                       organism = synthetic construct
SEQUENCE: 264
QDLVYKPVNP AFGGDTFNYQ WLLSSAEAQN KFTD                                              34

SEQ ID NO: 265         moltype = AA  length = 34
FEATURE                Location/Qualifiers
source                 1..34
                       mol_type = protein
                       organism = synthetic construct
SEQUENCE: 265
QDLVYRAKNP AFGGDTFNYQ WLLSSAEAQN KFTD                                              34

SEQ ID NO: 266         moltype = AA  length = 34
FEATURE                Location/Qualifiers
source                 1..34
                       mol_type = protein
                       organism = synthetic construct
SEQUENCE: 266
QDLVYKPKNP AFGGDTFNYQ WLASSAESQN SFKD                                              34

SEQ ID NO: 267         moltype = AA  length = 34
FEATURE                Location/Qualifiers
source                 1..34
                       mol_type = protein
                       organism = synthetic construct
SEQUENCE: 267
QGLIYKPKNP AFGGDTFNYQ WLASSAESQN KFTD                                              34

SEQ ID NO: 268         moltype = AA  length = 34
FEATURE                Location/Qualifiers
source                 1..34
                       mol_type = protein
                       organism = synthetic construct
SEQUENCE: 268
QELVYKPRNP AFGGDTFNYQ WLLSSAESQN LYKD                                              34

SEQ ID NO: 269         moltype = AA  length = 34
FEATURE                Location/Qualifiers
source                 1..34
                       mol_type = protein
                       organism = synthetic construct
SEQUENCE: 269
QDLVYKPRNP NFGGDTFNYQ WLLSSAEAQN KLKD                                              34
```

```
SEQ ID NO: 270          moltype = AA  length = 34
FEATURE                 Location/Qualifiers
source                  1..34
                        mol_type = protein
                        organism = synthetic construct
SEQUENCE: 270
QALVYKPVNP AFGGDTFNYQ WLLSSAEAQN KQKD                                    34

SEQ ID NO: 271          moltype = AA  length = 34
FEATURE                 Location/Qualifiers
source                  1..34
                        mol_type = protein
                        organism = synthetic construct
SEQUENCE: 271
QDLVYRPTNP AFGGNPYNYQ WLLSSAEAQN SFKD                                    34

SEQ ID NO: 272          moltype = AA  length = 33
FEATURE                 Location/Qualifiers
source                  1..33
                        mol_type = protein
                        organism = synthetic construct
SEQUENCE: 272
LVYHPNNPAF GGNTFNYQWM LSSAQAQDRL TDP                                     33

SEQ ID NO: 273          moltype = AA  length = 35
FEATURE                 Location/Qualifiers
source                  1..35
                        mol_type = protein
                        organism = synthetic construct
SEQUENCE: 273
QALVYHPNNP AFGGNTFNYQ WMLSSAQAQD RLTDP                                   35

SEQ ID NO: 274          moltype = AA  length = 35
FEATURE                 Location/Qualifiers
source                  1..35
                        mol_type = protein
                        organism = synthetic construct
SEQUENCE: 274
QAFVYHPYNP AFGGNTFNYQ WMLSSAQAQD KTKDP                                   35

SEQ ID NO: 275          moltype = AA  length = 35
FEATURE                 Location/Qualifiers
source                  1..35
                        mol_type = protein
                        organism = synthetic construct
SEQUENCE: 275
QAFVYHPNNP NFGGNTFNYS WMLSSAQAQD RTTDP                                   35

SEQ ID NO: 276          moltype = AA  length = 35
FEATURE                 Location/Qualifiers
source                  1..35
                        mol_type = protein
                        organism = synthetic construct
SEQUENCE: 276
QQLIYRPVNP SFGGNTFNYA WMLSSAQAQD KLKDP                                   35

SEQ ID NO: 277          moltype = AA  length = 35
FEATURE                 Location/Qualifiers
source                  1..35
                        mol_type = protein
                        organism = synthetic construct
SEQUENCE: 277
QDLIYQAKNP AFGGETFNYQ WLQSSAQAQD KLKDP                                   35

SEQ ID NO: 278          moltype = AA  length = 35
FEATURE                 Location/Qualifiers
source                  1..35
                        mol_type = protein
                        organism = synthetic construct
SEQUENCE: 278
QDLVYQPKNP AFGGDTFNYQ WLLSSAQAQD KIADP                                   35

SEQ ID NO: 279          moltype = AA  length = 35
FEATURE                 Location/Qualifiers
source                  1..35
                        mol_type = protein
                        organism = synthetic construct
```

```
SEQUENCE: 279
QDLVYTPKNP AFGGNPYNYS WMQSSAQAQD KLKDP                              35

SEQ ID NO: 280         moltype = AA   length = 35
FEATURE                Location/Qualifiers
source                 1..35
                       mol_type = protein
                       organism = synthetic construct
SEQUENCE: 280
QDFVYEPKNP AFGGNPFNYQ WLQSSAQSQD KLKDP                              35

SEQ ID NO: 281         moltype = AA   length = 35
FEATURE                Location/Qualifiers
source                 1..35
                       mol_type = protein
                       organism = synthetic construct
SEQUENCE: 281
QRLVYTPQNP AFGGDTFNYQ WLLSSAQAQD TFEDP                              35

SEQ ID NO: 282         moltype = AA   length = 36
FEATURE                Location/Qualifiers
source                 1..36
                       mol_type = protein
                       organism = synthetic construct
SEQUENCE: 282
QDLVYEPKNP SFGGGNTFNY QWLLSSASAQ NTIEDT                             36

SEQ ID NO: 283         moltype = AA   length = 36
FEATURE                Location/Qualifiers
source                 1..36
                       mol_type = protein
                       organism = synthetic construct
SEQUENCE: 283
QDFVYEPKNP SFGGGNTFNY SWLLSSAQSQ NKIEDP                             36

SEQ ID NO: 284         moltype = AA   length = 36
FEATURE                Location/Qualifiers
source                 1..36
                       mol_type = protein
                       organism = synthetic construct
SEQUENCE: 284
QDLVYEPKNP AFGGGNTFNY SWLLSSAQSQ NKLEDK                             36

SEQ ID NO: 285         moltype = AA   length = 35
FEATURE                Location/Qualifiers
source                 1..35
                       mol_type = protein
                       organism = synthetic construct
SEQUENCE: 285
QDFVYQPINP AFGGSYLNYS WLLNSAQVQN THEEK                              35

SEQ ID NO: 286         moltype = AA   length = 35
FEATURE                Location/Qualifiers
source                 1..35
                       mol_type = protein
                       organism = synthetic construct
SEQUENCE: 286
QDFTYQPKNP AFGGNYLNYS WMLNSANVQN GLTDP                              35

SEQ ID NO: 287         moltype = AA   length = 35
FEATURE                Location/Qualifiers
source                 1..35
                       mol_type = protein
                       organism = synthetic construct
SEQUENCE: 287
QDFVYTPKNP AFGGSPYNYS WMLSSAESQN TIEAP                              35

SEQ ID NO: 288         moltype = AA   length = 34
FEATURE                Location/Qualifiers
source                 1..34
                       mol_type = protein
                       organism = synthetic construct
SEQUENCE: 288
QQFSYQAKNP AFGGDTFNYQ WLQSSATAQN GLTA                               34
```

```
SEQ ID NO: 289           moltype = AA   length = 35
FEATURE                  Location/Qualifiers
source                   1..35
                         mol_type = protein
                         organism = synthetic construct
SEQUENCE: 289
QQLIYQPTNP SFGGYAANTT HLFATANAQK TATVG                                    35

SEQ ID NO: 290           moltype = AA   length = 35
FEATURE                  Location/Qualifiers
source                   1..35
                         mol_type = protein
                         organism = synthetic construct
SEQUENCE: 290
RKRQLADTVP SFGGSPLNGN WLQSQATAQN IFVRK                                    35

SEQ ID NO: 291           moltype = AA   length = 28
FEATURE                  Location/Qualifiers
source                   1..28
                         mol_type = protein
                         organism = synthetic construct
SEQUENCE: 291
YFGIGADTQY CLDQIAVNLR CTMTFQFE                                            28

SEQ ID NO: 292           moltype = DNA   length = 45
FEATURE                  Location/Qualifiers
source                   1..45
                         mol_type = other DNA
                         organism = synthetic construct
SEQUENCE: 292
aaaaaaaaaa aaaaaaaaaa aaaaaaaaaa aaaaaaaaaa aaaaa                         45

SEQ ID NO: 293           moltype = DNA   length = 45
FEATURE                  Location/Qualifiers
source                   1..45
                         mol_type = other DNA
                         organism = synthetic construct
modified_base            44
                         mod_base = OTHER
                         note = abasic site
SEQUENCE: 293
aaaaaaaaaa aaaaaaaaaa aaaaaaaaaa aaaaaaaaaa aaana                         45

SEQ ID NO: 294           moltype = DNA   length = 45
FEATURE                  Location/Qualifiers
source                   1..45
                         mol_type = other DNA
                         organism = synthetic construct
modified_base            43
                         mod_base = OTHER
                         note = abasic site
SEQUENCE: 294
aaaaaaaaaa aaaaaaaaaa aaaaaaaaaa aaaaaaaaaa aanaa                         45

SEQ ID NO: 295           moltype = DNA   length = 45
FEATURE                  Location/Qualifiers
source                   1..45
                         mol_type = other DNA
                         organism = synthetic construct
modified_base            42
                         mod_base = OTHER
                         note = abasic site
SEQUENCE: 295
aaaaaaaaaa aaaaaaaaaa aaaaaaaaaa aaaaaaaaaa anaaa                         45

SEQ ID NO: 296           moltype = DNA   length = 45
FEATURE                  Location/Qualifiers
source                   1..45
                         mol_type = other DNA
                         organism = synthetic construct
modified_base            41
                         mod_base = OTHER
                         note = abasic site
SEQUENCE: 296
aaaaaaaaaa aaaaaaaaaa aaaaaaaaaa aaaaaaaaaa naaaa                         45

SEQ ID NO: 297           moltype = DNA   length = 45
FEATURE                  Location/Qualifiers
```

```
source                  1..45
                        mol_type = other DNA
                        organism = synthetic construct
modified_base           40
                        mod_base = OTHER
                        note = abasic site
SEQUENCE: 297
aaaaaaaaaa aaaaaaaaaa aaaaaaaaaa aaaaaaaaan aaaaa                45

SEQ ID NO: 298          moltype = DNA  length = 45
FEATURE                 Location/Qualifiers
source                  1..45
                        mol_type = other DNA
                        organism = synthetic construct
modified_base           39
                        mod_base = OTHER
                        note = abasic site
SEQUENCE: 298
aaaaaaaaaa aaaaaaaaaa aaaaaaaaaa aaaaaaaana aaaaa                45

SEQ ID NO: 299          moltype = DNA  length = 45
FEATURE                 Location/Qualifiers
source                  1..45
                        mol_type = other DNA
                        organism = synthetic construct
modified_base           38
                        mod_base = OTHER
                        note = abasic site
SEQUENCE: 299
aaaaaaaaaa aaaaaaaaaa aaaaaaaaaa aaaaaaanaa aaaaa                45

SEQ ID NO: 300          moltype = DNA  length = 45
FEATURE                 Location/Qualifiers
source                  1..45
                        mol_type = other DNA
                        organism = synthetic construct
modified_base           37
                        mod_base = OTHER
                        note = abasic site
SEQUENCE: 300
aaaaaaaaaa aaaaaaaaaa aaaaaaaaaa aaaaaanaaa aaaaa                45

SEQ ID NO: 301          moltype = DNA  length = 45
FEATURE                 Location/Qualifiers
source                  1..45
                        mol_type = other DNA
                        organism = synthetic construct
modified_base           36
                        mod_base = OTHER
                        note = abasic site
SEQUENCE: 301
aaaaaaaaaa aaaaaaaaaa aaaaaaaaaa aaaaanaaaa aaaaa                45

SEQ ID NO: 302          moltype = DNA  length = 45
FEATURE                 Location/Qualifiers
source                  1..45
                        mol_type = other DNA
                        organism = synthetic construct
modified_base           35
                        mod_base = OTHER
                        note = abasic site
SEQUENCE: 302
aaaaaaaaaa aaaaaaaaaa aaaaaaaaaa aaaanaaaaa aaaaa                45

SEQ ID NO: 303          moltype = DNA  length = 45
FEATURE                 Location/Qualifiers
source                  1..45
                        mol_type = other DNA
                        organism = synthetic construct
modified_base           34
                        mod_base = OTHER
                        note = abasic site
SEQUENCE: 303
aaaaaaaaaa aaaaaaaaaa aaaaaaaaaa aaanaaaaaa aaaaa                45
```

```
SEQ ID NO: 304          moltype = DNA  length = 45
FEATURE                 Location/Qualifiers
source                  1..45
                        mol_type = other DNA
                        organism = synthetic construct
modified_base           33
                        mod_base = OTHER
                        note = abasic site
SEQUENCE: 304
aaaaaaaaaa aaaaaaaaaa aaaaaaaaaa aanaaaaaaa aaaaa             45

SEQ ID NO: 305          moltype = DNA  length = 45
FEATURE                 Location/Qualifiers
source                  1..45
                        mol_type = other DNA
                        organism = synthetic construct
modified_base           32
                        mod_base = OTHER
                        note = abasic site
SEQUENCE: 305
aaaaaaaaaa aaaaaaaaaa aaaaaaaaaa anaaaaaaaa aaaaa             45

SEQ ID NO: 306          moltype = DNA  length = 45
FEATURE                 Location/Qualifiers
source                  1..45
                        mol_type = other DNA
                        organism = synthetic construct
modified_base           31
                        mod_base = OTHER
                        note = abasic site
SEQUENCE: 306
aaaaaaaaaa aaaaaaaaaa aaaaaaaaaa naaaaaaaaa aaaaa             45

SEQ ID NO: 307          moltype = DNA  length = 45
FEATURE                 Location/Qualifiers
source                  1..45
                        mol_type = other DNA
                        organism = synthetic construct
modified_base           30
                        mod_base = OTHER
                        note = abasic site
SEQUENCE: 307
aaaaaaaaaa aaaaaaaaaa aaaaaaaaan aaaaaaaaaa aaaaa             45

SEQ ID NO: 308          moltype = DNA  length = 45
FEATURE                 Location/Qualifiers
source                  1..45
                        mol_type = other DNA
                        organism = synthetic construct
modified_base           29
                        mod_base = OTHER
                        note = abasic site
SEQUENCE: 308
aaaaaaaaaa aaaaaaaaaa aaaaaaaana aaaaaaaaaa aaaaa             45

SEQ ID NO: 309          moltype = DNA  length = 45
FEATURE                 Location/Qualifiers
source                  1..45
                        mol_type = other DNA
                        organism = synthetic construct
modified_base           28
                        mod_base = OTHER
                        note = abasic site
SEQUENCE: 309
aaaaaaaaaa aaaaaaaaaa aaaaaaanaa aaaaaaaaaa aaaaa             45

SEQ ID NO: 310          moltype = DNA  length = 45
FEATURE                 Location/Qualifiers
source                  1..45
                        mol_type = other DNA
                        organism = synthetic construct
modified_base           27
                        mod_base = OTHER
                        note = abasic site
SEQUENCE: 310
aaaaaaaaaa aaaaaaaaaa aaaaaanaaa aaaaaaaaaa aaaaa             45
```

```
SEQ ID NO: 311          moltype = DNA  length = 28
FEATURE                 Location/Qualifiers
source                  1..28
                        mol_type = other DNA
                        organism = synthetic construct
SEQUENCE: 311
cagtcgcatc ggttttact gcgggctg                                              28

SEQ ID NO: 312          moltype = DNA  length = 38
FEATURE                 Location/Qualifiers
source                  1..38
                        mol_type = other DNA
                        organism = synthetic construct
SEQUENCE: 312
ttttttttt ggaattttt ttttggaatt tttttttt                                    38

SEQ ID NO: 313          moltype = AA  length = 119
FEATURE                 Location/Qualifiers
source                  1..119
                        mol_type = protein
                        organism = synthetic construct
SEQUENCE: 313
GTMTFQFRNP MFGGNPNNGA FLLNSAQAQN SYKIPSTNDD FGIETPSALD NFTQAIQSQI          60
LGGLLSNINI GKPGRMVIND YIVDIAHRDG QLQLNVTDRK TGQTSTIQVS GLQNNSTDF          119

SEQ ID NO: 314          moltype = AA  length = 116
FEATURE                 Location/Qualifiers
source                  1..116
                        mol_type = protein
                        organism = synthetic construct
SEQUENCE: 314
TELVYTPVNP AFGGNPLNGT HLLNNAQAQN DYDDPDLDKD RASAFTGTTA LERFSNQLES          60
RMLSQLLDNI SNGMTGSMAT DAFLIDVIDD SGALSIKVTD AATGEISIIE VSGLMP             116

SEQ ID NO: 315          moltype = AA  length = 113
FEATURE                 Location/Qualifiers
source                  1..113
                        mol_type = protein
                        organism = synthetic construct
SEQUENCE: 315
TELIVEPVNP NFGGNPLNGS YLLNNAQAQQ RHRDPDLSLY EQPSALDRFT DSLETRLLNQ          60
LLTDVGNGNS GELITDDFIV QIVDNDGVLI VLVTDRSTGD KSEIIVSGLN PTN                113

SEQ ID NO: 316          moltype = AA  length = 113
FEATURE                 Location/Qualifiers
source                  1..113
                        mol_type = protein
                        organism = synthetic construct
SEQUENCE: 316
SELVYTPVNP NFGGNPLNTS HLFGGANAIN DYKGPDEDSL FEQESALDRL TSSLQSRLIS          60
QLLADVGNGN TGQLITDDFI LNIVDQSGAL LIQIVDKATG ETSEIQVSGL TPD                113

SEQ ID NO: 317          moltype = AA  length = 114
FEATURE                 Location/Qualifiers
source                  1..114
                        mol_type = protein
                        organism = synthetic construct
SEQUENCE: 317
TQLVYTPVNP AFGGSYLNGS YLLANASAQN EMQGGSSYVA PTALQRLASS LQSRLMSQLF          60
MDAAMGGEGY LKTDDFEIMV VNEDGSLLVH ITDLLTGETT IIEVGGIVGT TTGG               114

SEQ ID NO: 318          moltype = AA  length = 114
FEATURE                 Location/Qualifiers
source                  1..114
                        mol_type = protein
                        organism = synthetic construct
SEQUENCE: 318
TQLIVTPVNP NFGGSYLNGS YLLAMASVQN DHKTSSGYTP PTALERMANS LESRLMSQLF          60
NDAANGGEGY LKTTDFEINV VNEDGTLLVH ITDIVTGETT VIEVGGLVNT GTGG               114

SEQ ID NO: 319          moltype = AA  length = 109
FEATURE                 Location/Qualifiers
source                  1..109
                        mol_type = protein
                        organism = synthetic construct
SEQUENCE: 319
TELVYTPKNP AFGGSPLNGS YLLGNAQAQN DYDQPMAKKA TTLSALERFT NQLQSSLSDV          60
LAKRKGEAGS LQTDDFIVMM LKDETGQLVI HITDRATGEI SEIVTGTTV                     109
```

```
SEQ ID NO: 320          moltype = AA   length = 105
FEATURE                 Location/Qualifiers
source                  1..105
                        mol_type = protein
                        organism = synthetic construct
SEQUENCE: 320
SSLVVEPVNP TFGGNPLNTT HLFSRAEAIN DYEGSSGSSS SSSVLSSLTS SLQSRLISQL   60
LATGEAGSLE TNDYSLVITD NDGYLTITIT DKATGESTDI DVSGL                  105

SEQ ID NO: 321          moltype = AA   length = 113
FEATURE                 Location/Qualifiers
source                  1..113
                        mol_type = protein
                        organism = synthetic construct
SEQUENCE: 321
GQLIYQPINP SFGGDPLLGN HLLNKAQAQD TKKIPNAPDF GRFSETEFFI QDLRAKLIND   60
RIQDAVDGGD GESTIDSSTL RVELRSSGGG SFSMTILDKT TGETTTVNFG QPF         113

SEQ ID NO: 322          moltype = AA   length = 126
FEATURE                 Location/Qualifiers
source                  1..126
                        mol_type = protein
                        organism = synthetic construct
SEQUENCE: 322
TELVYEPINP SFGGNPLNGS FLLSKANSQN AHTAPYSERS YDERLQESLE RAYINRIVRE   60
ITDIAFGEQE YDEDGNPIDS IFNQDSIFVS GDFQVELITS NPDSIVVNIT NLLIGEVIVV  120
EIPRFG                                                             126

SEQ ID NO: 323          moltype = AA   length = 108
FEATURE                 Location/Qualifiers
source                  1..108
                        mol_type = protein
                        organism = synthetic construct
SEQUENCE: 323
TEIVYQPINP SFGGNPMNGS FLLQKAQSQN AHTAPDEGRS FVDAFRDALE RNITNSLTRR   60
IADGEIVEGL YDTGEYTVEV IGQPDGSVLV YITHNETGEQ TVITMPAI               108

SEQ ID NO: 324          moltype = AA   length = 113
FEATURE                 Location/Qualifiers
source                  1..113
                        mol_type = protein
                        organism = synthetic construct
SEQUENCE: 324
TELVFSFTNP SFGGDPMIGN FLLNKADSQK AFAEDEYEED PLSDFEDGLN RRYLGLIADK   60
IVQDAFGDEG NLSNGTYTIG SYVISIDMNG KVIKVAVTDS LSGDSTVVEV PVF         113

SEQ ID NO: 325          moltype = AA   length = 127
FEATURE                 Location/Qualifiers
source                  1..127
                        mol_type = protein
                        organism = synthetic construct
SEQUENCE: 325
SSLVVQPVNP AFGGPQLNGS WLQAEANAQN TPQAAAQRRQ QITGAAASDA REGILTPGDA   60
FAQQLQTQLY SSLANQITRA IFEENAQPNE QFSFQGTTIS YIRVGSNVSI TINGGSTVTT  120
VTVPAIP                                                            127

SEQ ID NO: 326          moltype = AA   length = 117
FEATURE                 Location/Qualifiers
source                  1..117
                        mol_type = protein
                        organism = synthetic construct
SEQUENCE: 326
GSLVYIPINP AFGGSPLNGS WQMQQATAGN HFHRAAPTSG PQQLIQSQIF AQQLQSQLYA   60
SLANQVTQAI FGANAQQSGT FSFQGTTISF AKVDGQTNIT INDGSTVTQI SLPTVTH     117

SEQ ID NO: 327          moltype = AA   length = 133
FEATURE                 Location/Qualifiers
source                  1..133
                        mol_type = protein
                        organism = synthetic construct
SEQUENCE: 327
QQLIVQPTNP SFGGYAANTT HLFATANAQK TATVGGSHKY GSGSGSGNDG SGSSLADLFV   60
RQLQNRLIYA LADQVSQAIF GDDPKDSGTV SFGDQKVSFV RGSDSIQLQI IDESTGAITQ  120
ITVPVLQTDT PIN                                                     133

SEQ ID NO: 328          moltype = AA   length = 169
FEATURE                 Location/Qualifiers
source                  1..169
```

```
                           mol_type = protein
                           organism = synthetic construct
SEQUENCE: 328
GDLVVTPVNP SFGGSPLNSA HLLSTAGRQK NATASDYKKP VDSTSAGTTG SGTKTQSDAD    60
LFVRQLQGRL LSALASQVTD AIFGENPQDS GTVQFGDTKV TFDRTLTTIR LRIENATDGT   120
VTDIVVPQLV TSKPATTTAS TASSSASASQ LSTATPVLSG SALTPLSIN              169

SEQ ID NO: 329             moltype = AA   length = 118
FEATURE                    Location/Qualifiers
source                     1..118
                           mol_type = protein
                           organism = synthetic construct
SEQUENCE: 329
RELGYTPVNP SFGGSPLNGS TLLSEASAQK PNAPTSKTAS STTSASQQFL QMLQSQLYAS    60
LASSVAQRVI GATTGGTIVL DNLTVTWAIA STGKVITMTD ASTGQVTKIT VPIVTTSN    118

SEQ ID NO: 330             moltype = AA   length = 117
FEATURE                    Location/Qualifiers
source                     1..117
                           mol_type = protein
                           organism = synthetic construct
SEQUENCE: 330
QQLVVKSTNP FFGGGDSFAY QQLLASANAQ NDFVEENSSL FSQSSEIENF TDNLNRQLLN    60
SLSQGLFQEQ FGSQGLSEGT YVYGSLVVEV NPGVGGLSVS ILNTSTGEQT QITIPNN     117

SEQ ID NO: 331             moltype = AA   length = 115
FEATURE                    Location/Qualifiers
source                     1..115
                           mol_type = protein
                           organism = synthetic construct
SEQUENCE: 331
QGLIVKPKNP AFGGDTFNYQ WLASSAESQN KFTDKTISQV EQTELERFTS SLNSLLLSQI    60
SSSLFRQQFG SDGIKIGSYT FGSLSVEVYP SSGGLTVDIL DTKTGETTQV IIPNR       115

SEQ ID NO: 332             moltype = AA   length = 121
FEATURE                    Location/Qualifiers
source                     1..121
                           mol_type = protein
                           organism = synthetic construct
SEQUENCE: 332
QALVVHPMMP AFGGNTFNYQ AMLSSAQAQD RLTDPTLKKT TATATKTSNQ LSDLATSIQR    60
QLLSRITNDL LKHQFGENSS LKEGTYKYGD FTVTIRNQYD GIYIRIVDNQ GGETSIQVPY  120
F                                                                 121

SEQ ID NO: 333             moltype = AA   length = 120
FEATURE                    Location/Qualifiers
source                     1..120
                           mol_type = protein
                           organism = synthetic construct
SEQUENCE: 333
QAFVYHPNNP NFGGNTFNYS WMLSSAQAQD RTTDPTATVR TANGTTQTGS LNSFAQSLQS    60
QLLSRITSSL VGSQFGEGTL KPGTYKFGEY QVDISNGASG VVVRIVDGKG GETSITIPYY  120
```

PROTEIN PORES

RELATED APPLICATIONS

This Application is a Continuation of U.S. application Ser. No. 16/624,341, filed Dec. 19, 2019, entitled "NOVEL PROTEIN PORES", which is a national stage filing under 35 U.S.C. § 371 of International Patent Application Serial No. PCT/GB2018/051858, filed Jul. 2, 2018, entitled "NOVEL PROTEIN PORES". Foreign priority benefits are claimed under 35 U.S.C. § 119(a)-(d) or 35 U.S.C. § 365(b) of European application number 17179099.1, filed Jun. 30, 2017. The entire contents of these applications are incorporated herein by reference in their entirety.

REFERENCE TO AN ELECTRONIC SEQUENCE LISTING

The contents of the electronic sequence listing (0036670093US02-SUBSEQ-MSB.xml; Size: 357,163 bytes; and date of Creation: Jul. 31, 2023) are herein incorporated by reference in their entirety.

FIELD

The present invention relates to novel protein pores and their uses in analyte detection and characterisation. The invention further relates to a transmembrane pore complex and methods for production of the pore complex and for use in molecular sensing and nucleic acid sequencing applications.

BACKGROUND

Nanopore sensing is an approach to analyte detection and characterization that relies on the observation of individual binding or interaction events between the analyte molecules and an ion conducting channel. Nanopore sensors can be created by placing a single pore of nanometer dimensions in an electrically insulating membrane and measuring voltage-driven ion currents through the pore in the presence of analyte molecules. The presence of an analyte inside or near the nanopore will alter the ionic flow through the pore, resulting in altered ionic or electric currents being measured over the channel. The identity of an analyte is revealed through its distinctive current signature, notably the duration and extent of current blocks and the variance of current levels during its interaction time with the pore. Analytes can be organic and inorganic small molecules as well as various biological or synthetic macromolecules and polymers including polynucleotides, polypeptides and polysaccharides. Nanopore sensing can reveal the identity and perform single molecule counting of the sensed analytes, but can also provide information on the analyte composition such as nucleotide, amino acid or glycan sequence, as well as the presence of base, amino acid or glycan modifications such as methylation and acylation, phosphorylation, hydroxylation, oxidation, reduction, glycosylation, decarboxylation, deamination and more. Nanopore sensing has the potential to allow rapid and cheap polynucleotide sequencing, providing single molecule sequence reads of polynucleotides of tens to tens of thousands bases length.

Two of the essential components of polymer characterization using nanopore sensing are (1) the control of polymer movement through the pore and (2) the discrimination of the composing building blocks as the polymer is moved through the pore. During nanopore sensing, the narrowest part of the pore forms the reader head, the most discriminating part of the nanopore with respect to the current signatures as a function of the passing analyte. CsgG was identified as an ungated, non-selective protein secretion channel from Escherichia coli (Goyal et al., 2014) and has been used as a nanopore for detecting and characterising analytes. Mutations to the wild-type CsgG pore that improve the properties of the pore in this context have also been disclosed (WO2016/034591, WO2017/149316, WO2017/149317 and WO2017/149318, PCT/GB2018/051191, all incorporated by reference herein).

For analytes being polynucleotides, nucleotide discrimination is achieved via passage through such a mutant pore, but current signatures have been shown to be sequence dependent, and multiple nucleotides contributed to the observed current, so that the height of the channel constriction and extent of the interaction surface with the analyte affect the relationship between observed current and polynucleotide sequence. While the current range for nucleotide discrimination has been improved through mutation of the CsgG pore, a sequencing system would have higher performance if the current differences between nucleotides could be improved further. Accordingly, there is a need to identify novel ways to improve nanopore sensing features.

SUMMARY

The disclosure relates to modified CsgF peptides, in particular truncated CsgF fragments, binding the CsgG pore and thereby introducing another additional channel or pore constriction within the CsgG pore. Other aspects of the invention also relate to an isolated transmembrane pore complex, and the use of said CsgG:CsgF complexes and modified CsgF peptides or fragments in a nanopore sensing platform with two consecutive reader heads.

The first aspect of the invention relates to a pore comprising a CsgG pore and a CsgF peptide. In one aspect, the CsgF peptide comprises a CsgG-binding region, and a region that forms a constriction in the pore. In one aspect the CsgF peptide is a truncated CsgF peptide lacking the C-terminal head domain of CsgF. In another aspect the CsgF peptide is a truncated CsgF peptide lacking the C-terminal head and a portion of the neck domain of CsgF. In another aspect the CsgF peptide is a truncated CsgF peptide lacking the C-terminal head and neck domains of CsgF. The pore is also referred to herein as a pore complex and as an isolated pore complex. The isolated pore complex comprising a CsgG pore, or a homologue or mutant thereof, and a modified CsgF peptide, or a homologue or mutant thereof, in particular truncated CsgF fragments, or homologues or mutants thereof. In one embodiment, said modified CsgF peptide, or homologues or mutants, is located in the lumen of the CsgG pore, or homologues or mutants thereof. In another embodiment, said isolated pore complex has two or more channel constrictions, one located or provided by the CsgG pore, formed by its constriction loop, and another additional channel constriction or reader head, introduced by the modified CsgF peptide or its homologues or mutants. In one embodiment, said CsgG-pore or CsgG-like pore, is not a wild-type pore, it is a mutant CsgG pore, with in particular embodiments mutations being present, for example, in said channel constriction loop. In another embodiment, the isolated pore complex, comprising the modified CsgF peptide, or a homologue or mutant thereof, has a CsgF channel constriction with a diameter in the range from 0.5 nm to 2.0 nm. In one embodiment, the pore complex comprises: (i) a CsgG pore comprising a first opening, a mid-section comprising a beta barrel, a second opening, and a lumen extending from the first opening through the mid-section to the second opening, wherein a luminal surface of the mid-section defines a CsgG constriction; and (ii) a plurality of modified CsgF peptides, each having a CsgF constriction region and a CsgF binding region (also referred to herein as a CsgG-binding domain or region of CsgF), wherein the modified CsgF peptides form a CsgF constriction within the beta barrel of the CsgG pore and wherein the CsgG constriction and the CsgF constriction are co-axially spaced apart within the beta barrel of the CsgG pore. The luminal surface of the CsgG pore may comprise one or more loop regions of CsgG monomers that define the CsgG constriction. The CsgF constriction region and the CsgF binding region typically correspond to a N-terminal portion of a CsgF mature peptide. In one embodiment, the pore complex excludes CsgA, CsgB and CsgE.

In a second aspect, the invention relates to a modified CsgF peptide, or a homologue or mutant thereof, wherein the protein or peptide is modified via a truncation or deletion of part of the protein, resulting in a CsgF fragment of SEQ ID NO:6 or of a homologue or mutant thereof. One embodiment relates to a modified or truncated CsgF peptide, or a modified peptide of a CsgF homologue or mutant, said modified peptide comprising SEQ ID NO:39, or SEQ ID NO:40, or a homologue or mutant thereof, alternatively, said modified peptide comprises SEQ ID NO:15, or a homologue or mutant thereof, alternatively SEQ ID NO: 54, or SEQ ID NO: 55 or a homologue or mutant thereof. Another embodiment discloses a modified CsgF peptide wherein one or more positions in the region comprising SEQ ID NO:15 are modified, and wherein said mutation(s) required to retain a minimal of 35% amino acid identity to SEQ ID NO:15, in the peptide fragment corresponding to the region comprising SEQ ID NO:15.

One embodiment relates to a pore comprising a CsgG pore and a modified CsgF peptide, wherein the modified CsgF peptide is bound to CsgG and forms a constriction in the pore One embodiment relates to a polynucleotide encoding said modified CsgF peptide, or homologue or mutant thereof, according to the second aspect of the invention. In another embodiment, the isolated pore complex comprising a CsgG pore and a modified CsgF peptide, or homologues or mutants thereof, are characterized in that said modified CsgF peptide is a peptide provided by the peptides disclosed in the second aspect of the invention.

Another embodiment relates to the isolated pore complex wherein the modified CsgF peptide and the CsgG pore or a monomer of said pore, or homologues or mutants thereof, are covalently coupled. And even more particularly, said coupling is made via a cysteine residue or via a non-native reactive or photo-reactive amino acid in a CsgG monomer at a position corresponding to 132, 133, 136, 138, 140, 142, 144, 145, 147, 149, 151, 153, 155, 183, 185, 187, 189, 191, 201, 203, 205, 207 or 209 of SEQ ID NO: 3, or of a homologue thereof.

A preferred embodiment relates to an isolated transmembrane pore complex, or a membranous composition, which comprises the isolated pore complex of the invention, and the components of a membrane. Particularly, said transmembrane pore complex or membranous composition consists of the isolated pore complex of the invention, and the components of a membrane or an insulating layer.

One embodiment relates to a method for producing a pore as disclosed herein, the method comprising co-expressing one or more CsgG monomers as disclosed herein and a CsgF peptide as disclosed herein in a host cell, thereby allowing transmembrane pore complex formation in the cell. The CsgF peptide may be produced in the cell by cleaving a modified CsgF peptide or protein comprising an enzyme cleavage site at a suitable position in the amino acid sequence.

One embodiment relates to a method for producing a pore as disclosed herein, the method comprising contacting one or more purified CsgG monomers with one or more purified modified CsgF peptides, thereby allowing in vitro formation of the pore. The modified CsgF peptide may be a peptide comprising an enzyme cleavage site at a suitable position in the amino acid sequence, that is cleaved before or after formation of the pore.

A third aspect of the invention relates to a method for producing said transmembrane pore complex, wherein the pore is an isolated complex formed by a CsgG pore, or a homologue or mutant thereof, and a modified CsgF peptide, or a homologue or mutant thereof, the method comprising the steps of co-expressing CsgG SEQ ID NO:2, or a homologue or mutant thereof, and modified or truncated CsgF, comprising a fragment of SEQ ID NO:5, or a homologue or mutant thereof, in a suitable host cell, thereby allowing in vivo pore complex formation. In specific embodiments, said modified CsgF peptide, or homologue or mutant thereof, comprises SEQ ID NO: 12 or SEQ ID NO:14, or a homologue or mutant thereof. Alternatively, a method for producing an isolated pore complex comprises the steps of contacting CsgG monomers of SEQ ID NO:3, or a homologue or mutant thereof, with modified CsgF peptide(s), or a homologue or mutant thereof, for in vitro reconstitution of the pore complex. In particular embodiments, modified CsgF peptides of said method comprise SEQ ID NO:15 or SEQ ID NO:16, or homologues or mutants thereof.

Another aspect of the invention relates to a method for determining the presence, absence or one or more characteristics of a target analyte, comprising the steps of:
 (i) contacting the target analyte with said isolated pore complex or transmembrane pore complex, such that the target analyte moves into the pore channel; and
 (ii) taking one or more measurements as the analyte moves through the pore channel and thereby determining the presence, absence or one or more characteristics of the analyte.

In one embodiment, said analyte is a polynucleotide. In particular, said method using a polynucleotide as an analyte alternatively comprises determining one or more characteristics selected from (i) the length of the polynucleotide, (ii) the identity of the polynucleotide, (iii) the sequence of the polynucleotide, (iv) the secondary structure of the polynucleotide and (v) whether or not the polynucleotide is modified.

In another embodiment, the analyte is a protein, or peptide, and in further embodiments, said analyte is a polysaccharide, or a small organic or inorganic compound, such as for instance but not limited to pharmacologically active compounds, toxic compounds and pollutants.

In another embodiment, a method for characterising a polynucleotide or a (poly)peptide using an isolated transmembrane pore complex is described, wherein the pore complex is an isolated complex comprising a CsgG pore, or a homologue or mutant thereof, and a modified CsgF peptide, or a homologue or mutant thereof. In particular, said CsgG pore, or homologue or mutant thereof, comprising six to ten CsgG monomers forming the CsgG pore channel.

A further aspect of the invention discloses the use of said isolated pore complex or transmembrane pore complex according to the previous aspects of the invention to determine the presence, absence or one or more characteristics of a target analyte. Furthermore, the invention also relates to a kit for characterising a target analyte comprising (a) said isolated pore complex and (b) the components of a membrane.

DESCRIPTION OF THE FIGURES

The drawings described are only schematic and are non-limiting. In the drawings, the size of some of the elements may be exaggerated and not drawn on scale for illustrative purposes.

FIGS. 1A-1E Structure of CsgG pore and the interface for complex formation with CsgF. Cross-sectional (FIG. 1A), side (FIG. 1B) and top (FIG. 1C) views of CsgG oligomers (e.g., nonamers) (gold) in surface (FIG. 1A) and ribbon (FIG. 1B, FIG. 1C) representation, with a single CsgG protomer colored light blue (FIG. 1D) (based on the CsgG X-ray structure PDB entry: 4uv3). The CsgG constriction loop (CL loop) spans residues 46 to 61 according SEQ ID NO:3, and is indicated in dark grey in all panels, and corresponds to the loop provided in the bottom left of (FIG. 1E). CsgG residues for which the side chain faces the inner lumen of the CsgG beta-barrel are colored mid-grey as indicated and labelled in the β strands in (FIG. 1E) and (FIG. 1D). These residues represent sites that can be used for substitution to natural or non-natural amino acids, e.g., amenable for attachment (e.g., covalent crosslinking) of a pore-resident peptide, (including e.g., a modified CsgF peptide, or a homologue thereof) to a CsgG pore or monomer. In some embodiments crosslinking residues include Cys and reactive and photo-reactive amino acids, acids such as azidohomoalanine, homopropargylglycyine, homoallelglycine, p-acetyl-Phe, p-azido-Phe, p-propargyloxy-Phe and p-benzoyl-Phe (Wang et al. 2012; Chin et al. 2002) and can be substituted into positions 132, 133, 136, 138, 140, 142, 144, 145, 147, 149, 151, 153, 155, 183, 185, 187, 189, 191, 201, 203, 205, 207 or 209 according to SEQ ID NO:3. (FIG. 1E) shows a zoom of the CL loop and the transmembrane beta-strands of a CsgG monomer. The CsgG constriction loop (colored dark blue) forms the orifice or narrowest passage in the CsgG pore (FIG. 1A). In some embodiments, three positions in the CL loop, 56, 55 and 51 according to SED ID NO:3, are of particular importance to the diameter and chemical and physical properties of the CsgG channel orifice or "reader head". These represent preferred positions to alter the nanopore sensing properties of CsgG pores and homologues.

FIGS. 2A-2B CsgG:CsgF complex protein co-expression and complex purification. (FIG. 2A) Schematic representation of the purification protocol of the CsgG:CsgF complex starting from an E. coli culture co-expressing CsgG (SEQ ID NO:2+C-terminal StrepII tag) and CsgF (SEQ ID NO:4+C-terminal 6xHis tag). The protocol involves disrupting resuspended cells and performing a 1% DDM extraction of the membrane-bound proteins. The CsgG:CsgF complex and excess CsgF undergo a first enrichment by affinity purification on a nickel IMAC column, followed by a second affinity-based enrichment of the CsgG:CsgF complex on a Streptavidin column. (FIG. 2B) Coommassie stained SDS-PAGE of the IMAC (left) and Streptavidin (right) purification steps. Protein bands corresponding to CsgG and CsgF are labelled. Notably, the IMAC eluate contains a N-terminally truncated CsgF fragment (labelled *) that was not retained in the affinity pulldown using the CsgG-bound Strep tag, indicating that the CsgF N-terminus is required for complex formation with CsgG.

(FIG. 3A) Superimposed chromatograms of Size Exclusion Chromatography (SEC) runs (using BioRad Enrich 650 10/300 column) of CsgG (light grey) and CsgG supplemented with an excess CsgF (dark grey). The chromatograms show elution peaks corresponding to a CsgG 9-mer (a) and CsgG 18-mer (b) for the CsgG run; and an excess free CsgF (c), as well as a 9-mer CsgG:CsgF complex (d) and 18-mer CsgG:CsgF complex (e) that elute at higher hydrodynamic radius (molecular mass) due the incorporation of CsgF in the complex. (FIG. 3B) Native PAGE analysis of the representative species labelled in panel (A), confirming the shift to higher molecular mass due to incorporation of CsgF into the CsgG 9-mer and CsgG 18-mer complexes. These experiments demonstrate that CsgG:CsgF complex can be reconstituted in vitro starting from the purified components. (FIG. 3C) Ribbon representation of the CsgG 9-mer and CsgG 18-mer as previously reported in Goyal et al. 2014 (PDB entry 4uv3). The CsgG 18-mer is formed of a dimer of CsgG 9-mers. The SEC and native PAGE analyses shown in panels A and B demonstrate that the CsgG 18-mer is amenable to complex formation with CsgF.

(FIG. 4A) A cryo electron micrograph of the CsgG:CsgF complex shows the presence of 9-mer and 18-mer CsgG:CsgF complexes, with a number of single particles of the 9- and 18-mer forms highlighted by full and dashed circles, respectively. (FIG. 4B) Two representative class averages of the CsgG:CsgF 9-mer complex, viewed from the side. Class averages include 6020 and 4159 individual particles, respectively. The class averages reveal the presence of additional density on top of the CsgG particle, corresponding to an oligomeric complex of CsgF. Three distinct regions can be seen in the CsgF oligomer: a "head" and "neck" region, as well as a region that resides inside lumen of the CsgG beta-barrel and forms a constriction or narrow passage (labelled F) that is stacked on top of the constriction formed by the CsgG CL loop (labelled G). This latter CsgF region is referred to as CsgF Constriction Peptide (FCP).

(FIG. 6A) Schematic representation of the CsgG nanopore in cross-sectional view, harbouring a single constriction, labelled (1). CsgG-based nanopores form 3.5-4 nm wide channels that contain a 0.5-1.5 nm orifice made by the CsgG constriction loop (residues 46 to 61 according SEQ ID No:3). When in complex with CsgF, a second constriction or orifice is introduced into the CsgG channel, labelled (2)/F, and the channel exit becomes occluded by the CsgF head domain (see FIG. 5). When using modified CsgF peptides, e.g., corresponding to a CsgF constriction peptide (FCP), which lacks the neck and head regions, a CsgG:CsgF pore complex is formed with two consecutive channel constrictions or orifices ((1) and (2)), as shown in the cross-sectional view of the CsgG:CsgF cryo-EM density in panel (FIG. 6B) and in schematic representation in panel (FIG. 6C). Removal of the neck and head regions in the modified CsgF peptide alleviates their blockage of the channel exit.

(FIG. 7C) Schematic representation of theoretical channel conductance profiles of small molecules (indicated by hexagonals or triangles) passing and interacting with the consecutive CsgG (1) and CsgF (2) constrictions or reader heads.

FIG. 8 Multiple sequence alignments of exemplary CsgF homologues. Aligned sequences are shown as mature proteins (i.e. lacking their N-terminal signal peptide (SP)). The boxed sequences indicate a CsgF region of sequence conservation (between 35 and 100% pairwise sequence identity—see FIG. 10) that corresponds to a CsgF constriction peptide (FCP) in some embodiments. CsgF homologues included in the multiple sequence alignment are Q88H88; A0A143HJA0; Q5E245; Q084E5; FOLZU2; A0A136HQR0; A0A0W1SRL3; BOUH01; Q6NAU5; G8PUY5; A0AOS2ETP7; E311Z1; F3Z094; A0A176T7M2; D2QPP8; N21YT1; W7QHV5; D4ZLW2; D2QT92; A0A167UJA2. The FCP regions of *E. coli* CsgF (SEQ ID No:15) and the shown CsgF homologues correspond to SEQ ID Nos 18-36. Top to bottom, left to right, the sequences depicted in FIG. 8 correspond to SEQ ID NOs: 313-333.

FIG. 9A-9C Experimental evaluation of the *E. coli* CsgF region forming the CsgG-interaction sequence and CsgF constriction peptide (FCP). Panel (FIG. 9A) shows the mature sequences (i.e. after removal of the CsgF signal peptide, corresponding to residues 1-19 of SEQ ID NO:5) of the four N-terminal CsgF fragments (SEQ ID NO:8_ CsgF residues 1-27; SEQ ID NO: 10; SEQ ID NO: 12 and SEQ ID NO: 14) that were co-expressed with *E. coli* CsgG (SEQ ID NO:2). Top to bottom, left to right, the sequences depicted in FIG. 9 correspond to SEQ ID NOs: 37-40. (FIG. 9B) Anti-Strep (left) and anti-His (right) Western blot analysis of SDS-PAGE runs of crude cell lysates of CsgG and CsgF co-expression experiments. Anti-strep analysis demonstrates the expression of CsgG in all co-expression experiments, whereas anti-his western blot analysis shows detectible levels of CsgF fragments only for the truncation mutant CsgF 1-64 (SEQ ID NO: 14). A His-tagged nanobody (Nb) was used as positive control. (FIG. 9C) Anti-His dot blot analysis of the presence of CsgF fragments in CsgG:CsgF co-expression experiments. Top row shows whole cell lysates, middle and bottom rows show the eluate and flow-through of a Strep affinity pulldown experiment. These data demonstrate that CsgF fragment 1-64, and to a much lesser extent CsgF 1-48, is specifically pulled down as a complex with Strep-tagged CsgG. CsgF fragments 1-27 and 1-38 do not result in detectable levels of the corresponding CsgF fragments and show no sign of complex formation with CsgG.

FIGS. 10A-10C Multiple sequence alignment of the CsgF region forming the CsgG-interaction sequence and CsgF constriction peptide (FCP). The figures show a multiple sequence alignment and consensus sequence of the CsgF peptides and known homologues thereof in the region that corresponds to the CsgG-interaction. CsgF homologues are defined by the PFAM domain PF03783. These peptides bind CsgG, and localize to the lumen of the CsgG β-barrel where they form an additional constriction in the CsgG channel. These peptides and homologues thereof are examples of CsgF Constriction Peptides or FCPs. The pairwise sequence identity in the shown FCPs ranges between 35 and 98%. Top to bottom, left to right, the sequences depicted in FIG. 10A correspond to SEQ ID NOs: 55, 55, 55, 121, 122, 122, 122, 122, 122, 123, 123-140, 140-142, 142-168, 168-171, 171-178. Top to bottom, left to right, the sequences depicted in FIG. 10B correspond to SEQ ID NOs: 178-196, 196-206, 206-211, 211-212, 212-236, 25, 25, 237, 237-238, 238-239. Top to bottom, left to right, the sequences depicted in FIG. 10C correspond to SEQ ID NOs: 240-289, 289-290.

FIG. 11A Final electron density map of the CsgG:CsgF complex at 3.4 Å resolution. Side view. FIG. 11B Top view of the cryoEM structure to show CsgG:CsgF comprises a 9:9 stoichiometry, with C9 symmetry. FIG. 11C Internal architecture of the CsgG:CsgF complex. GC, CsgG constriction, FC, CsgF constriction. FIG. 11D Interactions between CsgG and CsgF proteins. CsgG and the CsgG constriction are coloured light grey and grey respectively. CsgF is coloured dark grey. Residues in CsgG and CsgF are labelled in light grey and black respectively.

FIG. 15A TEV or C3 or any other protease cleavage site can be Incorporated into the CsgF peptide at required sites (eg: between 30 and 31, 35 and 36, 40 and 41, 45 and 46 of seq ID no. 6) CsgG is shown in gold and CsgF domains in red. 1-35 of one CsgF subunit is coloured in green for clarity. 36-45 is shown in purple. 10 Histidine tag is shown in pink and the strep tag on CsgG is shown in blue. FIG. 15B SDS-PAGE (4-20% TGX) for protease cleavage of the full length CsgG:CsgF complex where TEV protease cleavage site is inserted between 35-36 of seq ID 6. M: molecular weight marker, Lane 1: post strep purification of CsgG:CsgF full length complex, Lane 2: post strep concentrated, Lane 3: post gel filtrated, Lane 4: cleaved with TEV protease to generate CsgG:CsgF complex, Lane 5: flow through of CsgG:CsgF after strep purification, Lane 6: CsgG:CsgF heated at 60° C. for 10 minutes. Lane 7: Eluted CsgG:CsgF complex from strep column, Lane 8: CsgG pore as the control, Lane 9: TEV protease as the control.

FIGS. 16A-16C Heat stability of CsgG:CsgF complexes. M: Molecular weight marker, Lane 1: CsgG pore, Lane 2: CsgG:CsgF complex at room temperature: Lanes 3-9: CsgG:CsgF sample was heated at different temperatures (40, 50, 60, 70, 80, 90, 100° ° C. respectively) for 10 minutes. Lane 1:

FIG. 16A. Y51A/F56Q/N55V/N91R/K94Q/R97W-del(V105-I107):CsgF-(1-45).

FIG. 16B. Y51A/F56Q/N55V/N91R/K94Q/R97W-del(V105-I107):CsgF-(1-35).

FIG. 16C. Y51A/F56Q/N55V/N91R/K94Q/R97W-del(V105-I107):CsgF-(1-30).

Figure 3A:
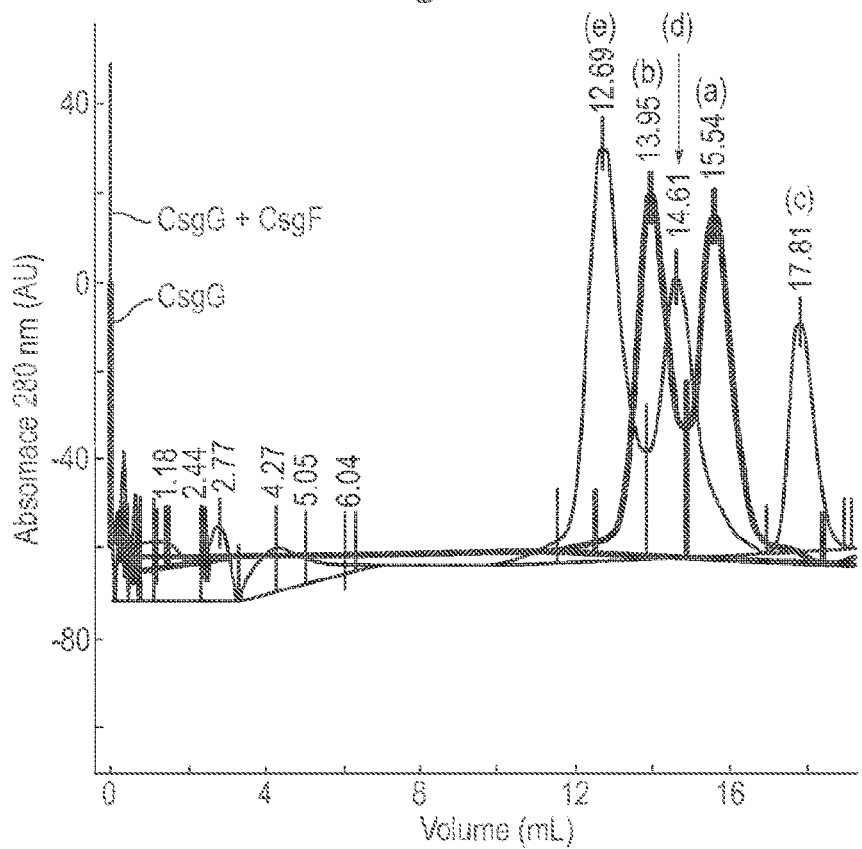
FIGS. 3A-3C CsgG:CsgF complex protein purification upon in vitro reconstitution.

Samples were subjected to SDS-PAGE on a 7.5% TGX gel. CsgG:CsgF complexes with both CsgF-(1-45) and CsgF-(1-35) shows a shift from the CsgG pore band in lanes 1. Therefore, it is clear that both those complexes are heat stable up to 90° C. The complex and the pore breaks down to CsgG monomers at 100° C. (lanes 9). Although the same heat stability pattern is seen with the CsgG:CsgF complex with CsgF-(1-30), its difficult to see the shift between the protein bands of the CsgG pore (lane 1) and CsgG-CsgF complexes (lanes 2-8).

FIG. 17 CsgG:CsgF formation via in vitro reconstitution using synthetic CsgF peptides. Native PAGE showing CsgG:CsgF formation via in vitro reconstitution using wildtype CsgG or a CsgG mutant with altered constriction Y51A/F56Q/K94Q/R97W/R192D-del(V105-I107). An Alexa 594-labelled CsgF peptide corresponding to the first 34 residues of mature CsgF (Seq ID No 6) was added to purified Strep-tagged CsgG or Y51A/F56Q/K94Q/R97W/R192D-del(V105-I107) in 50 mM Tris, 100 mM NaCl, 1 mM EDTA, 5 mM LDAO/C8D4 in a 2:1 molar ratio during 15 minutes at room temperature to allow reconstitution. After pull down of CsgG-strep on StrepTactin beads, the sample was analysed on native-PAGE. Both WT and Y51A/F56Q/K94Q/R97W/R192D-del(V105-I107) CsgG bind the CsgF N-terminal peptide as visualised by the fluorescence tag.

Figures 18A, 18B:
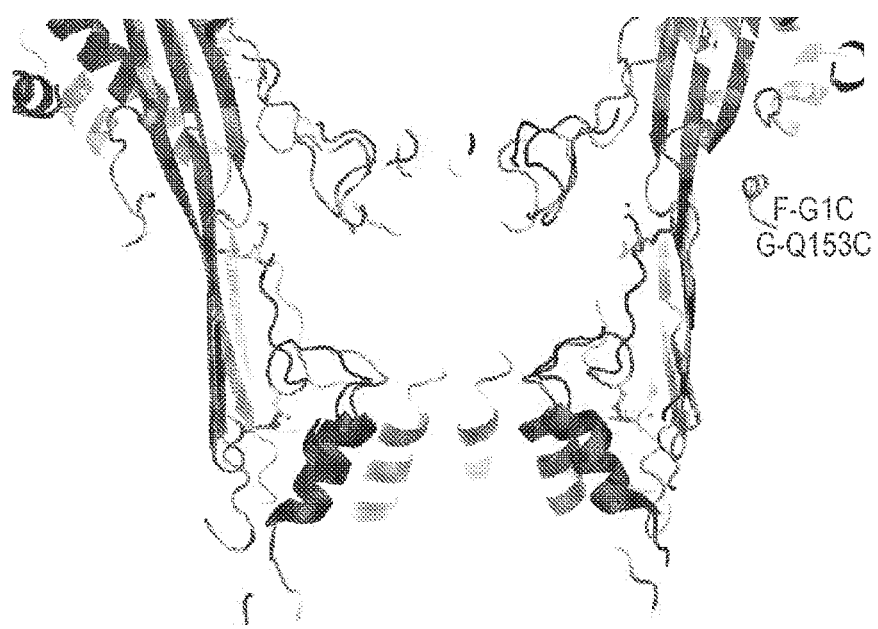

FIGS. 18A-18B Stabilising CsgG:CsgF or CsgG:FCP complexes. FIG. 18A Identified amino acid positions of CsgG (SEQ ID NO: 3 and CsgF (SEQ ID NO: 6) pairs where S—S bonds can be made. FIG. 18B Schematic representation to show the S—S bond between CsgG-Q153C and CsgF-G1C.

Figure 19A:
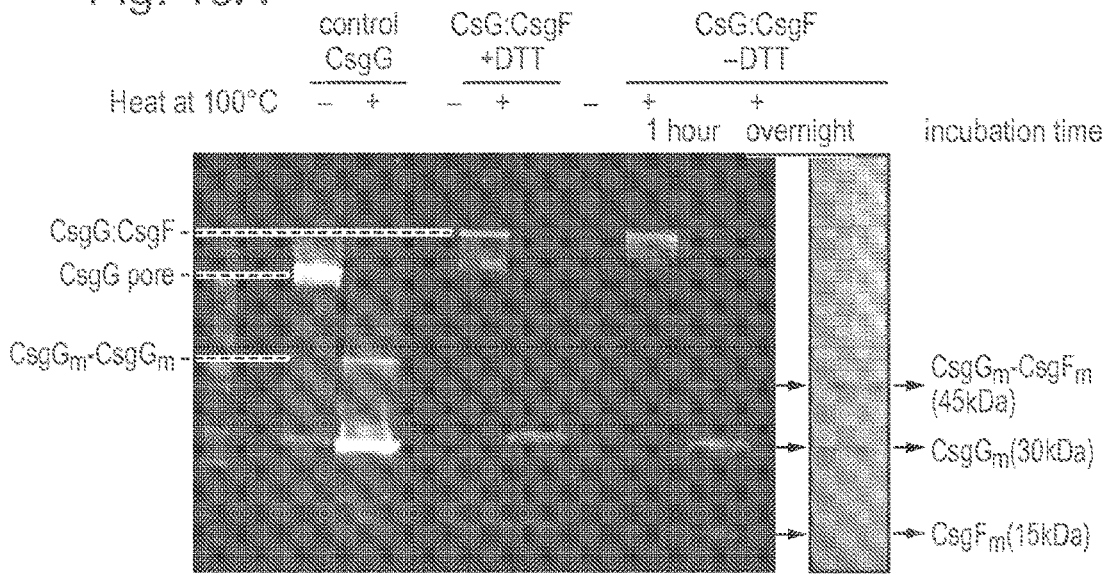
Figure 19B:
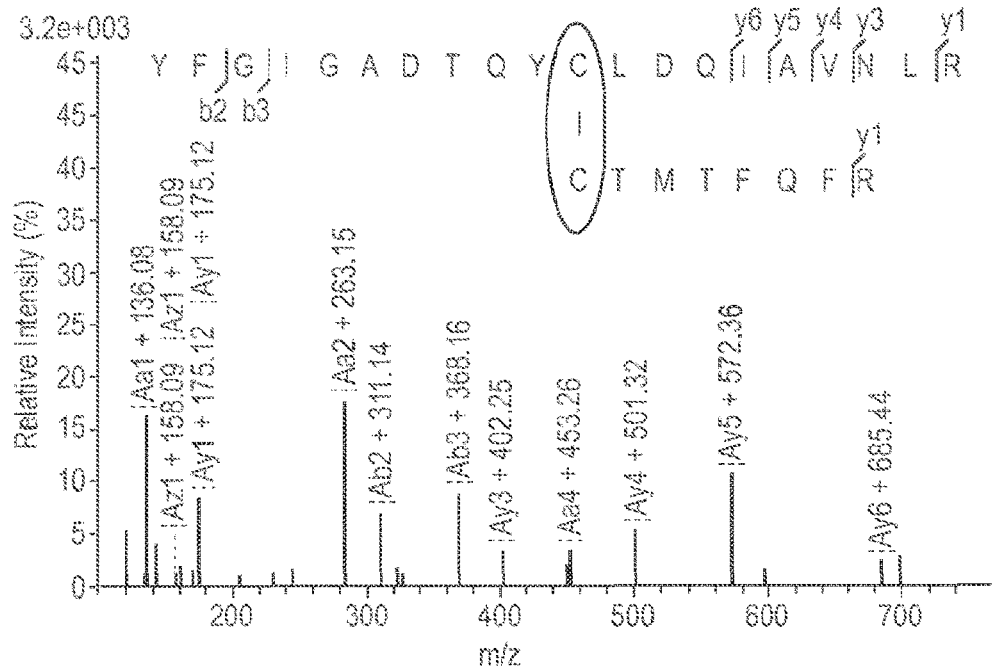

FIGS. 19A-19B Cysteine cross linking of the CsgG:CsgF complex. FIG. 19A Y51A/F56Q/N91R/K94Q/R97W/Q153C-del(V105-I107) and CsgF-G1C proteins were purified separately and incubated together at 4° C. for 1 hour or overnight to form the complex and allow S—S formation. No oxidising were promote S—S Control CsgG pore agents added to formation. (Y51A/F56Q/N91R/K94Q/R97W/Q153C-DEL(V105-I107)) and complex (with and without DTT) were heated at 100° C. for 10 minutes to breakdown the complex into CsgG monomer (CsgG$_m$, 30 KDa) and CsgF monomer (CsgF$_m$, 15 KDa). A dimer between the CsgG$_m$ and CsgF$_m$ (CsgG$_m$-CsgF$_m$, 45 KDa) can be seen in the absence of the reducing agents confirming the S—S bond formation. Increased dimer formation can be seen in overnight incubation compared to one hour incubation. FIG. 19B Mass spectrometry analysis was carried out on the gel purified CsgG$_m$-CsgF$_m$ band from overnight incubation. Protein was proteolytically cleaved to generate tryptic peptides. LC-MS/MS sequencing methods were performed, resulting in the identification of the precursor ion above, corresponding to the linked peptides shown. This precursor ion was fragmented to give the fragment ions observed. These include ions for each of the peptides, as well as fragments incorporating the intact disulphide bond. This data provides strong evidence for the presence of a disulphide bond between C1 of CsgF and C153 of CsgG. The sequence depicted in FIG. 19B corresponds to SEQ ID NO: 291).

Figure 20:
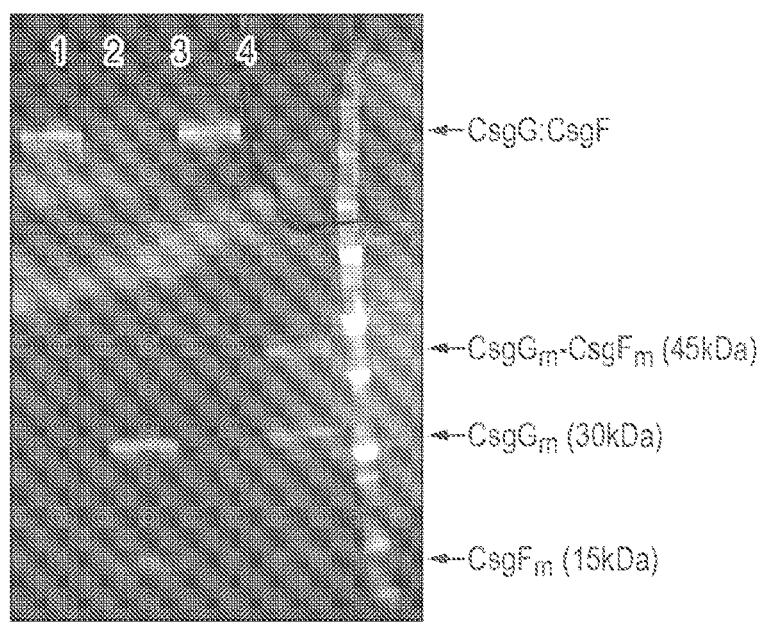

FIG. 20 Improving the efficiency of Cysteine cross linking of the CsgG:CsgF complex. Lane 1: Y51A/F56Q/N91R/K94Q/R97W/N133C-del(V105-I107) and CsgF-T4C proteins were co expressed the CsgG:CsgF complex was purified. Lane 2: The complex was heated in the presence of DTT to break down the complex into substituent monomers (CsgG$_m$ and CsgF$_m$). DTT will break down any S—S bonds between CsgG-N133C and CsgF-T4C if formed. Lane 3: The complex is incubated with the oxidising agent copper-orthophenanthroline to promote S—S bond formation. Lane 4: Oxidised sample was heated at 100° C. in the absence of DTT to break down the complex. A new band of 45 KDa corresponding to the CsgG$_m$-CsgF$_m$ appears confirming the S—S bond formation.

Figure 21A:
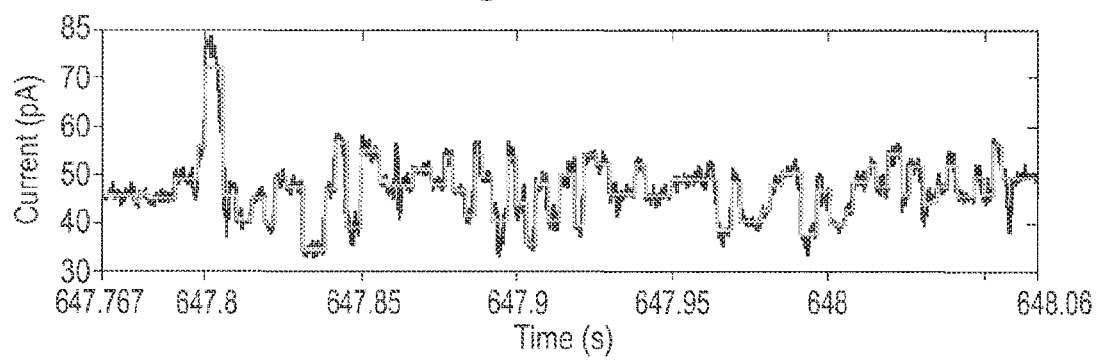
Figure 21B:
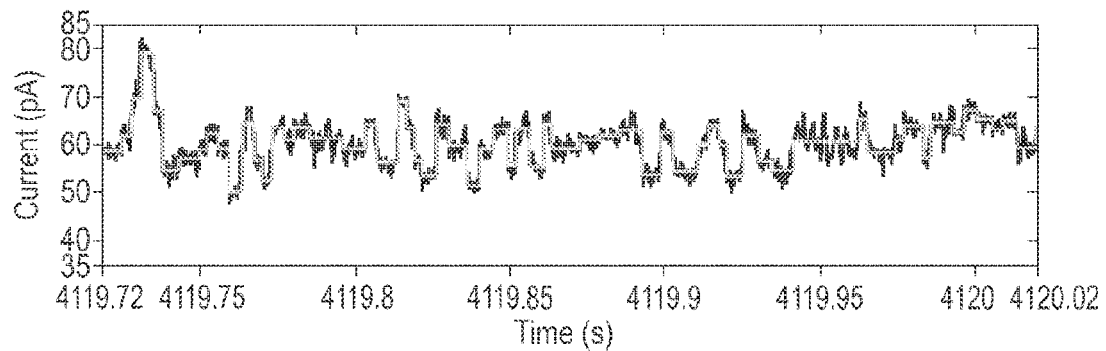

FIGS. 21A-21B Current signature when the DNA strand is passing through the CsgG:CsgF complex. The complexes were made by co-expressing the CsgG pore (Y51A/F56Q/N91R/K94Q/R97W-del(V105-I107)) containing the C terminal strep tag with the full length CsgF proteins containing C terminal His tag and TEV protease cleavage site between 35 and 36 of seq ID no. 6. Purified complexes were then cleaved by TEV protease to make the given CsgG:CsgF complexes. Note that TEV cleavage leaves ENLYFQ sequence at the cleavage site. FIG. 21A No mutations at 17 position of CsgF. FIG. 21B N17S mutation in CsgF.

Figure 22A:
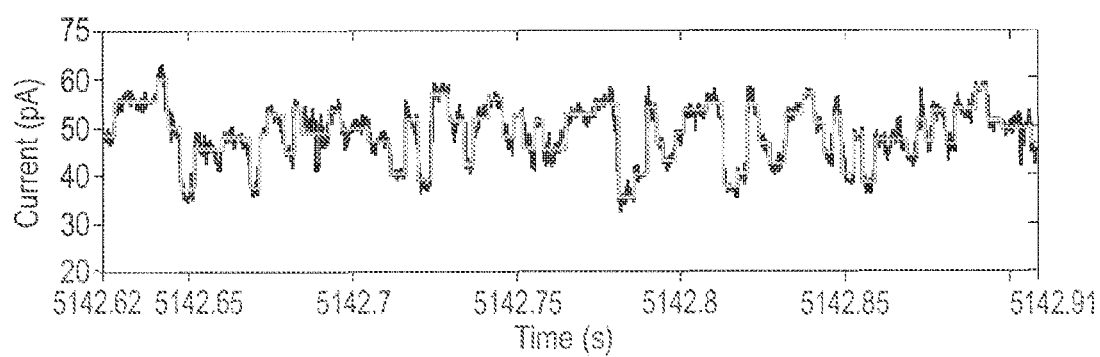
Figure 22B:
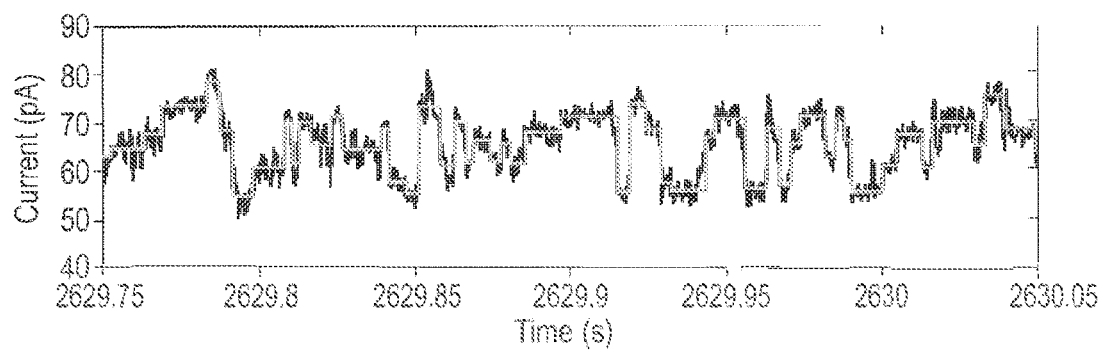

FIGS. 22A-22B Current signature when the DNA strand is passing through the CsgG:CsgF complex. The complexes were made by incubating Y51A/N55V/F56Q/N91R/K94Q/R97W-del(V105-I107) pore containing the C terminal strep tag with CsgF-(1-35) mutants. FIG. 22A CsgF-N17S-(1-35). FIG. 22B CsgF-N17V-(1-35).

FIGS. 23A-23F Current signature when the DNA strand is passing through the CsgG:CsgF complex.

Figure 23A:
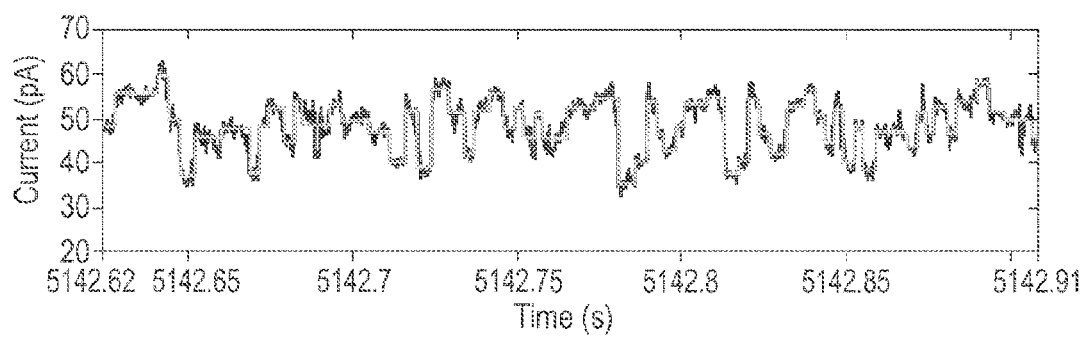
Figure 23B:
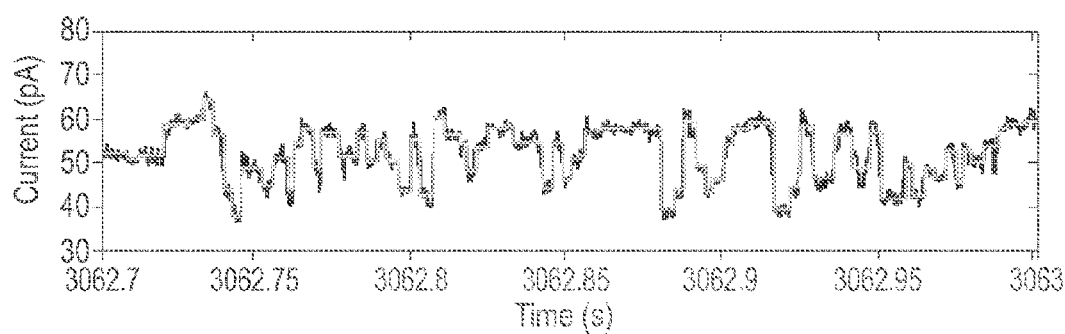
Figure 23C:
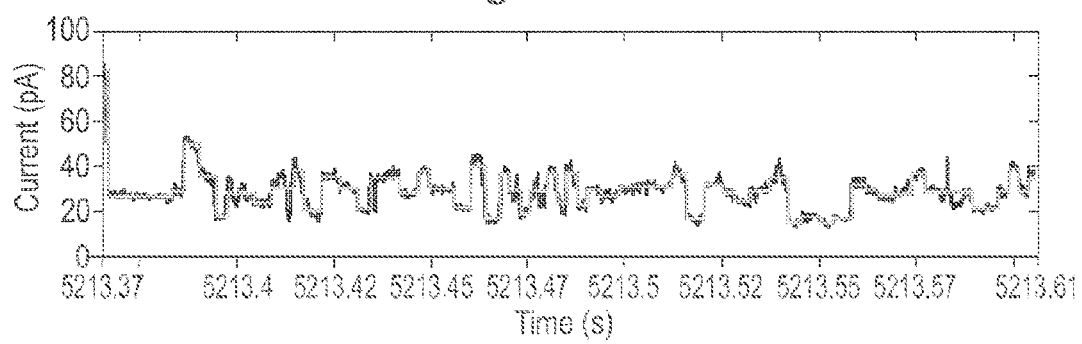
Figure 23D:
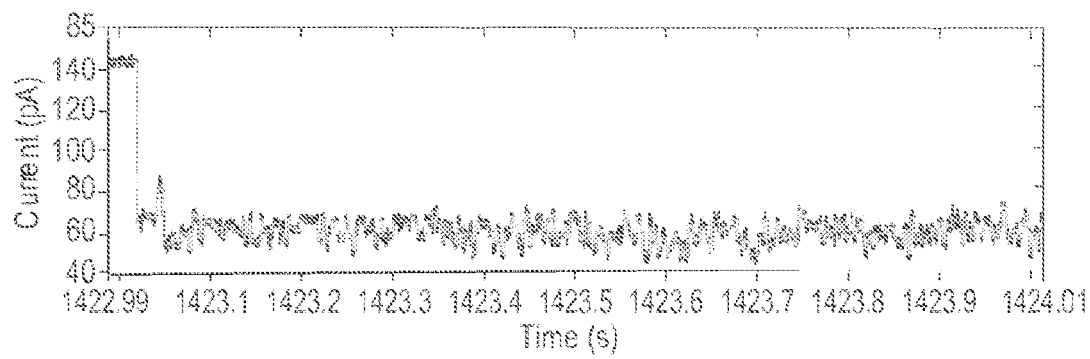
Figure 23E:
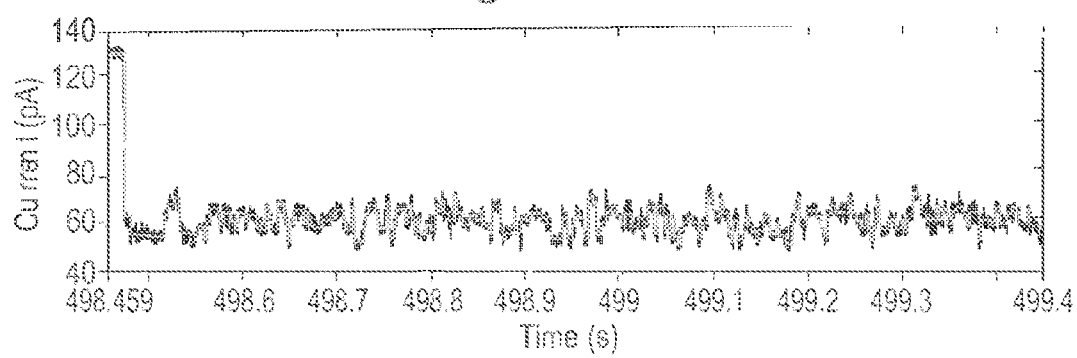
Figure 23F:
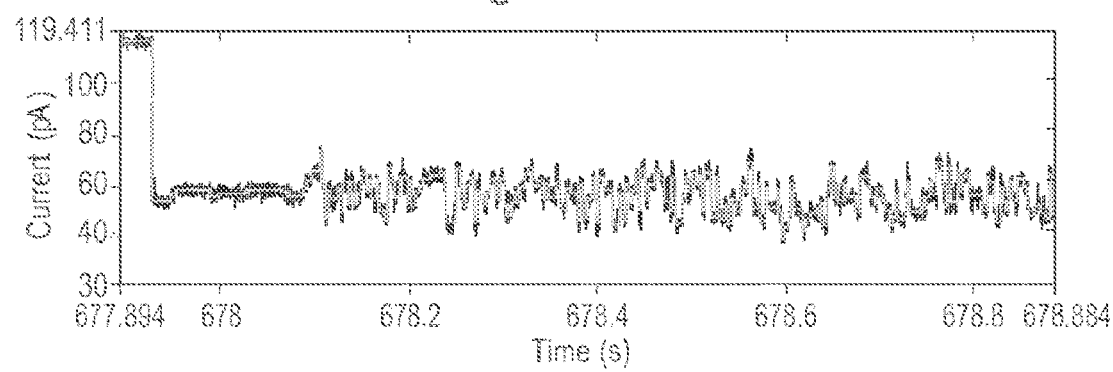

The complexes were made by incubating different CsgG pores containing the C terminal strep tag with CsgF-N17S-(1-35). FIG. 23A CsgG pore is Y51A/N55V/F56Q/N91R/K94Q/R97W-del(V105-I107). FIG. 23B CsgG pore is Y51T/N55V/F56Q/N91R/K94Q/R97W-del(V105-I107). FIG. 23C CsgG pore is Y51A/N55I/F56Q/N91R/K94Q/R97W-del(V105-I107). FIG. 23D CsgG pore is Y51A/F56A/N91R/K94Q/R97W-del(V105-I107). FIG. 23E CsgG pore is Y51A/F56I/N91R/K94Q/R97W-del(V105-I107). FIG. 23F CsgG pore is Y51S/N55V/F56Q/N91R/K94Q/R97W-del(V105-I107).

FIGS. 24A-24C Current signature when the DNA strand is passing through the CsgG:CsgF complex.

Complexes were made by incubating the E. coli purified Y51A/N55V/F56Q/N91R/K94Q/R97W-del(V105-I107) pore containing the C terminal strep with CsgF of three different lengths. FIG. 24A CsgF-(1-29), FIG. 24B CsgF-(1-35), FIG. 24C CsgF-(1-45). The arrow indicates the range of the signal. Surprisingly, complex with the CsgF-(1-29) produces the signal with the largest range.

Figure 25:
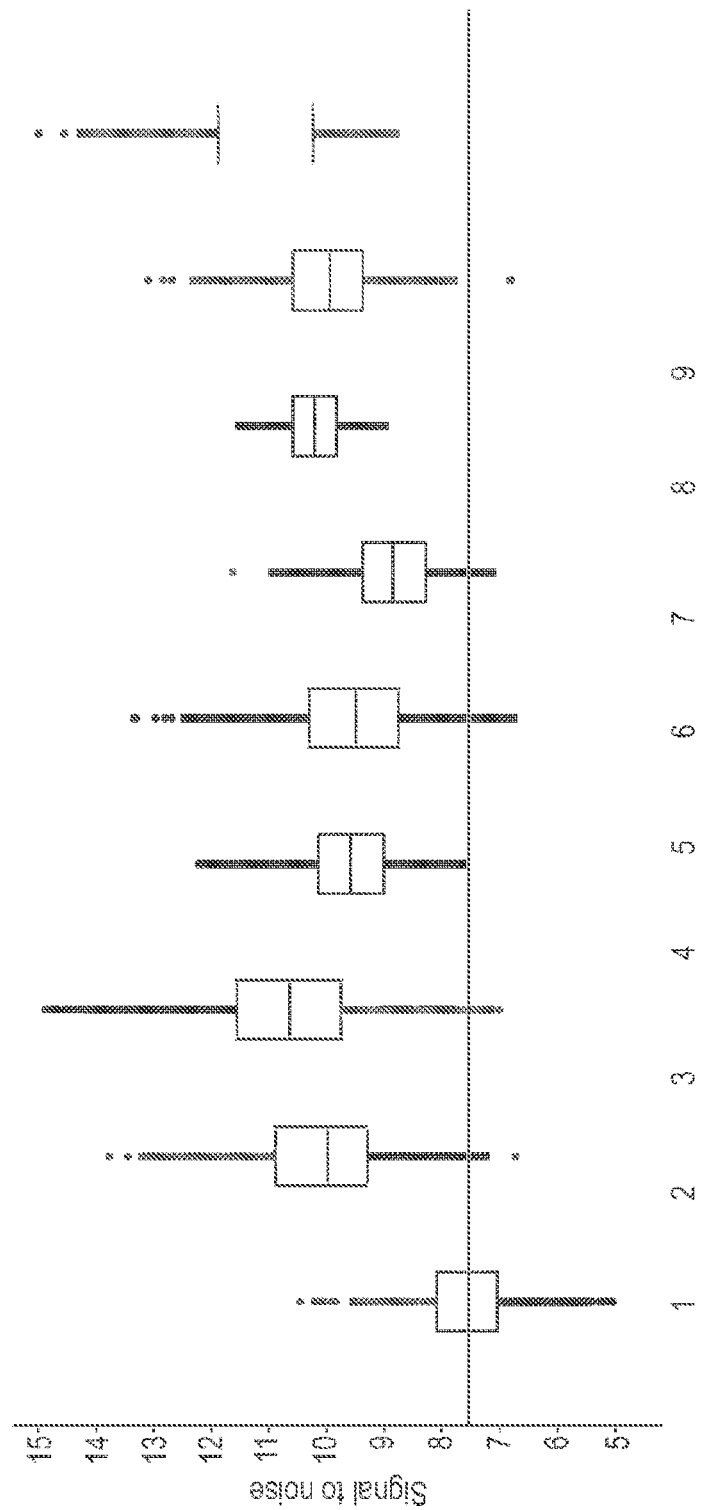

FIG. 25 Signal:noise of the current signature when the DNA strand is passing through the CsgG:CsgF complex. Different CsgG:CsgF complexes were made by incubating different CsgG pores (1-Y51A/F56Q/N91R/K94Q/R97W-del(V105-I107) 2-Y51A/N55I/F56Q/N91R/K94Q/R97W-del(V105-I107) 3-Y51A/N55V/F56Q/N91R/K94Q/R97W-del(V105-I107) 4-Y51A/F56A/N91R/K94Q/R97W-del(V105-I107) 5-Y51A/F56I/N91R/K94Q/R97W-del(V105-I107) 6-Y51A/F56V/N91R/K94Q/R97W-del(V105-I107) 7-Y51S/N55A/F56Q/N91R/K94Q/R97W-del(V105-I107) 8-Y51S/N55V/F56Q/N91R/K94Q/R97W-del(V105-I107) 9-Y51T/N55V/F56Q/N91R/K94Q/R97W-del(V105-I107)) with the same CsgF peptide CsgF-(1-35). Different squiggle patterns were observed in DNA translocation experiments and their signal:noise is measured. Higher accuracies can be obtained with larger signal:noise ratios.

Figure 26A:
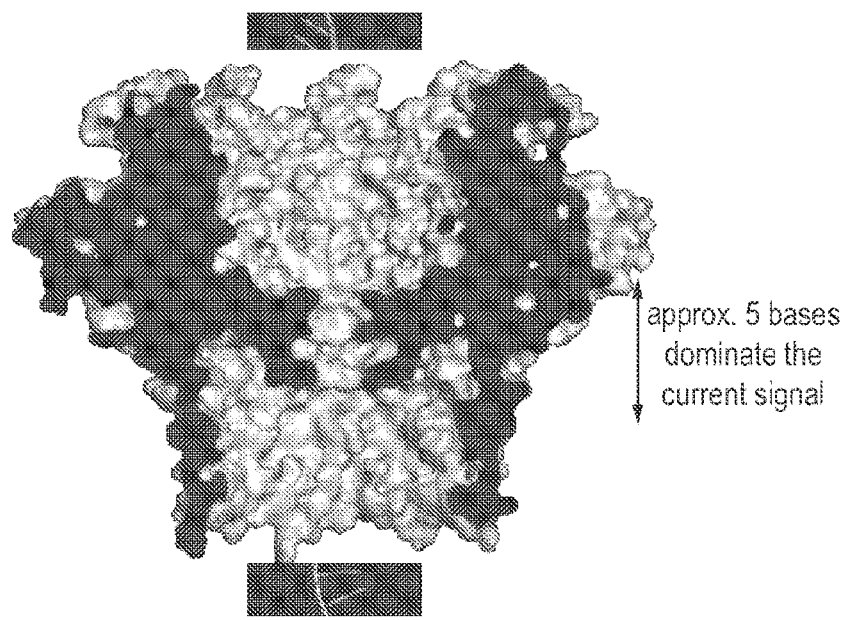
Figure 26B:
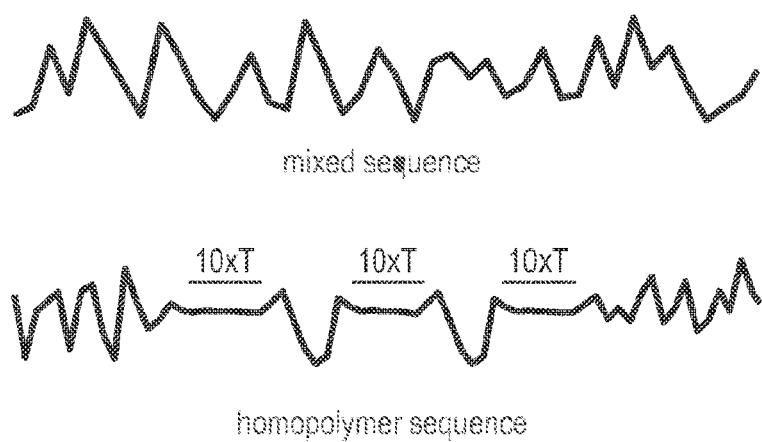

FIGS. 26A-26B Sequencing errors with narrow reader-heads. FIG. 26A Representation of DNA base interaction with the reader head of the CsgG pore. Approximately, 5 bases dominate the current signal at any given time when the DNA strand is translocating through the pore. FIG. 26B Mapping plots of the signal. Event-detected signal for multiple reads mapped to modelled signal using a custom HMM, for a mixed sequence lacking homopolymer runs, and for a sequence containing three homopolymer runs of 10 T.

Figure 27C:
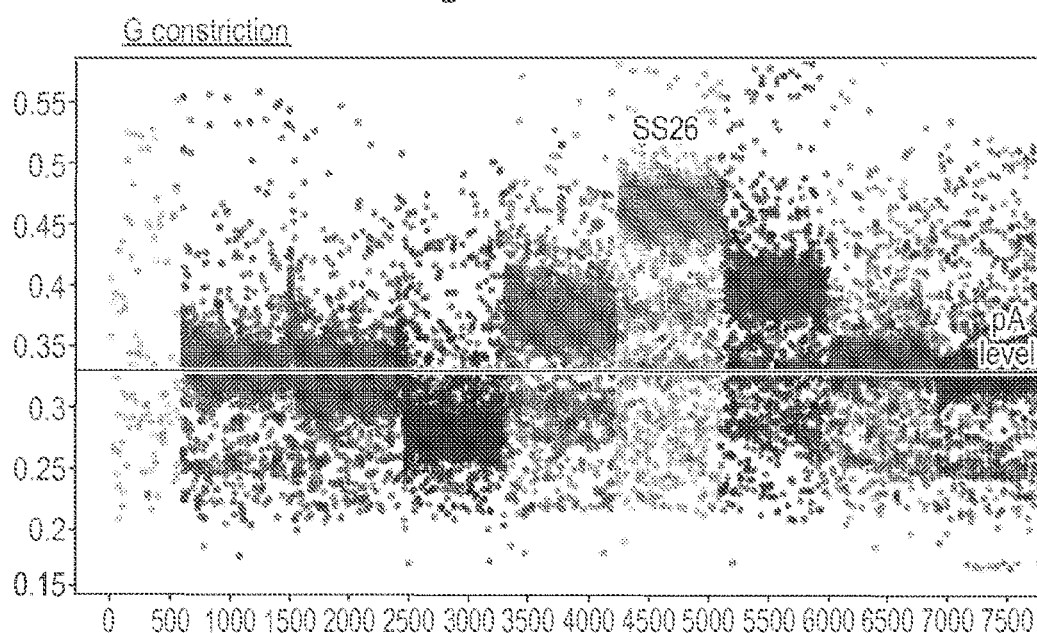
Figure 27D:
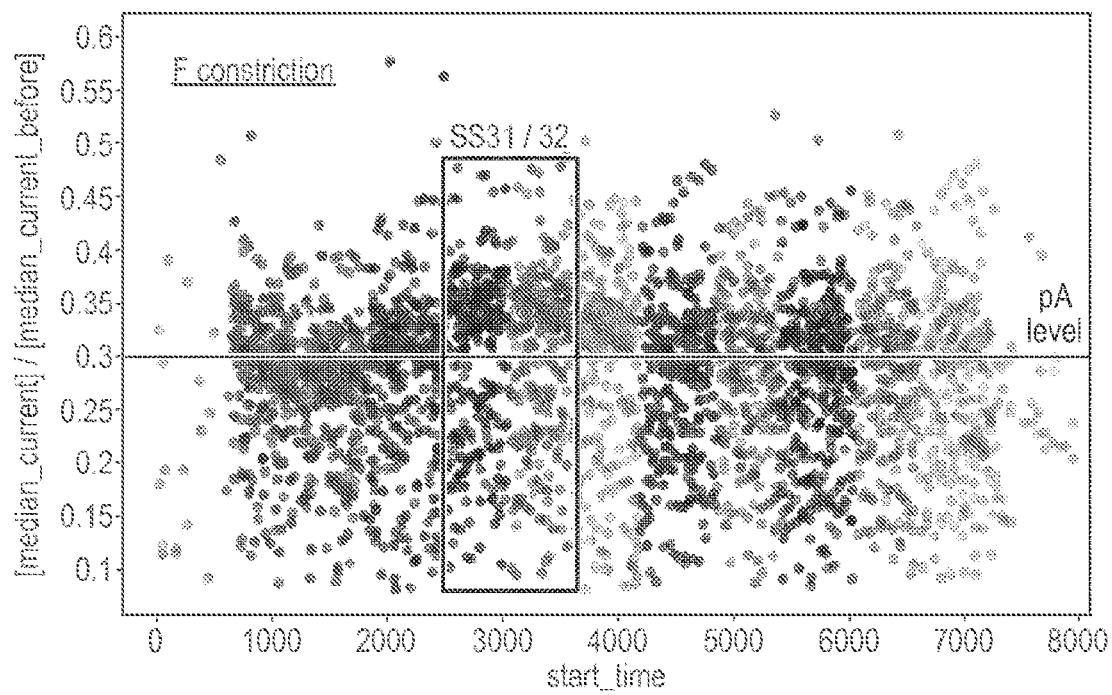

FIGS. 27A-27D Mapping the reader heads of the CsgG: CsgF complex. FIG. 27A Reader head discrimination plot for the CsgG:CsgF complex. The average variation in modelled current when the base at each read head position is varied. To calculate the read head discrimination at position i for a model of length k with alphabet of length n, we define the discrimination at read-head position i as the median of the standard deviations in current level for each of the nk-1 groups of size n where position i is varied while other positions are held constant. FIG. 27B Static DNA strands to map the reader head: A set of polyA DNA strands (SS20 to SS38) in which one base is missing from the DNA backbone (iSpc3) is created. In each strand, the position of iSpc3 moves from 3' end towards the 5' end. Based on previous experiments with the CsgG pore, 7th position of the DNA is expected to be located within the CsgG constriction. SS26 corresponds to this DNA is highlighted. Top to bottom, left to right, the sequences depicted in FIG. 27B correspond to SEQ ID NOs: 292-310. Based on the model from FIG. 27A, 4-5 bases are expected to separate CsgG and CsgF reader heads. Therefore, approximately, position 12 and 13 are expected to be within the CsgF constriction. SS31 and SS32 DNA strands corresponding to those positions are highlighted. FIGS. 27C-27D Mapping the two reader heads: Biotin modification at the 3' end of each strand is complexed with monovalent streptavidin and the current blockage generated from each strand is recorded in a MinION set up. When the iSpc3 position is present above or below the constriction within the pore, no deflection is expected. However, when the iSpc3 is located within the constriction, a higher current level is expected to pass through the pore—the extra space created by the lack of base lets more ions to pass through. Therefore, by plotting the current passing through with each DNA strand, the locations of the two reader heads can be mapped. As expected, the highest deflection in the current is seen when the position 7 of the DNA strand is occupied by iSpc3 (FIG. 27C). iSpc3 at positions 6 and 8 also produce a higher deflection over the average polyA current level. Therefore, positions 6, 7 and 8 of the DNA strand represent the first reader head—CsgG reader head. As expected, when positions 12th and 13th are occupied by iCsp3, another deviation from baseline polyA is observed (FIG. 27D). This indicates the second reader head of the pore—CsgF reader head. Results also confirm that the two reader heads are apart by approximately 4-5 bases.

Figure 28A:
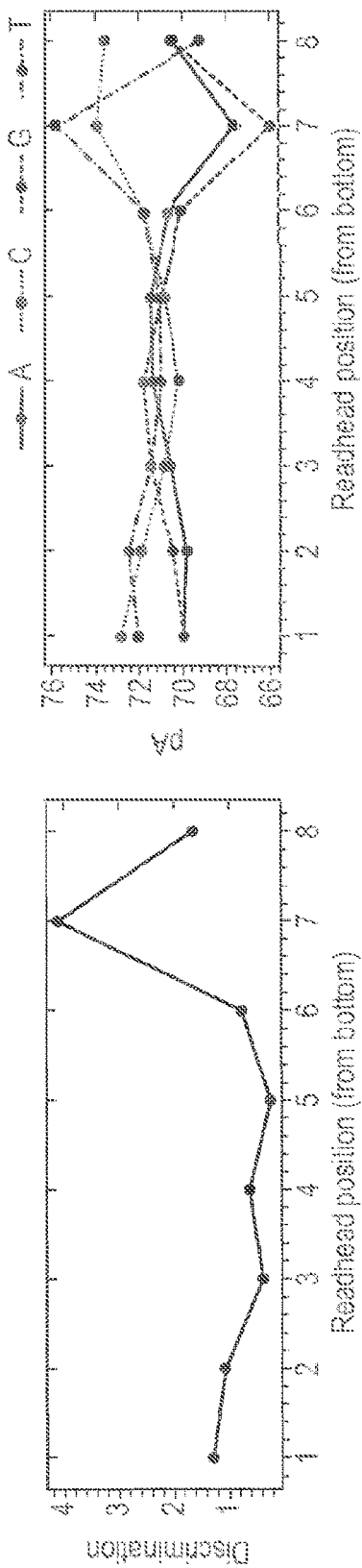
Figure 28B:
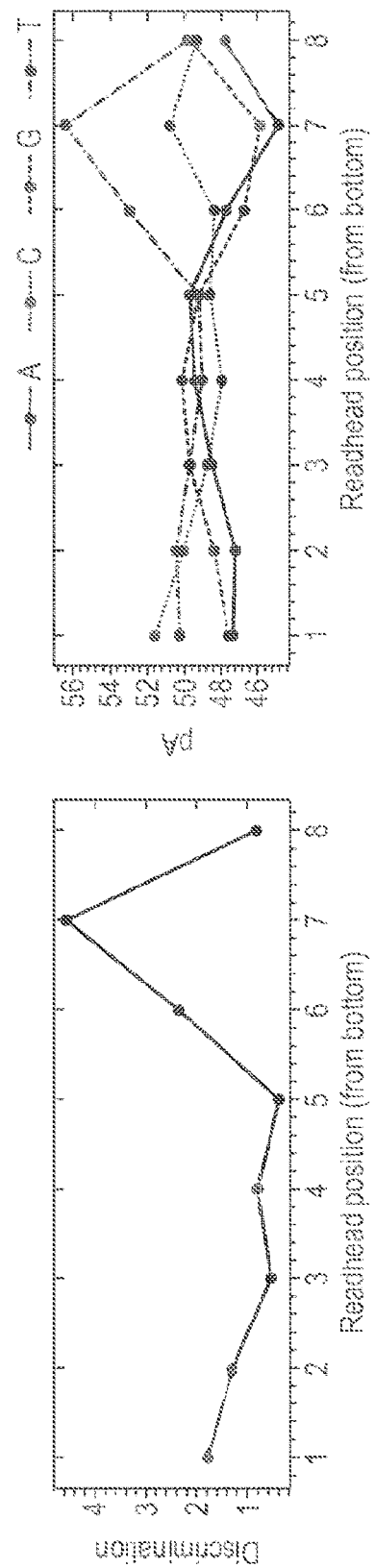

FIGS. 28A-28B Reader head discrimination and base contribution. Left hand panel demonstrates the read-head discrimination of each mutant pore: the average variation in modelled current when the base at each read head position is varied. To calculate the read head discrimination at position i for a model of length k with alphabet of length n, we define the discrimination at read-head position i as the median of the standard deviations in current level for each of the nk-1 groups of size n where position i is varied while other positions are held constant. Right hand panel demonstrates the base contribution plot: Median current over all sequence contexts with base b (A, T, G or C) at position i of the reader head.

Figure 29A:
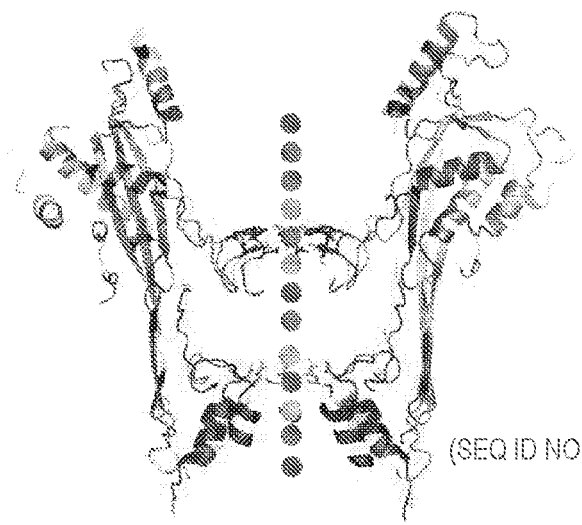
Figure 29B:
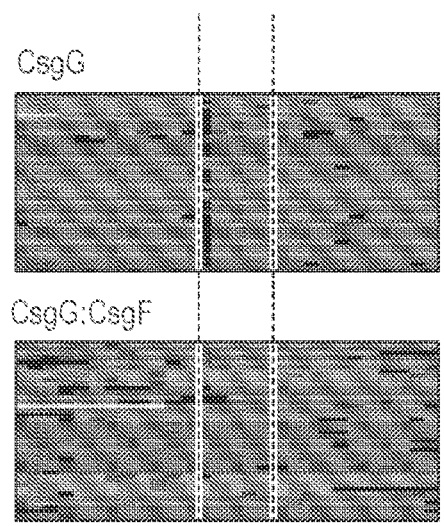
Figure 29C:
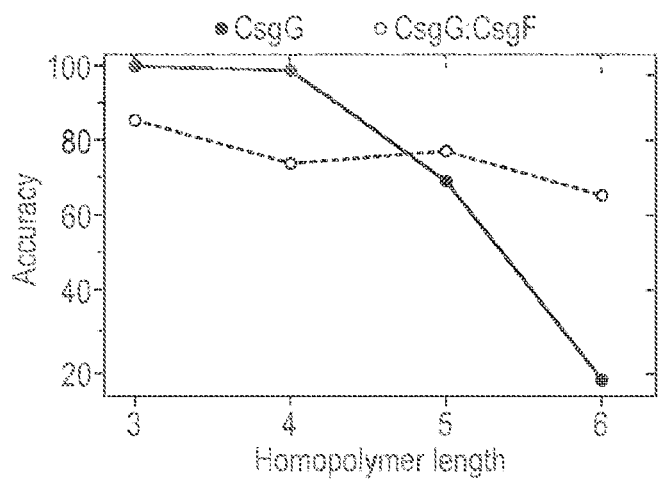

FIGS. 29A-29C Error profiles of the double reader head pore. FIG. 29A Schematic representation of the CsgG:CsgF complex and the interaction of bases of the DNA with the two reader heads. Red: strong interactions, orange: weak interactions, grey: no interactions. FIG. 29B Comparison of errors in deletions. Reads from Y51A/F56Q/N91R/K94Q/R97W/R192D-del(V105-I107) and Y51A/N55V/F56Q/N91R/K94Q/R97W-del(V105-I107): CsgF-N17S-(1-35) pores were basecalled from the same region of E. coli DNA. Reads were aligned to the reference genome using Minimap2 (arxiv.org/abs/1708.01492), and the resultant alignments were visualised in Savant Genome Browser (ncbi.nlm.nih.gov/pubmed/20562449). The majority of Y51A/F56Q/N91R/K94Q/R97W/R192D-del(V105-I107) reads contain a single base deletion (black boxes) in the T homopolymer, which is not present in the majority of CsgG:CsgF reads. The sequence depicted in FIG. 29B corresponds to SEQ ID NO: 311. FIG. 29C Comparison of the consensus accuracy from unpolished data generated from Y51A/F56Q/N91R/K94Q/R97W/R192D-del(V105-I107) (blue) and Y51A/N55V/F56Q/N91R/K94Q/R97W-del(V105-I107):CsgF-N17S-(1-35) pores (green) against the length of homopolymers.

Figure 30C:
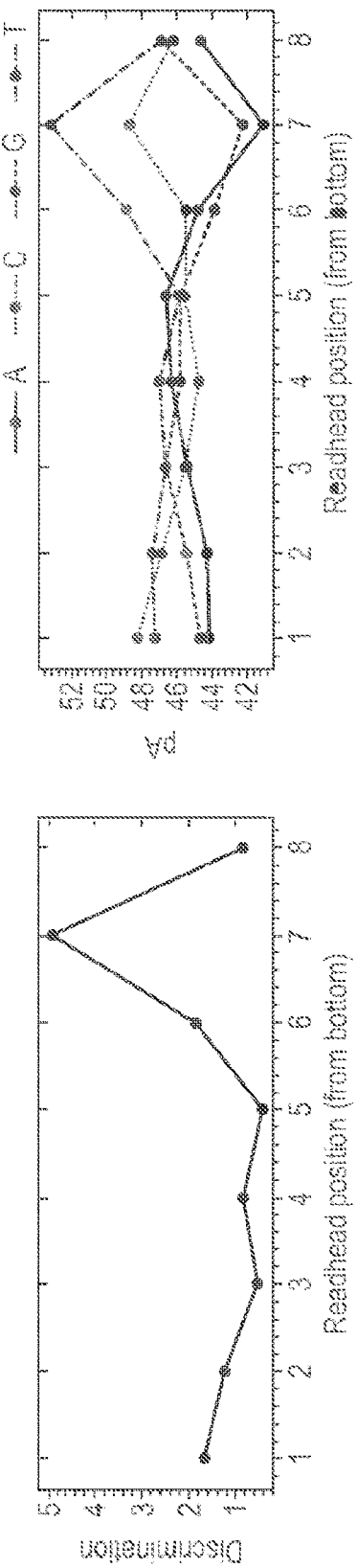
Figure 30D:
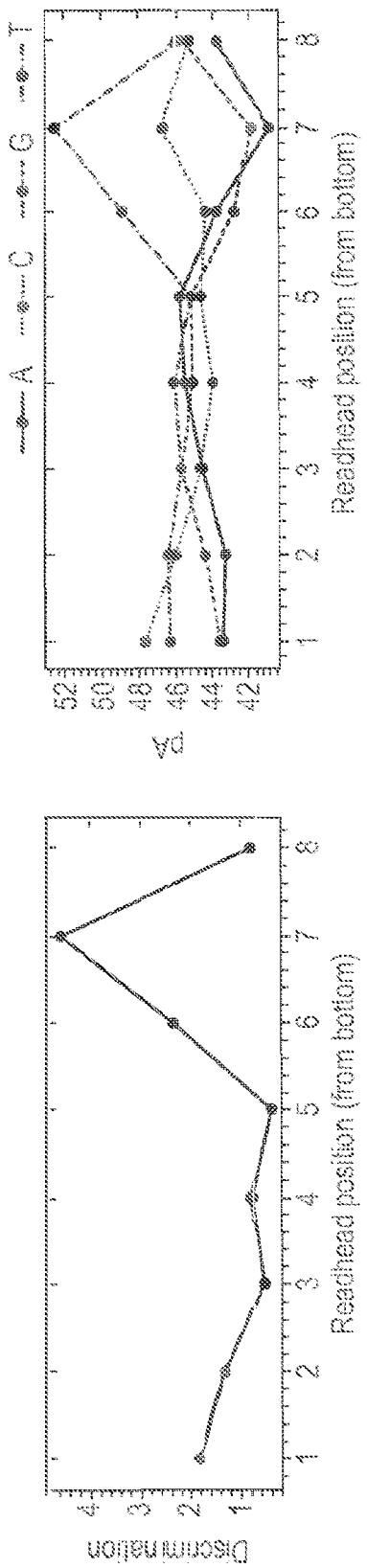
Figure 30E:
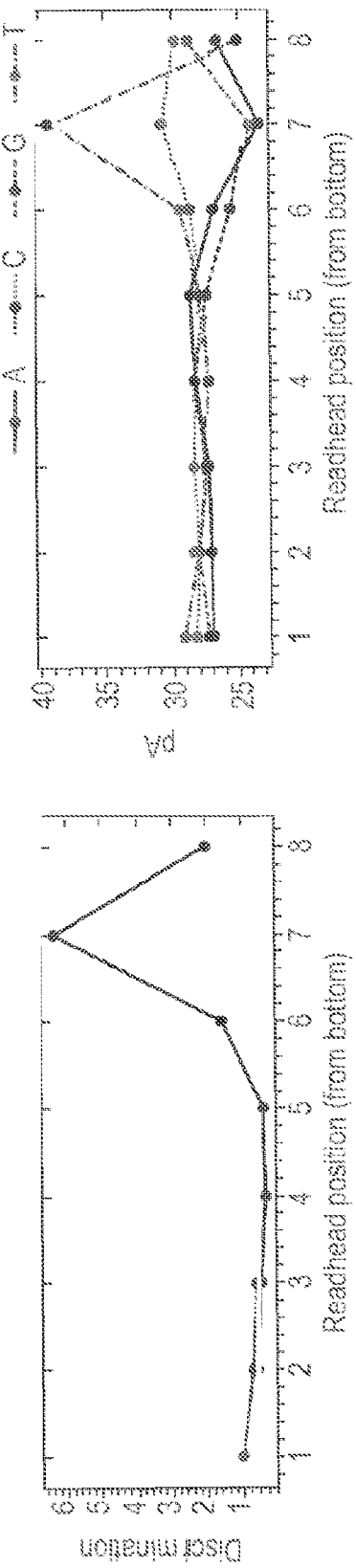
Figure 30F:
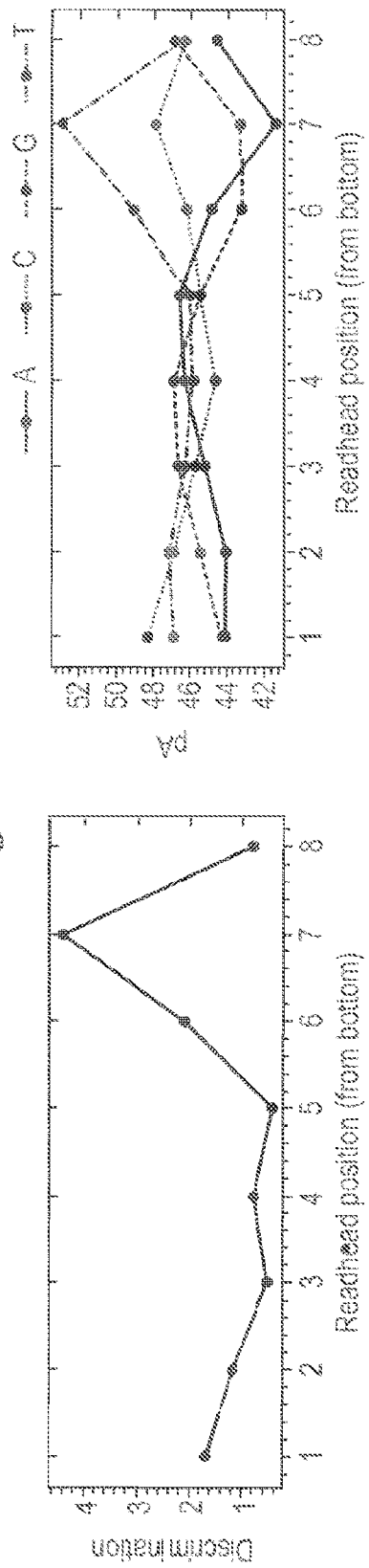

FIGS. 30A-30H Homopolymer calling of CsgG:CsgF complex. FIG. 30A DNA with the sequence shown in (A) is translocated through the Y51A/F56Q/N91R/K94Q/R97W/R192D-del(V105-I107) pore (B) and the Y51A/N55V/F56Q/N91R/K94Q/R97W-del(V105-I107):CsgF-N17S-(1-35) pore (C) and their signal was analysed for the first polyT section shown in red in (A). FIGS. 30B-30H When the polyT section is passing through the CsgG pore which contains a single reader head (model is based on 5 bases located in the reader head), it generates a flat line in the signal. Therefore, it is difficult to determine the exact number of bases in this region which usually causes deletion errors. When the DNA is passing through the CsgG:CsgF complex which contains two reader heads (model is based on 9 bases located within and in between the two reader heads), polyT section shows multiple steps instead of a flat line. Information in these steps can be used to correctly identify the number of bases in the homopolymeric region. This additional information significantly reduce deletion errors and improves overall consensus accuracy. The sequence depicted in FIG. 30B corresponds to SEQ ID NO: 312.

Figure 31A:
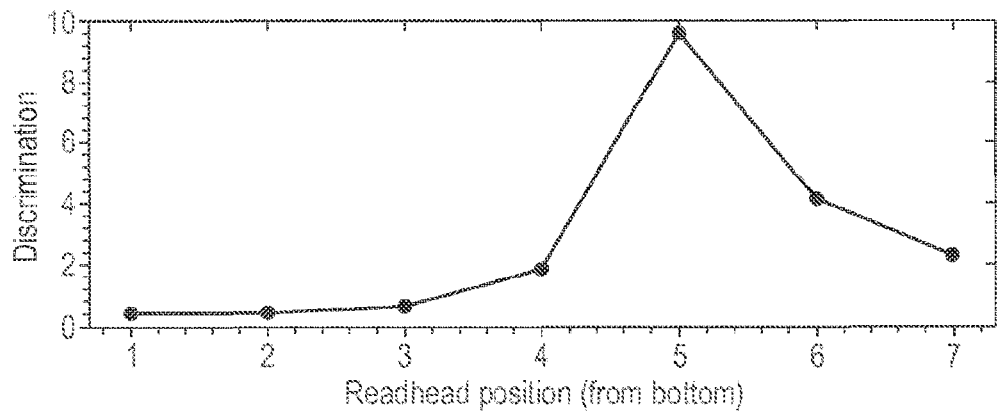
Figure 31B:
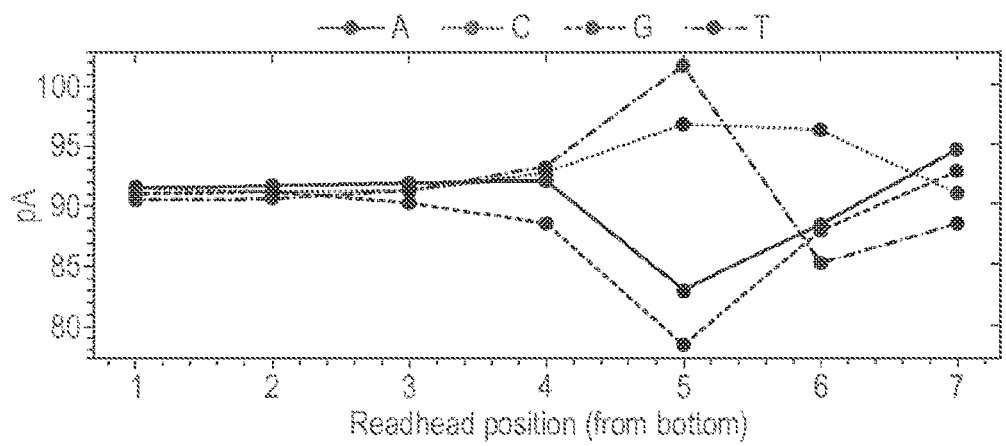
Figure 31C:
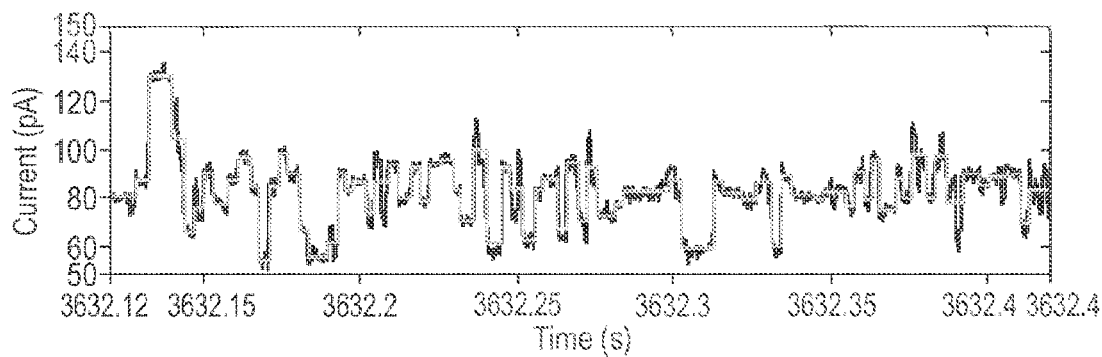

FIGS. 31A-31C Characterisation of the CsgG pore (Y51A/F56Q/N91R/K94Q/R97W/-del(V105-I107). FIG. 31A Reader head discrimination of the CsgG pore. The average variation in modelled current when the base at each read head position is varied. To calculate the read head discrimination at position i for a model of length k with alphabet of length n, we define the discrimination at readhead position i as the median of the standard deviations in current level for each of the $n^{k-1}$ groups of size n where position i is varied while other positions are held constant. FIG. 31B Base contribution plot of the CsgG pore. Median current over all kmers with base b (A, T, G or C) at position / of the reader head. FIG. 31C Current signature when the DNA strand is passing through the CsgG pore.

DETAILED DESCRIPTION

The present invention will be described with respect to particular embodiments and with reference to certain drawings but the invention is not limited thereto but only by the claims. Any reference signs in the claims shall not be construed as limiting the scope. Of course, it is to be understood that not necessarily all aspects or advantages may be achieved in accordance with any particular embodiment of the invention. Thus, for example those skilled in the art will recognize that the invention may be embodied or carried out in a manner that achieves or optimizes one advantage or group of advantages as taught herein without necessarily achieving other aspects or advantages as may be taught or suggested herein.

The invention, both as to organization and method of operation, together with features and advantages thereof, may best be understood by reference to the following detailed description when read in conjunction with the accompanying drawings. The aspects and advantages of the invention will be apparent from and elucidated with reference to the embodiment(s) described hereinafter. Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment.

In addition as used in this specification and the appended claims, the singular forms "a", "an", and "the" include plural referents unless the content clearly dictates otherwise. Thus, for example, reference to "a polynucleotide" includes two or more polynucleotides, reference to "a polynucleotide binding protein" includes two or more such proteins, reference to "a helicase" includes two or more helicases, reference to "a monomer" refers to two or more monomers, reference to "a pore" includes two or more pores and the like.

In all of the discussion herein, the standard one letter codes for amino acids are used. These are as follows: alanine (A), arginine (R), asparagine (N), aspartic acid (D), cysteine (C), glutamic acid (E), glutamine (Q), glycine (G), histidine (H), isoleucine (I), leucine (L), lysine (K), methionine (M), phenylalanine (F), proline (P), serine (S), threonine (T), tryptophan (W), tyrosine (Y) and valine (V). Standard substitution notation is also used, i.e. Q42R means that Q at position 42 is replaced with R.

In the paragraphs herein where different amino acids at a specific position are separated by the / symbol, the/symbol means "or". For instance, Q87R/K means Q87R or Q87K.

In the paragraphs herein where different positions are separated by the/symbol, the/symbol means "and" such that Y51/N55 is Y51 and N55.

All amino-acid substitutions, deletions and/or additions disclosed herein are with reference to a mutant CsgG monomer comprising a variant of the sequence shown in SEQ ID NO: 3, unless stated to the contrary.

Reference to a mutant CsgG monomer comprising a variant of the sequence shown in SEQ ID NO: 3 encompasses mutant CsgG monomers comprising variants of sequences as set out in the further SEQ ID NOS as disclosed below. Amino-acid substitutions, deletions and/or additions may be made to CsgG monomers comprising a variant of the sequence other than shown in SEQ ID NO: 3 that are equivalent to those substitutions, deletions and/or additions disclosed herein with reference to a mutant CsgG monomer comprising a variant of the sequence shown in SEQ ID NO: 3.

All publications, patents and patent applications cited herein, whether supra or infra, are hereby incorporated by reference in their entirety.

Definitions

Where an indefinite or definite article is used when referring to a singular noun e.g. "a" or "an", "the", this includes a plural of that noun unless something else is specifically stated. Where the term "comprising" is used in the present description and claims, it does not exclude other elements or steps. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 4th ed., Cold Spring Harbor Press, Plainsview, New York (2012); and Ausubel et al., Current Protocols in Molecular Biology (Supplement 114), John Wiley & Sons, New York (2016), for definitions and terms of the art. The definitions provided herein should not be construed to have a scope less than understood by a person of ordinary skill in the art.

"About" as used herein when referring to a measurable value such as an amount, a temporal duration, and the like, is meant to encompass variations of +20% or +10%, more preferably +5%, even more preferably +1%, and still more preferably +0.1% from the specified value, as such variations are appropriate to perform the disclosed methods.

"Nucleotide sequence", "DNA sequence" or "nucleic acid molecule(s)" as used herein refers to a polymeric form of nucleotides of any length, either ribonucleotides or deoxyribonucleotides. This term refers only to the primary structure of the molecule. Thus, this term includes double- and single-stranded DNA, and RNA. The term "nucleic acid" as used herein, is a single or double stranded covalently-linked sequence of nucleotides in which the 3' and 5' ends on each nucleotide are joined by phosphodiester bonds. The polynucleotide may be made up of deoxyribonucleotide bases or ribonucleotide bases. Nucleic acids may be manufactured synthetically in vitro or isolated from natural sources. Nucleic acids may further include modified DNA or RNA, for example DNA or RNA that has been methylated, or RNA that has been subject to post-translational modification, for example 5'-capping with 7-methylguanosine, 3'-processing such as cleavage and polyadenylation, and splicing. Nucleic acids may also include synthetic nucleic acids (XNA), such as hexitol nucleic acid (HNA), cyclohexene nucleic acid (CeNA), threose nucleic acid (TNA), glycerol nucleic acid (GNA), locked nucleic acid (LNA) and peptide nucleic acid (PNA). Sizes of nucleic acids, also referred to herein as "polynucleotides" are typically expressed as the number of base pairs (bp) for double stranded polynucleotides, or in the case of single stranded polynucleotides as the number of nucleotides (nt). One thousand bp or nt equal a kilobase (kb). Polynucleotides of less than around 40 nucleotides in length are typically called "oligonucleotides" and may comprise primers for use in manipulation of DNA such as via polymerase chain reaction (PCR).

"Gene" as used here includes both the promoter region of the gene as well as the coding sequence. It refers both to the genomic sequence (including possible introns) as well as to the cDNA derived from the spliced messenger, operably linked to a promoter sequence.

"Coding sequence" is a nucleotide sequence, which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances.

The term "amino acid" in the context of the present disclosure is used in its broadest sense and is meant to include organic compounds containing amine ($NH_2$) and carboxyl (COOH) functional groups, along with a side chain (e.g., a R group) specific to each amino acid. In some embodiments, the amino acids refer to naturally occurring L α-amino acids or residues. The commonly used one and three letter abbreviations for naturally occurring amino acids are used herein: A=Ala; C=Cys; D=Asp; E=Glu; F=Phe; G=Gly; H=His; I=Ile; K=Lys; L=Leu; M=Met; N=Asn; P=Pro; Q=Gln; R=Arg; S=Ser; T=Thr; V=Val; W=Trp; and Y=Tyr (Lehninger, A. L., (1975) Biochemistry, 2d ed., pp. 71-92, Worth Publishers, New York). The general term "amino acid" further includes D-amino acids, retro-inverso amino acids as well as chemically modified amino acids such as amino acid analogues, naturally occurring amino acids that are not usually incorporated into proteins such as norleucine, and chemically synthesised compounds having properties known in the art to be characteristic of an amino acid, such as β-amino acids. For example, analogues or mimetics of phenylalanine or proline, which allow the same conformational restriction of the peptide compounds as do natural Phe or Pro, are included within the definition of amino acid. Such analogues and mimetics are referred to herein as "functional equivalents" of the respective amino acid. Other examples of amino acids are listed by Roberts and Vellaccio, The Peptides: Analysis, Synthesis, Biology, Gross and Meiehofer, eds., Vol. 5 p. 341, Academic Press, Inc., N.Y. 1983, which is incorporated herein by reference.

The terms "protein", "polypeptide", and "peptide" are interchangeably used further herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers. Polypeptides can also undergo maturation or post-translational modification processes that may include, but are not limited to: glycosylation, proteolytic cleavage, lipidization, signal peptide cleavage, propeptide cleavage, phosphorylation, and such like. By "recombinant polypeptide" is meant a polypeptide made using recombinant techniques, e.g., through the expression of a recombinant or synthetic polynucleotide. When the chimeric polypeptide or biologically active portion thereof is recombinantly produced, it is also preferably substantially free of culture medium, e.g., culture medium represents less than about 20%, more preferably less than about 10%, and most preferably less than about 5% of the volume of the protein preparation. By "isolated" is meant material that is substantially or essentially free from components that normally accompany it in its native state. For example, an "isolated polypeptide", as used herein, refers to a polypeptide, which has been purified from the molecules which flank it in a naturally-occurring state, e.g., a protein complex or CsgF peptide which has been removed from the molecules present in the production host that are adjacent to said polypeptide. An isolated CsgF peptide (optionally a truncated CsgF peptide) can be generated by amino acid chemical synthesis or can be generated by recombinant production. An isolated complex can be generated by in vitro reconstitution after purification of the components of the complex, e.g. a CsgG pore and the CsgF peptide(s), or can be generated by recombinant co-expression.

"Orthologues" and "paralogues" encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

"Homologue", "Homologues" of a protein encompass peptides, oligopeptides, polypeptides, proteins and enzymes having amino acid substitutions, deletions and/or insertions relative to the unmodified or wild-type protein in question and having similar biological and functional activity as the unmodified protein from which they are derived. The term "amino acid identity" as used herein refers to the extent that sequences are identical on an amino acid-by-amino acid basis over a window of comparison. Thus, a "percentage of sequence identity" is calculated by comparing two optimally aligned sequences over the window of comparison, determining the number of positions at which the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

The term "CsgG pore" defines a pore comprising multiple CsgG monomers. Each CsgG momomer may be a wild-type monomer from E. coli (SEQ ID NO: 3), wild-type homologues of E. coli CsgG, such as for example, monomers having any one of the amino acid sequences shown in SEQ ID NOS: 68 to 88. or a variant of any thereof (e.g. a variant of any one of SEQ ID NOs: 3 and 68 to 88). The variant CsgG momomer may also be referred to as a modified CsgG monomer or a mutant CsgG monomer. The modifications, or mutations, in the variant include but are not limited to any one or more of the modifications disclosed herein, or combinations of said modifications.

For all aspects and embodiments of the present invention, a CsgG homologue is referred to as a polypeptide that has at least 50%, 60%, 70%, 80%, 90%, 95% or 99% complete sequence identity to wild-type E. coli CsgG as shown in SEQ ID NO: 3. A CsgG homologue is also referred to as a polypeptide that contains the PFAM domain PF03783, which is characteristic for CsgG-like proteins. A list of presently known CsgG homologues and CsgG architectures can be found at pfam.xfam.org//family/PF03783. Likewise, a CsgG homologous polynucleotide can comprise a polynucleotide that has at least 50%, 60%, 70%, 80%, 90%, 95% or 99% complete sequence identity to wild-type E. coli CsgG as shown in SEQ ID NO: 1. Examples of homologues of CsgG shown in SEQ ID NO:3 have the sequences shown in SEQ ID NOS: 68 to 88.

The term "modified CsgF peptide" or "CsgF peptide" defines CsgF peptide that has been truncated from its C-terminal end (e.g. is an N-terminal fragment) and/or is modified to include a cleavage site. The CsgF peptide may be a fragment of wild-type E. coli CsgF (SEQ ID NO: 5 or SEQ ID NO: 6), or of a wild-type homologue of E. coli CsgF, such as for example, a peptide comprising any one of the amino acid sequences shown in SEQ ID NOS: 17 to 36. or a variant (e.g. one modified to include a cleavage site) of any thereof.

For all aspects and embodiments of the present invention, a CsgF homologue is referred to as a polypeptide that has at least 50%, 60%, 70%, 80%, 90%, 95% or 99% complete sequence identity to wild-type E. coli CsgF as shown in SEQ ID NO: 6. In some embodiments, a CsgF homologue is also referred to as a polypeptide that contains the PFAM domain PF10614, which is characteristic for CsgF-like proteins. A list of presently known CsgF homologues and CsgF architectures can be found at pfam.xfam.org//family/PF10614. Likewise, a CsgF homologous polynucleotide can comprise a polynucleotide that has at least 50%, 60%, 70%, 80%, 90%, 95% or 99% complete sequence identity to wild-type E. coli CsgF as shown in SEQ ID NO: 4. Examples of truncated regions of homologues of CsgF shown in SEQ ID NO:6 have the sequences shown in SEQ ID NOs:17 to 36.

The term "N-terminal portion of a CsgF mature peptide" refers to a peptide having an amino acid sequence that corresponds to the first 60, 50, or 40 amino acid residues starting from the N-terminus of a CsgF mature peptide (without a signal sequence). The CsgF mature peptide can be a wild-type or mutant (e.g., with one or more mutations).

Sequence identity can also be to a fragment or portion of the full length polynucleotide or polypeptide. Hence, a sequence may have only 50% overall sequence identity with a full length reference sequence, but a sequence of a particular region, domain or subunit could share 80%, 90%, or as much as 99% sequence identity with the reference sequence. Homology to the nucleic acid sequence of SEQ ID NO: 1 for CsgG homologues or SEQ ID NO:4 for CsgF homologues, respectively, is not limited simply to sequence identity. Many nucleic acid sequences can demonstrate biologically significant homology to each other despite having apparently low sequence identity. Homologous nucleic acid sequences are considered to be those that will hybridise to each other under conditions of low stringency (M. R. Green, J. Sambrook, 2012, Molecular Cloning: A Laboratory Manual, Fourth Edition, Books 1-3, Cold Spring Harbor Laboratory Press, Cold Spring Harbor, NY).

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified", "mutant" or "variant" refers to a gene or gene product that displays modifications in sequence (e.g., substitutions, truncations, or insertions), post-translational modifications and/or functional properties (e.g., altered characteristics) when compared to the wild-type gene or gene product. It is noted that naturally occurring mutants can be isolated; these are identified by the fact that they have altered characteristics when compared to the wild-type gene or gene product. Methods for introducing or substituting naturally-occurring amino acids are well known in the art. For instance, methionine (M) may be substituted with arginine (R) by replacing the codon for methionine (ATG) with a codon for arginine (CGT) at the relevant position in a polynucleotide encoding the mutant monomer. Methods for introducing or substituting non-naturally-occurring amino acids are also well known in the art. For instance, non-naturally-occurring amino acids may be introduced by including synthetic aminoacyl-tRNAs in the IVTT system used to express the mutant monomer. Alternatively, they may be introduced by expressing the mutant monomer in E. coli that are auxotrophic for specific amino acids in the presence of synthetic (i.e. non-naturally-occurring) analogues of those specific amino acids. They may also be produced by naked ligation if the mutant monomer is produced using partial peptide synthesis. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 1 below. Where amino acids have similar polarity, this can also be determined by reference to the hydropathy scale for amino acid side chains in Table 2.

TABLE 1

| Chemical properties of amino acids | | | |
| --- | --- | --- | --- |
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |

TABLE 1-continued

Chemical properties of amino acids

| | | | |
|---|---|---|---|
| Leu | aliphatic, hydrophobic, neutral | Tyr | aromatic, polar, hydrophobic |

TABLE 2

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

A mutant or modified protein, monomer or peptide can also be chemically modified in any way and at any site. A mutant or modified monomer or peptide is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The mutant of modified protein, monomer or peptide may be chemically modified by the attachment of any molecule. For instance, the mutant of modified protein, monomer or peptide may be chemically modified by attachment of a dye or a fluorophore. In some embodiments, the mutant or modified monomer or peptide is chemically modified with a molecular adaptor that facilitates the interaction between a pore comprising the monomer or peptide and a target nucleotide or target polynucleotide sequence. The molecular adaptor is preferably a cyclic molecule, a cyclodextrin, a species that is capable of hybridization, a DNA binder or interchelator, a peptide or peptide analogue, a synthetic polymer, an aromatic planar molecule, a small positively-charged molecule or a small molecule capable of hydrogen-bonding.

The presence of the adaptor improves the host-guest chemistry of the pore and the nucleotide or polynucleotide sequence and thereby improves the sequencing ability of pores formed from the mutant monomer. The principles of host-guest chemistry are well-known in the art. The adaptor has an effect on the physical or chemical properties of the pore that improves its interaction with the nucleotide or polynucleotide sequence. The adaptor may alter the charge of the barrel or channel of the pore or specifically interact with or bind to the nucleotide or polynucleotide sequence thereby facilitating its interaction with the pore. Hence a modified CsgF peptide, as provided in the disclosure, may be coupled to enzymes or proteins providing better proximity of said proteins or enzymes to the pore, which may facilitate certain applications of the pore complex comprising the modified CsgF peptide.

In this context, proteins can also be fusion proteins, referring in particular to genetic fusion, made e.g., by recombinant DNA technology. Proteins can also be conjugated, or "conjugated to", as used herein, which refers, in particular, to chemical and/or enzymatic conjugation resulting in a stable covalent link.

Proteins may form a protein complex when several polypeptides or protein monomers bind to or interact with each other. "Binding" means any interaction, be it direct or indirect. A direct interaction implies a contact between the binding partners, for instance through a covalent link or coupling. An indirect interaction means any interaction whereby the interaction partners interact in a complex of more than two compounds. The interaction can be completely indirect, with the help of one or more bridging molecules, or partly indirect, where there is still a direct contact between the partners, which is stabilized by the additional interaction of one or more compounds. The "complex" as referred to in this disclosure is defined as a group of two or more associated proteins, which might have different functions. The association between the different polypeptides of the protein complex might be via non-covalent interactions, such as hydrophobic or ionic forces, or may as well be a covalent binding or coupling, such as disulphide bridges, or peptidic bounds. Covalent "binding" or "coupling" are used interchangeably herein, and may also involve "cysteine coupling" or "reactive or photoreactive amino acid coupling", referring to a bioconjugation between cysteines or between (photo)reactive amino acids, respectively, which is a chemical covalent link to form a stable complex. Examples of photoreactive amino acids include azidohomoalanine, homopropargylglycyine, homoallelglycine, p-acetyl-Phe, p-azido-Phe, p-propargyloxy-Phe and p-benzoyl-Phe (Wang et al. 2012, in Protein Engineering, DOI: 10.5772/28719; Chin et al. 2002, Proc. Nat. Acad. Sci. USA 99(17); 11020-24).

A "biological pore" is a transmembrane protein structure defining a channel or hole that allows the translocation of molecules and ions from one side of the membrane to the other. The translocation of ionic species through the pore may be driven by an electrical potential difference applied to either side of the pore. A "nanopore" is a biological pore in which the minimum diameter of the channel through which molecules or ions pass is in the order of nanometres (10-9 metres). In some embodiments, the biological pore can be a transmembrane protein pore. The transmembrane protein structure of a biological pore may be monomeric or oligomeric in nature. Typically, the pore comprises a plurality of polypeptide subunits arranged around a central axis thereby forming a protein-lined channel that extends substantially perpendicular to the membrane in which the nanopore resides. The number of polypeptide subunits is not limited. Typically, the number of subunits is from 5 to up to 30, suitably the number of subunits is from 6 to 10. Alternatively, the number of subunits is not defined as in the case of perfringolysin or related large membrane pores. The portions of the protein subunits within the nanopore that form protein-lined channel typically comprise secondary structural motifs that may include one or more trans-membrane β-barrel, and/or α-helix sections.

The term "pore", "pore complex", or "complex pore", as used interchangeably herein, refer to an oligomeric pore, wherein for instance at least a CsgG monomer (including, e.g., one or more CsgG monomers such as two or more CsgG monomers, three or more CsgG monomers) or a CsgG pore (comprised of CsgG monomers), and a CsgF peptide (e.g., a modified or truncated CsgF peptide) are associated in the complex and together form a pore or a nanopore. The pore complex of the disclosure has the features of a biological pore, i.e. it has a typical transmembrane protein structure. When the pore complex is provided in an environment having membrane components, membranes, cells, or an insulating layer, the pore complex will insert in the membrane or the insulating layer, and form a "transmembrane pore complex".

The pore complex or transmembrane pore complex of the disclosure is suited for analyte characterization. In some embodiments, the pore complex or transmembrane complex described herein can be used for sequencing polynucleotide sequences e.g., because it can discriminate between different nucleotides with a high degree of sensitivity. The pore complex of the disclosure may be an isolated pore complex, substantially isolated, purified or substantially purified. A pore complex of the disclosure is "isolated" or purified if it is completely free of any other components, such as lipids or other pores, or other proteins with which it is normally associated in its native state e.g., CsgE, CsgA CsgB, or if it is sufficiently enriched from a membranous compartment. A pore complex is substantially isolated if it is mixed with carriers or diluents which will not interfere with its intended use. For instance, a pore complex is substantially isolated or substantially purified if it is present in a form that comprises less than 10%, less than 5%, less than 2% or less than 1% of other components, such as triblock copolymers, lipids or other pores. Alternatively, a pore complex of the disclosure may be a transmembrane pore complex, when present in a membrane. The disclosure provides isolated pore complexes comprising a homo-oligomeric pore derived from CsgG comprising identical mutant monomers, which may also contain a mutant form of the CsgG monomer, as a homologue thereof. Alternatively, an isolated pore complex comprising a hetero-oligomeric CsgG pore is provided, which can be CsgG pore consisting of mutant and wild-type CsgG monomers, or of different forms of CsgG variants, mutants or homologues. The isolated pore complex typically comprises at least 7, at least 8, at least 9 or at least 10 CsgG monomers, and 1 or more (modified) CsgF peptides, such as 2, 3, 4, 5, 6, 7, 8, 9, 10 CsgF peptides. The pore complex may comprise any ratio of CsG monomer:CsgF peptide. In one embodiment, the ratio of CsG monomer:CsgF peptide is 1:1.

The "constriction", "orifice", "constriction region", "channel constriction", or "constriction site", as used interchangeably herein, refers to an aperture defined by a luminal surface of a pore or pore complex, which acts to allow the passage of ions and target molecules (e.g., but not limited to polynucleotides or individual nucleotides) but not other non-target molecules through the pore complex channel. In some embodiments, the constriction(s) are the narrowest aperture(s) within a pore or pore complex. In this embodiment, the constriction(s) may serve to limit the passage of molecules through the pore. The size of the constriction is typically a key factor in determining suitability of a nanopore for nucleic acid sequencing applications. If the constriction is too small, the molecule to be sequenced will not be able to pass through. However, to achieve a maximal effect on ion flow through the channel, the constriction should not be too large. For example, the constriction should not be wider than the solvent-accessible transverse diameter of a target analyte. Ideally, any constriction should be as close as possible in diameter to the transverse diameter of the analyte passing through. For sequencing of nucleic acids and nucleic acid bases, suitable constriction diameters are in the nanometre range (10-9 meter range). Suitably, the diameter should be in the region of 0.5 to 2.0 nm, typically, the diameter is in the region of 0.7 to 1.2 nm. The constriction in wild type E. coli CsgG has a diameter of approximately 9 Å (0.9 nm). The CsgF constriction formed in the pore complex comprising the CsgG-like pore and the modified CsgF peptide, or homologues or mutants thereof, has a diameter in the range of 0.5 to 2 nm or in the range of 0.7 to 1.2 nm and is hence suitable for nucleic acid sequencing.

When two or more constrictions are present and spaced apart each constriction may interact or "read" separate nucleotides within the nucleic acid strand at the same time. In this situation, the reduction in ion flow through the channel will be the result of the combined restriction in flow of all the constrictions containing nucleotides. Hence, in some instances a double constriction may lead to a composite current signal. In certain circumstances, the current read-out for one constriction, or "reading head", may not be able to be determined individually when two such reading heads are present. The constriction of wildtype E. coli CsgG (SEQ ID NO:3) is composed of two annular rings formed by juxtaposition of tyrosine residues at position 51 (Tyr 51) in the adjacent protein monomers, and also the phenylalanine and asparagine residues at positions 56 and 55 respectively (Phe 56 and Asn 55) (FIG. 1). The wild-type pore structure of CsgG is in most cases being re-engineered via recombinant genetic techniques to widen, alter, or remove one of the two annular rings that make up the CsgG constriction (mentioned as "CsgG channel constriction" herein), to leave a single well-defined reading head. The constriction motif in the CsgG oligomeric pore is located at amino acid residues at position 38 to 63 in the wild type monomeric E. coli CsgG polypeptide, depicted in SEQ ID NO: 3. In considering this region, mutations at any of the amino acid residue positions 50 to 53, 54 to 56 and 58 to 59, as well as key of positioning of the sidechains of Tyr51, Asn55, and Phe56 within the channel of the wild-type CsgG structure, was shown to be advantageous in order to modify or alter the characteristics of the reading head. The present disclosure relating to a pore complex comprising a CsgG-pore and a modified CsgF peptide, or homologues or mutants thereof, surprisingly added another constriction (mentioned as "CsgF channel constriction" herein) to the CsgG-containing pore complex, forming a suitable additional, second reader head in the pore, via complex formation with the modified CsgF peptide. Said additional CsgF channel constriction or reader head is positioned adjacent to the constriction loop of the CsgG pore, or of the mutated GcsG pore. Said additional CsgF channel constriction or reader head is positioned approximately 10 nm or less, such as 5 nm or less, such as 1, 2, 3, 4, 5, 6, 7, 8, 9 nm from the constriction loop of the CsgG pore, or of the mutated GcsG pore. The pore complex or transmembrane pore complex of the disclosure includes pore complexes with two reader heads, meaning, channel constrictions positioned in such a way to provide a suitable separate reader head without interfering the accuracy of other constriction channel reader heads. Said pore complexes therefore may include CsgG mutant pores (see incorporated references WO2016/034591, WO2017/149316, WO2017/149317, WO2017/149318 and International patent application no. PCT/GB2018/051191 each of which lists mutations to the wild-type CsgG pore that improve the properties of the pore) as well as wild-type CsgG pores, or homologues thereof, together with a modified CsgF peptide, or homologue or mutant thereof, wherein said CsgF peptide has another constriction channel forming a reader head.

Pores

The invention relates to CsgG pores complexed with an extracellularly located CsgF peptide that surprisingly introduces an additional channel constriction or reader head in the pore complex. Moreover, the disclosure provides positional information for the constriction made by the CsgF peptide within the pore complex, the peptide being inserted in the lumen of the CsgG pore, and the constriction site being in the N-terminal part of the CsgF protein. Furthermore, modified or truncated CsgF peptides of the disclosure were shown to be sufficient for pore complex formation, and provide means and methods for biosensing applications. The disclosure comprises wildtype and mutant CsgG pores (as disclosed in e.g., WO2016/034591, WO2017/149316, WO2017/149317, WO2017/149318 and International patent application no. PCT/GB2018/051191), or homologues or mutants thereof, combined with modified or truncated CsgF peptides and its mutants or homologues, all together improving the ability of the CsgG-like pore complex to interact with an analyte, such as a polynucleotide. The additional constriction introduced in the CsgG-like nanopore channel by complex formation with (modified or truncated) CsgF peptides expands the contact surface with passing analytes and can act as a second reader head for analyte detection and characterization. Pores comprising mutant CsgG monomers combined with novel mutant or modified forms of CsgF can improve the characterisation of analytes, such as polynucleotides, providing a more discriminating direct relationship between the observed current as the polynucleotide moves through the pore. In particular, by having two stacked reader heads spaced at a defined distance, the CsgG:CsgF pore complex may facilitate characterization of polynucleotides that contain at least one homopolymeric stretch, e.g., several consecutive copies of the same nucleotide that otherwise exceed the interaction length of the single CsgG reader head. Additionally, by having two stacked constrictions at a defined distance, small molecule analytes including organic or inorganic drugs and pollutants passing through the CsgG:CsgF complex pore will consecutively pass two independent reader heads. The chemical nature of either reader head can be independently modified, each giving unique interaction properties with the analyte, thus providing additional discriminating power during analyte detection.

In a first aspect, the invention relates to an isolated pore complex, comprising a CsgG pore, or a homologue or mutant thereof, or a CsgG-like pore, and a modified CsgF peptide, or a homologue or mutant thereof. In fact, the disclosure relates to a modified CsgG biological pore, comprising a modified CsgF peptide, which can be a truncated, mutant and/or variant thereof. In one embodiment, the interaction region between said modified CsgF peptide or homologue or mutant thereof, is located at the lumen of the CsgG pore, or its homologues or mutants. In another embodiment, the pore complex has two or more constriction sites or reader heads, provided by at least one constriction of the CsgG pore, and by at least one being introduced by the CsgF peptide, forming a complex with the CsgG pore. N-terminal CsgF positions with the inclusion of positions in the range of amino acid residues 39-64 of SEQ ID NO:5, or more particularly of amino acid residues 49-64 of SEQ ID NO:5, were shown to allow detectable amounts of a stable CsgG:CsgF complex. In one embodiment, the CsgF constriction produced by a modified CsgF peptide (e.g., the ones described herein) is adjacent or head-to-head of the first constriction in the CsgG pore of the pore complex. For CsgG or CsgG-like protein pores, the constriction site has been determined to be formed by a loop region of a beta strand (see FIG. 1).

In one embodiment, the modified CsgF peptide is a peptide wherein said modification in particular refers to a truncated CsgF protein or fragment, comprising an N-terminal CsgF peptide fragment defined by the limitation to contain the constriction region and to bind CsgG monomers, or homologues or mutants thereof. Said modified CsgF peptide may additionally comprise mutations or homologous sequences, which may facilitate certain properties of the pore complex. In a particular embodiment, modified CsgF peptides comprise CsgF protein truncations as compared to the wild-type preprotein (SEQ ID NO:5) or mature protein (SEQ ID NO:6) sequence, or homologues thereof. These modified peptides are intended to function as a pore complex component introducing an additional constriction site or reader head, within the CsgG-like pore formed by CsgG and the modified or truncated CsgF peptide. Examples of truncated modified peptides are described below.

Examples of homologues of the modified CsgF peptides are for instance determined in Example 3, and reveal CsgF-like proteins or CsgF peptides comprising a homologous or similar constriction region in different bacterial strains, which may be useful in the use of similar pore complexes. The structural properties and CsgG-binding elements in the CsgF peptides derived from various CsgF homologues are conserved, such that CsgF peptides can be used in combination with different wildtype or mutant CsgG pores. This includes complexes of CsgG pores with non-cognate CsgF, meaning that the CsgG pore and the parental CsgF homologue from which the CsgF is derived do not need to originate from the same operon, bacterial species or strain.

In alternative embodiments, the CsgG pore within the pore complex is not a wild-type pore, but comprises mutations or modifications to increase pore properties as well. The isolated pore complex of the disclosure, formed by the CsgG pore, or a homologue thereof, and the modified CsgF peptide, or a homologue thereof, may be formed by the wild-type form of the CsgG pore or may be further modified in the CsgG pore, such as by directed mutagenesis of particular amino acid residues, to further enhance the desired properties of the CsgG pore for use within the pore complex. For example, in embodiments of the present invention mutations are contemplated to alter the number, size, shape, placement or orientation of the constriction within the channel. The pore complex comprising a modified mutant CsgG pore may be prepared by known genetic engineering techniques that result in the insertion, substitution and/or deletion of specific targeted amino acid residues in the polypeptide sequence. In the case of the oligomeric CsgG pore, the mutations may be made in each monomeric polypeptide subunit, or any one of the monomers, or all of the monomers. Suitably, in one embodiment of the invention the mutations described are made to all monomeric polypeptides within the oligomeric protein structure. A mutant CsgG monomer is a monomer whose sequence varies from that of a wild-type CsgG monomer and which retains the ability to form a pore. Methods for confirming the ability of mutant monomers to form pores are well-known in the art. The disclosure comprises wild type and mutant CsgG pores (e.g., as disclosed in WO2016/034591, WO2017/149316, WO2017/149317, WO2017/149318 and International patent application no. PCT/GB2018/051191), or homologues thereof, combined with modified or truncated CsgF peptides and their mutants or homologues, all together improving the ability of the CsgG-like pore complex to interact with an analyte, such as a polynucleotide. Mutant CsgG pores may comprise one or more mutant monomers. The CsgG pore may be a homopolymer comprising identical monomers, or a heteropolymer comprising two or more different monomers. The monomers may have one or more of the mutations described below in any combination.

The nanopore complex comprising a modified CsgF peptide differs as compared to the wild-type CsgF protein depicted in SEQ ID NO:6 since the modified CsgF peptide only comprises N-terminal fragments or truncates of the wild-type CsgF protein in certain embodiments. The modified CsgF peptide however may be additionally or alternatively mutated CsgF peptide in the sense that mutations as amino acid substitutions are made to allow for a better second constriction site in the pore formed by the complex comprising the CsgG pore and the modified CsgF peptide. The mutant monomers might as such have improved polynucleotide reading properties when said complex is used in nucleotide sequencing i.e. display improved polynucleotide capture and nucleotide discrimination, in addition to the improved feature of the complex to comprise two reader heads. In particular, pores constructed from the mutant peptides capture nucleotides and polynucleotides more easily than the wild type. In addition, pores constructed from the mutant peptides may display an increased current range, which makes it easier to discriminate between different nucleotides, and a reduced variance of states, which increases the signal-to-noise ratio. In addition, the number of nucleotides contributing to the current as the polynucleotide moves through pores constructed from the mutants may be decreased. This makes it easier to identify a direct relationship between the observed current as the polynucleotide moves through the pore and the polynucleotide sequence. In addition, pores constructed from the mutant peptides may display an increased throughput, e.g., are more likely to interact with an analyte, such as a polynucleotide. This makes it easier to characterise analytes using the pores. Pores constructed from the mutant peptides may insert into a membrane more easily, or may provide easier way to retain additional proteins in close vicinity of the pore complex.

In an alternative embodiment, the CsgF constriction site provided in the pore complex of the invention has a diameter in the range of 0.5 nm to 2.0 nm, thereby providing a pore complex suitable for nucleic acid sequencing, as described above.

The pore may be stabilised by covalent attachment of the CsgF peptide to the CsgG pore. The covalent linkage may for example be a disulphide bond, or click chemistry. The CsgF peptide and CsgG pore may, for example, be covalently linked via residues at a position corresponding to one or more of the following pairs of positions of SEQ ID NO: 6 and SEQ ID NO: 3, respectively: 1 and 153, 4 and 133, 5 and 136, 8 and 187, 8 and 203, 9 and 203, 11 and 142, 11 and 201, 12 and 149, 12 and 203, 26 and 191, and 29 and 144.

In the pore, the interaction between the CsgF peptide and the CsgG pore may, for example, be stabilised by hydrophobic interactions or electrostatic interactions at a position corresponding to one or more of the following pairs of positions of SEQ ID NO: 6 and SEQ ID NO: 3, respectively: 1 and 153, 4 and 133, 5 and 136, 8 and 187, 8 and 203, 9 and 203, 11 and 142, 11 and 201, 12 and 149, 12 and 203, 26 and 191, and 29 and 144.

The residues in CsgF and/or CsgG at one or more of the positions listed above may be modified in order to enhance the interaction between CsgG and CsgF in the pore.

In one embodiment, the pore of the invention may be isolated, substantially isolated, purified or substantially purified. A pore of the invention is isolated or purified if it is completely free of any other components, such as lipids or other pores. A pore is substantially isolated if it is mixed with carriers or diluents which will not interfere with its intended use. For instance, a pore is substantially isolated or substantially purified if it is present in a form that comprises less than 10%, less than 5%, less than 2% or less than 1% of other components, such as triblock copolymers, lipids or other pores. Alternatively, a pore of the invention may be present in a membrane. Suitable membranes are discussed below.

A pore of the invention may be present as an individual or single pore. Alternatively, a pore of the invention may be present in a homologous or heterologous population of two or more pores.

CsgF Peptide

A second aspect of the invention relates to novel modified CsgF monomers (peptides), or truncated CsgF proteins, or a modified or truncated peptide of a CsgF homologue or mutant. Those novel modified CsgF peptides may be used in a pore complex to integrate a second or additional reader head. Said modification or truncation is preferably resulting in a fragment of the wild-type CsgF, or of mutant or homologue CsgF protein, more preferably an N-terminal fragment.

Figure 4A:
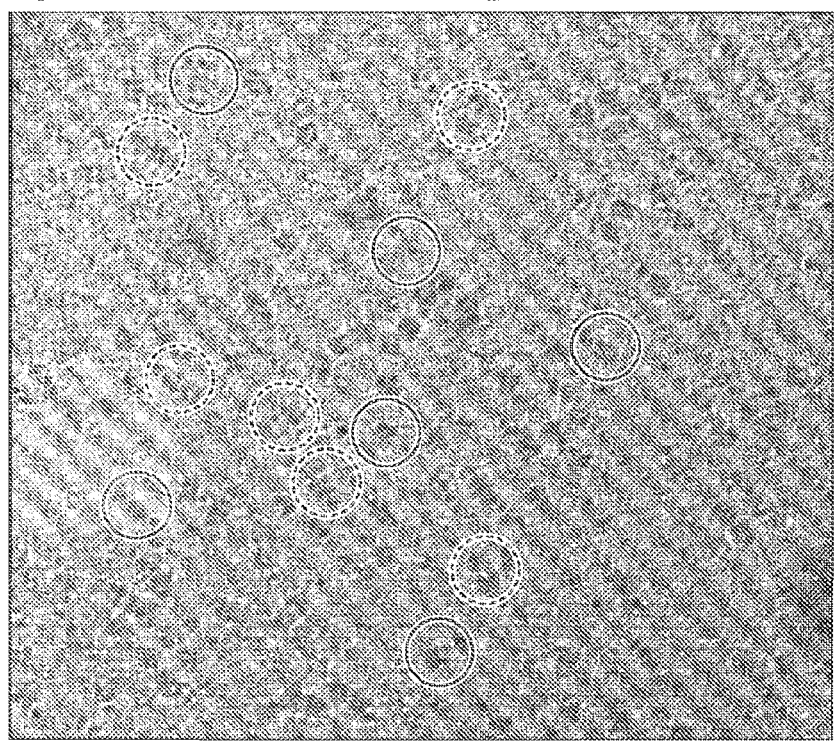
FIGS. 4A-4B CsgG:CsgF structure as determined in cryo-EM.
Figure 4B:
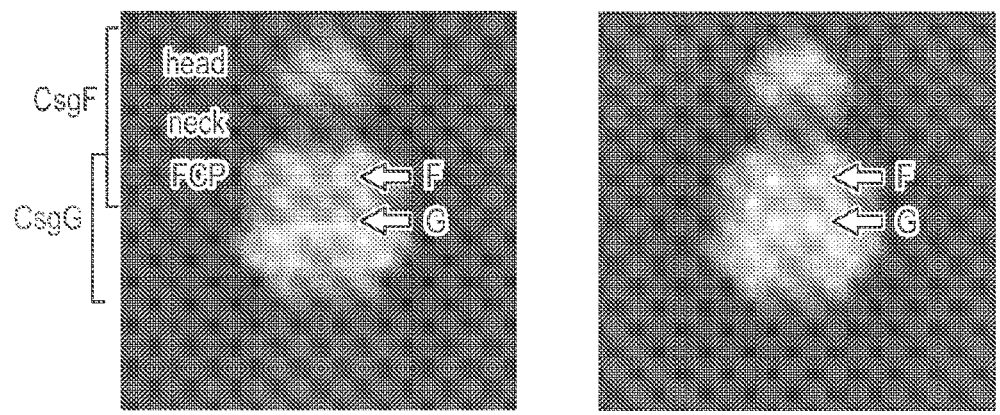
Figure 5:
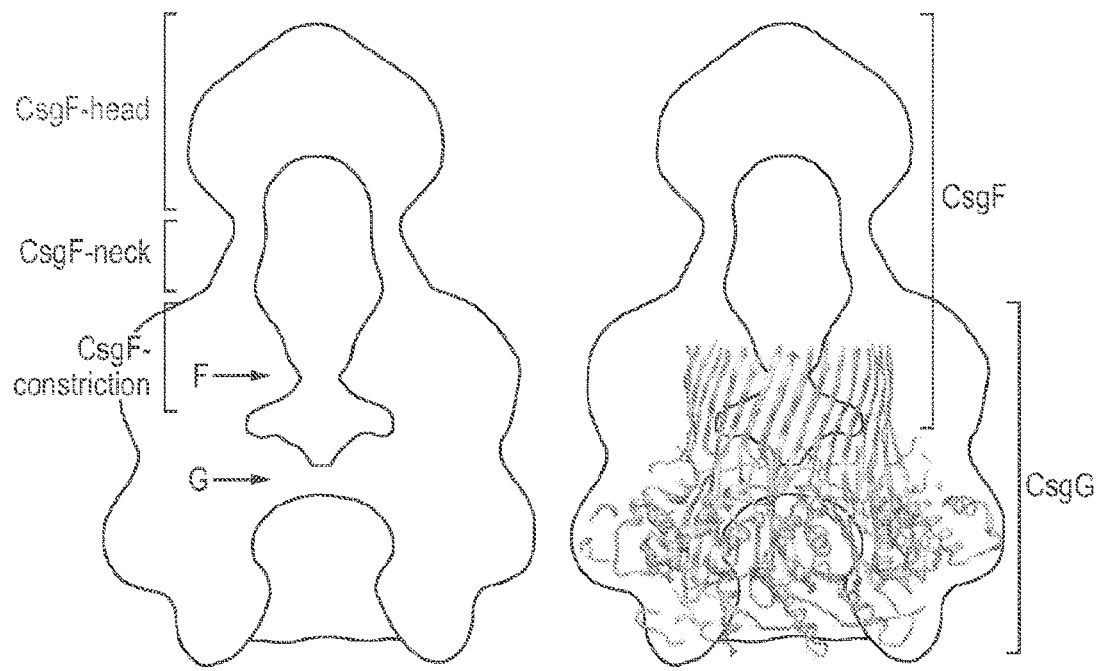
FIG. 5 Three-dimensional structural model of a CsgG:CsgF complex. Cross-sectional views of the 3D cryoEM electron density of the CsgG:CsgF 9-mer complex calculated from 20.000 particles assigned to 21 class averages. The right picture shows a superimposition with the CsgG 9-mer X-ray structure (PDB entry: 4uv3) docked into the cryoEM density. The regions corresponding to CsgG, CsgF and the CsgF head, neck and FCP domains are indicated. The cross-sections show the CsgF FCP regions forms an additional constriction (labelled F) in the CsgG channel, approximately 2 nm above the CsgG constriction loop (labelled G).

Mature CsgF (shown in SEQ ID NO:6) can be divided into three main regions: a "CsgF constriction peptide" (FCP), a "neck" region and a "head" region (as shown in FIGS. 4 and 5). The "head" region of the CsgF peptide is distinct from a reader head of a pore as described herein. The "head" region of the CsgF peptide may also be referred to as the "C-terminal head domain".

The FCP forms the contact region with the CsgG β-barrel, where it gives rise to an additional constriction. The neck region protrudes out of the β-barrel. In the CsgG:CsgF oligomer it forms a thin-walled hollow tube that connects the FCP to a globular head region.

Based on multiple sequence alignments (FIG. 8), co-purification experiments (FIG. 9) and the cryoEM reconstruction of the CsgG:CsgF complex at 3.4 Å resolution (FIG. 11) the CsgF constriction peptide, neck and head regions can be defined as three consecutive residue stretches in mature CsgF.

Figure 8:
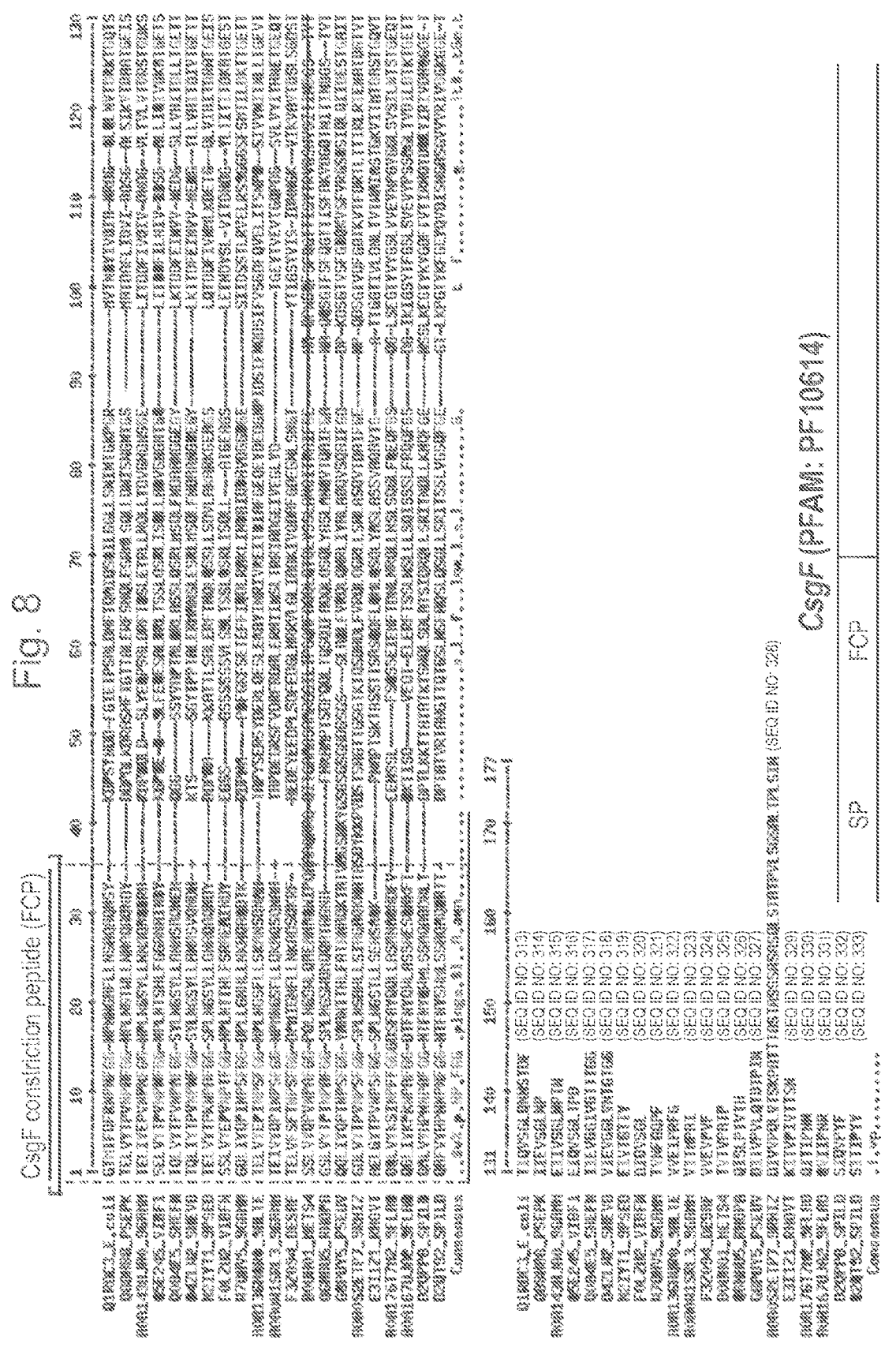
Figure 10A:
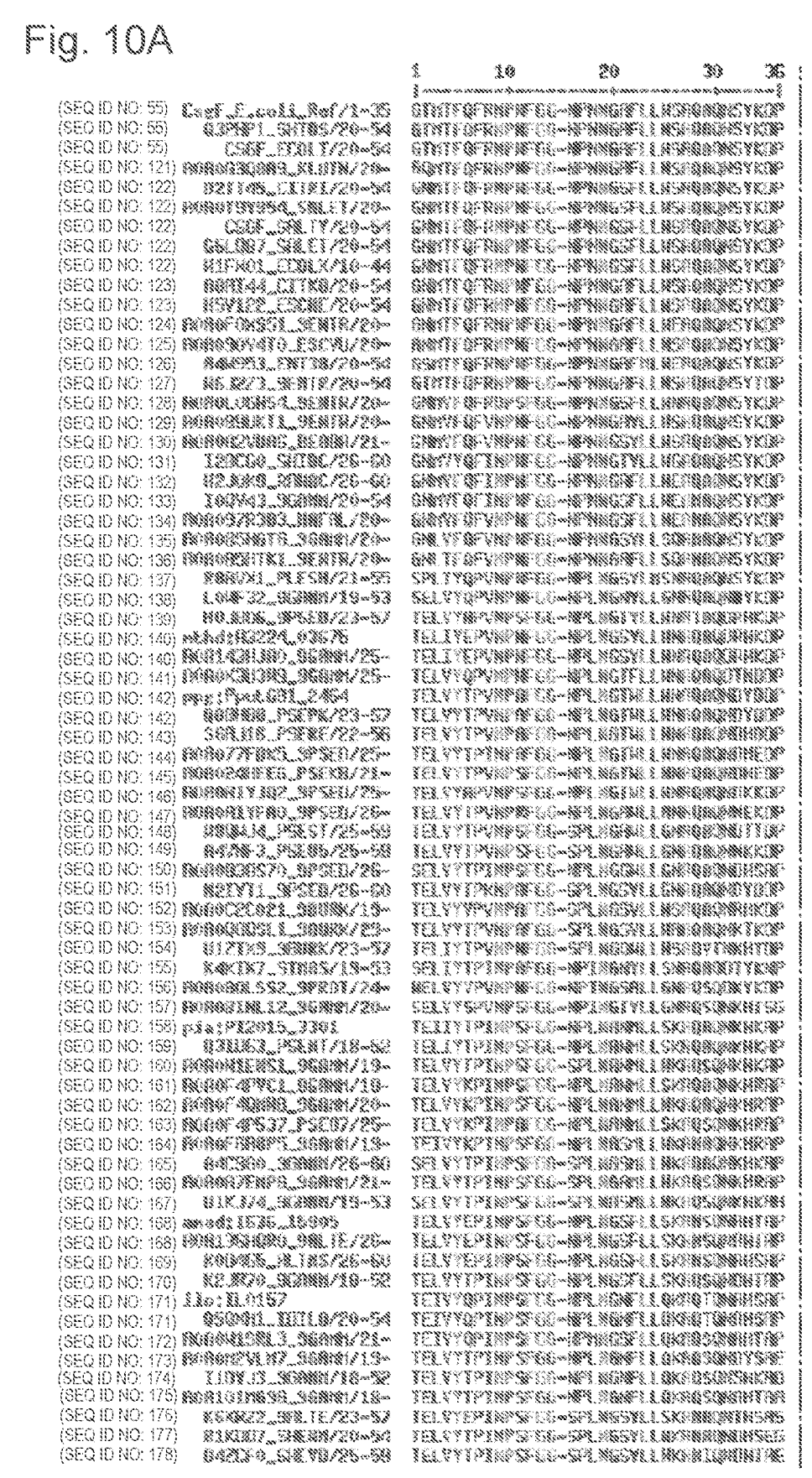
Figure 10B:
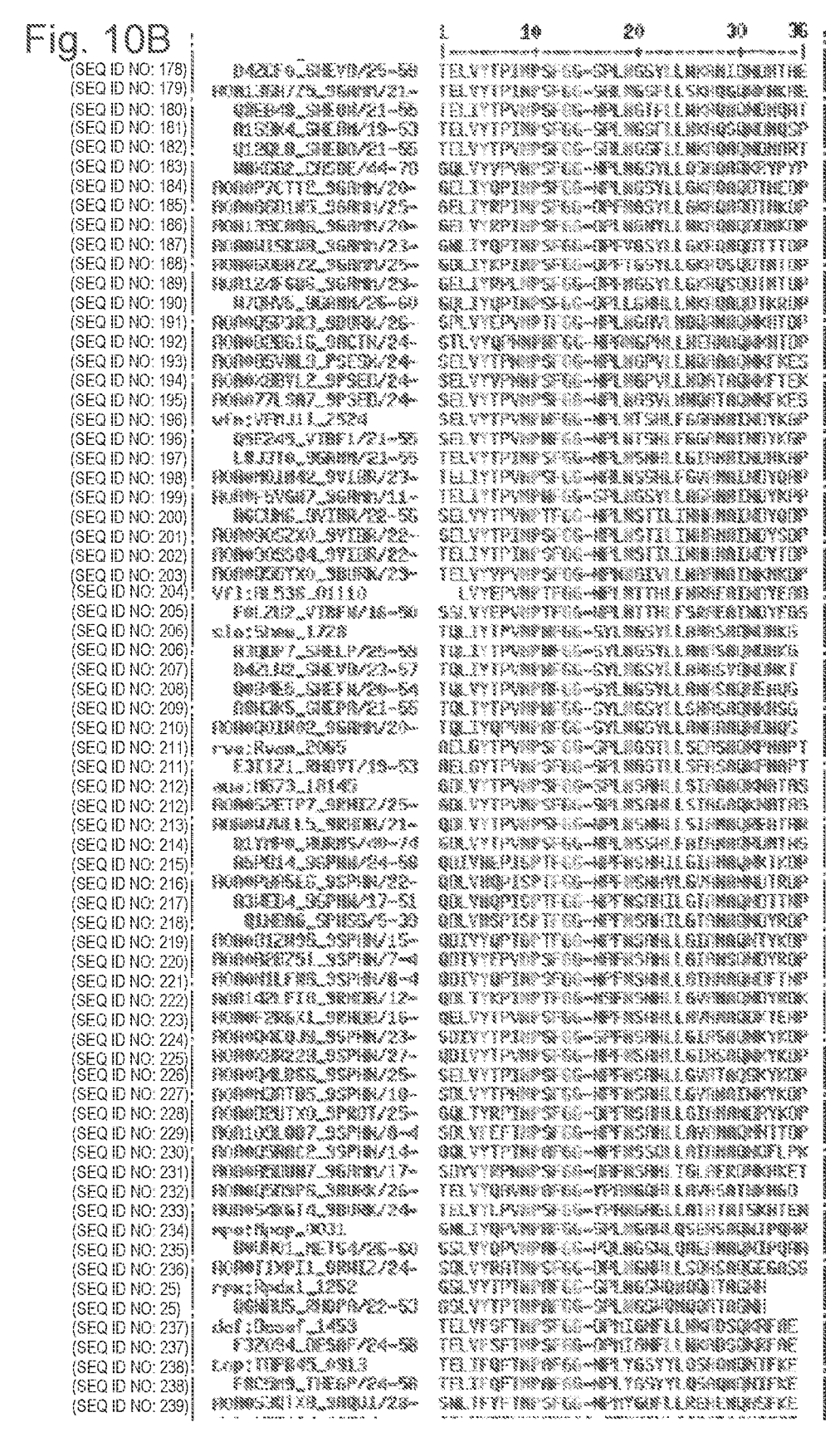
Figure 10C:
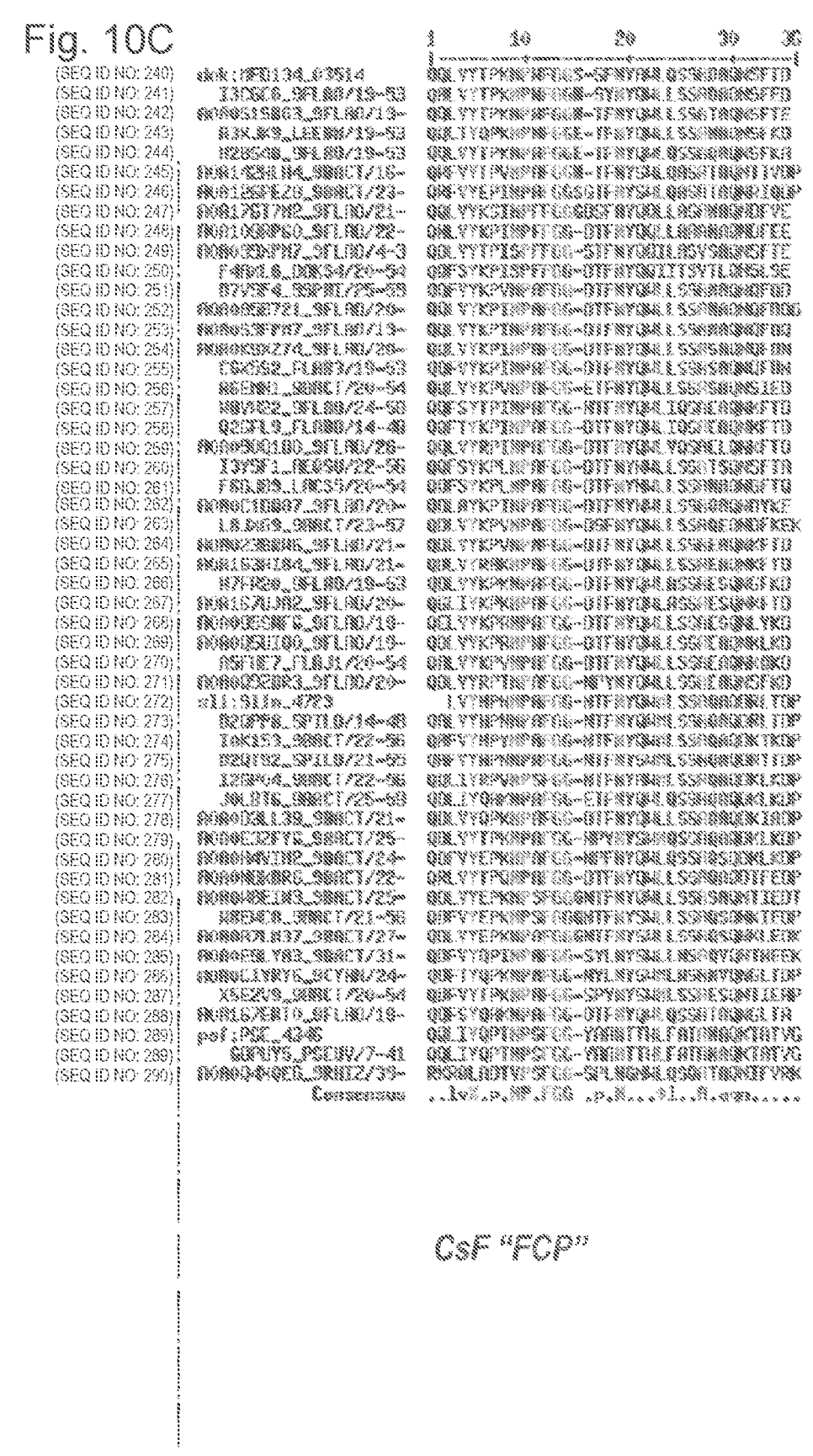

The FCP spans from approximately residues 1 to 35 of the mature CsgF (Seq ID NO:6). The FCP forms the most conserved region of the protein when comparing different CsgF orthologues (FIG. 8, FIG. 10). CryoEM 3D reconstruction shows the FCP forms a well-defined structure that binds the inside the CsgG β-barrel through non-covalent contacts with the CsgG transmembrane hairpins TM1 (residues 134 to 154 of Seq ID NO:3) and TM2 (residues 184 to 208 of Seq ID NO:3) (FIG. 1E; 11) (TM1 and TM2 are defined in Goyal P, et al., 2014). In the reconstruction, nine copies of the FCP bind the CsgG oligomer (comprising 9 monomers) and together give rise to an additional constriction approximately 2 nm above the top of CsgG constriction formed by a continuous loop spanning residues 46 to 61 of mature CsgG (Seq ID NO:3; FIG. 1E; FIG. 11).

The cryoEM 3D reconstruction also shows the CsgF N-terminal residue binds near the base or the top (depending on the orientation) of the CsgG β-barrel and exits the β-barrel at residue 32. This is in good agreement with MD simulations that show the average contact time of residue pairs in the CsgG:CsgF binding interface (Table 4). The cryoEM structure and MD simulations show residues 33-34 reside outside the CsgG β-barrel, where a well, though not strictly, conserved Pro residue (Pro 35 in Seq ID NO:6)

makes the transition to the CsgF neck regions. The CsgF neck is not resolved in atomic detail in the CsgG:CsgF 3D reconstruction pointing to its conformational flexibility. The CsgF neck is predicted to span from residue 36 to approximately residue 50 (SEQ ID NO:6) based on multiple sequence alignment and secondary structure prediction. The CsgF head region forms the C-terminal part of CsgF and is predicted to span from approximately residue 51 to the CsgF C-terminus. In the CsgG:CsgF complex, this region oligomerizes to give rise to a globular structure that appears to cap the CsgG:CsgF channel (FIGS. 4, 5). Multiple sequence alignment of CsgF orthologues shows the CsgF neck to be the least conserved region and suggests it may vary in length from one orthologue to another (FIG. 8).

The CsgF peptide which forms part of the invention is a truncated CsgF peptide lacking the C-terminal head; lacking the C-terminal head and a part of the neck domain of CsgF (e.g., the truncated CsgF peptide may comprise only a portion of the neck domain of CsgF); or lacking the C-terminal head and neck domains of CsgF. The CsgF peptide may lack part of the CsgF neck domain, e.g. the CsgF peptide may comprise a portion of the neck domain, such as for example, from amino acid residue 36 at the N-terminal end of the neck domain (see SEQ ID:NO:6) (e.g. residues 36-40, 36-41, 36-42, 36-43, 36-45,36-46 up to residues 36-50 or 36-60 of SEQ ID NO: 6). The CsgF peptide preferably comprises a CsgG-binding region and a region that forms a constriction in the pore. The CsgG-binding region typically comprises residues 1 to 8 and/or 29 to 32 of the CsgF protein (SEQ ID NO: 6 or a homologue from another species) and may include one or more modifications. The region that forms a constriction in the pore typically comprises residues 9 to 28 of the CsgF protein (SEQ ID NO: 6 or a homologue from another species) and may include one or more modifications. Residues 9 to 17 comprise the conserved motif $N_9PXFGGXXX_{17}$ and form a turn region. Residues 9 to 28 form an alpha-helix. $X_{17}$ (N17 in SEQ ID NO: 6) forms the apex of the constriction region, corresponding to the narrowest part of the CsgF constriction in the pore. The CsgF constriction region also makes stabilising contacts with the CsgG beta-barrel, primarily at residues 9, 11, 12, 18, 21 and 22 of SEQ ID NO: 6.

The CsgF peptide typically has a length of from 28 to 50 amino acids, such as 29 to 49, 30 to 45 or 32 to 40 amino acids. Preferably the CsgF peptide comprises from 29 to 35 amino acids, or 29 to 45 amino acids. The CsgF peptide comprises all or part of the FCP, which corresponds to residues 1 to 35 of SEQ ID NO: 6. Where the CsgF peptide is shorter that the FCP, the truncation is preferably made at the C-terminal end.

The CsgF fragment of SEQ ID NO:6 or of a homologue or mutant thereof may have a length of 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 amino acids.

The CsgF peptide may comprise the amino acid sequence of SEQ ID NO: 6 from residue 1 up to any one of residues 25 to 60, such as 27 to 50, for example, 28 to 45 of SEQ ID NO: 6, or the corresponding residues from a homologue of SEQ ID NO: 6, or variant of either thereof. More specifically, the CsgF peptide may comprise SEQ ID NO: 39 (residues 1 to 29 of SEQ ID NO: 6), or a homologue or variant thereof.

Examples of such CsgF peptides comprises, consist essentially of or consist of SEQ ID NO: 15 (residues 1 to 34 of SEQ ID NO: 6), SEQ ID NO: 54 (residues 1 to 30 of SEQ ID NO: 6), SEQ ID NO: 40 (residues 1 to 45 of SEQ ID NO: 6), or SEQ ID NO: 55 (residues 1 to 35 of SEQ ID NO: 6) and homologues or variants of any thereof. Other Examples of CsgF peptides comprise, consist essentially of or consist of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 16.

In the CsgF peptide, one or more residues e.g., in SEQ ID NO: 15, SEQ ID NO: 39, SEQ ID NO: 40, SEQ ID NO: 54, or SEQ ID NO: 55 may be modified.

For example, the CsgF peptide may comprise a modification at a position corresponding to one or more of the following positions in SEQ ID NO: 6: G1, T4, F5, R8, N9, N11, F12, A26 and Q29.

The CsgF peptide may be modified to introduce a cysteine, a hydrophobic amino acid, a charged amino acid, a non-native reactive amino acid, or photoreactive amino acid, for example at a position corresponding to one or more of the following positions in SEQ ID NO: 6: G1, T4, F5, R8, N9, N11, F12, A26 and Q29.

For example, the CsgF peptide may comprise a modification at a position corresponding to one or more of the following positions in SEQ ID NO: 6: N15, N17, A20, N24 and A28. The CsgF peptide may comprise a modification at a position corresponding to D34 to stabilise the CsgG-CsgF complex. In particular embodiments, the CsgF peptide comprises one or more of the substitutions: N15S/A/T/Q/G/L/V/I/F/Y/W/R/K/D/C, N17S/A/T/Q/G/L/V/I/F/Y/W/R/K/D/C, A20S/T/Q/N/G/L/V/I/F/Y/W/R/K/D/C, N24S/T/Q/A/G/L/V/I/F/Y/W/R/K/D/C, A28S/T/Q/N/G/L/V/I/F/Y/W/R/K/D/C and D34F/Y/W/R/K/N/Q/C. The CsgF peptide may, for example, comprise one or more of the following substitutions: G1C, T4C, N17S, and D34Y or D34N.

The CsgF peptide may be produced by cleavage of a longer protein, such as full-length CsgF using an enzyme. Cleavage at a particular site may be directed by modifying the longer protein, such as full-length CsgF, to include an enzyme cleavage site at an appropriate position. Examples of CsgF amino acid sequences that have been modified to include such enzyme cleavage sites are shown in SEQ ID NOs: 56 to 67. Following cleavage all or part of the added enzyme cleavage site may be present in the CsgF peptide that associates with CsgG to form a pore. Thus the CsgF peptide may further comprise all or part of an enzyme cleavage site at its C-terminal end. 5

Some examples of suitable CsgF peptides are shown in Table 3 below:

TABLE 3

CsgF peptides

| Technical description | Protein sequence | SEQ ID NO: |
|---|---|---|
| CsgF-(1-45) | GTMTFQFRNPNFGGNPNNGAFLLNSAQAQNSYKDPSYNDDFGIET | 40 |
| CsgF-(1-29) | GTMTFQFRNPNFGGNPNNGAFLLNSAQAQ | 39 |

TABLE 3-continued

CsgF peptides

| Technical description | Protein sequence | SEQ ID NO: |
|---|---|---|
| CsgF-(1-35) | GTMTFQFRNPNFGGNPNNGAFLLNSAQAQNSYKDP | 55 |
| CsgF-G1C-(1-45) | CTMTFQFRNPNFGGNPNNGAFLLNSAQAQNSYKDPSYNDDFGIET | 89 |
| CsgF-G1C-(1-30) | GTMTFQFRNPNFGGNPNNGAFLLNSAQAQ | 90 |
| CsgF-G1C-(1-35) | CTMTFQFRNPNFGGNPNNGAFLLNSAQAQNSYKDP | 91 |
| CsgF-N17S-(1-35) | GTMTFQFRNPNFGGNPSNGAFLLNSAQAQNSYKDP | 92 |
| CsgF-G1C/D34Y-(1-35) | CTMTFQFRNPNFGGNPNNGAFLLNSAQAQNSYKYP | 93 |
| CsgF-N17S-(1-45) | GTMTFQFRNPNFGGNPSNGAFLLNSAQAQNSYKDPSYNDDFGIET | 94 |
| CsgF-G1C/N17S/D34Y-(1-35) | CTMTFQFRNPNFGGNPSNGAFLLNSAQAQNSYKYP | 95 |
| CsgF-G1C-(1-30)-H10 | CTMTFQFRNPNFGGNPNNGAFLLNSAQAQHHHHHHHHHH | 96 |
| CsgF-G1C-(1-35)-H10 | CTMTFQFRNPNFGGNPNNGAFLLNSAQAQNSYKDPHHHHHHHHHH | 97 |
| CsgF-N17S/D34Y-(1-35) | GTMTFQFRNPNFGGNPSNGAFLLNSAQAQNSYKYP | 98 |
| CsgF-N17S/D34N-(1-35) | GTMTFQFRNPNFGGNPSNGAFLLNSAQAQNSYKNP | 99 |
| CsgF-T4C/N17S-(1-35) | GTMCFQFRNPNFGGNPSNGAFLLNSAQAQNSYKDP | 100 |
| CsgF-T4C/N17S/D34Y-(1-35) | GTMCFQFRNPNFGGNPSNGAFLLNSAQAQNSYKYP | 101 |
| CsgF-T4C/N17S/D34N-(1-35) | GTMCFQFRNPNFGGNPSNGAFLLNSAQAQNSYKNP | 102 |
| CsgF-G1C/T4C/N17S-(1-35) | CTMCFQFRNPNFGGNPSNGAFLLNSAQAQNSYKDP | 103 |
| CsgF-G1C/T4C/N17S/D34N-(1-35) | CTMCFQFRNPNFGGNPSNGAFLLNSAQAQNSYKNP | 104 |
| CsgF-G1C/T4C/N17S/D34Y-(1-35) | CTMCFQFRNPNFGGNPSNGAFLLNSAQAQNSYKYP | 105 |
| CsgF-N17V-(1-35) | GTMTFQFRNPNFGGNPVNGAFLLNSAQAQNSYKDP | 106 |
| CsgF-N17A-(1-35) | GTMTFQFRNPNFGGNPANGAFLLNSAQAQNSYKDP | 107 |
| CsgF-N17F-(1-35) | GTMTFQFRNPNFGGNPFNGAFLLNSAQAQNSYKDP | 108 |
| CsgF-N17S-(1-30) | GTMTFQFRNPNFGGNPSNGAFLLNSAQAQN | 109 |
| CsgF-N17V-(1-30) | GTMTFQFRNPNFGGNPVNGAFLLNSAQAQN | 110 |
| CsgF-N17A-(1-30) | GTMTFQFRNPNFGGNPANGAFLLNSAQAQN | 111 |
| CsgF-N17F-(1-30) | GTMTFQFRNPNFGGNPFNGAFLLNSAQAQN | 112 |
| CsgF-N17V/D34Y-(1-35) | GTMTFQFRNPNFGGNPVNGAFLLNSAQAQNSYKYP | 113 |
| CsgF-N17A/D34Y-(1-35) | GTMTFQFRNPNFGGNPANGAFLLNSAQAQNSYKYP | 114 |
| CsgF-N17F/D34Y-(1-35) | GTMTFQFRNPNFGGNPFNGAFLLNSAQAQNSYKYP | 115 |
| CsgF-N17S/A20Q-(1-35) | GTMTFQFRNPNFGGNPSNGQFLLNSAQAQNSYKDP | 116 |

In particular embodiments, said CsgF fragment comprises the amino acid sequence SEQ ID NO:39, or mutant or homologue thereof. In particular, SEQ ID NO:39 comprises the first 29 amino acids of the mature CsgF peptide (SEQ ID NO:6). In another embodiment, the modified CsgF peptide of the invention is a truncated peptide comprising SEQ ID NO:40. In particular, SEQ ID NO:40 comprises the first 45 amino acids of the mature CsgF peptide (SEQ ID NO:6). In particular, the CsgF constriction site and binding site to the CsgG are located within the N-terminal CsgF peptide region, further characterised in that amino acid 39 to 64 of SEQ ID NO:5 (present in SEQ ID NO:39 and SEQ ID NO:40), or in particular amino acid 49 to 64 of SEQ ID NO:5 (present in SEQ ID NO:40, but not in SEQ ID NO:39, the latter fragment encoded by SEQ ID NO:39 showing a weaker interaction with CsgG (see Examples)), confer a higher stability to the complex. Hence, the disclosure provides a modification of the CsgF protein by truncating the protein to said peptides or peptides comprising said N-terminal fragments or constriction site region to allow complex formation with the CsgG pore, or homologues or mutants thereof, in vivo. Further limitation is provided in one embodiment relating to a modified CsgF peptide comprising SEQ ID NO:37 or SEQ ID NO:38. Finally, identification of CsgF homologous peptides, especially aligned within the constriction region (FCP peptides), also provide modified CsgF peptide homologues that may form a part of said isolated complex (e.g.; see FIGS. 8 and 10).

A further embodiment relates to the modified or truncated CsgF peptides comprising SEQ ID NO:15, wherein said SEQ ID NO:15 contains the region of the CsgF protein including several residues from the region of the CsgG binding and/or constriction site, sufficient for in vitro reconstitution of the complex pore comprising CsgG or a homologue thereof, and a modified CsgF peptide, to result in an isolated pore complex comprising a CsgF channel constriction. Another embodiment describes said modified CsgF peptide comprising SEQ ID NO:16, which contains an N-terminal fragment of the CsgF protein, and two additional amino acids (KD), which will increase solubility and stability of the (synthetic) peptide, as well to allow in vitro reconstitution of said complex pore. Further embodiments are provided wherein said modified CsgF peptide comprises SEQ ID NO:15, SEQ ID NO:16 or a homologue or mutant thereof, wherein said modified CsgF peptide is further mutated, but still retains a minimal of 35% amino acid identity to SEQ ID NO:15, or SEQ ID NO:16, respectively, within the region of the modified CsgF peptide corresponding to said SEQ ID NO:15 or 16 e.g., 40%, 50%, 60%, 70%, 80% 85%, 90% amino acid identity. Further embodiments are provided wherein said modified CsgF peptide comprises SEQ ID NO:15, SEQ ID NO: 16 or a homologue or mutant thereof, wherein said modified CsgF peptide is further mutated, but still retains a minimal of 40%, 45%, 50%, 60%, 70%, 80% 85% or 90% amino acid identity to SEQ ID NO:15, or SEQ ID NO:16, respectively, within the region of the modified CsgF peptide corresponding to said SEQ ID NO:15 or 16. Those mutated regions are intended to alter and/or improve the characteristics of the CsgF constriction site, as discussed above, so for instance a more accurate target analysis can be obtained. Another embodiment discloses modified CsgF peptides wherein one or more positions in the regions comprising SEQ ID NO:39, SEQ ID NO:40, SEQ ID NO:54 or SEQ ID NO:55 are modified, and wherein said mutation(s) retain a minimal of 35% amino acid identity, or 40%, 50%, 60%, 70%, 80%, 85%, 90%, 95% amino acid identity to SEQ ID NO:39, SEQ ID NO:40, SEQ ID NO:54 or SEQ ID NO:55 in the peptide fragment corresponding to the region comprising SEQ ID NO:39, SEQ ID NO:40, SEQ ID NO:54 or SEQ ID NO:55.

So further embodiments of the invention involve the isolated pore complex comprising a CsgG pore, or homologue or mutant thereof, and modified CsgF peptide(s), or homologues or mutants thereof, wherein said modified CsgF peptide(s) are defined as described in the second aspect of the invention.

Additional embodiments relate to an isolated pore complex, wherein said CsgG pore, at least via one monomer, and the modified CsgF peptide, are coupled via covalent binding. Said covalent link or binding is in one instance possible via cysteine linkage, wherein the sulfhydryl side group of cysteine covalently links with another amino acid residue or moiety. In a second possibility, the covalent linkage is obtained via an interaction between non-native (photo) reactive amino acids. (Photo-)reactive amino acids are referring to artificial analogs of natural amino acids that can be used for crosslinking of protein complexes, and may be incorporated into proteins and peptides in vivo or in vitro. Photo-reactive amino acid analogs in common use are photoreactive diazirine analogs to leucine and methionine, and para-benzoyl-phenyl-alanine, as well as azidohomoalanine, homopropargylglycyine, homoallelglycine, p-acetyl-Phe, p-azido-Phe, p-propargyloxy-Phe and p-benzoyl-Phe (Wang et al. 2012; Chin et al. 2002). Upon exposure to ultraviolet light, they are activated and covalently bind to interacting proteins that are within a few angstroms of the photo-reactive amino acid analog. However, the positions in the CsgG monomer where said covalent linkages may take place is dependent on the exposure to the modified CsgF peptide. As shown in FIG. 1, several amino acids are in the position to provide the covalent linkage, namely positions 132, 133, 136, 138, 140, 142, 144, 145, 147, 149, 151, 153, 155, 183, 185, 187, 189, 191, 201, 203, 205, 207 or 209 of SEQ ID NO: 3, or of homologues thereof.

Another aspect of the invention relates to constructs comprising said modified CsgF peptide, wherein said peptide is covalently attached. A "construct" comprises two or more covalently attached monomers derived from modified CsgF and/or CsgG, or a homologue thereof. In other words, a construct may contain more than one monomer. In another aspect, the invention also provides a pore complex comprising at least one construct of the invention. The pore complex contains sufficient constructs and, if necessary, monomers to form the pore. For instance, an octameric pore may comprise (a) four constructs each comprising two monomers, (b) two constructs each comprising four monomers, (c) one construct comprising two monomers and six monomers that do not form part of a construct, or (d) one or two CsgF monomers in one construct, and one construct with six to seven CsgG monomers or even (e) a construct with CsgF and CsgG monomer in addition to another construct solely comprising CsgG monomers. Same and additional possibilities are provided for a nonameric pore for instance. Other combinations of constructs and monomers can be envisaged by the skilled person. One or more constructs of the invention may be used to form a pore complex for characterising, such as sequencing, polynucleotides. The construct may comprise at least 2, at least 3, at least 4, at least 5, at least 6, at least 7, at least 8, at least 9 or at least 10 monomers. The construct preferably comprises two monomers. The two or more monomers may be the same or different, may be CsgF, CsgG, CsgG/CsgF fusion monomers or homologues thereof, or any combination thereof.

Another embodiment relates to the polynucleotide or nucleic acid molecule encoding said modified CsgF peptides of the invention, or homologues or mutants thereof, or polynucleotides encoding a construct as described above.

Certain embodiments relate to an isolated transmembrane pore complex comprising the isolated pore complex according to the first and second aspect of the invention, and the components of a membrane. Said isolated transmembrane pore complex is directly applicable for use in molecular sensing, such as nucleic acid sequencing. Alternatively, a membranous composition is provided, comprising a modified CsgG/CsgF biological pore as described herein, according to the isolated pore complex of the invention, and a membrane, membrane components, or an insulating layer. One embodiment relates to an isolated transmembrane pore complex consisting of the isolated pore complex according to the invention, and the components of a membrane.

Although the CsgG:CsgF complex is very stable, when CsgF is truncated, the stability of CsgG:CsgF complexes decrease compared to a complex comprising full length CsgF. Therefore, disulphide bonds can be made between CsgG and CsgF to make the complex more stable, for example following introduction of cysteine residues at the positions identified herein. The pore complex can be made in any of the previously mentioned methods and disulphide bond formation can be induced by using oxidising agents (eg: Copper-orthophenanthroline). Other interactions (eg: hydrophobic interactions, charge-charge interactions/electrostatic interactions) can also be used in those positions instead of cysteine interactions.

In another embodiment, unnatural amino acids can also be incorporated in those positions. In this embodiment, covalent bonds made be made by via click chemistry. For example, unnatural amino acids with azide or alkyne or with a dibenzocyclooctyne (DBCO) group and/or a bicyclo [6.1.0]nonyne (BCN) group may be introduced at one or more of these positions.

Such stabilising mutations can be combined with any other modifications to CsgG and/or CsgF, for example the modifications disclosed herein.

The CsgG pore may comprise at least one, such as 2, 3, 4, 5, 6, 7, 8, 9 or 10, CsgG monomers that is/are modified to facilitate attachment to the CsgF peptide. For example a cysteine residue may be introduced at one or more of the positions corresponding to positions 132, 133, 136, 138, 140, 142, 144, 145, 147, 149, 151, 153, 155, 183, 185, 187, 189, 191, 201, 203, 205, 207 and 209 of SEQ ID NO: 3, and/or at any one of the positions identified in Table 4 as being predicted to make contact with CsgF, to facilitate covalent attachment to CsgG. As an alternative or addition to covalent attachment via cysteine residues, the pore may be stabilised by hydrophobic interactions or electrostatic interactions. To facilitate such interactions, a non-native reactive or photoreactive amino acid at a position corresponding to one or more of positions 132, 133, 136, 138, 140, 142, 144, 145, 147, 149, 151, 153, 155, 183, 185, 187, 189, 191, 201, 203, 205, 207 and 209 of SEQ ID NO: 3, and/or at any one of the positions identified in Table 4 as being predicted to make contact with CsgF.

The CsgF peptide may be modified to facilitate attachment to the CsgG pore. For example a cysteine residue may be introduced at one or more of the positions corresponding to positions 1, 4, 5, 8, 9, 11, 12, 26 or 29 of SEQ ID NO: 6, and/or at any one of the positions identified in Table 4 as being predicted to make contact with CsgF, to facilitate covalent attachment to CsgG. As an alternative or addition to covalent attachment via cysteine residues, the pore may be stabilised by hydrophobic interactions or electrostatic interactions. To facilitate such interactions, a non-native reactive or photoreactive amino acid at a position corresponding to one or more of positions 1, 4, 5, 8, 9, 11, 12, 26 or 29 of SEQ ID NO: 6, and/or at any one of the positions identified in Table 4 as being predicted to make contact with CsgF.

Preferred exemplary CsgF peptides include comprise the following mutations relative to SEQ ID NO: 6: N15$X_1$/ N17$X_2$/A20$X_3$/N24$X_4$/A28$X_5$/D34$X_6$, wherein $X_1$ is N/S/ A/T/Q/G/L/V/I/F/Y/W/R/K/D/C, $X_2$ is N/S/A/T/Q/G/L/V/I/ F/Y/W/R/K/D/C, $X_3$ is A/S/T/Q/N/G/L/V/I/F/Y/W/R/K/D/ C, $X_4$ is N/S/T/Q/A/G/L/V/I/F/Y/W/R/K/D/C, $X_5$ is A/S/T/ Q/N/G/L/V/I/F/Y/W/R/K/D/C and $X_5$ is D/F/Y/W/R/K/N/ Q/C. The mutations at positions N15, N17, A20, N24 and A28 are constriction mutations and the mutation at position 34 affects the interaction pf CsgF with the bottom of the CsgG pore to stabilise the interaction.

CsgG Pore

The CsgG pore may be a homo-oligomeric pore comprising identical mutant monomers of the invention. The CsgG pore may be a hetero-oligomeric pore derived from CsgG, for example comprising at least one mutant monomer as disclosed herein.

The CsgG pore may contain any number of mutant monomers. The pore typically comprises at least 7, at least 8, at least 9 or at least 10 identical mutant monomers, such as 7, 8, 9 or 10 mutant monomers. The CsgG pore preferably comprises eight or nine identical mutant monomers.

In a preferred embodiment, all of the monomers in the hetero-oligomeric CsgG pore (such as 10, 9, 8 or 7 of the monomers) are mutant monomers as disclosed herein, wherein at least one of them differs from the others. They may all differ from one another.

The mutant monomers in the CsgG pore are preferably all approximately the same length or are the same length. The barrels of the mutant monomers of the invention in the pore are preferably approximately the same length or are the same length. Length may be measured in number of amino acids and/or units of length.

A mutant monomer may be a variant of SEQ ID NO: 3. Over the entire length of the amino acid sequence of SEQ ID NO: 3, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 3 over the entire sequence. There may be at least 80%, for example at least 85%, 90% or 95%, amino acid identity over a stretch of 100 or more, for example 125, 150, 175 or 200 or more, contiguous amino acids ("hard homology").

CsgG monomers are highly conserved (as can be readily appreciated from FIGS. 45 to 47 of WO2017/149317). Furthermore, from knowledge of the mutations in relation to SEQ ID NO: 3 it is possible to determine the equivalent positions for mutations of CsgG monomers other than that of SEQ ID NO: 3.

Thus reference to a mutant CsgG monomer comprising a variant of the sequence as shown in SEQ ID NO: 3 and specific amino-acid mutations thereof as set out in the claims and elsewhere in the specification also encompasses a mutant CsgG monomer comprising a variant of the sequence as shown in SEQ ID NOs: 68 to 88 and corresponding amino-acid mutations thereof. Likewise reference to a construct, pore or method involving the use of a pore relating to a mutant CsgG monomer comprising a variant of the sequence as shown in SEQ ID NO: 3 and specific amino-acid mutations thereof as set out in the claims and elsewhere in the specification also encompasses a construct, pore or method relating to a mutant CsgG monomer comprising a variant of the sequence according the above disclosed SEQ ID NOs and corresponding amino-acid mutations thereof. If will further be appreciated that the invention extends to other variant CsgG monomers not expressly identified in the specification that show highly conserved regions.

Standard methods in the art may be used to determine homology. For example the UWGCG Package provides the BESTFIT program which can be used to calculate homology, for example used on its default settings (Devereux et al (1984) Nucleic Acids Research 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (ncbi.nlm.nih.gov/).

SEQ ID NO: 3 is the wild-type CsgG monomer from Escherichia coli Str. K-12 substr. MC4100. A variant of SEQ ID NO: 3 may comprise any of the substitutions present in another CsgG homologue. Preferred CsgG homologues are shown in SEQ ID NOs: 68 to 88. The variant may comprise combinations of one or more of the substitutions present in SEQ ID NOs: 68 to 88 compared with SEQ ID NO: 3. For example, mutations may be made at any one or more of the positions in SEQ ID NO: 3 that differ between SEQ ID NO: 3 and any one of SEQ ID NOs: 68 to 88. Such a mutation may be a substitution of an amino acid in SEQ ID NO: 3 with an amino acid from the corresponding position in any one of SEQ ID NOs: 68 to 88. Alternatively, the mutation at any one of these positions may be a substitution with any amino acid, or may be a deletion or insertion mutation, such as deletion or insertion of 1 to 10 amino acids, such as of 2 to 8 or 3 to 6 amino acids. Other than the mutations disclosed herein, the amino acids that are conserved between SEQ ID NO: 3 and all of SEQ ID NOs: 66 to 88 are preferably present in a variant of the invention. However, conservative mutations may be made at any one or more of these positions that are conserved between SEQ ID NO: 3 and all of SEQ ID NOs: 66 to 88.

The invention provides a pore-forming CsgG mutant monomer that comprises any one or more of the amino acids described herein as being substituted into a specific position of SEQ ID NO: 3 at a position in the structure of the CsgG monomer that corresponds to the specific position in SEQ ID NO: 3. Corresponding positions may be determined by standard techniques in the art. For example, the PILEUP and BLAST algorithms mentioned above can be used to align the sequence of a CsgG monomer with SEQ ID NO: 3 and hence to identify corresponding residues.

The pore-forming mutant monomer typically retains the ability to form the same 3D structure as the wild-type CsgG monomer, such as the same 3D structure as a CsgG monomer having the sequence of SEQ ID NO: 3. The 3D structure of CsgG is known in the art and is disclosed, for example, in Goyal et al (2014) Nature 516(7530):250-3. Any number of mutations may be made in the wild-type CsgG sequence in addition to the mutations described herein provided that the CsgG mutant monomer retains the improved properties imparted on it by the mutations of the present invention.

Typically the CsgG monomer will retain the ability to form a structure comprising three alpha-helicies and five beta-sheets. Mutations may be made at least in the region of CsgG which is N-terminal to the first alpha helix (which starts at S63 in SEQ ID NO:3), in the second alpha helix (from G85 to A99 of SEQ ID NO: 3), in the loop between the second alpha helix and the first beta sheet (from Q100 to N120 of SEQ ID NO: 3), in the fourth and fifth beta sheets (S173 to R192 and R198 to T107 of SEQ ID NO: 3, respectively) and in the loop between the fourth and fifth beta sheets (F193 to Q197 of SEQ ID NO: 3) without affecting the ability of the CsgG monomer to form a transmembrane pore, which transmembrane pore is capable of translocating polypeptides. Therefore, it is envisaged that further mutations may be made in any of these regions in any CsgG monomer without affecting the ability of the monomer to form a pore that can translocate polynucleotides. It is also expected that mutations may be made in other regions, such as in any of the alpha helicies (S63 to R76, G85 to A99 or V211 to L236 of SEQ ID NO: 3) or in any of the beta sheets (1121 to N133, K135 to R142, I146 to R162, S173 to R192 or R198 to T107 of SEQ ID NO: 3) without affecting the ability of the monomer to form a pore that can translocate polynucleotides. It is also expected that deletions of one or more amino acids can be made in any of the loop regions linking the alpha helicies and beta sheets and/or in the N-terminal and/or C-terminal regions of the CsgG monomer without affecting the ability of the monomer to form a pore that can translocate polynucleotides.

Amino acid substitutions may be made to the amino acid sequence of SEQ ID NO: 3 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 1 above. Where amino acids have similar polarity, this can also be determined by reference to the hydropathy scale for amino acid side chains in Table 2.

One or more amino acid residues of the amino acid sequence of SEQ ID NO: 3 may additionally be deleted from the polypeptides described above. Up to 1, 2, 3, 4, 5, 10, 20 or 30 or more residues may be deleted.

Variants may include fragments of SEQ ID NO: 3. Such fragments retain pore forming activity. Fragments may be at least 50, at least 100, at least 150, at least 200 or at least 250 amino acids in length. Such fragments may be used to produce the pores. A fragment preferably comprises the membrane spanning domain of SEQ ID NO: 3, namely K135-Q153 and S183-S208.

One or more amino acids may be alternatively or additionally added to the polypeptides described above. An extension may be provided at the amino terminal or carboxy terminal of the amino acid sequence of SEQ ID NO: 3 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

A CsgG pore as described herein includes a wild type CsgG pore, or a homologue or a mutant/variant thereof. A variant is a polypeptide that has an amino acid sequence which varies from that of SEQ ID NO: 3 and which retains its ability to form a pore. A variant typically contains the regions of SEQ ID NO: 3 that are responsible for pore formation. The pore forming ability of CsgG, which contains a β-barrel, is provided by β-sheets in each subunit. A variant of SEQ ID NO: 3 typically comprises the regions in SEQ ID NO: 3 that form β-sheets, namely K134-Q154 and S183-S208. One or more modifications can be made to the regions of SEQ ID NO: 3 that form β-sheets as long as the resulting variant retains its ability to form a pore. A variant of SEQ ID NO: 3 preferably includes one or more modifications, such as substitutions, additions or deletions, within its α-helices and/or loop regions.

The mutant CsgG monomers may be a mutant CsgG monomer, which is a monomer whose sequence varies from that of a wild-type CsgG monomer and which retains the ability to form a pore. A mutant monomer may also be referred to herein as a variant. Methods for confirming the ability of mutant monomers to form pores are well-known in the art and are discussed in more detail below.

Particular pore-forming CsgG mutant monomers that may be included in the CsgG pore may comprise any one or more of the following modifications:
a W at a position corresponding to R97 in SEQ ID NO:3;
a W at a position corresponding to R93 in SEQ ID NO:3;
a Y at a position corresponding to R97 in SEQ ID NO: 3;
a Y at a position corresponding to R93 in SEQ ID NO: 3;
a Y at each of the positions corresponding to R93 and R97 in SEQ ID NO: 3;
a D at the position corresponding to R192 in SEQ ID NO:3;
deletion of the residues at the positions corresponding to V105-I107 in SEQ ID NO:3;
deletion of the residues at one or more of the positions corresponding to F193 to L199 in SEQ ID NO: 3;
deletion of the residues the positions corresponding to F195 to L199 in SEQ ID NO: 3;
deletion of the residues the positions corresponding to F193 to L199 in SEQ ID NO: 3;
a T at the position corresponding to F191 in SEQ ID NO: 3;
a Q at the position corresponding to K49 in SEQ ID NO: 3;
a N at the position corresponding to K49 in SEQ ID NO: 3;
a Q at the position corresponding to K42 in SEQ ID NO: 3;
a Q at the position corresponding to E44 in SEQ ID NO: 3;
a N at the position corresponding to E44 in SEQ ID NO: 3;
a R at the position corresponding to L90 in SEQ ID NO: 3;
a R at the position corresponding to L91 in SEQ ID NO: 3;
a R at the position corresponding to I95 in SEQ ID NO: 3;
a R at the position corresponding to A99 in SEQ ID NO: 3;
a H at the position corresponding to E101 in SEQ ID NO: 3;
a K at the position corresponding to E101 in SEQ ID NO: 3;
a N at the position corresponding to E101 in SEQ ID NO: 3;
a Q at the position corresponding to E101 in SEQ ID NO: 3;
a T at the position corresponding to E101 in SEQ ID NO: 3;
a K at the position corresponding to Q114 in SEQ ID NO: 3.

The CsgG pore-forming monomer preferably further comprises an A at the position corresponding to Y51 in SEQ ID NO: 3 and/or a Q at the position corresponding to F56 in SEQ ID NO: 3.

Pores constructed from the CsgG monomers comprising a R to W substitution at the position corresponding to position 97 of SEQ ID NO: 3 display an increased accuracy as compared to otherwise identical pores without the modification at 97 when characterizing (or sequencing) target polynucleotides. An increased accuracy is also seen when instead of R97W the CsgG monomers comprise the modification R to W at a position corresponding to position 97 of SEQ ID NO: 3 or the modifications R to Y at positions corresponding to positions 93 and 97 of SEQ ID NO: 3. Accordingly, pores may be constructed from one or more mutant CsgG monomers that comprise a modification at positions corresponding to R97 or R93 of SEQ ID NO: 3 such that the modification increases the hydrophobicity of the amino acid. For example, such modification may include an amino acid substitution with any amino acid containing a hydrophobic side chain, including, e.g., but not limited to W and Y.

CsgG monomers that comprise a R to D, Q, F, S or T mutation at a position corresponding to position 192 of SEQ ID NO: 3 are easier to express than monomers which do not have a substitution at position 192 which may be due to the reduction of positive charge. Accordingly position 192 may be substituted with an amino-acid which reduces the positive charge. Monomers that comprise R192D/Q/F/S/T may also comprise additional modifications which improve the ability of mutant pores formed from the monomers to interact with and characterise analytes, such as polynucleotides. However, in one embodiment it is preferred that the residue at the position corresponding to position 193 of SEQ ID NO: 3 is R or K, more preferably R.

Pores comprising CsgG monomers that comprise a deletion of V105, A106 and I107, a deletion of F193, I194, D195, Y196, Q197, R198 and L199 or a deletion of D195, Y196, Q197, R198 and L199, and/or F191T display an increased accuracy when characterizing (or sequencing) target polynucleotides. The amino-acids at positions 105 to 107 correspond to the cis-loops in the cap of the nanopore and the amino-acids at positions 193 to 199 correspond to the trans-loops at the other end of the pore. Without wishing to be bound by theory it is thought that deletion of the cis-loops improves the interaction of the enzyme with the pore and removal of the trans-loops decreases any unwanted interaction between DNA on the trans side of the pore.

Pores comprising CsgG monomers that comprise a K to Q or K to N mutations at a position corresponding to K94 of SEQ ID NO: 3 show a reduction in the number of noisy pores (namely those pores that give rise to an increased signal:noise ratio) as compared to identical pores without the mutation at 94 when characterizing (or sequencing) target polynucleotides. Position 94 is found within the vestibule of the pore and was found to be a particularly sensitive position in relation to the noise of the current signal.

Pores comprising the CsgG monomers that comprise T104K or T104R, N91R, E101K/N/Q/T/H, E44N/Q, Q114K, A99R, I95R, N91R, L90R, E44Q/N and/or Q42K, or corresponding mutations, all demonstrate an improved ability to capture target polynucleotides when used to characterize (or sequence) target polynucleotides as compared to identical pores without substitutions at these positions.

In one embodiment, the CsgG pore comprises one or more monomers that are variants of SEQ ID NO: 3 comprising (a) one or more mutations at the following positions (i.e. mutations at one or more of the following positions) I41, R93, A98, Q100, G103, T104, A106, I107, N108, L113, S115, T117, Y130, K135, E170, S208, D233, D238 and E244 and/or (b) one or more of D43S, E44S, F48S/N/Q/Y/W/I/V/H/R/K, Q87N/R/K, N91K/R, K94R/F/Y/W/L/S/N, R97F/Y/W/V/I/K/S/Q/H, E101I/L/A/H, N102K/Q/L/I/V/S/H, R110F/G/N, Q114R/K, R142Q/S, T150Y/A/V/L/S/Q/N, R192D/Q/F/S/T and D248S/N/Q/K/R. The variant may comprise (a); (b); or (a) and (b). In some embodiments, the variant comprises R97W. In some embodiments, the variant comprises R192D/Q/F/S/T, such as R192D/Q. In (a), the variant may comprise modifications at any number and combination of the positions, such as 1, 2, 3, 4, 5, 6, 7, 8, 9, 10, 11, 12, 13, 14, 15, 16, 17, 18 or 19 of the positions.

In (a), the variant preferably comprises one or more of I41N, R93F/Y/W/L/I/V/N/Q/S, A98K/R, Q100K/R, G103F/W/S/N/K/R, T104R/K, A106R/K, I107R/K/W/F/Y/L/V, N108R/K, L113K/R, S115R/K, T117R/K, Y130W/F/H/Q/N, K135L/V/N/Q/S, E170S/N/Q/K/R, S208V/I/F/W/Y/L/T, D233S/N/Q/K/R, D238S/N/Q/K/R and E244S/N/Q/K/R.

In (a), the variant preferably comprises one or more modifications which provide more consistent movement of a target polynucleotide with respect to, such as through, a transmembrane pore comprising the monomer. In particular, in (a), the variant preferably comprises one or more mutations at the following positions (i.e. mutations at one or more of the following positions) R93, G103 and I107. The variant may comprise R93; G103; I107; R93 and G103; R93 and I107; G103 and I107; or R93, G103 and I107. The variant preferably comprises one or more of R93F/Y/W/L/I/V/N/Q/S, G103F/W/S/N/K/R and I107R/K/W/F/Y/L/V. These may be present in any combination shown for the positions R93, G103 and I107.

In (a), the variant preferably comprises one or modifications which allow pores constructed from the mutant monomers preferably capture nucleotides and polynucleotides more easily. In particular, in (a), the variant preferably comprises one or more mutations at the following positions (i.e. mutations at one or more of the following positions) I41, T104, A106, N108, L113, S115, T117, E170, D233, D238 and E244. The variant may comprise modifications at any number and combination of the positions, such as 1, 2, 3, 4, 5, 6, 7, 8, 9, 10 or 11 of the positions. The variant preferably comprises one or more of I41N, T104R/K, A106R/K, N108R/K, L113K/R, S115R/K, T117R/K, E170S/N/Q/K/R, D233S/N/Q/K/R, D238S/N/Q/K/R and E244S/N/Q/K/R. Additionally or alternatively the variant may comprise (c) Q42K/R, E44N/Q, L90R/K, N91R/K, I95R/K, A99R/K, E101H/K/N/Q/T and/or Q114K/R.

In (a), the variant preferably comprises one or more modifications which provide more consistent movement and increase capture. In particular, in (a), the variant preferably comprises one or more mutations at the following positions (i.e. mutations at one or more of the following positions) (i) A98, (ii) Q100, (iii) G103 and (iv) I107. The variant preferably comprises one or more of (i) A98R/K, (ii) Q100K/R, (iii) G103K/R and (iv) I107R/K.

Particularly preferred mutant monomers which provide for increased capture of analytes, such as a polynucleotides include a mutation at one or more of positions Q42, E44, E44, L90, N91, I95, A99, E101 and Q114, which mutation removes the negative charge and/or increases the positive charge at the mutated positions. In particular, the following mutations may be included in a mutant monomer of the invention to produce a CsgG pore that has an improved ability to capture an analyte, preferably a polynucleotide: Q42K, E44N, E44Q, L90R, N91R, I95R, A99R, E101H, E101K, E101N, E101Q, E101T and Q114K. Examples of particular mutant monomers which comprise one of these mutations in combination with other beneficial mutations are:

CsgG-(WT-Y51A/F56Q/K94Q/R97W/R192D-del(V105-I107)-Q42K
CsgG-(WT-Y51A/F56Q/K94Q/R97W/R192D-del(V105-I107)-E44N
CsgG-(WT-Y51A/F56Q/K94Q/R97W/R192D-del(V105-I107)-E44Q
CsgG-(WT-Y51A/F56Q/K94Q/R97W/R192D-del(V105-I107)-L90R
CsgG-(WT-Y51A/F56Q/K94Q/R97W/R192D-del(V105-I107)-N91R
CsgG-(WT-Y51A/F56Q/K94Q/R97W/R192D-del(V105-I107)-I95R
CsgG-(WT-Y51A/F56Q/K94Q/R97W/R192D-del(V105-I107)-A99R
CsgG-(WT-Y51A/F56Q/K94Q/R97W/R192D-del(V105-I107)-E101H
CsgG-(WT-Y51A/F56Q/K94Q/R97W/R192D-del(V105-I107)-E101K
CsgG-(WT-Y51A/F56Q/K94Q/R97W/R192D-del(V105-I107)-E101N
CsgG-(WT-Y51A/F56Q/K94Q/R97W/R192D-del(V105-I107)-E101Q
CsgG-(WT-Y51A/F56Q/K94Q/R97W/R192D-del(V105-I107)-E101T
CsgG-(WT-Y51A/F56Q/K94Q/R97W/R192D-del(V105-I107)-Q114K.

In (a), the variant preferably comprises one or more modifications which provide increased characterisation accuracy. In particular, in (a), the variant preferably comprises one or more mutations at the following positions (i.e. mutations at one or more of the following positions) Y130, K135 and S208, such as Y130; K135; S208; Y130 and K135; Y130 and S208; K135 and S208; or Y130, K135 and S208. The variant preferably comprises one or more of Y130W/F/H/Q/N, K135L/V/N/Q/S and R142Q/S. These substitutions may be present in any number and combination as set out for Y130, K135 and S208.

In (b), the variant may comprise any number and combination of the substitutions, such as 1, 2, 3, 4, 5, 6, 7, 8, 9, 10, 11 or 12 of the substitutions. In (b), the variant preferably comprises one or more modifications which provide more consistent movement of a target polynucleotide with respect to, such as through, a transmembrane pore comprising the monomer. In particular, in (b), the variant preferably comprises one or more one or more of (i) Q87N/R/K, (ii) K94R/F/Y/W/L/S/N, (iii) R97F/Y/W/V/I/K/S/Q/H, (iv) N102K/Q/L/I/V/S/H and (v) R110F/G/N. More preferably, the variant comprises K94D or K94Q and/or R97W or R97Y. Other preferred variants that are modified to provide more consistent movement of a target polynucleotide with respect to, such as through, a transmembrane pore comprising the monomer include (vi) R93W and R93Y. A preferred variant may comprise R93W and R97W, R93Y and R97W, R93W and R97W, or more preferably R93Y and R97Y.

In (b), the variant preferably comprises one or modifications which allow pores constructed from the mutant monomers preferably capture nucleotides and polynucleotides more easily. In particular, in (b), the variant preferably comprises one or more of (i) D43S, (ii) E44S, (iii) N91K/R, (iv) Q114R/K and (v) D248S/N/Q/K/R.

In (b), the variant preferably comprises one or more modifications which provide more consistent movement and increase capture. In particular, in (b), the variant preferably comprises one or more of Q87R/K, E101I/L/A/H and N102K, such as Q87R/K; E101I/L/A/H; N102K; Q87R/K and E101I/L/A/H; Q87R/K and N102K; E101I/L/A/H and N102K; or Q87R/K, E101I/L/A/H and N102K.

In (b), the variant preferably comprises one or more modifications which provide increased characterisation accuracy. In particular, in (a), the variant preferably comprises F48S/N/Q/Y/W/I/V.

In (b), the variant preferably comprises one or more modifications which provide increased characterisation accuracy and increased capture. In particular, in (a), the variant preferably comprises F48H/R/K.

The variant may comprise modifications in both (a) and (b) which provide more consistent movement. The variant may comprise modifications in both (a) and (b) which provide increased capture.

The invention provides variants of SEQ ID NO: 3 which provide an increased throughput of an assay for characterising an analyte, such as a polynucleotide, using a pore comprising the variant. Such variants may comprise a mutation at K94, preferably K94Q or K94N, more preferably K94Q. Examples of particular mutant monomers which comprise a K94Q or K94N mutation in combination with other beneficial mutations are:

CsgG-(WT-Y51A/F56Q/R97W/R192D-StrepII)9-K94N
CsgG-(WT-Y51A/F56Q/R97W/R192D-StrepII)9-K94Q.

Using monomers that are variants of SEQ ID NO: 3 to form the CsgG pore can provide increased characterisation accuracy in an assay for characterising an analyte, such as a polynucleotide. Such variants include variants that comprise: a mutation at F191, preferably F191T; deletion of V105-I107; deletion of F193-L199 or of D195-L199; and/or a mutation at R93 and/or R97, preferably R93Y, R97Y, or more preferably, R97W, R93W or both R97Y and R97Y. Examples of particular mutant monomers which comprise one or more of these mutations in combination with other beneficial mutations are:

CsgG-(WT-Y51A/F56Q/R97W/R192D-StrepII)9-del (D195-L199)
CsgG-(WT-Y51A/F56Q/R97W/R192D-StrepII)9-del (F193-L199)
CsgG-(WT-Y51A/F56Q/R97W/R192D-StrepII)9-F191T
CsgG-(WT-Y51A/F56Q/R97W/R192D-del(V105-I107)-StrepII)9
CsgG-(WT-Y51A/F56Q/K94Q/R97W/R192D-del(V105-I107)
CsgG-(WT-Y51A/F56Q/R192D-StrepII)9-R93W
CsgG-(WT-Y51A/F56Q/R192D-StrepII)9-R93W-del (D195-L199)
CsgG-(WT-Y51A/F56Q/R192D-StrepII)9-R93Y/R97Y.

In another embodiment, the variant of SEQ ID NO: 3 comprises (A) deletion of one or more positions R192, F193, I194, D195, Y196, Q197, R198, L199, L200 and E201 and/or (B) deletion of one or more of V139/G140/D149/T150/V186/Q187/V204/G205 (called band 1 herein), G137/G138/Q151/Y152/Y184/E185/Y206/T207 (called band 2 herein) and A141/R142/G147/A148/A188/G189/G202/E203 (called band 3 herein).

In (A), the variant may comprise deletion of any number and combination of the positions, such as 1, 2, 3, 4, 5, 6, 7, 8, 9 or 10 of the positions. In (A), the variant preferably comprises deletion of D195, Y196, Q197, R198 and L199;
R192, F193, I194, D195, Y196, Q197, R198, L199 and L200;
Q197, R198, L199 and L200;
I194, D195, Y196, Q197, R198 and L199;
D195, Y196, Q197, R198, L199 and L200;
Y196, Q197, R198, L199, L200 and E201;
Q197, R198, L199, L200 and E201;
Q197, R198, L199; or
F193, I194, D195, Y196, Q197, R198 and L199.

More preferably, the variant comprises deletion of D195, Y196, Q197, R198 and L199 or F193, I194, D195, Y196, Q197, R198 and L199. In (B), any number and combination of bands 1 to 3 may be deleted, such as band 1; band 2; band 3; bands 1 and 2; bands 1 and 3; bands 2 and 3; or bands 1, 2 and 3. The variant may comprise deletions according to (A); (B); or (A) and (B).

The variants comprising deletion of one or more positions according to (A) and/or (B) above may further comprise any of the modifications or substitutions discussed above and below. If the modifications or substitutions are made at one or more positions which appear after the deletion positions in SEQ ID NO: 3, the numbering of the one or more positions of the modifications or substitutions must be adjusted accordingly. For instance, if L199 is deleted, E244 becomes E243. Similarly, if band 1 is deleted, R192 becomes R186.

In another embodiment, the variant of SEQ ID NO: 3 comprises (C) deletion of one or more positions V105, A106 and I107. The deletions in accordance with (C) may be made in addition to deletions according to (A) and/or (B).

The above-described deletions typically reduce the noise associated with the movement of the target polynucleotide with respect to, such as through, a transmembrane pore comprising the monomer. As a result the target polynucleotide can be characterised more accurately.

In the paragraphs above where different amino acids at a specific positon are separated by the / symbol, the/symbol means "or". For instance, Q87R/K means Q87R or Q87K.

The variants of SEQ ID NO: 3 which provide increased capture of an analyte, such as a polynucleotide may comprise a mutation at T104, preferably T104R or T104K, a mutation at N91, preferably N91R, a mutation at E101, preferably E101K/N/Q/T/H, a mutation at position E44, preferably E44N or E44Q and/or a mutation at position Q42, preferably Q42K.

The mutations at different positions in SEQ ID NO: 3 may be combined in any possible way. In particular, a monomer in the CsgG pore may comprise one or more mutation that improves accuracy, one ore more mutation that reduces noise and/ore one or more mutation that enhances capture of an analyte.

The variant of SEQ ID NO: 3 preferably comprises one or more of the following (i) one or more mutations at the following positions (i.e. mutations at one or more of the following positions) N40, D43, E44, S54, S57, Q62, R97, E101, E124, E131, R142, T150 and R192, such as one or more mutations at the following positions (i.e. mutations at one or more of the following positions) N40, D43, E44, S54, S57, Q62, E101, E131 and T150 or N40, D43, E44, E101 and E131; (ii) mutations at Y51/N55, Y51/F56, N55/F56 or Y51/N55/F56; (iii) Q42R or Q42K; (iv) K49R; (v) N102R, N102F, N102Y or N102W; (vi) D149N, D149Q or D149R; (vii) E185N, E185Q or E185R; (viii) D195N, D195Q or D195R; (ix) E201N, E201Q or E201R; (x) E203N, E203Q or E203R; and (xi) deletion of one or more of the following positions F48, K49, P50, Y51, P52, A53, S54, N55, F56 and S57. The variant may comprise any combination of (i) to (xi).

If the variant comprises any one of (i) and (iii) to (xi), it may further comprise a mutation at one or more of Y51, N55 and F56, such as at Y51, N55, F56, Y51/N55, Y51/F56, N55/F56 or Y51/N55/F56.

In (i), the variant may comprises mutations at any number and combination of N40, D43, E44, S54, S57, Q62, R97, E101, E124, E131, R142, T150 and R192. In (i), the variant preferably comprises one or more mutations at the following positions (i.e. mutations at one or more of the following positions) N40, D43, E44, S54, S57, Q62, E101, E131 and T150. In (i), the variant preferably comprises one or more mutations at the following positions (i.e. mutations at one or more of the following positions) N40, D43, E44, E101 and E131. In (i), the variant preferably comprises a mutation at S54 and/or S57. In (i), the variant more preferably comprises a mutation at (a) S54 and/or S57 and (b) one or more of Y51, N55 and F56, such as at Y51, N55, F56, Y51/N55, Y51/F56, N55/F56 or Y51/N55/F56. If S54 and/or S57 are deleted in (xi), it/they cannot be mutated in (i) and vice versa. In (i), the variant preferably comprises a mutation at T150, such as T150I. Alternatively the variant preferably comprises a mutation at (a) T150 and (b) one or more of Y51, N55 and F56, such as at Y51, N55, F56, Y51/N55, Y51/F56, N55/F56 or Y51/N55/F56. In (i), the variant preferably comprises a mutation at Q62, such as Q62R or Q62K. Alternatively the variant preferably comprises a mutation at (a) Q62 and (b) one or more of Y51, N55 and F56, such as at Y51, N55, F56, Y51/N55, Y51/F56, N55/F56 or Y51/N55/F56. The variant may comprise a mutation at D43, E44, Q62 or any combination thereof, such as D43, E44, Q62, D43/E44, D43/Q62, E44/Q62 or D43/E44/Q62. Alternatively the variant preferably comprises a mutation at (a) D43, E44, Q62, D43/E44, D43/Q62, E44/Q62 or D43/E44/Q62 and (b) one or more of Y51, N55 and F56, such as at Y51, N55, F56, Y51/N55, Y51/F56, N55/F56 or Y51/N55/F56.

In (ii) and elsewhere in this application where different positions are separated by the/symbol, the/symbol means "and" such that Y51/N55 is Y51 and N55. In (ii), the variant preferably comprises mutations at Y51/N55. It has been proposed that the constriction in CsgG is composed of three stacked concentric rings formed by the side chains of residues Y51, N55 and F56 (Goyal et al, 2014, Nature, 516, 250-253). Mutation of these residues in (ii) may therefore decrease the number of nucleotides contributing to the current as the polynucleotide moves through the pore and thereby make it easier to identify a direct relationship between the observed current (as the polynucleotide moves through the pore) and the polynucleotide. F56 may be mutated in any of the ways discussed below with reference to variants and pores useful in the method of the invention.

In (v), the variant may comprise N102R, N102F, N102Y or N102W. The variant preferably comprises (a) N102R, N102F, N102Y or N102W and (b) a mutation at one or more of Y51, N55 and F56, such as at Y51, N55, F56, Y51/N55, Y51/F56, N55/F56 or Y51/N55/F56.

In (xi), any number and combination of K49, P50, Y51, P52, A53, S54, N55, F56 and S57 may be deleted. Preferably one or more of K49, P50, Y51, P52, A53, S54, N55 and S57 may be deleted. If any of Y51, N55 and F56 are deleted in (xi), it/they cannot be mutated in (ii) and vice versa.

In (i), the variant preferably comprises one of more of the following substitutions N40R, N40K, D43N, D43Q, D43R, D43K, E44N, E44Q, E44R, E44K, S54P, S57P, Q62R, Q62K, R97N, R97G, R97L, E101N, E101Q, E101R, E101K, E101F, E101Y, E101W, E124N, E124Q, E124R, E124K, E124F, E124Y, E124W, E131D, R142E, R142N, T150I, R192E and R192N, such as one or more of N40R, N40K, D43N, D43Q, D43R, D43K, E44N, E44Q, E44R, E44K, S54P, S57P, Q62R, Q62K, E101N, E101Q, E101R, E101K, E101F, E101Y, E101W, E131D and T150I, or one or more of N40R, N40K, D43N, D43Q, D43R, D43K, E44N, E44Q, E44R, E44K, E101N, E101Q, E101R, E101K, E101F, E101Y, E101W and E131D. The variant may comprise any number and combination of these substitutions. In (i), the variant preferably comprises S54P and/or S57P. In (i), the variant preferably comprises (a) S54P and/or S57P and (b) a mutation at one or more of Y51, N55 and F56, such as at Y51, N55, F56, Y51/N55, Y51/F56, N55/F56 or Y51/N55/F56. The mutations at one or more of Y51, N55 and F56 may be any of those discussed below. In (i), the variant preferably comprises F56A/S57P or S54P/F56A. The variant preferably comprises T150I. Alternatively the variant preferably comprises a mutation at (a) T150I and (b) one or more of Y51, N55 and F56, such as at Y51, N55, F56, Y51/N55, Y51/F56, N55/F56 or Y51/N55/F56.

In (i), the variant preferably comprises Q62R or Q62K. Alternatively the variant preferably comprises (a) Q62R or Q62K and (b) a mutation at one or more of Y51, N55 and F56, such as at Y51, N55, F56, Y51/N55, Y51/F56, N55/F56 or Y51/N55/F56. The variant may comprise D43N, E44N, Q62R or Q62K or any combination thereof, such as D43N, E44N, Q62R, Q62K, D43N/E44N, D43N/Q62R, D43N/Q62K, E44N/Q62R, E44N/Q62K, D43N/E44N/Q62R or D43N/E44N/Q62K. Alternatively the variant preferably comprises (a) D43N, E44N, Q62R, Q62K, D43N/E44N, D43N/Q62R, D43N/Q62K, E44N/Q62R, E44N/Q62K, D43N/E44N/Q62R or D43N/E44N/Q62K and (b) a mutation at one or more of Y51, N55 and F56, such as at Y51, N55, F56, Y51/N55, Y51/F56, N55/F56 or Y51/N55/F56.

In (i), the variant preferably comprises D43N.

In (i), the variant preferably comprises E101R, E101S, E101F or E101N.

In (i), the variant preferably comprises E124N, E124Q, E124R, E124K, E124F, E124Y, E124W or E124D, such as E124N.

In (i), the variant preferably comprises R142E and R142N.

In (i), the variant preferably comprises R97N, R97G or R97L.

In (i), the variant preferably comprises R192E and R192N.

In (ii), the variant preferably comprises F56N/N55Q, F56N/N55R, F56N/N55K, F56N/N55S, F56N/N55G, F56N/N55A, F56N/N55T, F56Q/N55Q, F56Q/N55R, F56Q/N55K, F56Q/N55S, F56Q/N55G, F56Q/N55A, F56Q/N55T, F56R/N55Q, F56R/N55R, F56R/N55K, F56R/N55S, F56R/N55G, F56R/N55A, F56R/N55T, F56S/N55Q, F56S/N55R, F56S/N55K, F56S/N55S, F56S/N55G, F56S/N55A, F56S/N55T, F56G/N55Q, F56G/N55R, F56G/N55K, F56G/N55S, F56G/N55G, F56G/N55A, F56G/N55T, F56A/N55Q, F56A/N55R, F56A/N55K, F56A/N55S, F56A/N55G, F56A/N55A, F56A/N55T, F56K/N55Q, F56K/N55R, F56K/N55K, F56K/N55S, F56K/N55G, F56K/N55A, F56K/N55T, F56N/Y51L, F56N/Y51V, F56N/Y51A, F56N/Y51N, F56N/Y51Q, F56N/Y51S, F56N/Y51G, F56Q/Y51L, F56Q/Y51V, F56Q/Y51A, F56Q/Y51N, F56Q/Y51Q, F56Q/Y51S, F56Q/Y51G, F56R/Y51L, F56R/Y51V, F56R/Y51A, F56R/Y51N, F56R/Y51Q, F56R/Y51S, F56R/Y51G, F56S/Y51L, F56S/Y51V, F56S/Y51A, F56S/Y51N, F56S/Y51Q, F56S/Y51S, F56S/Y51G, F56G/Y51L, F56G/Y51V, F56G/Y51A, F56G/Y51N, F56G/Y51Q, F56G/Y51S, F56G/Y51G, F56A/Y51L, F56A/Y51V, F56A/Y51A, F56A/Y51N, F56A/Y51Q, F56A/Y51S, F56A/Y51G, F56K/Y51L, F56K/Y51V, F56K/Y51A, F56K/Y51N, F56K/Y51Q, F56K/Y51S, F56K/Y51G, N55Q/Y51L, N55Q/Y51V, N55Q/Y51A, N55Q/Y51N, N55Q/Y51Q, N55Q/Y51S, N55Q/Y51G, N55R/Y51L, N55R/Y51V, N55R/Y51A, N55R/Y51N, N55R/Y51Q, N55R/Y51S, N55R/Y51G, N55K/Y51L, N55K/Y51V, N55K/Y51A, N55K/Y51N, N55K/Y51Q, N55K/Y51S, N55K/Y51G, N55S/Y51L, N55S/Y51V, N55S/Y51A, N55S/Y51N, N55S/Y51Q, N55S/Y51S, N55S/Y51G, N55G/Y51L, N55G/Y51V, N55G/Y51A, N55G/Y51N, N55G/Y51Q, N55G/Y51S, N55G/Y51G, N55A/Y51L, N55A/Y51V, N55A/Y51A, N55A/Y51N, N55A/Y51Q, N55A/Y51S, N55A/Y51G, N55T/Y51L, N55T/Y51V, N55T/Y51A, N55T/Y51N, N55T/Y51Q, N55T/Y51S, N55T/Y51G, F56N/N55Q/Y51L, F56N/N55Q/Y51V, F56N/N55Q/Y51A, F56N/

N55Q/Y51N, F56N/N55Q/Y51Q, F56N/N55Q/Y51S, F56N/N55Q/Y51G, F56N/N55R/Y51L, F56N/N55R/Y51V, F56N/N55R/Y51A, F56N/N55R/Y51N, F56N/N55R/Y51Q, F56N/N55R/Y51S, F56N/N55R/Y51G, F56N/N55K/Y51L, F56N/N55K/Y51V, F56N/N55K/Y51A, F56N/N55K/Y51N, F56N/N55K/Y51Q, F56N/N55K/Y51S, F56N/N55K/Y51G, F56N/N55S/Y51L, F56N/N55S/Y51V, F56N/N55S/Y51A, F56N/N55S/Y51N, F56N/N55S/Y51Q, F56N/N55S/Y51S, F56N/N55S/Y51G, F56N/N55G/Y51L, F56N/N55G/Y51V, F56N/N55G/Y51A, F56N/N55G/Y51N, F56N/N55G/Y51Q, F56N/N55G/Y51S, F56N/N55G/Y51G, F56N/N55A/Y51L, F56N/N55A/Y51V, F56N/N55A/Y51A, F56N/N55A/Y51N, F56N/N55A/Y51Q, F56N/N55A/Y51S, F56N/N55A/Y51G, F56N/N55T/Y51L, F56N/N55T/Y51V, F56N/N55T/Y51A, F56N/N55T/Y51N, F56N/N55T/Y51Q, F56N/N55T/Y51S, F56N/N55T/Y51G, F56Q/N55Q/Y51L, F56Q/N55Q/Y51V, F56Q/N55Q/Y51A, F56Q/N55Q/Y51N, F56Q/N55Q/Y51Q, F56Q/N55Q/Y51S, F56Q/N55Q/Y51G, F56Q/N55R/Y51L, F56Q/N55R/Y51V, F56Q/N55R/Y51A, F56Q/N55R/Y51N, F56Q/N55R/Y51Q, F56Q/N55R/Y51S, F56Q/N55R/Y51G, F56Q/N55K/Y51L, F56Q/N55K/Y51V, F56Q/N55K/Y51A, F56Q/N55K/Y51N, F56Q/N55K/Y51Q, F56Q/N55K/Y51S, F56Q/N55K/Y51G, F56Q/N55S/Y51L, F56Q/N55S/Y51V, F56Q/N55S/Y51A, F56Q/N55S/Y51N, F56Q/N55S/Y51Q, F56Q/N55S/Y51S, F56Q/N55S/Y51G, F56Q/N55G/Y51L, F56Q/N55G/Y51V, F56Q/N55G/Y51A, F56Q/N55G/Y51N, F56Q/N55G/Y51Q, F56Q/N55G/Y51S, F56Q/N55G/Y51G, F56Q/N55A/Y51L, F56Q/N55A/Y51V, F56Q/N55A/Y51A, F56Q/N55A/Y51N, F56Q/N55A/Y51Q, F56Q/N55A/Y51S, F56Q/N55A/Y51G, F56Q/N55T/Y51L, F56Q/N55T/Y51V, F56Q/N55T/Y51A, F56Q/N55T/Y51N, F56Q/N55T/Y51Q, F56Q/N55T/Y51S, F56Q/N55T/Y51G, F56R/N55Q/Y51L, F56R/N55Q/Y51V, F56R/N55Q/Y51A, F56R/N55Q/Y51N, F56R/N55Q/Y51Q, F56R/N55Q/Y51S, F56R/N55Q/Y51G, F56R/N55R/Y51L, F56R/N55R/Y51V, F56R/N55R/Y51A, F56R/N55R/Y51N, F56R/N55R/Y51Q, F56R/N55R/Y51S, F56R/N55R/Y51G, F56R/N55K/Y51L, F56R/N55K/Y51V, F56R/N55K/Y51A, F56R/N55K/Y51N, F56R/N55K/Y51Q, F56R/N55K/Y51S, F56R/N55K/Y51G, F56R/N55S/Y51L, F56R/N55S/Y51V, F56R/N55S/Y51A, F56R/N55S/Y51N, F56R/N55S/Y51Q, F56R/N55S/Y51S, F56R/N55S/Y51G, F56R/N55G/Y51L, F56R/N55G/Y51V, F56R/N55G/Y51A, F56R/N55G/Y51N, F56R/N55G/Y51Q, F56R/N55G/Y51S, F56R/N55G/Y51G, F56R/N55A/Y51L, F56R/N55A/Y51V, F56R/N55A/Y51A, F56R/N55A/Y51N, F56R/N55A/Y51Q, F56R/N55A/Y51S, F56R/N55A/Y51G, F56R/N55T/Y51L, F56R/N55T/Y51V, F56R/N55T/Y51A, F56R/N55T/Y51N, F56R/N55T/Y51Q, F56R/N55T/Y51S, F56R/N55T/Y51G, F56S/N55Q/Y51L, F56S/N55Q/Y51V, F56S/N55Q/Y51A, F56S/N55Q/Y51N, F56S/N55Q/Y51Q, F56S/N55Q/Y51S, F56S/N55Q/Y51G, F56S/N55R/Y51L, F56S/N55R/Y51V, F56S/N55R/Y51A, F56S/N55R/Y51N, F56S/N55R/Y51Q, F56S/N55R/Y51S, F56S/N55R/Y51G, F56S/N55K/Y51L, F56S/N55K/Y51V, F56S/N55K/Y51A, F56S/N55K/Y51N, F56S/N55K/Y51Q, F56S/N55K/Y51S, F56S/N55K/Y51G, F56S/N55S/Y51L, F56S/N55S/Y51V, F56S/N55S/Y51A, F56S/N55S/Y51N, F56S/N55S/Y51Q, F56S/N55S/Y51S, F56S/N55S/Y51G, F56S/N55G/Y51L, F56S/N55G/Y51V, F56S/N55G/Y51A, F56S/N55G/Y51N, F56S/N55G/Y51Q, F56S/N55G/Y51S, F56S/N55G/Y51G, F56S/N55A/Y51L, F56S/N55A/Y51V, F56S/N55A/Y51A, F56S/N55A/Y51N, F56S/N55A/Y51Q, F56S/N55A/Y51S, F56S/N55A/Y51G, F56S/N55T/Y51L, F56S/N55T/Y51V, F56S/N55T/Y51A, F56S/N55T/Y51N, F56S/N55T/Y51Q, F56S/N55T/Y51S, F56S/N55T/Y51G, F56G/N55Q/Y51L, F56G/N55Q/Y51V, F56G/N55Q/Y51A, F56G/N55Q/Y51N, F56G/N55Q/Y51Q, F56G/N55Q/Y51S, F56G/N55Q/Y51G, F56G/N55R/Y51L, F56G/N55R/Y51V, F56G/N55R/Y51A, F56G/N55R/Y51N, F56G/N55R/Y51Q, F56G/N55R/Y51S, F56G/N55R/Y51G, F56G/N55K/Y51L, F56G/N55K/Y51V, F56G/N55K/Y51A, F56G/N55K/Y51N, F56G/N55K/Y51Q, F56G/N55K/Y51S, F56G/N55K/Y51G, F56G/N55S/Y51L, F56G/N55S/Y51V, F56G/N55S/Y51A, F56G/N55S/Y51N, F56G/N55S/Y51Q, F56G/N55S/Y51S, F56G/N55S/Y51G, F56G/N55G/Y51L, F56G/N55G/Y51V, F56G/N55G/Y51A, F56G/N55G/Y51N, F56G/N55G/Y51Q, F56G/N55G/Y51S, F56G/N55G/Y51G, F56G/N55A/Y51L, F56G/N55A/Y51V, F56G/N55A/Y51A, F56G/N55A/Y51N, F56G/N55A/Y51Q, F56G/N55A/Y51S, F56G/N55A/Y51G, F56G/N55T/Y51L, F56G/N55T/Y51V, F56G/N55T/Y51A, F56G/N55T/Y51N, F56G/N55T/Y51Q, F56G/N55T/Y51S, F56G/N55T/Y51G, F56A/N55Q/Y51L, F56A/N55Q/Y51V, F56A/N55Q/Y51A, F56A/N55Q/Y51N, F56A/N55Q/Y51Q, F56A/N55Q/Y51S, F56A/N55Q/Y51G, F56A/N55R/Y51L, F56A/N55R/Y51V, F56A/N55R/Y51A, F56A/N55R/Y51N, F56A/N55R/Y51Q, F56A/N55R/Y51S, F56A/N55R/Y51G, F56A/N55K/Y51L, F56A/N55K/Y51V, F56A/N55K/Y51A, F56A/N55K/Y51N, F56A/N55K/Y51Q, F56A/N55K/Y51S, F56A/N55K/Y51G, F56A/N55S/Y51L, F56A/N55S/Y51V, F56A/N55S/Y51A, F56A/N55S/Y51N, F56A/N55S/Y51Q, F56A/N55S/Y51S, F56A/N55S/Y51G, F56A/N55G/Y51L, F56A/N55G/Y51V, F56A/N55G/Y51A, F56A/N55G/Y51N, F56A/N55G/Y51Q, F56A/N55G/Y51S, F56A/N55G/Y51G, F56A/N55A/Y51L, F56A/N55A/Y51V, F56A/N55A/Y51A, F56A/N55A/Y51N, F56A/N55A/Y51Q, F56A/N55A/Y51S, F56A/N55A/Y51G, F56A/N55T/Y51L, F56A/N55T/Y51V, F56A/N55T/Y51A, F56A/N55T/Y51N, F56A/N55T/Y51Q, F56A/N55T/Y51S, F56A/N55T/Y51G, F56K/N55Q/Y51L, F56K/N55Q/Y51V, F56K/N55Q/Y51A, F56K/N55Q/Y51N, F56K/N55Q/Y51Q, F56K/N55Q/Y51S, F56K/N55Q/Y51G, F56K/N55R/Y51L, F56K/N55R/Y51V, F56K/N55R/Y51A, F56K/N55R/Y51N, F56K/N55R/Y51Q, F56K/N55R/Y51S, F56K/N55R/Y51G, F56K/N55K/Y51L, F56K/N55K/Y51V, F56K/N55K/Y51A, F56K/N55K/Y51N, F56K/N55K/Y51Q, F56K/N55K/Y51S, F56K/N55K/Y51G, F56K/N55S/Y51L, F56K/N55S/Y51V, F56K/N55S/Y51A, F56K/N55S/Y51N, F56K/N55S/Y51Q, F56K/N55S/Y51S, F56K/N55S/Y51G, F56K/N55G/Y51L, F56K/N55G/Y51V, F56K/N55G/Y51A, F56K/N55G/Y51N, F56K/N55G/Y51Q, F56K/N55G/Y51S, F56K/N55G/Y51G, F56K/N55A/Y51L, F56K/N55A/Y51V, F56K/N55A/Y51A, F56K/N55A/Y51N, F56K/N55A/Y51Q, F56K/N55A/Y51S, F56K/N55A/Y51G, F56K/N55T/Y51L, F56K/N55T/Y51V, F56K/N55T/Y51A, F56K/N55T/Y51N, F56K/N55T/Y51Q, F56K/N55T/Y51S, F56K/N55T/Y51G, F56E/N55R, F56E/N55K, F56D/N55R, F56D/N55K, F56R/N55E, F56R/N55D, F56K/N55E or F56K/N55D.

In (ii), the variant preferably comprises Y51R/F56Q, Y51N/F56N, Y51M/F56Q, Y51L/F56Q, Y511/F56Q, Y51V/F56Q, Y51A/F56Q, Y51P/F56Q, Y51G/F56Q, Y51C/F56Q, Y51Q/F56Q, Y51N/F56Q, Y51S/F56Q, Y51E/F56Q, Y51D/F56Q, Y51K/F56Q or Y51H/F56Q.

In (ii), the variant preferably comprises Y51T/F56Q, Y51Q/F56Q or Y51A/F56Q.

In (ii), the variant preferably comprises Y51T/F56F, Y51T/F56M, Y51T/F56L, Y51T/F561, Y51T/F56V, Y51T/F56A, Y51T/F56P, Y51T/F56G, Y51T/F56C, Y51T/F56Q, Y51T/F56N, Y51T/F56T, Y51T/F56S, Y51T/F56E, Y51T/ F56D, Y51T/F56K, Y51T/F56H or Y51T/F56R.

In (ii), the variant preferably comprises Y51T/N55Q, Y51T/N55S or Y51T/N55A.

In (ii), the variant preferably comprises Y51A/F56F, Y51A/F56L, Y51A/F56I, Y51A/F56V, Y51A/F56A, Y51A/ F56P, Y51A/F56G, Y51A/F56C, Y51A/F56Q, Y51A/F56N, Y51A/F56T, Y51A/F56S, Y51A/F56E, Y51A/F56D, Y51A/ F56K, Y51A/F56H or Y51A/F56R.

In (ii), the variant preferably comprises Y51C/F56A, Y51E/F56A, Y51D/F56A, Y51K/F56A, Y51H/F56A, Y51Q/F56A, Y51N/F56A, Y51S/F56A, Y51P/F56A or Y51V/F56A.

In (xi), the variant preferably comprises deletion of Y51/ P52, Y51/P52/A53, P50 to P52, P50 to A53, K49 to Y51, K49 to A53 and replacement with a single proline (P), K49 to S54 and replacement with a single P, Y51 to A53, Y51 to S54, N55/F56, N55 to S57, N55/F56 and replacement with a single P, N55/F56 and replacement with a single glycine (G), N55/F56 and replacement with a single alanine (A), N55/F56 and replacement with a single P and Y51N, N55/ F56 and replacement with a single P and Y51Q, N55/F56 and replacement with a single P and Y51S, N55/F56 and replacement with a single G and Y51N, N55/F56 and replacement with a single G and Y51Q, N55/F56 and replacement with a single G and Y51S, N55/F56 and replacement with a single A and Y51N, N55/F56 and replacement with a single A/Y51Q or N55/F56 and replacement with a single A and Y51S.

The variant more preferably comprises D195N/E203N, D195Q/E203N, D195N/E203Q, D195Q/E203Q, E201N/ E203N, E201Q/E203N, E201N/E203Q, E201Q/E203Q, E185N/E203Q, E185Q/E203Q, E185N/E203N, E185Q/ E203N, D195N/E201N/E203N, D195Q/E201N/E203N, D195N/E201Q/E203N, D195N/E201N/E203N, D195Q/ E201Q/E203N, D195Q/E201N/E203Q, D195N/E201Q/ E203Q, D195Q/E201Q/E203Q, D149N/E201N, D149Q/ E201N, D149N/E201Q, D149Q/E201Q, D149N/E201N/ D195N, D149Q/E201N/D195N, D149N/E201Q/D195N, D149N/E201N/D195Q, D149Q/E201Q/D195N, D149Q/ E201N/D195Q, D149N/E201Q/D195Q, D149Q/E201Q/ D195Q, D149N/E203N, D149Q/E203N, D149N/E203Q, D149Q/E203Q, D149N/E185N/E201N, D149Q/E185N/ E201N, D149N/E185Q/E201N, D149N/E185N/E201Q, D149Q/E185Q/E201N, D149Q/E185N/E201Q, D149N/ E185Q/E201Q, D149Q/E185Q/E201Q, D149N/E185N/ E203N, D149Q/E185N/E203N, D149N/E185Q/E203N, D149N/E185N/E203Q, D149Q/E185Q/E203N, D149Q/ E185N/E203Q, D149N/E185Q/E203Q, D149Q/E185Q/ E203Q, D149N/E185N/E201N/E203N, D149Q/E185N/ E201N/E203N, D149N/E185Q/E201N/E203N, D149N/ E185N/E201Q/E203N, D149N/E185N/E201N/E203Q, D149Q/E185Q/E201N/E203N, D149Q/E185N/E201Q/ E203N, D149Q/E185N/E201N/E203Q, D149N/E185Q/ E201Q/E203N, D149N/E185Q/E201N/E203Q, D149N/ E185N/E201Q/E203Q, D149Q/E185Q/E201Q/E203Q, D149Q/E185Q/E201N/E203Q, D149Q/E185N/E201Q/ E203Q, D149N/E185Q/E201Q/E203Q, D149Q/E185N/ E201Q/E203N, D149N/E185N/D195N/E201N/E203N, D149Q/E185N/D195N/E201N/E203N, D149N/E185Q/ D195N/E201N/E203N, D149N/E185N/D195Q/E201N/ E203N, D149N/E185N/D195N/E201Q/E203N, D149N/ E185N/D195N/E201N/E203Q, D149Q/E185Q/D195N/ E201N/E203N, D149Q/E185N/D195Q/E201N/E203N, D149Q/E185N/D195N/E201Q/E203N, D149N/E185Q/ D195N/E201N/E203Q, D149N/E185Q/D195Q/E201N/ E203N, D149N/E185Q/D195N/E201Q/E203N, D149N/ E185Q/D195N/E201N/E203Q, D149N/ E185Q/D195N/E201N/E203N, D149N/E185N/D195Q/E201Q/E203N, D149N/ E185Q/D195N/E201N/E203Q, D149N/E185N/D195Q/ E201Q/E203N, D149N/E185N/D195Q/E201N/E203Q, D149N/E185N/D195N/E201Q/E203Q, D149Q/E185Q/ D195Q/E201N/E203N, D149Q/E185Q/D195N/E201Q/ E203N, D149Q/E185Q/D195N/E201N/E203Q, D149Q/ E185N/D195Q/E201Q/E203N, D149Q/E185N/D195Q/ E201N/E203Q, D149Q/E185N/D195N/E201Q/E203Q, D149N/E185Q/D195Q/E201Q/E203N, D149N/E185Q/ D195Q/E201N/E203Q, D149N/E185Q/D195N/E201Q/ E203Q, D149N/E185N/D195Q/E201Q/E203Q, D149Q/ E185Q/D195Q/E201Q/E203N, D149Q/E185Q/D195Q/ E201N/E203Q, D149Q/E185N/D195Q/E201Q/E203Q, D149Q/E185Q/D195N/E201Q/E203Q, D149N/E185Q/ D195Q/E201Q/E203Q, D149Q/E185Q/D195Q/E201Q/E203Q, D149N/E185R/E201N/E203N, D149Q/E185R/ E201N/E203N, D149N/E185R/E201Q/E203N, D149N/ E185R/E201N/E203Q, D149Q/E185R/E201Q/E203N, D149Q/E185R/E201N/E203Q, D149N/E185R/E201Q/ E203Q, D149Q/E185R/E201Q/E203Q, D149R/E185N/ E201N/E203N, D149R/E185Q/E201N/E203N, D149R/ E185N/E201Q/E203N, D149R/E185N/E201N/E203Q, D149R/E185Q/E201Q/E203N, D149R/E185Q/E201N/ E203Q, D149R/E185N/E201Q/E203Q, D149R/E185Q/ E201Q/E203Q, D149R/E185N/D195N/E201N/E203N, D149R/E185Q/D195N/E201N/E203N, D149R/E185N/ D195Q/E201N/E203N, D149R/E185N/D195N/E201Q/ E203N, D149R/E185Q/D195N/E201N/E203Q, D149R/ E185Q/D195Q/E201N/E203N, D149R/E185Q/D195N/ E201Q/E203N, D149R/E185Q/D195N/E201N/E203Q, D149R/E185N/D195Q/E201Q/E203N, D149R/E185N/ D195Q/E201N/E203Q, D149R/E185N/D195N/E201Q/ E203Q, D149R/E185Q/D195Q/E201Q/E203N, D149R/ E185Q/D195Q/E201N/E203Q, D149R/E185Q/D195N/ E201Q/E203Q, D149R/E185N/D195Q/E201Q/E203Q, D149R/E185Q/D195Q/E201Q/E203Q, D149N/E185R/ D195N/E201N/E203N, D149Q/E185R/D195N/E201N/ E203N, D149N/E185R/D195Q/E201N/E203N, D149N/ E185R/D195N/E201Q/E203N, D149N/E185R/D195N/ E201N/E203Q, D149Q/E185R/D195Q/E201N/E203N, D149Q/E185R/D195N/E201Q/E203N, D149Q/E185R/ D195N/E201N/E203Q, D149N/E185R/D195Q/E201Q/ E203N, D149N/E185R/D195Q/E201N/E203Q, D149N/ E185R/D195N/E201Q/E203Q, D149Q/E185R/D195Q/ E201Q/E203N, D149Q/E185R/D195Q/E201N/E203Q, D149Q/E185R/D195N/E201Q/E203Q, D149N/E185R/ D195Q/E201Q/E203Q, D149Q/E185R/D195Q/E201Q/ E203Q, D149N/E185R/D195N/E201R/E203N, D149Q/ E185R/D195N/E201R/E203N, D149N/E185R/D195Q/ E201R/E203N, D149N/E185R/D195N/E201R/E203Q, D149Q/E185R/D195Q/E201R/E203N, D149Q/E185R/ D195N/E201R/E203Q, D149N/E185R/D195Q/E201R/ E203Q, D149Q/E185R/D195Q/E201R/E203Q, E131D/ K49R, E101N/N102F, E101N/N102Y, E101N/N102W, E101F/N102F, E101F/N102Y, E101F/N102W, E101Y/ N102F, E101Y/N102Y, E101Y/N102W, E101W/N102F, E101W/N102Y, E101W/N102W, E101N/N102R, E101F/ N102R, E101Y/N102R or E101W/N102F.

Preferred variants of the invention which form pores in which fewer nucleotides contribute to the current as the polynucleotide moves through the pore comprise Y51A/ F56A, Y51A/F56N, Y51I/F56A, Y51L/F56A, Y51T/F56A, Y51I/F56N, Y51L/F56N or Y51T/F56N or more preferably Y51I/F56A, Y51L/F56A or Y51T/F56A. As discussed above, this makes it easier to identify a direct relationship between the observed current (as the polynucleotide moves through the pore) and the polynucleotide.

Preferred variants which form pores displaying an increased range comprise mutations at the following positions:
Y51, F56, D149, E185, E201 and E203;
N55 and F56;
Y51 and F56;
Y51, N55 and F56; or
F56 and N102.

Preferred variants which form pores displaying an increased range comprise:
Y51N, F56A, D149N, E185R, E201N and E203N;
N55S and F56Q;
Y51A and F56A;
Y51A and F56N;
Y51I and F56A;
Y51L and F56A;
Y51T and F56A;
Y51I and F56N;
Y51L and F56N;
Y51T and F56N;
Y51T and F56Q;
Y51A, N55S and F56A;
Y51A, N55S and F56N;
Y51T, N55S and F56Q; or
F56Q and N102R.

Preferred variants which form pores in which fewer nucleotides contribute to the current as the polynucleotide moves through the pore comprise mutations at the following positions:
N55 and F56, such as N55X and F56Q, wherein X is any amino acid; or
Y51 and F56, such as Y51X and F56Q, wherein X is any amino acid.

Particularly preferred variants comprise Y51A and F56Q.

Preferred variants which form pores displaying an increased throughput comprise mutations at the following positions:
D149, E185 and E203;
D149, E185, E201 and E203; or
D149, E185, D195, E201 and E203.

Preferred variants which form pores displaying an increased throughput comprise:
D149N, E185N and E203N;
D149N, E185N, E201N and E203N;
D149N, E185R, D195N, E201N and E203N; or
D149N, E185R, D195N, E201R and E203N.

Preferred variants which form pores in which capture of the polynucleotide is increased comprise the following mutations:
D43N/Y51T/F56Q;
E44N/Y51T/F56Q;
D43N/E44N/Y51T/F56Q;
Y51T/F56Q/Q62R;
D43N/Y51T/F56Q/Q62R;
E44N/Y51T/F56Q/Q62R; or
D43N/E44N/Y51T/F56Q/Q62R.

Preferred variants comprise the following mutations:
D149R/E185R/E201R/E203R or Y51T/F56Q/D149R/E185R/E201R/E203R;
D149N/E185N/E201N/E203N or Y51T/F56Q/D149N/E185N/E201N/E203N;
E201R/E203R or Y51T/F56Q/E201R/E203R
E201N/E203R or Y51T/F56Q/E201N/E203R;
E203R or Y51T/F56Q/E203R;
E203N or Y51T/F56Q/E203N;
E201R or Y51T/F56Q/E201R;
E201N or Y51T/F56Q/E201N;
E185R or Y51T/F56Q/E185R;
E185N or Y51T/F56Q/E185N;
D149R or Y51T/F56Q/D149R;
D149N or Y51T/F56Q/D149N;
R142E or Y51T/F56Q/R142E;
R142N or Y51T/F56Q/R142N;
R192E or Y51T/F56Q/R192E; or
R192N or Y51T/F56Q/R192N.

Preferred variants comprise the following mutations:
Y51A/F56Q/E101N/N102R;
Y51A/F56Q/R97N/N102G;
Y51A/F56Q/R97N/N102R;
Y51A/F56Q/R97N;
Y51A/F56Q/R97G;
Y51A/F56Q/R97L;
Y51A/F56Q/N102R;
Y51A/F56Q/N102F;
Y51A/F56Q/N102G;
Y51A/F56Q/E101R;
Y51A/F56Q/E101F;
Y51A/F56Q/E101N; or
Y51A/F56Q/E101G The variant preferably further comprises a mutation at T150. A preferred variant which forms a pore displaying an increased insertion comprises T150I. A mutation at T150, such as T150I, may be combined with any of the mutations or combinations of mutations discussed above.

A preferred variant of SEQ ID NO: 3 comprises (a) R97W and (b) a mutation at Y51 and/or F56. A preferred variant of SEQ ID NO: 3 comprises (a) R97W and (b) Y51R/H/K/D/E/S/T/N/Q/C/G/P/A/V/I/L/M and/or F56 R/H/K/D/E/S/T/N/Q/C/G/P/A/V/I/L/M. A preferred variant of SEQ ID NO: 3 comprises (a) R97W and (b) Y51L/V/A/N/Q/S/G and/or F56A/Q/N. A preferred variant of SEQ ID NO: 3 comprises (a) R97W and (b) Y51A and/or F56Q. A preferred variant of SEQ ID NO: 3 comprises R97W, Y51A and F56Q.

The variant of SEQ ID NO: 3 preferably comprises a mutation at R192. The variant preferably comprises R192D/Q/F/S/T/N/E, R192D/Q/F/S/T or R192D/Q. A preferred variant of SEQ ID NO: 3 comprises (a) R97W, (b) a mutation at Y51 and/or F56 and (c) a mutation at R192, such as R192D/Q/F/S/T/N/E, R192D/Q/F/S/T or R192D/Q. A preferred variant of SEQ ID NO: 3 comprises (a) R97W, (b) Y51R/H/K/D/E/S/T/N/Q/C/G/P/A/V/I/L/M and/or F56 R/H/K/D/E/S/T/N/Q/C/G/P/A/V/I/L/M and (c) a mutation at R192, such as R192D/Q/F/S/T/N/E, R192D/Q/F/S/T or R192D/Q. A preferred variant of SEQ ID NO: 3 comprises (a) R97W, (b) Y51L/V/A/N/Q/S/G and/or F56A/Q/N and (c) a mutation at R192, such as R192D/Q/F/S/T/N/E, R192D/Q/F/S/T or R192D/Q. A preferred variant of SEQ ID NO: 3 comprises (a) R97W, (b) Y51A and/or F56Q and (c) a mutation at R192, such as R192 D/Q/F/S/T/N/E, R192D/Q/F/S/T or R192D/Q. A preferred variant of SEQ ID NO: 3 comprises R97W, Y51A, F56Q and R192D/Q/F/S/T or R192D/Q. A preferred variant of SEQ ID NO: 3 comprises R97W, Y51A, F56Q and R192D. A preferred variant of SEQ ID NO: 3 comprises R97W, Y51A, F56Q and R192Q. In the paragraphs above where different amino acids at a specific positon are separated by the/symbol, the / symbol means "or". For instance, R192D/Q means R192D or R192Q.

Any of the above preferred variants of SEQ ID NO: 3 described above may further comprises a mutation at R93. A preferred variant of SEQ ID NO: 3 comprise (a) R93W and (b) a mutation at Y51 and/or F56, preferably Y51A and F56Q.

Any of the above preferred variants of SEQ ID NO: 3 may comprise a K94N/Q mutation. Any of the above preferred variants of SEQ ID NO: 3 may comprise a F191T mutation.

The CsgG monomer may be modified to facilitate attachment to the CsgF peptide. For example a cysteine residue may be introduced at one or more of the positions corresponding to positions 132, 133, 136, 138, 140, 142, 144, 145, 147, 149, 151, 153, 155, 183, 185, 187, 189, 191, 201, 203, 205, 207 and 209 of SEQ ID NO: 3, and/or at any one of the positions identified in Table 4 as being predicted to make contact with CsgF, to facilitate covalent attachment to CsgG. As an alternative or addition to covalent attachment via cysteine residues, the pore may be stabilised by hydrophobic interactions or electrostatic interactions. To facilitate such interactions, a non-native reactive or photoreactive amino acid at a position corresponding to one or more of positions 132, 133, 136, 138, 140, 142, 144, 145, 147, 149, 151, 153, 155, 183, 185, 187, 189, 191, 201, 203, 205, 207 and 209 of SEQ ID NO: 3, and/or at any one of the positions identified in Table 4 as being predicted to make contact with CsgF.

Preferred exemplary pores include at least one CsgG monomer having the following mutations relative to SEQ ID NO: 3: Y51X$_1$/N55X$_2$/F56X$_3$/N91R/K94Q/R97W/R192D-del(V105-I107), wherein X$_1$ is I/V/S/T, X$_2$ is N/I/V/S/T and/or X$_3$ is Q/I/V/S/T.

Methods for introducing or substituting naturally-occurring amino acids are well known in the art. For instance, methionine (M) may be substituted with arginine (R) by replacing the codon for methionine (ATG) with a codon for arginine (CGT) at the relevant position in a polynucleotide encoding the mutant monomer. The polynucleotide can then be expressed as discussed below.

Double Pores

The CsgG/CsgF pore may be a double pore comprising a first pore and a second pore. At least the first pore is a CsgG/CsgF pore disclosed herein. The second pore may be a CsgG pore or a CsgG/CsgF pore. In one embodiment both the first pore and the second pore are CsgG/CsgF pores as disclosed herein. The first and second pores may be the same or different. In addition to any of the mutations disclosed herein, in a double pore, the CsgG monomer may comprise one or more of the additional mutations described below.

In the double pore, the first pore may be attached to the second CsgG pore by hydrophobic interactions and/or by one or more disulphide bond. One or more, such as 2, 3, 4, 5, 6, 8, 9, for example all, of the monomers in the first pore and/or the second pore may be modified to enhance such interactions. This may be achieved in any suitable way.

At least one cysteine residue in the amino acid sequence of the first pore at the interface between the first and second pores may be disulphide bonded to at least one cysteine residue in the amino acid sequence of the second pore at the interface between the first and second pores. The cysteine residue in the first pore and/or the cysteine residue in the second pore may be a cysteine residue that is not present in the wild type CsgG monomer. Multiple disulphide bonds, such as from 2, 3, 4, 5, 6, 7, 8 or 9 to 16, 18, 24, 27, 32, 36, 40, 45, 48, 54, 56 or 63, may form between the two pores in the double pore. One or both the first or second pore may comprise at least one monomer, such as up to 8, 9 or 10 monomers, that comprises a cysteine residue at the interface between the first and second pores at a position corresponding to R97, I107, R110, Q100, E101, N102 and/or L113 of SEQ ID NO: 3.

At least one monomer in the first pore and/or at least one monomer in the second pore may comprise at least one residue at the interface between the first and second pores, which residue is more hydrophobic than the residue present at the corresponding position in the wild type CsgG monomer. For example, from 2 to 10, such as 3, 4, 5, 6, 7, 8 or 9, residues in the first pore and/or the second pore may be more hydrophobic that the residues at the same positions in the corresponding wild type CsgG monomer. Such hydrophobic residues strengthen the interaction between the two pores in the double pore. The at least one residue at the interface between the first and second pores may be at a position corresponding to R97, I107, R110, Q100, E101, N102 and or L113 of SEQ ID NO: 3. Where the residue at the interface in the wild type CsgG monomer is R, Q, N or E, the hydrophobic residue is typically I, L, V, M, F, W or Y. Where the residue at the interface in the wild type CsgG monomer is I, the hydrophobic residue is typically L, V, M, F, W or Y. Where the residue at the interface in the wild type CsgG monomer is L, the hydrophobic residue is typically I, V, M, F, W or Y.

The double pore may comprise one or more monomer that comprises one or more cysteine residue at the interface between the pores and one or more monomer that comprises one or more introduced hydrophobic residue at the interface between the pores, or may comprise one or more monomer that comprises such cysteine residues and such hydrophobic residues. For example, one or more, such as any 2, 3, or 4, of the positions in the monomer corresponding to the positions at R97, I107, R110, Q100, E101, N102 and or L113 of SEQ ID NO: 3 may comprise a cysteine (C) residue and one or more, such as any 2, 3 or 4, of the positions in the monomer corresponding to the positions at R97, I107, R110, Q100, E101, N102 and or L113 of SEQ ID NO: 3 may comprise a hydrophobic residue, such as I, L, V, M, F, W or Y.

The double pore according may contain bulky residues at one or more, such as 2, 3, 4, 5, 6 or 7, positions in the tail region, which residues are typically at the interface between the first and second pores and are bulkier than the residues present at the corresponding positions in the wild type CsgG monomer. The bulk of these residues prevents holes from forming in the walls of the pore at the interface between the first and second pore in the double pore. The at least one bulky residue at the interface between the first and second pores is typically at a position corresponding to A98, A99, T104, V105, L113, Q114 or S115 of SEQ ID NO: 3. Where the residue at the interface in the wild type CsgG monomer is A, the bulky residue is typically I, L, V, M, F, W, Y, N, Q, S or T. Where the residue present at the interface in the wild type CsgG monomer is T, the bulky residue is typically L, M, F, W, Y, N, Q, R, D or E. Where the residue present at the interface in the wild type CsgG monomer is V, the bulky residue is typically I, L, M, F, W, Y, N, Q. Where the residue present at the interface in the wild type CsgG monomer is L, the bulky residue is typically M, F, W, Y, N, Q, R, D or E. Where the residue present at the interface in the wild type CsgG monomer is Q, the bulky residue is typically F, W or Y. Where the residue present at the interface in the wild type CsgG monomer is S, the bulky residue is typically M, F, W, Y, N, Q, E or R.

Particularly where the second pore is located outside the membrane, the second pore, and optionally the first pore, preferably comprises residues in the barrel region of the pore that reduce the negative charge inside the barrel compared to the charge in the barrel of the wild type CsgG pore. These mutations make the barrel more hydrophilic. At least one monomer in the first pore and/or at least one monomer in the second pore of the double pore may comprise at least one residue in the barrel region of the pore, which residue has less negative charge than the residue present at the corresponding position in the wild type CsgG monomer. The charge inside the barrel is sufficiently neutral or positive such that negatively charged analytes, such as polynucleotides, are not repelled from entering the pore by electrostatic charges. At least one residue, such as 2, 3, 4 or 5 residues, in the barrel region of the pore at a position corresponding to D149, E185, D195, E210 and/or E203 of SEQ ID NO: 3 may be a neutral or positively charged amino acid. At least one residue, such as 2, 3, 4 or 5 residues, in the barrel region of the pore at a position corresponding to D149, E185, D195, E210 and/or E203 of SEQ ID NO: 3 is preferably N, Q, R or K.

Particular examples of charge-removing mutations in SEQ ID NO: 3 include the following: E185N/E203N; D149N/E185R/D195N/E201R/E203N, D149N/E185R/ D195N/E201N/E203N, D149R/E185N/D195N/E201N/ E203N, D149R/E185N/E201N/E203N, D149N/E185N/ D195/E201N/E203N, D149N/E185N/E201N/E203N, D149N/E185N/E203N, D149N/E185N/E201N, D149N/ E203N, D149N/E201N/D195N, D149N/E201N, D195N/ E201N/E203N, E201N/E203N, D195N/E203, E203R, E203N, E201R, E201N, D195R, D195N, E185R, E185N, D149R and D149N.

At least one CsgG monomer in the first pore may comprise at least one residue in the constriction of the barrel region of the first pore, which residue decreases, maintains or increases the length of the constriction compared to the wild type CsgG pore and/or at least one monomer in the second CsgG pore may comprise at least one residue in the constriction of the barrel region of the second pore, which residue decreases, maintains or increases the length of the constriction compared to the wild type CsgG pore. Preferably, the length of the constriction in the first pore and/or the length of the constriction in the second pore is at least as long as in the wild-type pore and more preferably longer.

The length of the pore may be increased by inserting residues into the region corresponding to the region between positions K49 and F56 of SEQ ID NO: 3. From 1 to 5, such as 2, 3, or 4 amino acid residues may be inserted at any one or more of the following positions defined by reference to SEQ ID NO: 3: K49 and P50, P50 and Y51, Y51 and P52, P52 and A53, A53 and S54, S54 and N55 and/or N55 F56. Preferably from 1 to 10, such as 2 to 8, or 3 to 5 amino acid residues in total are inserted into the sequence of a monomer. Preferably, all of the monomers in the first pore and/or all of the monomers in the second pore have the same number of insertions in this region. The inserted residues may increase the length of the loop between the residues corresponding to Y51 and N55 of SEQ ID NO: 3. The inserted residues may be any combination of A, S, G or T to maintain flexibility; P to add a kink to the loop; and/or S, T, N, Q, M, F, W, Y, V and/or I to contribute to the signal produced when a analyte interacts with the barrel of the pore under an applied potential difference. The inserted amino acids may be any combination of S, G, SG, SGG, SGS, GS, GSS and/or GSG.

In the double pore, the constriction in the barrel of the first pore and/or the second pore may comprise at least one residue, such as 2, 3, 4 or 5 residues, which influences the properties of the pore when used to detect or characterise an analyte compared to when a first pore or a second pore with a wild-type constriction is used, wherein the at least one residue in the constriction of the barrel region of the pore is at a position corresponding to Y51, N55, Y51, P52 and/or A53 of SEQ ID NO: 3. The at least one residue may be Q or V at a position corresponding to F56 of SEQ ID NO: 3; A or Q at a position corresponding to Y51 of SEQ ID NO: 3; and/or V at a position corresponding to N55 of SEQ ID NO: 3.

The double pore may comprise at least one monomer in the first CsgG pore and/or at least one monomer in the second CsgG pore, which monomer comprises two or more of the mutations defined above.

A CsgG monomer in the double pore may comprise a cysteine residue at a position corresponding to R97, I107, R110, Q100, E101, N102 and or L113 of SEQ ID NO: 3.

A CsgG monomer in the double pore may comprise a residue at a position corresponding to any one or more of R97, Q100, I107, R110, E101, N102 and L113 of SEQ ID NO: 3, which residue is more hydrophobic than the residue present at the corresponding position of SEQ ID NO: 3, such as the corresponding position of any one of SEQ ID NOs: 68 to 88, wherein the residue at the position corresponding to R97 and/or I107 is M, the residue at the position corresponding to R110 is I, L, V, M, W or Y, and/or the residue at the position corresponding to E101 or N102 is V or M. The residue at a position corresponding to Q100 is typically I, L, V, M, F, W or Y; and or the residue at a position corresponding to L113 is typically I, V, M, F, W or Y.

Particular monomers may have the sequence shown in SEQ ID NO 3 comprising Y51A, F56Q substitutions and R97I/V/L/M/F/W/Y, I107L/V/M/F/W/Y, R110I/V/L/M/F/ W/Y, Q100I/V/L/M/F/W/Y, E101I/V/L/M/F/W/Y, N102I/V/ L/M/F/W/Y and L113CI/V/L/M/F/W/Y in combination, R97I/V/L/M/F/W/Y and N102I/V/L/M/F/W/Y in combination and/or R97I/V/L/M/F/W/Y and E101I/V/L/M/F/W/Y in combination. I107 may already form hydrophobic interactions between two pores.

The CsgG monomer in at least one of the pores in the double pore may comprise a residue at a position corresponding to any one or more of A98, A99, T104, V105, L113, Q114 and S115 of SEQ ID NO: 3 which is bulkier than the residue present at the corresponding position of SEQ ID NO: 3, such as the corresponding position of any one of SEQ ID NOs: 68 to 88, wherein the residue at the position corresponding to T104 is L, M, F, W, Y, N, Q, D or E, the residue at the position corresponding to L113 is M, F, W, Y, N, G, D or E and/or the residue at the position corresponding to S115 is M, F, W, Y, N, Q or E. The residue at a position corresponding to A98 or A99, is typically I, L, V, M, F, W, Y, N, Q, S or T. The residue at a position corresponding to V105 is I, L, M, F, W, Y, N or Q. The residue at a position corresponding to Q114 is F, W or Y. The residue at a position corresponding to E210 is N, Q, R or K.

Particular monomers may have the sequence shown in SEQ ID NO 3 comprising Y51A, F56Q substitutions and 1, 2, 3, 4, 5, 6 or all of the following substitutions: A98I/L/ V/M/F/W/Y/N/Q/S/T; A99I/L/V/M/F/W/Y/N/Q/S/T; T104N/Q/L/R/D/E/M/F/W/Y; V105I/L/M/F/W/Y/N/Q; L113M/F/W/Y/N/Q/D/E/L/R; Q114Y/F/W; and S115N/Q/ M/F/W/Y/E/R.

The CsgG monomer in at least one of the pores in the double pore may comprise a residue in the barrel region of the pore at a position corresponding to any one ore more of D149, E185, D195, E210 and E203 less negative charge than the residue present at the corresponding position of SEQ ID NO: 3, such as the corresponding position of any one of SEQ ID NOs: 68 to 88, wherein the residue at the position corresponding to D149, E185, D195 and/or E203 is K.

The CsgG monomer in at least one of the pores in the double pore may comprise at least one residue in the constriction of the barrel region of the pore, which residue increases the length of the constriction compared to the wild type CsgG pore. The at least one residue is additional to the residues present in the constriction of the wild type CsgG pore.

The length of the pore may be increased by inserting residues into the region corresponding to the region between positions K49 and F56 of SEQ ID NO: 3. From 1 to 5, such as 2, 3, or 4 amino acid residues may be inserted at any one or more of the following positions defined by reference to SEQ ID NO: 3: K49 and P50, P50 and Y51, Y51 and P52, P52 and A53, A53 and S54, S54 and N55 and/or N55 and F56. Preferably from 1 to 10, such as 2 to 8, or 3 to 5 amino acid residues in total are inserted into the sequence of the monomer. The inserted residues may increase the length of the loop between the residues corresponding to Y51 and N55 of SEQ ID NO: 3. The inserted residues may be any combination of A, S, G or T to maintain flexibility; P to add a kink to the loop; and/or S, T, N, Q, M, F, W, Y, V and/or I to contribute to the signal produced when a analyte interacts with the barrel of the pore under an applied potential difference. The inserted amino acids may be any combination of S, G, SG, SGG, SGS, GS, GSS and/or GSG.

The CsgG monomer in at least one of the pores in the double pore may comprise at least one residue in the constriction of the barrel region of the pore at a position corresponding to N55, P52 and/or A53 of SEQ ID NO: 3 that is different from the residue present in the corresponding wild type monomer, wherein the residue at a position corresponding to N55 is V.

Any two or more of the above described residues may be present in the same monomer. In particular the monomer may comprise at least one said cysteine residue, at least one said hydrophobic residue, at least one said bulky residue, at least one said neutral or positively charged residue and/or at least one said residue that increases the length of the constriction.

A CsgG monomer in the double pore may additionally comprise one or more, such as 2, 3, 4 or 5 residues, which influence the properties of the pore when used to detect or characterise an analyte compared to when a first pore or a second pore with a wild-type constriction is used, wherein the at least one residue in the constriction of the barrel region of the pore is at a position corresponding to Y51, N55, Y51, P52 and/or A53 of SEQ ID NO: 3. The at least one residue may be Q or V at a position corresponding to F56 of SEQ ID NO: 3; A or Q at a position corresponding to Y51 of SEQ ID NO: 3; and/or V at a position corresponding to N55 of SEQ ID NO: 3.

Method for Making Modified Proteins

Methods for introducing or substituting non-naturally-occurring amino acids are also well known in the art. For instance, non-naturally-occurring amino acids may be introduced by including synthetic aminoacyl-tRNAs in the IVTT system used to express the mutant monomer. Alternatively, they may be introduced by expressing the mutant monomer in E. coli that are auxotrophic for specific amino acids in the presence of synthetic (i.e. non-naturally-occurring) analogues of those specific amino acids. They may also be produced by naked ligation if the mutant monomer is produced using partial peptide synthesis.

The monomers derived from CsgG may be modified to assist their identification or purification, for example by the addition of a streptavidin tag or by the addition of a signal sequence to promote their secretion from a cell where the monomer does not naturally contain such a sequence. Other suitable tags are discussed in more detail below. The monomer may be labelled with a revealing label. The revealing label may be any suitable label which allows the monomer to be detected. Suitable labels are described below.

The monomer derived from CsgG may also be produced using D-amino acids. For instance, the monomer derived from CsgG may comprise a mixture of L-amino acids and D-amino acids. This is conventional in the art for producing such proteins or peptides.

The monomer derived from CsgG contains one or more specific modifications to facilitate nucleotide discrimination. The monomer derived from CsgG may also contain other non-specific modifications as long as they do not interfere with pore formation. A number of non-specific side chain modifications are known in the art and may be made to the side chains of the monomer derived from CsgG. Such modifications include, for example, reductive alkylation of amino acids by reaction with an aldehyde followed by reduction with $NaBH_4$, amidination with methylacetimidate or acylation with acetic anhydride.

The monomer derived from CsgG can be produced using standard methods known in the art. The monomer derived from CsgG may be made synthetically or by recombinant means. For example, the monomer may be synthesised by in vitro translation and transcription (IVTT). Suitable methods for producing pores and monomers are discussed in the International applications WO 2010/004273, WO 2010/004265 or WO 2010/086603. Methods for inserting pores into membranes are known.

Two or more CsgG monomers in the pore may be covalently attached to one another. For example, at least 2, at least 3, at least 4, at least 5, at least 6, at least 7, at least 8, at least 9 or at least 10 monomers may be covalently attached. The covalently attached monomers may be the same or different.

The monomers may be genetically fused, optionally via a linker, or chemically fused, for instance via a chemical crosslinker. Methods for covalently attaching monomers are disclosed in WO2017/149316, WO2017/149317 and WO2017/149318.

In some embodiments, the mutant monomer is chemically modified. The mutant monomer can be chemically modified in any way and at any site. The mutant monomer is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The mutant monomer may be chemically modified by the attachment of any molecule. For instance, the mutant monomer may be chemically modified by attachment of a dye or a fluorophore.

In some embodiments, the mutant monomer is chemically modified with a molecular adaptor that facilitates the interaction between a pore comprising the monomer and a target nucleotide or target polynucleotide sequence. The presence of the adaptor improves the host-guest chemistry of the pore and the nucleotide or polynucleotide sequence and thereby improves the sequencing ability of pores formed from the mutant monomer. The principles of host-guest chemistry are well-known in the art. The adaptor has an effect on the physical or chemical properties of the pore that improves its interaction with the nucleotide or polynucleotide sequence. The adaptor may alter the charge of the barrel or channel of the pore or specifically interact with or bind to the nucleotide or polynucleotide sequence thereby facilitating its interaction with the pore.

The molecular adaptor is preferably a cyclic molecule, a cyclodextrin, a species that is capable of hybridization, a DNA binder or interchelator, a peptide or peptide analogue, a synthetic polymer, an aromatic planar molecule, a small positively-charged molecule or a small molecule capable of hydrogen-bonding.

The adaptor may be cyclic. A cyclic adaptor preferably has the same symmetry as the pore. The adaptor preferably has eight-fold or nine-fold symmetry since CsgG typically has eight or nine subunits around a central axis. This is discussed in more detail below.

The adaptor typically interacts with the nucleotide or polynucleotide sequence via host-guest chemistry. The adaptor is typically capable of interacting with the nucleotide or polynucleotide sequence. The adaptor comprises one or more chemical groups that are capable of interacting with the nucleotide or polynucleotide sequence. The one or more chemical groups preferably interact with the nucleotide or polynucleotide sequence by non-covalent interactions, such as hydrophobic interactions, hydrogen bonding, Van der Waal's forces, x-cation interactions and/or electrostatic forces. The one or more chemical groups that are capable of interacting with the nucleotide or polynucleotide sequence are preferably positively charged. The one or more chemical groups that are capable of interacting with the nucleotide or polynucleotide sequence more preferably comprise amino groups. The amino groups can be attached to primary, secondary or tertiary carbon atoms. The adaptor even more preferably comprises a ring of amino groups, such as a ring of 6, 7 or 8 amino groups. The adaptor most preferably comprises a ring of eight amino groups. A ring of protonated amino groups may interact with negatively charged phosphate groups in the nucleotide or polynucleotide sequence.

The correct positioning of the adaptor within the pore can be facilitated by host-guest chemistry between the adaptor and the pore comprising the mutant monomer. The adaptor preferably comprises one or more chemical groups that are capable of interacting with one or more amino acids in the pore. The adaptor more preferably comprises one or more chemical groups that are capable of interacting with one or more amino acids in the pore via non-covalent interactions, such as hydrophobic interactions, hydrogen bonding, Van der Waal's forces, x-cation interactions and/or electrostatic forces. The chemical groups that are capable of interacting with one or more amino acids in the pore are typically hydroxyls or amines. The hydroxyl groups can be attached to primary, secondary or tertiary carbon atoms. The hydroxyl groups may form hydrogen bonds with uncharged amino acids in the pore. Any adaptor that facilitates the interaction between the pore and the nucleotide or polynucleotide sequence can be used.

Suitable adaptors include, but are not limited to, cyclodextrins, cyclic peptides and cucurbiturils. The adaptor is preferably a cyclodextrin or a derivative thereof. The cyclodextrin or derivative thereof may be any of those disclosed in Eliseev, A. V., and Schneider, H-J. (1994) *J. Am. Chem. Soc.* 116, 6081-6088. The adaptor is more preferably heptakis-6-amino-β-cyclodextrin ($am_7$-βCD), 6-monodeoxy-6-monoamino-β-cyclodextrin ($am_1$-□CD) or heptakis-(6-deoxy-6-guanidino)-cyclodextrin ($gu_7$-βCD). The guanidino group in $gu_7$-βCD has a much higher pKa than the primary amines in $am_7$-βCD and so it is more positively charged. This $gu_7$-βCD adaptor may be used to increase the dwell time of the nucleotide in the pore, to increase the accuracy of the residual current measured, as well as to increase the base detection rate at high temperatures or low data acquisition rates.

If a succinimidyl 3-(2-pyridyldithio)propionate (SPDP) crosslinker is used as discussed in more detail below, the adaptor is preferably heptakis(6-deoxy-6-amino)-6-N-mono (2-pyridyl)dithiopropanoyl-β-cyclodextrin ($am_6amPDP_1$-βCD).

More suitable adaptors include γ-cyclodextrins, which comprise 9 sugar units (and therefore have nine-fold symmetry). The γ-cyclodextrin may contain a linker molecule or may be modified to comprise all or more of the modified sugar units used in the β-cyclodextrin examples discussed above.

The molecular adaptor may be covalently attached to the mutant monomer. The adaptor can be covalently attached to the pore using any method known in the art. The adaptor is typically attached via chemical linkage. If the molecular adaptor is attached via cysteine linkage, the one or more cysteines have preferably been introduced to the mutant, for instance in the barrel, by substitution. The mutant monomer may be chemically modified by attachment of a molecular adaptor to one or more cysteines in the mutant monomer. The one or more cysteines may be naturally-occurring, i.e. at positions 1 and/or 215 in SEQ ID NO: 3. Alternatively, the mutant monomer may be chemically modified by attachment of a molecule to one or more cysteines introduced at other positions. The cysteine at position 215 may be removed, for instance by substitution, to ensure that the molecular adaptor does not attach to that position rather than the cysteine at position 1 or a cysteine introduced at another position.

The reactivity of cysteine residues may be enhanced by modification of the adjacent residues. For instance, the basic groups of flanking arginine, histidine or lysine residues will change the pKa of the cysteines thiol group to that of the more reactive S group. The reactivity of cysteine residues may be protected by thiol protective groups such as dTNB. These may be reacted with one or more cysteine residues of the mutant monomer before a linker is attached.

The molecule may be attached directly to the mutant monomer. The molecule is preferably attached to the mutant monomer using a linker, such as a chemical crosslinker or a peptide linker.

Suitable chemical crosslinkers are well-known in the art. Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2-yldisulfanyl)octananoate. The most preferred crosslinker is succinimidyl 3-(2-pyridyldithio)propionate (SPDP). Typically, the molecule is covalently attached to the bifunctional crosslinker before the molecule/crosslinker complex is covalently attached to the mutant monomer but it is also possible to covalently attach the bifunctional crosslinker to the monomer before the bifunctional crosslinker/monomer complex is attached to the molecule.

The linker is preferably resistant to dithiothreitol (DTT). Suitable linkers include, but are not limited to, iodoacetamide-based and Maleimide-based linkers.

In other embodiment, the monomer may be attached to a polynucleotide binding protein. This forms a modular sequencing system that may be used in the methods of sequencing of the invention. Polynucleotide binding proteins are discussed below.

The polynucleotide binding protein is preferably covalently attached to the mutant monomer. The protein can be covalently attached to the monomer using any method known in the art. The monomer and protein may be chemically fused or genetically fused. The monomer and protein are genetically fused if the whole construct is expressed from a single polynucleotide sequence. Genetic fusion of a monomer to a polynucleotide binding protein is discussed in WO 2010/004265.

If the polynucleotide binding protein is attached via cysteine linkage, the one or more cysteines have preferably been introduced to the mutant by substitution. The one or more cysteines are preferably introduced into loop regions which have low conservation amongst homologues indicating that mutations or insertions may be tolerated. They are therefore suitable for attaching a polynucleotide binding protein. In such embodiments, the naturally-occurring cysteine at position 251 may be removed. The reactivity of cysteine residues may be enhanced by modification as described above.

The polynucleotide binding protein may be attached directly to the mutant monomer or via one or more linkers. The molecule may be attached to the mutant monomer using the hybridization linkers described in as WO 2010/086602. Alternatively, peptide linkers may be used. Peptide linkers are amino acid sequences. The length, flexibility and hydrophilicity of the peptide linker are typically designed such that it does not to disturb the functions of the monomer and molecule. Preferred flexible peptide linkers are stretches of 2 to 20, such as 4, 6, 8, 10 or 16, serine and/or glycine amino acids. More preferred flexible linkers include $(SG)_1$, $(SG)_2$, $(SG)_3$, $(SG)_4$, $(SG)_5$ and (SG): wherein S is serine and G is glycine. Preferred rigid linkers are stretches of 2 to 30, such as 4, 6, 8, 16 or 24, proline amino acids. More preferred rigid linkers include $(P)_{12}$ wherein P is proline.

Chemical Modification

The mutant CsgG monomer or CsgF peptide may be chemically modified with a molecular adaptor and a polynucleotide binding protein.

The molecule (with which the monomer or peptide is chemically modified) may be attached directly to the monomer or peptide or attached via a linker as disclosed in WO 2010/004273, WO 2010/004265 or WO 2010/086603.

Any of the proteins described herein, such as the CsgG monomers and/or CsgF peptides, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the protein. An example of this would be to react a gel-shift reagent to a cysteine engineered on the outside of the protein. This has been demonstrated as a method for separating hemolysin hetero-oligomers (Chem Biol. 1997 July; 4(7):497-505).

Any of the proteins described herein, such as the CsgG monomers and/or CsgF peptides, may be labelled with a revealing label. The revealing label may be any suitable label which allows the protein to be detected. Suitable labels include, but are not limited to, fluorescent molecules, radioisotopes, e.g. $^{125}I$, $^{35}S$, enzymes, antibodies, antigens, polynucleotides and ligands such as biotin.

Any of the proteins described herein, such as the CsgG monomers and/or CsgF peptides, may be made synthetically or by recombinant means. For example, the protein may be synthesised by in vitro translation and transcription (IVTT). The amino acid sequence of the protein may be modified to include non-naturally occurring amino acids or to increase the stability of the protein. When a protein is produced by synthetic means, such amino acids may be introduced during production. The protein may also be altered following either synthetic or recombinant production.

Proteins may also be produced using D-amino acids. For instance, the protein may comprise a mixture of L-amino acids and D-amino acids. This is conventional in the art for producing such proteins or peptides.

The protein may also contain other non-specific modifications as long as they do not interfere with the function of the protein. A number of non-specific side chain modifications are known in the art and may be made to the side chains of the protein(s). Such modifications include, for example, reductive alkylation of amino acids by reaction with an aldehyde followed by reduction with $NaBH_4$, amidination with methylacetimidate or acylation with acetic anhydride.

Any of the proteins described herein, such as the CsgG monomers and/or CsgF peptides, can be produced using standard methods known in the art. Polynucleotide sequences encoding a protein may be derived and replicated using standard methods in the art. Polynucleotide sequences encoding a protein may be expressed in a bacterial host cell using standard techniques in the art. The protein may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, NY.

Proteins may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

Method of Producing Pores

In a third aspect, the invention provides methods to in vivo and in vitro produce CsgG: modified CsgF pore complex holding two or more constriction sites. One embodiment provides a method for producing a transmembrane pore complex, comprising a CsgG pore, or homologue or mutant form thereof, and the modified CsgF peptide, or its homologue or mutant, via co-expression. Said method comprising the steps of expressing CsgG monomers (expressed as preprotein provided in SEQ ID NO: 2, or a homologue or mutant thereof), and expressing modified or truncated CsgF monomers, both in a suitable host cell, allowing in vivo complex pore formation. Said complex comprises modified CsgF peptides, in complex with the CsgG pore, to provide the pore with an additional reader head. The resulting pore complex produced by said method using modified CsgF peptides provides a structure that is sufficient for a use of the pore complex in characterization of target analytes such as nucleic acid sequencing, as it allows passage of the analytes, in particular polynucleotide strands, and comprises two or more reader heads for improved reading of said polynucleotide sequence, when used in the appropriate settings for said application. More particularly, the modified CsgF peptide expressed in said method comprises the preprotein depicted in SEQ ID NO: 8, 10, 12, or 14, or homologues thereof. Those sequences limiting the method to those CsgF fragments capable of introducing a constriction site in the pore complex, and binding to the CsgG protein pore, to obtain a biological pore.

Another method for producing an isolated pore complex formed by the CsgG and CsgF proteins or the like, relates to in vitro reconstitution of said monomers to obtain a functional pore. Said method comprises the steps of contacting the mature CsgG monomer as depicted in SEQ ID NO:3 or a homologue or mutant thereof, with modified CsgF peptides, or homologues or mutants thereof, in a suitable system to allow complex formation. Said system may be an "in vitro system", which refers to a system comprising at least the necessary components and environment to execute said method, and makes use of biological molecules, organisms, a cell (or part of a cell) outside of their normal naturally-occurring environment, permitting a more detailed, more convenient, or more efficient analysis than can be done with whole organisms. An in vitro system may also comprise a suitable buffer composition provided in a test tube, wherein said protein components to form the complex have been added. A person skilled in the art is aware of the options to provide said system. Said modified CsgF peptides or the like applied in said method for in vitro reconstitution in particular embodiments are peptides comprising SEQ ID NO:15 or SEQ ID NO:16, or mutant or homologues thereof, which can be synthesized or recombinantly produced. Alternatively, modified CsgF peptides comprising SEQ ID NO:40, 39, 38, or 37, 15, 54, 55 or homologues or mutants thereof, are provided in said method for contacting with CsgG or CsgG-like pores to produce the pore complex.

The CsgG/CsgF pore can be made by any suitable method. Examples of such suitable methods are described.

In one embodiment, the CsgG/CsgF pore may be produced by co-expression. In this embodiment, at least one gene encoding a CsgG monomer polypeptide (which may be a mutant polypeptide) in one vector and a gene encoding at least one full length or truncated CsgF polypeptide (which may be a mutant polypeptide) in a second vector may be transformed together to express the proteins and make the complex within transformed cells. This could be in vivo or in vitro. Alternatively, the two genes encoding the polypetides of CsgG and CsgF can be placed in one vector under the control of a single promotor or under the control of two separate promoters, which may be the same or different.

In another embodiment, the CsgG/CsgF pore is produced by expressing the CsgG monomer(s) separately from the CsgF peptide. CsgG monomers or a CsgG pore may be purified from the cells transformed with a vector encoding at least one CsgG monomer, or with more than one vector each expressing a CsgG monomer. The CsgF peptide may be purified from the cells transformed with a vector encoding at least one CsgF peptide. The purified CsgG monomer(s)/pore may then be incubated together with the CsgF peptide(s) to make the pore complex.

Figure 14:
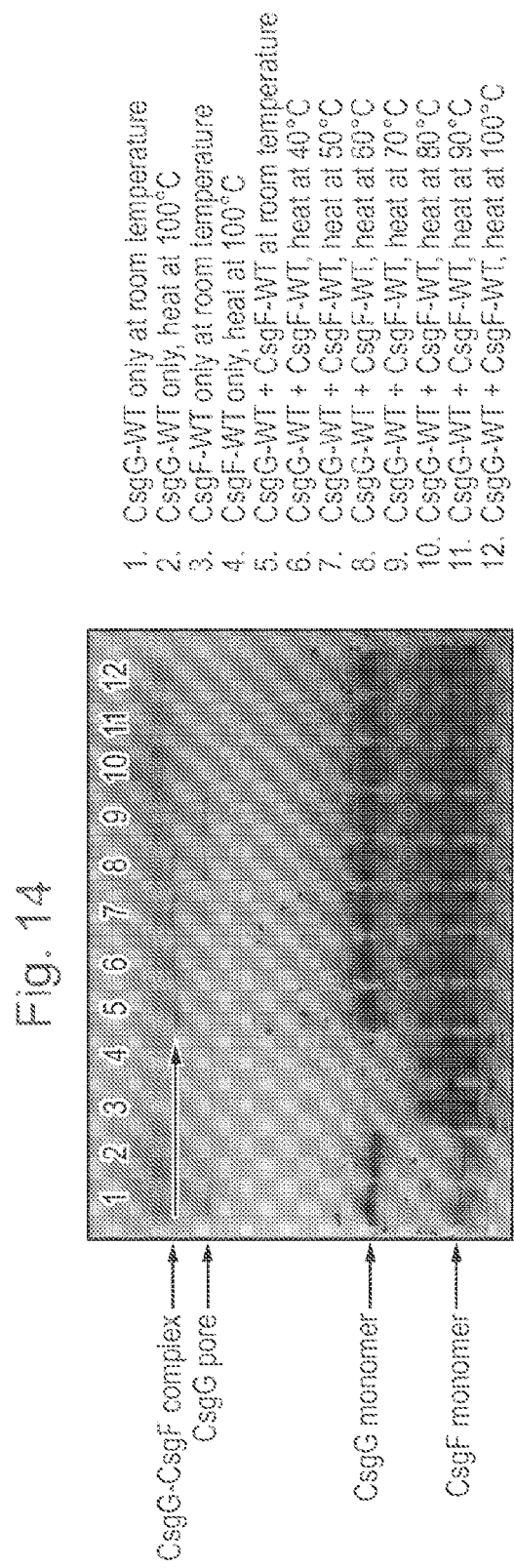
FIG. 14 Co-expression of CsgG and CsgF in vitro and the heat stability of the CsgG-CsgF complex. CsgG and CsgF DNA in different vectors are co-expressed in an in vitro transcription and translation reaction. Proteins are radio-labled with S-35 methionine and exposed onto a X-ray film. Stability of the complex is assessed by incubating the reaction mixture for 10 minutes at different temperatures.

In another embodiment, the CsgG monomer(s) and/or the CsgF peptide are produced separately by in vitro translation and transcription (IVTT). The CsgG monomer(s) may then be incubated together with the CsgF peptide(s) to make the pore complex. Use of this method is illustrated in FIG. 14.

The above embodiments may be combined, such that for example, (i) CsgG is produced in vivo and CsgF in vivo; (ii) CsgG is produced in vitro and CsgF in vivo; (iii) CsgG is produced in vivo and CsgF in vitro; or (iv) CsgG is produced in vitro and CsgF in vitro.

One or both of the CsgG momoner and the CsgF peptide may be tagged to facilitate purification. Purification can also be performed when the CsgG monomer and/or CsgF peptide are untagged. Methods known in the art (e.g. ion exchange, gel filtration, hydrophobic interaction column chromatography etc.) can be used alone or in different combinations to purify the components of the pore.

Any known tags can be used in any of the two proteins. In one embodiment, two tag purification can be used to purify the CsgG:CsgF complex from CsgG pore and CsgF. For example, a Strep tag can be used in CsgG and His tag can be used in CsgF or vice versa. This is exemplified in FIG. 13. A similar end result can be obtained when the two proteins are purified individually and mixed together followed by another round of Strep and His purification.

When the full length CsgF protein forms the complex with CsgG, the neck and head domains of CsgF (FIG. 4B) (shown in the red box) protrudes out from the beta barrel of the CsgG pore.

Therefore, if a pore comprising a CsgG pore and the full length CsgF were used in single channel recording experiments, the head domain may hinder or prevent pore insertion in to a membrane. They may also potentially block the passage of the pore for analytes to pass through. Thus, when inserting a pore into a membrane, it is better if the number of flexible polypeptides dangling down from the beta-barrel are reduced. Truncated versions of the CsgF protein that mimic the FCP region resolved in the cryo EM structure of the complex and that maintain structural integrity are provided herein.

The CsgG/CsgF pore can be made prior to insertion into a membrane or after insertion of the CsgG pore into a membrane. When the pore complex is made prior to insertion into a membrane, a truncation mutant is preferably used. However, the CsgG pore may be inserted into a membrane and the CsgF peptide may be added afterwards so that the CsgG and CsgF complex can form in situ. For example, in one embodiment a system where the trans side of the membrane is accessible (for example in a chip or chamber for electrophysiogy measurements), the CsgG pore may be inserted into the membrane, and then a CsgF peptide may be added from the trans side of the membrane, so that the complex can be formed in-situ. In any embodiment in which the CsgG pore is formed in situ, larger CsgF peptide may be used. For example, the CsgF peptide may comprise all or part of the neck domain of CsgF (from about residue 36 of SEQ ID NO: 6). In some embodiments the CsgF may comprise all of the neck domain and part of the head domain (residues 36 to XX of SEQ ID NO: 6)

Depending on the methods of making the complex and the stability of the complex with a particular truncation, CsgG:CsgF and CsgG:FCP complexes can be made in different methods.

In one embodiment, the truncated version of the CsgF polypeptide at the required length is used directly.

Another embodiment uses the full length polypeptide of CsgF or a longer than required truncation (enough to keep the complex stable) in which a protease cleavage sites is inserted (e.g. TEV, HRV 3 or any other protease cleavage site) so that cleavage by the protease produces a CsgF peptide of the required length. In this embodiment, once the CsgG/CsgF complex is formed, the protease is used to cleave the CsgF at the required site. Alternatively, the protease may be used to produce the CsgF peptide prior to complex assembly.

Figure 15A:
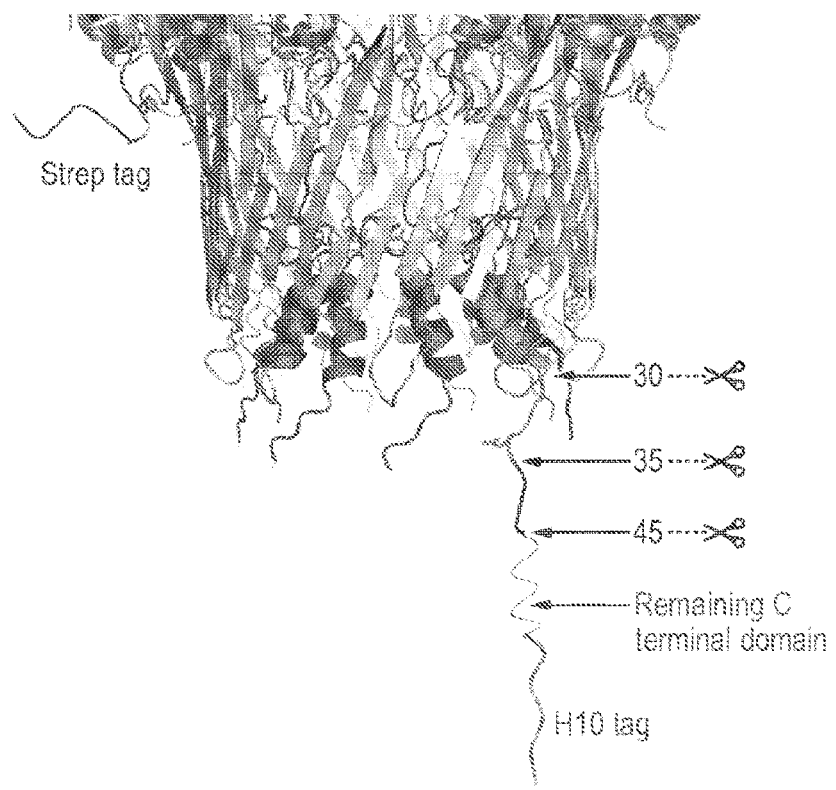
FIGS. 15A-15B Making CsgG:CsgF complexes using protease cleavage sites.
Figure 15B:

Some protease sites will leave an additional tag behind after cleavage. For example, the TEV protease cleavage sequence is ENLYFQS. TEV protease cleaves the protein between Q and S leaving ENLYFQ intact at the C-terminus of the CsgF peptide. FIG. 15 shows an example using a modified CsgF comprising a TEV cleavage site which is cleaved using TEV protease after complex formation. By way of another example, the HRV C3 cleavage site is LEVLFQGP and the enzyme cleaves between Q and G leaving LEVLFQ intact at the C-terminus of the CsgF peptide.

Methods of Characterising an Analyte

In a further aspect, the invention provides a method of determining the presence, absence or one or more characteristics of a target analyte. The method involves contacting the target analyte with an isolated pore complex, or transmembrane pore, such as a pore of the invention, such that the target analyte moves with respect to, such as into or through, the pore channel and taking one or more measurements as the analyte moves with respect to the pore and thereby determining the presence, absence or one or more characteristics of the analyte. The target analyte may also be called the template analyte or the analyte of interest. The isolated pore complex typically comprises at least 7, at least 8, at least 9 or at least 10 monomers, such as 7, 8, 9 or 10 CsgG monomers. The isolated pore complex preferably comprises eight or nine identical CsgG monomers. One or more, such as 2, 3, 4, 5, 6, 7, 8, 9 or 10, of the CsgG monomers is preferably chemically modified, or the CsgF peptide is chemically modified. The isolated pore complex monomers, such as the CsgG monomers, or homologues or mutants thereof, and the modified CsgF monomers, or homologues or mutants thereof, may be derived from any organism. The analyte may pass through the CsgG constriction, followed by the CsgF constriction. In an alternative embodiment the analyte may pass through the CsgF constriction, followed by the CsgG constriction, depending on the orientation of the CsgG/CsgF complex in the membrane.

The method is for determining the presence, absence or one or more characteristics of a target analyte. The method may be for determining the presence, absence or one or more characteristics of at least one analyte. The method may concern determining the presence, absence or one or more characteristics of two or more analytes. The method may comprise determining the presence, absence or one or more characteristics of any number of analytes, such as 2, 5, 10, 15, 20, 30, 40, 50, 100 or more analytes. Any number of characteristics of the one or more analytes may be determined, such as 1, 2, 3, 4, 5, 10 or more characteristics.

The binding of a molecule in the channel of the pore complex, or in the vicinity of either opening of the channel will have an effect on the open-channel ion flow through the pore, which is the essence of "molecular sensing" of pore channels. In a similar manner to the nucleic acid sequencing application, variation in the open-channel ion flow can be measured using suitable measurement techniques by the change in electrical current (for example, WO 2000/28312 and D. Stoddart et al., Proc. Natl. Acad. Sci., 2010, 106, 7702-7 or WO 2009/077734). The degree of reduction in ion flow, as measured by the reduction in electrical current, is related to the size of the obstruction within, or in the vicinity of, the pore. Binding of a molecule of interest, also referred to as an "analyte", in or near the pore therefore provides a detectable and measurable event, thereby forming the basis of a "biological sensor". Suitable molecules for nanopore sensing include nucleic acids; proteins; peptides; polysaccharides and small molecules (refers here to a low molecular weight (e.g., <900 Da or <500 Da) organic or inorganic compound) such as pharmaceuticals, toxins, cytokines, and pollutants. Detecting the presence of biological molecules finds application in personalised drug development, medicine, diagnostics, life science research, environmental monitoring and in the security and/or the defence industry.

In another aspect, the isolated pore complex, or the transmembrane pore complex containing a wild type or modified E. coli CsgG nanopore, or homologue or mutant thereof, and a modified CsgF peptide providing a channel constriction to the pore within the complex, may serve as a molecular or biological sensor. In some embodiments, the CsgG nanopore can be derived or isolated from bacterial proteins (e.g., E. coli, Salmonella typhi). In some embodiments, the CsgG nanopore can be recombinantly produced. Procedures for analyte detection are described in Howorka et al. Nature Biotechnology (2012) June 7; 30(6):506-7. The analyte molecule that is to be detected may bind to either face of the channel, or within the lumen of the channel itself. The position of binding may be determined by the size of the molecule to be sensed.

The target analyte is preferably a metal ion, an inorganic salt, a polymer, an amino acid, a peptide, a polypeptide, a protein, a nucleotide, an oligonucleotide, a polynucleotide, a polysaccharide, a dye, a bleach, a pharmaceutical, a diagnostic agent, a recreational drug, an explosive, a toxic compound, or an environmental pollutant. The method may concern determining the presence, absence or one or more characteristics of two or more analytes of the same type, such as two or more proteins, two or more nucleotides or two or more pharmaceuticals. Alternatively, the method may concern determining the presence, absence or one or more characteristics of two or more analytes of different types, such as one or more proteins, one or more nucleotides and one or more pharmaceuticals.

The target analyte can be secreted from cells. Alternatively, the target analyte can be an analyte that is present inside cells such that the analyte must be extracted from the cells before the method can be carried out.

A wild-type pore may act as sensor, but is often modified via recombinant or chemical methods to increase the strength of binding, the position of binding, or the specificity of binding of the molecule to be sensed. Typical modifications include addition of a specific binding moiety complimentary to the structure of the molecule to be sensed. Where the analyte molecule comprises a nucleic acid, this binding moiety may comprise a cyclodextrin or an oligonucleotide; for small molecules this may be a known complimentary binding region, for example the antigen binding portion of an antibody or of a non-antibody molecule, including a single chain variable fragment (scFv) region or an antigen recognition domain from a T-cell receptor (TCR); or for proteins, it may be a known ligand of the target protein. In this way the wild type or modified E. coli CsgG nanopore, or homologue thereof, may be rendered capable of acting as a molecular sensor for detecting presence in a sample of suitable antigens (including epitopes) that may include cell surface antigens, including receptors, markers of solid tumours or haematologic cancer cells (e.g. lymphoma or leukaemia), viral antigens, bacterial antigens, protozoal antigens, allergens, allergy related molecules, albumin (e.g. human, rodent, or bovine), fluorescent molecules (including fluorescein), blood group antigens, small molecules, drugs, enzymes, catalytic sites of enzymes or enzyme substrates, and transition state analogues of enzyme substrates. As described above, modifications may be achieved using known genetic engineering and recombinant DNA techniques. The positioning of any adaptation would be dependent on the nature of the molecule to be sensed, for example, the size, three-dimensional structure, and its biochemical nature. The choice of adapted structure may make use of computational structural design. Determination and optimization of protein-protein interactions or protein-small molecule interactions can be investigated using technologies such as a BIAcore® which detects molecular interactions using surface plasmon resonance (BIAcore, Inc., Piscataway, NJ; see also biacore.com).

In one embodiment, the analyte is an amino acid, a peptide, a polypeptides or protein. The amino acid, peptide, polypeptide or protein can be naturally-occurring or non-naturally-occurring. The polypeptide or protein can include within them synthetic or modified amino acids. Several different types of modification to amino acids are known in the art. Suitable amino acids and modifications thereof are above. It is to be understood that the target analyte can be modified by any method available in the art.

In another embodiment, the analyte is a polynucleotide, such as a nucleic acid, which is defined as a macromolecule comprising two or more nucleotides. Nucleic acids are particularly suitable for nanopore sequencing. The naturally-occurring nucleic acid bases in DNA and RNA may be distinguished by their physical size. As a nucleic acid molecule, or individual base, passes through the channel of a nanopore, the size differential between the bases causes a directly correlated reduction in the ion flow through the channel. The variation in ion flow may be recorded. Suitable electrical measurement techniques for recording ion flow variations are described in, for example, WO 2000/28312 and D. Stoddart et al., Proc. Natl. Acad. Sci., 2010, 106, pp 7702-7 (single channel recording equipment); and, for example, in WO 2009/077734 (multi-channel recording techniques). Through suitable calibration, the characteristic reduction in ion flow can be used to identify the particular nucleotide and associated base traversing the channel in real-time. In typical nanopore nucleic acid sequencing, the open-channel ion flow is reduced as the individual nucleotides of the nucleic sequence of interest sequentially pass through the channel of the nanopore due to the partial blockage of the channel by the nucleotide. It is this reduction in ion flow that is measured using the suitable recording techniques described above. The reduction in ion flow may be calibrated to the reduction in measured ion flow for known nucleotides through the channel resulting in a means for determining which nucleotide is passing through the channel, and therefore, when done sequentially, a way of determining the nucleotide sequence of the nucleic acid passing through the nanopore. For the accurate determination of individual nucleotides, it has typically required for the reduction in ion flow through the channel to be directly correlated to the size of the individual nucleotide passing through the constriction (or "reading head"). It will be appreciated that sequencing may be performed upon an intact nucleic acid polymer that is 'threaded' through the pore via the action of an associated polymerase, for example. Alternatively, sequences may be determined by passage of nucleotide triphosphate bases that have been sequentially removed from a target nucleic acid in proximity to the pore (see for example WO 2014/187924).

The polynucleotide or nucleic acid may comprise any combination of any nucleotides. The nucleotides can be naturally occurring or artificial. One or more nucleotides in the polynucleotide can be oxidized or methylated. One or more nucleotides in the polynucleotide may be damaged. For instance, the polynucleotide may comprise a pyrimidine dimer. Such dimers are typically associated with damage by ultraviolet light and are the primary cause of skin melanomas. One or more nucleotides in the polynucleotide may be modified, for instance with a label or a tag, for which suitable examples are known by a skilled person. The polynucleotide may comprise one or more spacers. A nucleotide typically contains a nucleobase, a sugar and at least one phosphate group. The nucleobase and sugar form a nucleoside. The nucleobase is typically heterocyclic. Nucleobases include, but are not limited to, purines and pyrimidines and more specifically adenine (A), guanine (G), thymine (T), uracil (U) and cytosine (C). The sugar is typically a pentose sugar. Nucleotide sugars include, but are not limited to, ribose and deoxyribose. The sugar is preferably a deoxyribose. The polynucleotide preferably comprises the following nucleosides: deoxyadenosine (dA), deoxyuridine (dU) and/or thymidine (dT), deoxyguanosine (dG) and deoxycytidine (dC). The nucleotide is typically a ribonucleotide or deoxyribonucleotide. The nucleotide typically contains a monophosphate, diphosphate or triphosphate. The nucleotide may comprise more than three phosphates, such as 4 or 5 phosphates. Phosphates may be attached on the 5' or 3' side of a nucleotide. The nucleotides in the polynucleotide may be attached to each other in any manner. The nucleotides are typically attached by their sugar and phosphate groups as in nucleic acids. The nucleotides may be connected via their nucleobases as in pyrimidine dimers. The polynucleotide may be single stranded or double stranded. At least a portion of the polynucleotide is preferably double stranded. The polynucleotide is most preferably ribonucleic nucleic acid (RNA) or deoxyribonucleic acid (DNA). In particular, said method using a polynucleotide as an analyte alternatively comprises determining one or more characteristics selected from (i) the length of the polynucleotide, (ii) the identity of the polynucleotide, (iii) the sequence of the polynucleotide, (iv) the secondary structure of the polynucleotide and (v) whether or not the polynucleotide is modified.

The polynucleotide can be any length (i). For example, the polynucleotide can be at least 10, at least 50, at least 100, at least 150, at least 200, at least 250, at least 300, at least 400 or at least 500 nucleotides or nucleotide pairs in length. The polynucleotide can be 1000 or more nucleotides or nucleotide pairs, 5000 or more nucleotides or nucleotide pairs in length or 100000 or more nucleotides or nucleotide pairs in length. Any number of polynucleotides can be investigated. For instance, the method may concern characterising 2, 3, 4, 5, 6, 7, 8, 9, 10, 20, 30, 50, 100 or more polynucleotides. If two or more polynucleotides are characterised, they may be different polynucleotides or two instances of the same polynucleotide. The polynucleotide can be naturally occurring or artificial. For instance, the method may be used to verify the sequence of a manufactured oligonucleotide. The method is typically carried out in vitro.

Nucleotides can have any identity (ii), and include, but are not limited to, adenosine monophosphate (AMP), guanosine monophosphate (GMP), thymidine monophosphate (TMP), uridine monophosphate (UMP), 5-methylcytidine monophosphate, 5-hydroxymethylcytidine monophosphate, cytidine monophosphate (CMP), cyclic adenosine monophosphate (CAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP), deoxycytidine monophosphate (dCMP) and deoxymethylcytidine monophosphate. The nucleotides are preferably selected from AMP, TMP, GMP, CMP, UMP, dAMP, dTMP, dGMP, dCMP and dUMP. A nucleotide may be abasic (i.e. lack a nucleobase). A nucleotide may also lack a nucleobase and a sugar (i.e. is a C3 spacer). The sequence of the nucleotides (iii) is determined by the consecutive identity of following nucleotides attached to each other throughout the polynucleotide strain, in the 5' to 3' direction of the strand.

The pores comprising a CsgG pore and CsgF peptides are particularly useful in analysing homopolymers. For example, the pores may be used to determine the sequence of a polynucleotide comprising two or more, such as at least 3, 4, 5, 6, 7, 8, 9 or 10, consecutive nucleotides that are identical. For example, the pores may be used to sequence a polynucleotide comprising a polyA, polyT, polyG and/or polyC region.

The CsgG pore constriction is made of the residues at the 51, 55 and 56 positions of SEQ ID NO: 3. The reader head of CsgG and its constriction mutants are generally sharp. When DNA is passing through the constriction, interactions of approximately 5 bases of DNA with the reader head of the pore at any given time dominate the current signal. Although these sharper reader heads are very good in reading mixed sequence regions of DNA (when A, T, G and C are mixed), the signal becomes flat and lack information when there is a homopolymeric region within the DNA (eg: polyT, polyG, polyA, polyC). Because 5 bases dominate the signal of the CsgG and its constriction mutants, its difficult to discriminate photopolymers longer than 5 without using additional dwell time information. However, if DNA is passing through a second reader head, more DNA bases will interact with the combined reader heads, increasing the length of the homopolymers that can be discriminated. The Examples and Figures show that such an increase in homopolymer sequencing accuracy is achieved using the pore comprising a CsgG pore and a CsgF peptide.

Kit

In a further aspect, the present invention also provides a kit for characterising a target polynucleotide. The kit comprises an isolated pore complex according to the invention, and the components of a membrane or an insulating layer. The membrane is preferably formed from the components. The isolated pore complex is preferably present in the membrane or in the insulating layer, together forming a transmembrane pore complex channel. The kit may comprise components of any type of membranes, such as an amphiphilic layer or a triblock copolymer membrane. The kit may further comprise a polynucleotide binding protein. The kit may further comprise one or more anchors for coupling the polynucleotide to the membrane. The kit may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides or voltage or patch clamp apparatus. Reagents may be present in the kit in a dry state such that a fluid sample resuspends the reagents. The kit may also, optionally, comprise instructions to enable the kit to be used in the method of the invention or details regarding for which organism the method may be used. Finally, the kit may also comprise additional components useful in peptide characterization.

In one embodiment, the isolated pore complex or transmembrane pore complex, as provided by the invention, is used for nucleic acid sequencing. For said use, the Phi29 DNA polymerase (DNAP) may be used as a molecular motor with a CsgG:CsgF Nanopore complex located within a membrane to allow controlled movement of an oligomeric probe DNA strand through the pore. A voltage may be applied across the pore and a current generated from the movement of ions in a salt solution on either side of the nanopore. As the probe DNA moves through the pore, the ionic flow through the pore changes with respect to the DNA. This information has been shown to be sequence dependent and allows for the sequence of the probe to be read with accuracy from current measurements.

It is to be understood that although particular embodiments, specific configurations as well as materials and/or molecules, have been discussed herein for engineered cells and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

Introduction

The CsgG pore is part of the multi-component type VIII secretion system, also known as the curli biosynthesis system, which is responsible for the formation of aggregative fibres known in E. coli as curli. Curli are extracellular proteinaceous fibres primarily involved in bacterial biofilm formation and attachment to non-biotic surfaces. Curli biosynthesis is directed by two operons, in E. coli called csgBAC and csgDEFG (curli-specific genes) (Hammar et al., 1995). Secretion of curli subunits CsgA and CsgB depends on CsgG, a dedicated lipoprotein found to form an oligomeric secretion channel in the outer membrane. For transport, CsgG works in coordination with the periplasmic and extracellular accessory proteins CsgE and CsgF. CsgE forms a specificity factor for CsgG-mediated transport, whilst CsgF appears to couple CsgA secretion to the CsgB-templated aggregation into extracellular fibers.

A crystal structure of the CsgG secretion channel demonstrated CsgG to form a nonameric transport complex 120 Å in diameter and 85 Å in height that traverses the OM through a 36-stranded β-barrel of 40 Å inner diameter (Goyal et al., 2014; FIG. 1). A periplasmic domain of the channel, separated from the transmembrane β-barrel by an iris-like diaphragm, forms a large solvent-accessible cavity of 24,000 Å3. This diaphragm is formed by a conserved 12-residue 'constriction loop' (CL) found in each subunit, and whose concentric organization in the CsgG oligomer forms an orifice with solvent-excluded diameter of ~0.6 nm and a height of ~1.5 nm (FIG. 1). When acting as a protein secretion channel, this orifice or constriction in the CsgG channel forms the primary site of interaction with the translocating polypeptide. When CsgG is used as a nanopore sensing platform, this orifice serves the role of primary reader head for analytes residing in or passing the channel. The diameter of the orifice as well as its physical and chemical properties can be modified by amino acid substitutions, deletions or insertions in a region of the protein corresponding to residues 46 to 61 of SEQ ID NO:3 (FIG. 1D). In particular, mutation of positions 51, 55, and 56 according to SEQ ID NO:3, together or individually, has a beneficial influence on the conductance characteristics of the nanopore and its interaction with analytes including polynucleotides.

The assembly factor CsgF represents a component to the curli secretion apparatus. The CsgF preprotein reaches the periplasm via the SEC pathway, after which mature CsgF (12.9 KDa) is found as a surface-exposed protein in a CsgG-dependent manner. In presence of CsgG, CsgF fractionates with the OM, and co-immunoprecipitation experiments suggested the two proteins are in direct contact. Available data demonstrate that CsgF is non-essential for productive subunit secretion, but rather suggest the protein forms a coupling factor between CsgA secretion and extracellular polymerization into curli fibers by coordinating or chaperoning the nucleating function of the CsgB subunit.

Example 1: CsgG:CsgF Complex Protein Production (Co-Expression, In Vitro Reconstitution, Coupled In-Vitro Transcription and Translation and Reconstitution of CsgG with CsgF Synthetic Peptides)

To produce the CsgG:CsgF complex, both proteins can be co-expressed in a suitable Gram-negative host such as E. coli, and extracted and purified as a complex from the outer membrane. The in vivo formation of the CsgG pore and the CsgG:CsgF complex requires targeting of the proteins to the outer membrane. To do so, CsgG is expressed as a preprotein with a lipoprotein signal peptide (Juncker et al. 2003, Protein Sci. 12(8): 1652-62) and Cys residue at the N-terminal position of the mature protein (SEQ ID No:3). An example of such lipoprotein signal peptide is residues 1-15 of full length E. coli CsgG as shown in SEQ ID No:2. Processing of prepro CsgG results in cleavage of the signal peptide and lipidatation of mature CsgG, following by transfer of the mature lipoprotein to the outer membrane, where it inserts as an oligomeric pore (Goyal et al. 2014, Nature 516(7530):250-3). To form the CsgG:CsgF complex, CsgF can be co-expressed with CsgG and targeted to the periplasm by means of a leader sequence such as the native signal peptide corresponding to residues 1-19 of SEQ ID No:5. CsgG:CsgF combination pores can then be extracted from the outer membrane using detergents, and purified to a homogeneous complex by chromatography (FIG. 2).

Figure 3B:
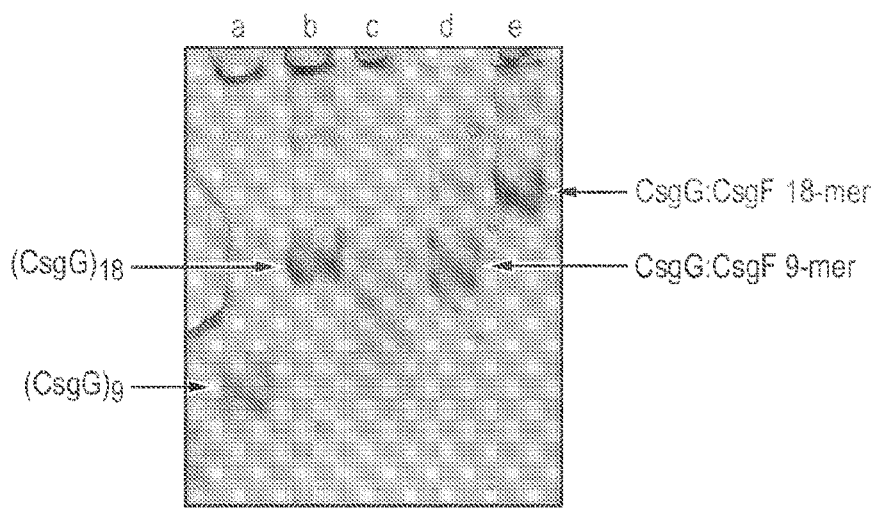
Figure 3C:
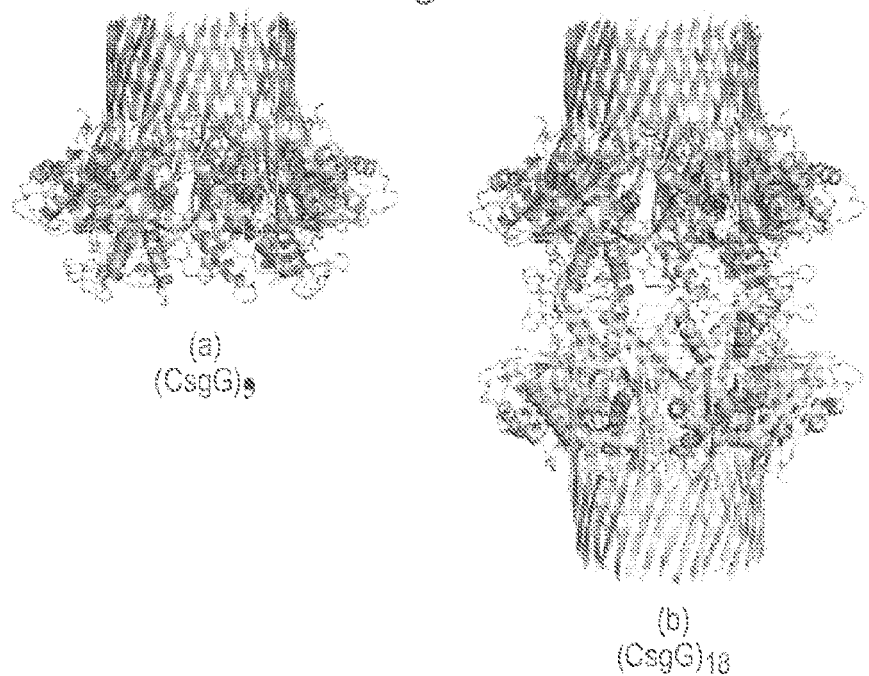

Alternatively, the CsgG:CsgF pore complex can be produced by in vitro reconstitution using the CsgG pore and CsgF—see below and FIG. 3.

For in vivo CsgG:CsgF complex formation in the example shown in FIG. 2, E. coli CsgF (SEQ ID NO:5) and CsgG (SEQ ID NO:2) were co-expressed using their native signal peptides to ensure periplasmic targeting of both proteins, as well as N-terminal lipidation of CsgG. Additionally, for ease of purification, CsgF was modified by introduction of a C-terminally 6× histidine tag and CsgG was fused C-terminally to a Strep-II tag. Co-expression and complex purification was performed as described in the Methods. SDS-PAGE analysis of the His affinity purification eluate revealed the enrichment of CsgF-His, as well as the co-purification of CsgG-Strep, suggesting the latter was in a complex with CsgF (FIG. 2B). Additionally, the SDS-PAGE revealed that a significant fraction of the eluted CsgF ran at lower molecular mass due to the loss of a N-terminal fragment of the protein (FIG. 2B, indicated with asterisk). SDS-PAGE analysis of the pooled fractions of the His-trap elution of the second affinity purification revealed the presence of CsgG and CsgF in an apparent equimolar concentrations, as well as the loss of the CsgF truncation fragment seen in the His-trap eluate (FIG. 2B). Co-elution of CsgF in the Strep-affinity purification indicated that the protein is present as a non-covalent complex with CsgG. Strikingly, the N-terminal truncation fragment of CsgF was lost in the Strep-affinity purification, suggesting that the CsgF N-terminus is required to bind CsgG (FIG. 2B).

Figure 13:
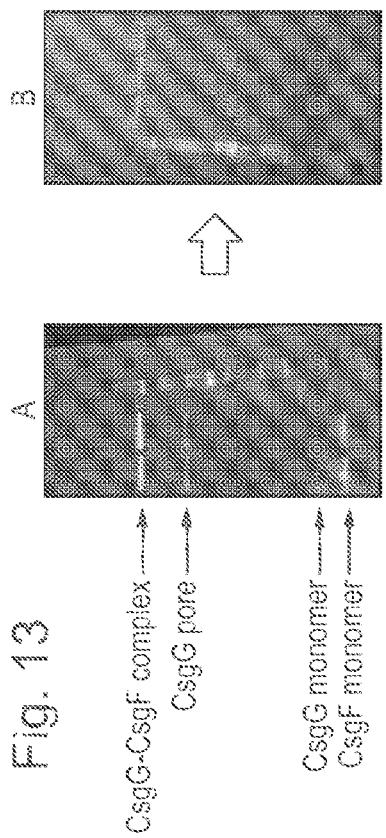
FIG. 13 Co-expression of CsgG with CsgF WT in vivo. Gene encoding the C-terminal strep tagged CsgG polypeptide in pT7 vector with ampicillin resistance and the gene encoding the C-terminal His tagged CsgF polypeptide in pRham vector with kanamycin resistance were transformed together into *E. coli* BL21DE3 cells in the presence of both ampicillin and kanamycin. Proteins were expressed for overnight at 18° C. at 250 rpm and the CsgG-CsgF complex was purified using the Strep tag purification followed by His tag purification. (Gel A) Protein sample (in duplicate) before strep purification. (Gel B). Protein sample (three elution fractions) after His purification. Proteins were run on a 4-20% Tris gel.

FIG. 13 shows another example of CsgG:CsgF complex formation by in vivo co-expression. In this example, CsgG protein is modified with a C terminal Strep-II tag and the CsgF full length protein is modified with a C terminal 10× Histidine tag. Co-expressed CsgG:CsgF complex is been purified away from its constituent components by Strep tag purification followed by a Histidine tag purification as shown in the materials and methods section for characterisation of analytes. Due to the differences in molecular weights, CsgG:CsgF complex can be clearly differentiated from the CsgG pore in SDS-PAGE analysis (FIG. 13A). As shown in FIG. 13.B, two tag purification method can be successfully applied to purify the CsgG:CsgF complex away from its constituent components.

To produce the CsgG:CsgF complex by in vitro reconstitution, CsgG and CsgF were expressed in separate E. coli cultures transformed with pPG1 and pNA101, respectively, and purified, followed by in vitro reconstitution of the CsgG:CsgF complex (see Methods). For comparison, purified CsgG was similarly run over the Superose 6 column as the complex. The CsgG Superose 6 run showed the existence of two discrete populations, corresponding to nonameric CsgG pores (FIG. 3A (a) and 3C) as well as dimers of nonameric CsgG pores (FIG. 3A (b) and 3C), as previously described in Goyal et al. (2014). The Superose 6 run of the CsgG:CsgF reconstitution revealed the existence of three discrete populations corresponding to excess CsgF (FIG. 3A (c)), nonameric CsgG:CsgF complex (FIG. 3A (d)) and dimers of nonameric CsgG:CsgF (FIG. 3A (e)). To provide independent confirmation of the formation of CsgG:CsgF complexes, the various Superose 6 elution peaks were analysed on native PAGE (FIG. 3B)

Surprisingly, CsgG:CsgF complex can also be made by coupled in vitro transcription and translation (IVTT) method as described in the materials and methods section for characterisation of analytes. The complex can be made either by expressing CsgG and CsgF proteins in the same IVTT reaction or reconstituting separately made CsgG and CsgF in two different IVTT reactions. In the example shown in FIG. 14, E. coli T7-S30 extract system for circular DNA (Promega) has been used to make the CsgG:CsgF complex in one reaction mixture and proteins were analysed on SDS-PAGE. Since the protein expression in IVTT does not use the natural molecular machinery of protein expression, DNA that are used to express proteins in IVTT lack the DNA encoding the signal peptide region. When the DNA of CsgG is expressed in IVTT in the absence of DNA of CsgF, only the monomers of CsgG can be produced. Surprisingly, these expressed monomers can be assembled into CsgG oligomeric pores in situ by using cell extract membranes present in the IVTT reaction mixture (FIG. 14, lane 1). Although the oligomer of CsgG is SDS stable, it breaks down into its constituent monomers when the sample is heated to 100° ° C. (FIG. 14, lane 2). When the DNA of CsgF is expressed in IVTT in the absence of DNA of CsgG, only CsgF monomers can be seen (FIG. 14, lane 3). When DNA of CsgG and CsgF are mixed in 1:1 ratio and expressed simultaneously in the same IVTT reaction mixture, CsgF proteins generated interact with the assembled CsgG pore with high efficiency to make CsgG:CsgF complex (FIG. 14, lane 5). This SDS stable complex made in IVTT is heat stable at least up to 70° C. (FIG. 14, lanes 6-12).

CsgG:CsgF complexes with truncated CsgF can also be made by any of the methods shown above by using DNA encoding truncated CsgF instead of the full length version. However, stability of the complex may be compromised when CsgF is truncated below the FCP domain. In addition, CsgG:CsgF complexes with truncated CsgF can be made by cleaving the full length CsgF in appropriate positions once the full length CsgG:CsgF complex is formed. Truncations can be done by modifying the DNA that encode CsgF protein by incorporating protease cleavage sites at positions where cleavage is needed (FIG. 15.A). Seq ID No. 56-67 show TEV or HCV C3 protease sites incorporated in various positions of CsgF to generate CsgG:CsgF complexes with truncated CsgF. SDS-PAGE analysis of TEV cleavage of the CsgG:CsgF complex made with the Seq ID No. 61 is shown (FIG. 15.B). When the CsgG:CsgF complex (with full length CsgF) is treated with TEV protease enzyme as described in the materials and methods section for characterisation of analytes, CsgF is being truncated at position 35 (FIG. 15.B, lanes 3 and 4). However, TEV cleavage leaves an extra 6 amino acids at the C terminal of the cleavage site. Therefore, remaining CsgF truncated protein in complex with the CsgG pore is 42 amino acids long. Molecular weight difference of this complex and the CsgG pore (without the CsgF) is still visible in SDS-PAGE (FIG. 15.B, lanes 7 and 8).

Surprisingly, CsgG:CsgF complexes with truncated CsgF can also be made by reconstituting purified CsgG pore (made by in vivo or in vitro) with synthetic peptides of appropriate length. Since the reconstitution takes place in vitro, signal peptide of CsgF is not required to make the CsgG:CsgF complex. Further, this method does not leave extra amino acids at the C terminus of the CsgF. Mutations and modifications can also be easily incorporated into synthetic CsgF peptides. Therefore, this method is a very convenient way to reconstitute different CsgG pores or mutants or homologues thereof with different CsgF peptides or mutants or homologues thereof to generate different CsgG:CsgF complex variants. Stability of the complex may be compromised when the CsgF is truncated beyond the FCP domain. Examples of truncated CsgF and FCP peptides used to generate CsgG:CsgF complex variants are shown in Table 3. Surprisingly, SDS-PAGE analysis of the heat stability of CsgG:CsgF complexes made by this method with CsgF-(1-45) (FIG. 16.A), CsgF-(1-35) (FIG. 16.B) and CsgF-(1-30) (FIG. 16.C) shows at least CsgF-(1-45) and CsgF-(1-35) peptides make complexes with CsgG that are heat stable at least to 90° C. Since the CsgG pore breaks down to its constituent monomers at 90° C., it is difficult to assess the stability of the complex beyond 90° C. Due to the minimal difference between the CsgG pore band and the CsgG:CsgF-(1-30) complex band in SDS-PAGE, this method is not sufficient to analyse the heat stability of the CsgG:CsgF-(1-30) complex (FIG. 16.C). However, CsgG:CsgF complexes have been observed in all three cases and even with CsgG:CsgF-(1-29) in electrophysiological experiments indicating that even CsgF-(1-29) peptide is producing at least some CsgG:CsgF complexes (FIG. 24).

Example 2: CsgG:CsgF Structural Analysis Via Cryo-EM

To gain structural insight in the CsgG:CsgF complex, co-purified or in vitro reconstituted CsgG:CsgF particles were analysed by transmission electron microscopy. In preparation of cryo-EM analysis, 500 μL of the peak fraction of the double-affinity purified CsgG:CsgF complex was injected onto a Superose 6 10/30 column (GE Healthcare) equilibrated with Buffer D (25 mM Tris pH8, 200 mM NaCl and 0.03% DDM), and run at 0.5 mL/min. Protein concentration was determined based on calculated absorbance at 280 nm and assuming 1:1 stoichiometry. Samples for electron cryomicroscopy were analysed as described in the Methods. A cryo-EM micrograph of the CsgG:CsgF complex as well as two selected class averages from the picked CsgG:CsgF particles are shown in FIG. 4. The micrograph shows the presence of nonameric pore as well as dimer of nonameric pore complexes. For image reconstruction, nonameric CsgG:CsgF particles were picked and aligned using RELION. Class averages of the CsgG:CsgF complex as side views, as well as the 3D reconstructed electron density show the presence of an additional density corresponding to CsgF, seen as a protrusion from the CsgG particle, located at the side of the CsgG β-barrel (FIG. 4B, 5). The additional density reveals three distinct regions, encompassing a globular head domain, a hollow neck domain and a domain that interacts with the CsgG β-barrel. The latter CsgF region, referred to as CsgF constriction peptide or FCP, inserts into the lumen of the CsgG β-barrel and can be seen to form an additional constriction (labeled F in FIG. 4B, 5) of the CsgG pore, located approximately 2 nm above the constriction formed by the CsgG constriction loop (labeled G in FIG. 4B, 5).

Figure 6A:
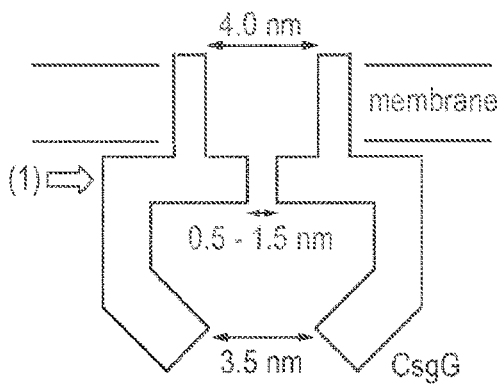
FIG. 6A-6C Schematic representation of the CsgG:CsgF pore complex based on the cryo-EM structure.
Figure 6B:
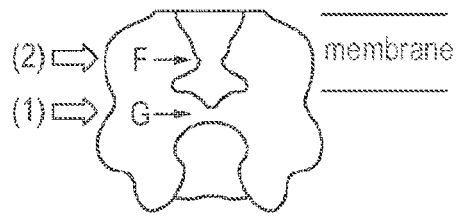
Figure 6C:
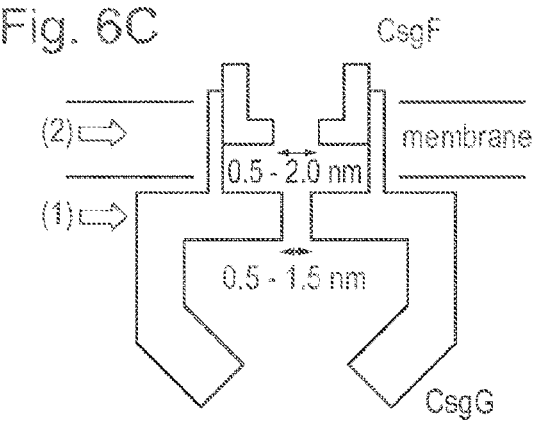
Figure 7A:
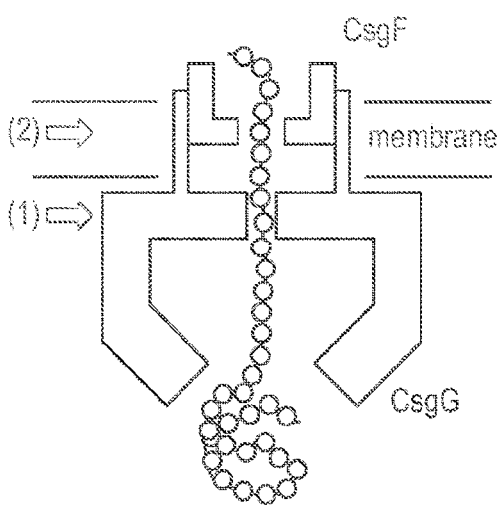
FIG. 7A-7C Schematic representation of the use of CsgG:CsgF pore complex for nanopore sensing applications of a (bio)polymer (FIG. 7A) or single molecule analytes (FIG. 7B). When used in polymer sensing, the second channel constriction introduced by the modified CsgF peptide increases the contact region with the analyte and forms a second interaction site and reader head. When used in single molecule nanopore sensing, the second channel constriction introduced by the modified CsgF peptide, creates a second independent analyte interaction site.
Figure 7B:
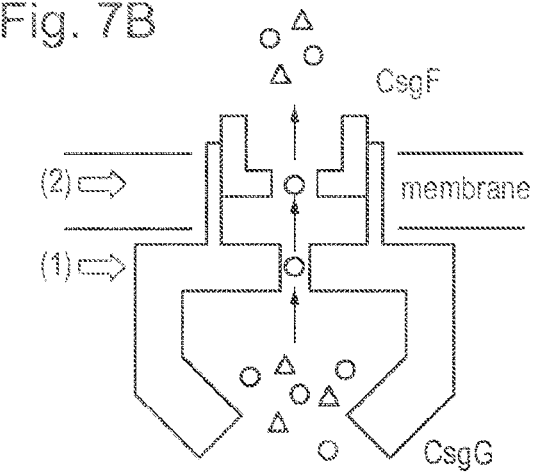
Figure 7C:
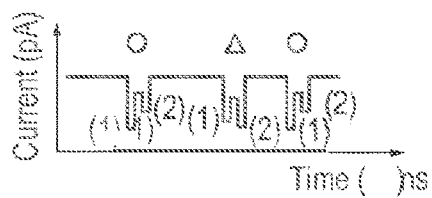

Example 3: Identification of the CsgF Interaction and Constriction Peptide by Truncation of CsgF The presence of a second constriction in the CsgG:CsgF pore complex as compared to the CsgG only pore provides opportunities for nanopore sensing applications, providing a second orifice in the nanopore that can be used as a second reader head or as an extension of the primary reader head provided by the CsgG constriction loop (FIG. 6, 7). However, when in complex with the full length CsgF, the exit side of CsgG:CsgF combination pore is blocked by the CsgF neck and head domains. Therefore, we sought to determine the CsgF region required to interact with and insert into the CsgG β-barrel. Our Strep-tactin affinity purification experiments hinted that the N-terminal region of CsgF was required for CsgG interaction, since an N-terminal truncation fragment of CsgF present in the His-trap affinity purification was lost and did not co-purify with CsgG (FIG. 2B). CsgF homologues are characterised by the presence of PFAM domain PF03783. When performing a multiple sequence alignment (MSA) of CsgG homologues found in Gram-negative bacteria (FIG. 8 shows a MSA of a selected CsgF homologues) a region of sequence conservation (between 35 and 100% pairwise sequence identity) was seen corresponding to the first ~30-35 amino acids of mature CsgF (SEQ ID NO:6). Based on the combined data, this N-terminal region of CsgF was hypothesised to form the CsgG interaction peptide or FCP. A multiple sequence alignment of the FCPs in known CsgF homologues is shown in FIG. 10.

To test the hypothesis that the CsgF N-terminus corresponds to the CsgG binding region and forms the CsgF constriction peptide residing in the CsgG β-barrel lumen, Strep-tagged CsgG and His-tagged CsgF truncates were co-overexpressed in E. coli (see Methods). pNA97, pNA98, pNA99 and pNA100 encode N-terminal CsgF fragments corresponding to residues 1-27, 1-38, 1-48 and 1-64 of CsgF (SEQ ID NO:5). These peptides include the CsgF signal peptide corresponding to residues 1-19 of SEQ ID NO: 5, and thus will produce periplasmic peptides corresponding to the first 8, 19, 29 and 45 residues of mature CsgF (SEQ ID NO:6; FIG. 9A), each including a C-terminal 6×His tag. SDS-PAGE analysis of whole cell lysates revealed the presence of CsgG in all samples, as well as the presence of CsgF fragment corresponding to the first 45 residues of mature CsgF (SEQ ID NO:6; FIG. 9B). For the shorter N-terminal CsgF fragments, no detectable expression of the peptides was seen in the whole cell lysates. After two freeze/thaw cycles, cell mass of the various CsgG:CsgF fragments were further enriched by purification. Whole cell lysates as well as the eluted fractions of the Strep affinity purification were spotted onto a nitrocellulose membrane for dot blot analysis using an anti-His antibody for the detection of the His-tagged CsgF fragments (FIG. 9C). The dot blot shows the CsgF 20:64 peptide co-purifies with CsgG, demonstrating this CsgF fragment is sufficient to form a stable non-covalent complex with CsgG. For the CsgG 20:48 fragment a small amount of peptide can be seen to co-purify with CsgG, whilst no detectable levels are seen for CsgF 20:27 or CsgF 20:38 in either the whole cell lysate or the Strep affinity purification (FIG. 9C), suggesting that the latter peptides are not stably expressed in E. coli, and/or do not form a stable complex with CsgG.

Example 4: Description of the CsgG:CsgF Interaction at Atomic Resolution

Figure 11A:
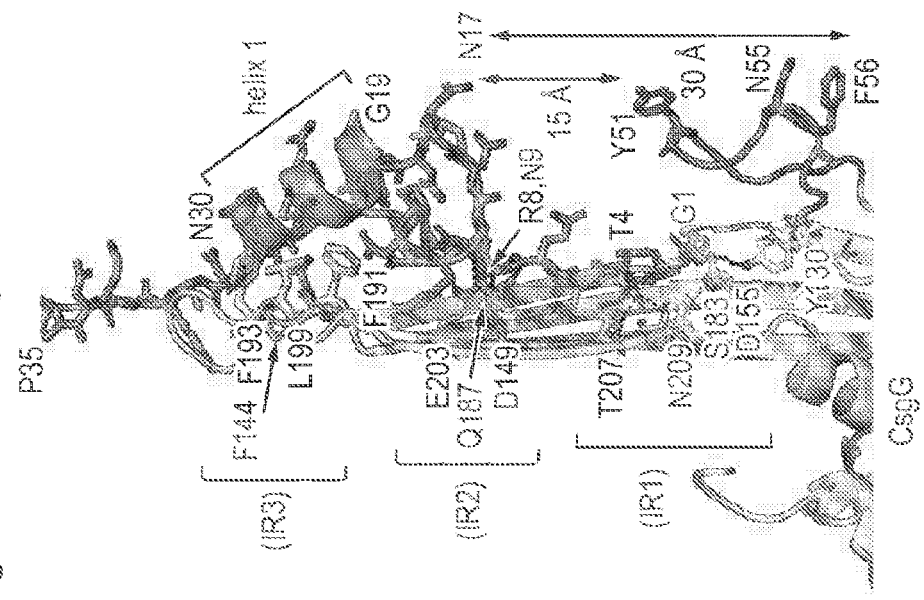
FIG. 11A-11D The high resolution cryoEM structure of the CsgG:CsgF complex. CsgG is shown in light grey and CsgF is shown in dark grey.
Figure 11B:
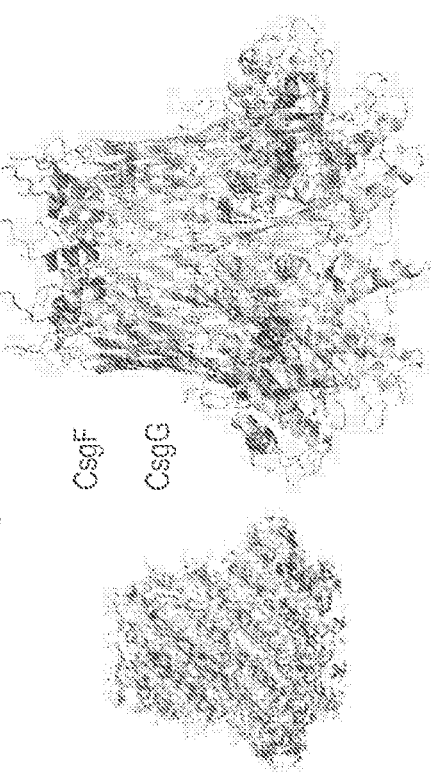
Figure 11C:
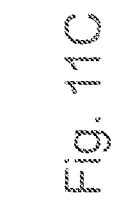
Figure 11D:
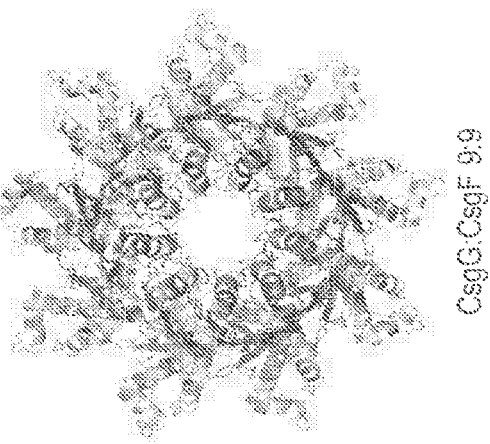

To gain an atomic level detail on the CsgG:CsgF interaction we determined the high resolution cryoEM structure of the CsgG:CsgF complex. For this purpose, CsgG and CsgF were co-expressed recombinantly in E. coli and the CsgG:CsgF complex was isolated from E. coli outer membranes by detergent extraction and purified using tandem affinity purification. Samples for electron cryo-microscopy were prepared by spotting 3 μl sample on R2/1 Holey grids (Quantifoil), coated with graphene oxide, and data was collected on a 300 KV TITAN Krios with Gatan K2 direct electron detector in counting mode. 62.000 single CsgG:CsgF particles were used to calculate a final electron density map at 3.4 Å resolution (FIG. 11A). The map allowed unambiguous docking and local rebuilding of the CsgG crystal structure, as well as the de novo building of the N-terminal 35 residues of mature CsgF (i.e. residues 20:54 of Seq ID No. 5), which encompass the FCP that binds CsgG and forms a second constriction at the height of the CsgG transmembrane β-barrel (FIG. 11C, D). The cryoEM structure shows CsgG:CsgF comprises a 9:9 stoichiometry, with C9 symmetry (FIG. 11B). The FCP binds the inside of the CsgG β-barrel, with the C-terminus of the CsgF pointing out of the CsgG β-barrel, and the CsgF N-terminus located near the CsgG constriction. The structure shows that P35 in mature CsgF lies outside the CsgG β-barrel and forms the connection between the CsgF FCP and neck regions. The CsgF neck and head regions are not resolved in the high resolution cryoEM maps due to flexibility relative to the main body of the CsgG:CsgF complex. Three regions in the CsgG β-barrel stabilize the CsgG:CsgF interaction: (IR1) residues Y130, D155, S183, N209 and T207 in mature CsgG (SEQ ID NO: 3) form an interaction network with the N-terminal amine and residues 1 to 4 of mature CsgF (SEQ ID NO: 6), comprising four H-bonds and an electrostatic interaction; (IR2) residues Q187, D149 and E203 in mature CsgG (SEQ ID NO: 3) form an interaction network with R8 and N9 in mature CsgF (SEQ ID NO 6), encompassing three H-bonds and two electrostatic interaction; and (IR3) residues F144, F191, F193 and L199 in mature CsgG (SEQ ID NO: 3) form a hydrophobic interaction surface with residues F21, L22 and A26 in mature CsgF (SEQ ID NO: 6). The latter are located in an α-helix (helix 1) formed by residues 19-30 of mature CsgF. The conserved sequence N-P-X-F-G-G (residues 9-14 in SEQ ID NO: 6) forms an inward turn that connects the loop region formed by residues 15-19 with the CsgF helix 1. Together, these elements give rise to a constriction in the CsgG:CsgF complex, of which residue 17 (N17 in mature E. coli CsgF, SEQ ID NO: 6) forms the narrowest point, resulting in an orifice with 15 Å diameter (FIG. 11C). The second constriction (F-constriction or FC) lies approximately 15 Å and 30 Å above the top and bottom, respectively, of the constriction formed by CsgG residues 46 to 59 (G-constriction or GC).

Example 5: Simulations to Improve CcgG-CsgF Complex Stability

Molecular dynamics simulations were performed to establish which residues in CsgG and CsgF come into close proximity. This information was used to design CsgG and CsgF mutants that could increase the stability of the complex.

Simulations were performed using the GROMACS package version 4.6.5, with the GROMOS 53a6 forcefield and the SPC water model. The cryo-EM structure of the CsgG-CsgF complex was used in the simulations. The complex was solvated and then energy minimised using the steepest descents algorithm. Throughout the simulation, restraints were applied to the backbone of the complex, however, the residue sidechains were free to move. The system was simulated in the NPT ensemble for 20 ns, using the Berendsen thermostat and Berendsen barostat to 300 K.

Contacts between CsgG and CsgF were analysed using both GROMACS analysis software and also locally written code. Two residues were defined as having made a contact if they came within 3 Angstroms. The results are shown in Table 4 below.

TABLE 4

Predicted contact frequencies of residue pairs in the CsgG/CsgF complex:

| CsgG residue | CsgF residue | % Time spent in contact |
|---|---|---|
| GLU 203 | ARG 8 | 88.8 |
| GLU 201 | ASN 11 | 87.4 |
| GLU 201 | PHE 12 | 84.3 |
| GLU 203 | ASN 9 | 83.6 |
| ASP 155 | GLY 1 | 81.2 |
| GLU 203 | PHE 7 | 81 |
| GLU 201 | ASN 9 | 77.2 |
| SER 183 | GLY 1 | 76.1 |
| ASN 209 | MET 3 | 70.8 |
| THR 207 | PHE 5 | 70.1 |
| ASP 149 | ARG 8 | 68.5 |
| GLN 187 | ARG 8 | 66.1 |
| ARG 142 | PHE 12 | 65.4 |
| GLU 185 | ARG 8 | 64.4 |
| ASP 149 | PHE 12 | 64.2 |
| GLN 187 | GLN 6 | 63.3 |
| GLY 205 | PHE 5 | 54 |
| GLN 197 | ASN 30 | 52.5 |
| GLN 197 | SER 31 | 51.4 |
| LYS 49 | THR 2 | 50.8 |
| PHE 144 | GLN 29 | 50.6 |
| GLU 201 | PHE 21 | 48 |
| GLN 151 | PHE 5 | 47 |
| PHE 191 | ASN 9 | 46.9 |
| ARG 142 | ASN 11 | 46.4 |
| GLN 151 | PHE 7 | 45.6 |
| TYR 196 | TYR 32 | 45.4 |
| PHE 191 | PHE 21 | 45.3 |
| PHE 193 | ALA 26 | 45.1 |
| GLU 201 | SER 25 | 44.9 |
| LEU 199 | GLN 29 | 44.7 |
| ARG 141 | PHE 12 | 43.1 |
| GLY 138 | PHE 7 | 43 |
| GLN 187 | PHE 5 | 43 |
| GLY 145 | GLN 29 | 42.4 |
| GLN 153 | GLY 1 | 42.1 |
| GLY 140 | PHE 7 | 40.5 |
| PHE 193 | TYR 32 | 39.9 |
| GLU 203 | PHE 12 | 39.7 |

TABLE 4-continued

Predicted contact frequencies of residue pairs in the CsgG/CsgF complex:

| CsgG residue | CsgF residue | % Time spent in contact |
|---|---|---|
| ASN 133 | PHE 5 | 35.9 |
| GLN 151 | MET 3 | 32 |
| PHE 193 | ASN 30 | 31.9 |
| SER 136 | PHE 5 | 31.7 |
| PHE 144 | SER 31 | 30.3 |
| TYR 130 | GLY 1 | 30 |
| GLN 187 | PHE 7 | 29.9 |
| PHE 192 | ASN 30 | 28.9 |
| GLY 138 | PHE 5 | 28.3 |
| ILE 194 | TYR 32 | 26.7 |
| ASN 209 | GLY 1 | 26.1 |
| PHE 192 | GLN 29 | 25.8 |
| PHE 193 | GLN 29 | 25.4 |
| PHE 193 | GLN 27 | 23.9 |
| ASP 149 | GLY 13 | 22.7 |
| TYR 196 | ASN 30 | 22.6 |
| PHE 192 | SER 31 | 22.2 |
| ASP 148 | PHE 12 | 22 |
| GLY 140 | PHE 12 | 21.7 |
| TYR 196 | ASP 34 | 21.6 |
| ARG 198 | SER 31 | 19.9 |
| VAL 139 | PHE 7 | 19.5 |
| PHE 191 | ALA 26 | 18.3 |
| ASN 132 | GLY 1 | 18.1 |
| TYR 195 | TYR 32 | 17.9 |
| GLN 197 | ALA 28 | 17.6 |
| GLN 151 | ARG 8 | 16.9 |
| PHE 191 | LEU 22 | 16.5 |
| PHE 191 | GLN 29 | 15.6 |
| THR 206 | PHE 5 | 14.7 |
| GLN 153 | MET 3 | 14.3 |
| PHE 192 | TYR 32 | 13.8 |
| GLU 201 | GLN 29 | 13.3 |
| ARG 142 | SER 25 | 13.3 |
| PHE 144 | ASN 30 | 12.6 |
| ARG 142 | ARG 8 | 12.6 |
| PHE 191 | ASN 11 | 12.3 |
| GLU 131 | THR 2 | 12.2 |
| ASN 133 | GLY 1 | 11.3 |
| GLY 205 | PHE 7 | 11.2 |
| GLN 151 | PHE 12 | 10.4 |
| ASN 132 | PHE 5 | 10.3 |
| GLU 202 | PHE 12 | 10.2 |
| ASP 149 | PHE 7 | 10.2 |

Materials and Methods for Structural Determination of the CsgG:CsgF Complex:

Cloning

For the expression of E. coli CsgG as outer membrane localized pore, the coding sequence of E. coli CsgG (SEQ ID NO:1) was cloned into pASK-Iba12, resulting in plasmid pPG1 (Goyal et al. 2013).

For the expression of C-terminally 6x-His tagged CsgF in the E. coli cytoplasm, the coding sequence for mature E. coli CsgF (SEQ ID NO:6; i.e. CsgF without its signal sequence) was cloned into pET22b via the NdeI and EcoRI sites, using a PCR product generated using the primers "CsgF-His_pET22b_FW" (SEQ ID NO:46) and "CsgF-His_pET22b_Rev" (SEQ ID NO:47), resulting in the CsgF-His expression plasmid pNA101.

The pNA62 plasmid, a pTrc99a based vector expressing csgF-His and csgG-strep, was created based on pGV5403 (pTrc99a with the pDEST14 Gateway® cassette integrated). The pGV5403 ampicillin resistance cassette was replaced by a streptomycin/spectinomycin resistance cassette. A PCR fragment encompassing part of the E. coli MC4100 csgDEFG operon corresponding to the coding sequences of csgE, csgF and csgG was generated with primers csgEFG_pDONR221_FW (SEQ ID NO:48) and csgEFG_pDONR221_Rev (SEQ ID NO:49), and inserted in pDONR221 (ThermoFisher Scientific) via BP Gateway® recombination. Next, this recombinant csgEFG operon from the pDONR221 donor plasmid was inserted via LR Gateway® recombination into pGV5403 with streptomycin/spectinomycin resistance cassette. Via PCR, a 6×His-tag was added to the CsgF C-terminus using primers Mut_csgF_His_FW (SEQ ID NO:50) and Mut_csgF_His_Rev (SEQ ID NO:51). Finally, csgE was removed by outwards PCR (primers DelCsgE_FW (SEQ ID NO:52) and DelCsgE_Rev (SEQ ID NO:53)) to obtain pNA62.

Constructs for the periplasmic expression of C-terminally His-tagged CsgF fragments corresponding to the putative constriction peptides (FIG. 9A) were created by outwards PCR on pNA62, a pTrc99a based vector expressing CsgF-his and CsgG-strep. Primer combinations were as follows: pNa62_CsgF_histag_Fw (SEQ ID NO:45) as forward primers, with CsgF_d27_end (SEQ ID NO:41), CsgF_d38_end (SEQ ID NO:42), CsgF_d48_end (SEQ ID NO:43) or CsgF_d64_end (SEQ ID NO:44) as reverse primers to create pNA97, pNA98, pNA99 and pNA100 respectively.

In pNA97 csgF is truncated to SEQ ID NO:7, encoding a CsgF fragment including residues 1-27 (SEQ ID NO:8); In pNA98 csgF is truncated to SEQ ID NO:9, encoding a CsgF fragment including residues 1-38 (SEQ ID NO:10); In pNA99 csgF is truncated to SEQ ID NO:11, encoding a CsgF fragment including residues 1-48 (SEQ ID NO:12); and in pNA100 csgF is truncated to SEQ ID NO:13, encoding a CsgF fragment including residues 1-64 (SEQ ID NO:14). Expression of pNA97, pNA98, pNA99 and pNA100 in E. coli does result in production of the CsgG pore (SEQ ID NO:3) in the outer membrane, as well as periplasmic targeting of CsgF-derived peptides with sequences:

"GTMTFQFRHHHHHH" (SEQ ID NO:37+6×His), "GTMTFQFRNPNFGGNPNNGHHHHHH" (SEQ ID NO:38+6×His), "GTMTFQFRNPNFGGNPNNGAFLLNSAQAQHHHHHH" (SEQ ID NO:39+6×His), and "GTMTFQFRNPNFGGNPNNGAFLLNSAQAQNSYKDPSYNDDFGIETHHHHHH" (SEQ ID NO:40+6×His), respectively.

Strains

E. coli Top10 (F⁻ mcrA Δ(mrrhsdRMS-mcrBC) Φ80lacZΔM15 Δ lacX74 recA1 araD139 Δ(araleu) 7697 galU galK rpsL (StrR) endA1 nupG) was used for all cloning procedures. E. coli C43(DE3) (F⁻ ompT hsdSB (rB⁻ mB⁻) gal dcm (DE3)) and Top10 were used for protein production.

Recombinant CsgG:CsgF Complex Production Via Co-Expression

For co-expression of E. coli CsgF (SEQ ID NO:5) and CsgG (SEQ ID NO:2), both recombinant genes including their native Shine Dalgarno sequences were placed under control of the inducible trc promotor in a pTrc99a-derived plasmid to form plasmid pNA62. CsgG and CsgF were overexpressed in E. coli C43(DE3) cells transformed with plasmid pNA62 and grown at 37° C. in Terrific Broth medium. When the cell culture reached an optical density (OD) at 600 nm of 0.7, recombinant protein expression was induced with 0.5 mM IPTG and left to grow for 15 hours at 28° C., before being harvested by centrifugation at 5500 g.

Recombinant CsgG:CsgF Complex Production Via In Vitro Reconstitution

Full-length E. coli CsgG (SEQ ID NO:2) modified with a C-terminal StrepII-tag was overexpressed in E. coli BL21 (DE3) cells transformed with plasmid pPG1 (Goyal et al.

2013). The cells were grown at 37° C. to an OD 600 nm of 0.6 in Terrific Broth medium. Recombinant protein production was induced with 0.0002% anhydrotetracyclin (Sigma) and the cells were grown at 25° C. for a further 16 h before being harvested by centrifugation at 5500 g.

E. coli CsgF (SEQ ID NO:6; i.e. lacking the CsgF signal sequence) in a C-terminal fusion with a 6×His-tag was overexpressed in the cytoplasm of E. coli BL21(DE3) cells transformed with plasmid pNA101 Cells were grown at 37° C. to an OD of 600 nm followed by induction by 1 mM IPTG and left to express protein 15h at 37° C. before being harvested by centrifugation at 5500 g.

Recombinant Protein Purification of the CsgG:CsgF Complex, CsgG, and CsgF

E. coli cells transformed with pNA62 and co-expressing CsgG-Strep and CsgF-His were resuspended in 50 mM Tris-HCl pH 8.0, 200 mM NaCl, 1 mM EDTA, 5 mM MgCl2, 0.4 mM AEBSF, 1 µg/mL Leupeptin, 0.5 mg/mL DNase I and 0.1 mg/mL lysozyme. The cells were disrupted at 20 kPsi using a TS series cell disruptor (Constant Systems Ltd) and the lysed cell suspension incubated 30' with 1% n-dodecyl-β-d-maltopyranoside (DDM; Inalco) for further cell lysis and extraction of outer membrane components. Next, remaining cell debris and membranes were spun down by ultracentrifugation at 100.000 g for 40'. Supernatant was loaded onto a 5 mL HisTrap column equilibrated in buffer A (25 mM Tris pH8, 200 mM NaCl, 10 mM imidazole, 10% sucrose and 0.06% DDM). Column was washed with >10 CVs 5% buffer B (25 mM Tris pH8, 200 mM NaCl, 500 mM imidazole, 10% sucrose and 0.06% DDM) ion buffer A and eluted with a gradient of 5-100% buffer B over 60 mL.

Eluens was diluted 2-fold before loading overnight on a 5 mL Strep-tactin column (IBA GmbH) equilibrated with buffer C (25 mM Tris pH8, 200 mM NaCl, 10% sucrose and 0.06% DDM). Column was washed with >10 CVs buffer C and protein was eluted by the addition of 2.5 mM desthiobiotin. Next 500 µL of the peak fraction of the double-affinity purified complex was injected on a Superose 6 10/30 (GE Healthcare) equilibrated with Buffer D (25 mM Tris pH8, 200 mM NaCl and 0.03% DDM), and run at 0.5 mL/min to prepare samples for electron microscopy. Protein concentration was determined based on calculated absorbance at 280 nm and assuming 1/1 stoichiometry. Buffer D (25 mM Tris pH8, 200 mM NaCl and 0.03% DDM)

CsgG-strep purification for in vitro reconstitution is identical to the protocol for CsgG:CsgF when omitting sucrose in the buffers and bypassing the IMAC and size exclusion steps.

CsgF-His purification for in vitro reconstitution was performed by resuspension of the cell mass in 50 mM Tris-HCl PH 8.0, 200 mM NaCl, 1 mM EDTA, 5 mM MgCl2, 0.4 mM AEBSF, 1 µg/mL Leupeptin, 0.5 mg/mL DNase I and 0.1 mg/mL lysozyme. The cells were disrupted at 20 kPsi using a TS series cell disruptor (Constant Systems Ltd) and the lysed cell suspension was centrifuged at 10.000 g for 30 min to remove intact cells and cell debris. Supernatant was added to 5 mL Ni-IMAC-beads (Workbeads 40 IDA, Bio-Works Technologies AB) equilibrated with buffer A (25 mM Tris pH8, 200 mM NaCl, 10 mM imidazole) and left incubating for 1 hour at 4° C. Ni-NTA beads were pooled in a gravity flow column and washed with 100 mL of 5% buffer B (25 mM Tris pH8, 200 mM NaCl, 500 mM imidazole diluted in buffer A. Bound protein was eluted by stepwise increase of Buffer B (10% steps of each 5 mL).

In Vitro Reconstitution of the CsgG:CsgF Complex

Purified CsgG and CsgF were pooled and used to in vitro reconstitute the complex. Therefore a molar ratio of 1 CsgG: 2 CsgF was mixed to saturate the CsgG barrel with CsgF. Next, the reconstituted mixture was injected on a Superose 6 10/30 column (GE Healthcare) equilibrated with Buffer D (25 mM Tris pH8, 200 mM NaCl and 0.03% DDM), and run at 0.5 mL/min to prepare samples for electron microscopy (FIG. 3). Protein concentration was determined based on calculated absorbance at 280 nm and assuming 1/1 stoichiometry.

Structural Analysis Using Electron Microscopy

Sample behavior of the size exclusion fraction is probed using negative stain electron microscopy. Samples are stained with 1% uranyl formate and imaged using an in-house 120 kV JEM 1400 (JEOL) microscope equipped with a LaB6 filament. Samples for electron cryomicroscopy were prepared by spotting 2 µL sample onto R2/1 continuous carbon (2 nm) coated grids (Quantifoil), manually blotted and plunged in liquid ethane using an in house plunging device. Sample quality was screened on the in-house JEOL JEM 1400 before collecting a dataset on a 200 kV TALOS ARCTICA (FEI) microscope equipped with a Falcon-3 direct electron detection camera. Images were motion corrected with MotionCor2.1 (Zheng et al. 2017), defocus values were determined using ctffind4 (Rohou and Grigorieff, 2015) and data was further analysed using a combination of RELION (Scheres, 2012) and EMAN2 (Ludtke, 2016). C9 Symmetry was imposed during 3D model generation and refinement on selected 2D class averages featuring additional density for a head group.

For high resolution cryoEM analysis, CsgG:CsgF samples were prepared for electron cryo-microscopy by spotting 3 µl sample on R2/1 Holey grids (Quantifoil), coated with graphene oxide (Sigma Aldrich), manually blotted and plunged in liquid ethane using CP3 plunger (Gatan). Sample quality was screened on the in-house JEOL JEM 1400 before collecting a dataset on a 300 kV TITAN KRIOS (FEI, Thermo-Scientific) microscope equipped K2 Summit direct electron detector (Gatan). The detector was used in counting mode with a cumulative electron dose of 56 electrons per Å2 spread over 50 frames. 2045 images were collected with a pixel size of 1.07 Å. Images were motion-corrected with MotionCor2.1 (Zheng et al. 2017) and defocus values were determined using ctffind4 (Rohou and Grigorieff, 2015). Particles were picked automatically using Gautomatch (Dr. Kai Zhang) and data was further analysed using a combination of RELION2.0 (Kimanius et al. 2016, Elife 5. pii: e18722) and EMAN2 (Ludtke, 2016). C9 Symmetry was imposed during 3D model generation and refinement on selected 2D class averages featuring additional density for the head group corresponding to CsgF. 62.000 particles were used to calculate the final map at 3.4 Å resolution. De novo model building of CsgF was done with COOT (Brown et al. 2015 Acta Crystallogr D Biol Crystallogr 71 (Pt 1):136-53) and iterative cycles of model building and refinement of the full complex was done with PHENIX (Afonine 2018, Acta Crystallogr D Struct Biol 74 (Pt 6):531-544) real-space refinement in combination with COOT.

Protein Expression and Purification of CsgG:CsgF Fragments

CsgF fragments and CsgG were co-expressed, with CsgF fragments being C-terminally His-tagged and CsgG fused C-terminally to a Strep tag. The CsgG: CsgF fragments complex was overexpressed in E. coli Top10 cells, transformed with plasmid pNA97, pNA98, pNA99 or pNA100. Plates were grown at 37° C. ON, and a colony was resuspended in LB medium supplemented with Streptomycin/ spectomycin. When the cell cultures reached an optical density (OD) at 600 nm of 0.7, recombinant protein expression was induced with 0.5 mM IPTG and left to grow for 15 hours at 28° C., before being harvested by centrifugation at 5500 g. Pellets were frozen at −20° C.

Cell mass for the various CsgG:CsgF fragment co-expressions was resuspended in 200 ml 50 mM Tris-HCl PH 8.0, 200 mM NaCl, 1 mM EDTA, 5 mM MgCl2, 0.4 mM AEBSF, 1 μg/mL Leupeptin, 0.5 mg/mL DNase I and 0.1 mg/mL lysozyme, sonicated and incubated with 1% n-dodecyl-β-d-maltopyranoside (DDM; Inalco) for further cell lysis and extraction of outer membrane components. Next, remaining cell debris and membranes were spun down by centrifugation at 15.000 g for 40'. The supernatant was incubated with 100 μL Strep-tactin beads at RT for 30 min. Strep beads were washed with buffer (25 mM Tris pH8, 200 mM NaCl, and 1% DDM) by centrifugation and bound proteins were eluted by the addition of 2.5 mM desthiobiotin in 25 mM Tris pH8, 200 mM NaCl, 0.01% DDM.

Production of CsgG:FCP by In Vitro Reconstitution.

A synthetic peptide corresponding to the N-terminal 34 residues of mature CsgF (SEQ ID NO: 6) was diluted to 1 mg/ml in buffer 0.1 M MES, 0.5 M NaCl, 0.4 mg/ml EDC (1-ethyl-3-(3-dimethylaminopropyl)carbodiimide), 0.6 mg/ml NHS (N-hydroxysuccinimide) and incubated for 15 min at room temperature to allow activation of the peptide carboxyterminus. Next, 1 mg/ml Cadaverin-Alexa594 in PBS was added during a 2h incubation to allow covalent coupling at room temperature. The reaction was quenched via buffer exchange to 50 mM Tris, NaCl, 1 mM EDTA, 0.1% DDM using Zeba Spin filters.

Labelled peptide was added to strep-affinity purified CsgG in 50 mM Tris, 100 mM NaCl, 1 mM EDTA, 5 mM LDAO/C8D4 in a 2:1 molar ratio during 15 minutes at room temperature to allow reconstitution of the CsgG:FCP complex. After pull down of CsgG-strep on StrepTactin beads, the sample was analysed on native-PAGE.

Example 6: Further Stabilization of CsgG:CsgF Complex by Covalent Cross Linking Although full length and some of the truncated versions of CsgF make stable CsgG:CsgF complexes with the CsgG pore, CsgF can still be dislodged from the barrel region of CsgG pore under certain conditions. Therefore, it is desirable to make a covalent link between the CsgG and CsgF subunits. Based on molecular simulation studies, positions of CsgG and CsgF that are in close proximity to each other have been identified (Example 5 and Table 4). Some of these identified positions have been modified to incorporate a Cysteine in both CsgG and CsgF. FIG. 19 shows an example of thiol-thiol bond formation between Q153 position of CsgG and G1 position of CsgF. CsgG pore containing Q153C mutation was reconstituted with CsgF containing G1C mutation and incubated for 1 hour enabling S—S bond formation. When the complex is heated to 100° C. in the absence of DTT, a 45 kDa band corresponding to dimer between CsgG monomer and CsgF monomer (CsgGm-CsgFm) can be seen indicating the S—S bond formation between the two monomers (CsgGm is 30 kDa and CsgFm is 15 kDa) (FIG. 19.A). This band disappears when the heating is done in the presence of DTT. DTT breaks down the S—S bond. When the CsgG:CsgF complex incubated overnight instead of 1 hour, the extend of CsgGm-CsgFm dimer formation increases (FIG. 19.A). Mass spectroscopy methods have been carried out to further identify the dimer band. Gel purified protein was proteolytically cleaved to generate tryptic peptides. LC-MS/MS sequencing methods were performed, resulting in the identification of S—S bond between the Q153 position of CsgG and G1 position of CsgF (FIG. 19.B). Oxidising agents such as copper-orthophenanthroline can be used to enhance the S—S bond formation. When CsgG pore containing N133C modification is reconstituted with CsgF containing T4C modification in the presence of copper-orthophenanthroline as described in methods section and then broken down to its constituent monomers by heating to 100° C. in the absence of DTT, a strong dimer band corresponding to CsgGm-CsgFm can be observed on SDS-PAGE (FIG. 20, lanes 3 and 4). When the heating was carried out in the presence of DTT, the dimer breaks down to its constituent monomers (FIG. 20, lanes 1 and 2).

Example 7: Electrophysiological Characterisation of CsgG:CsgF Complexes

Figure 12:
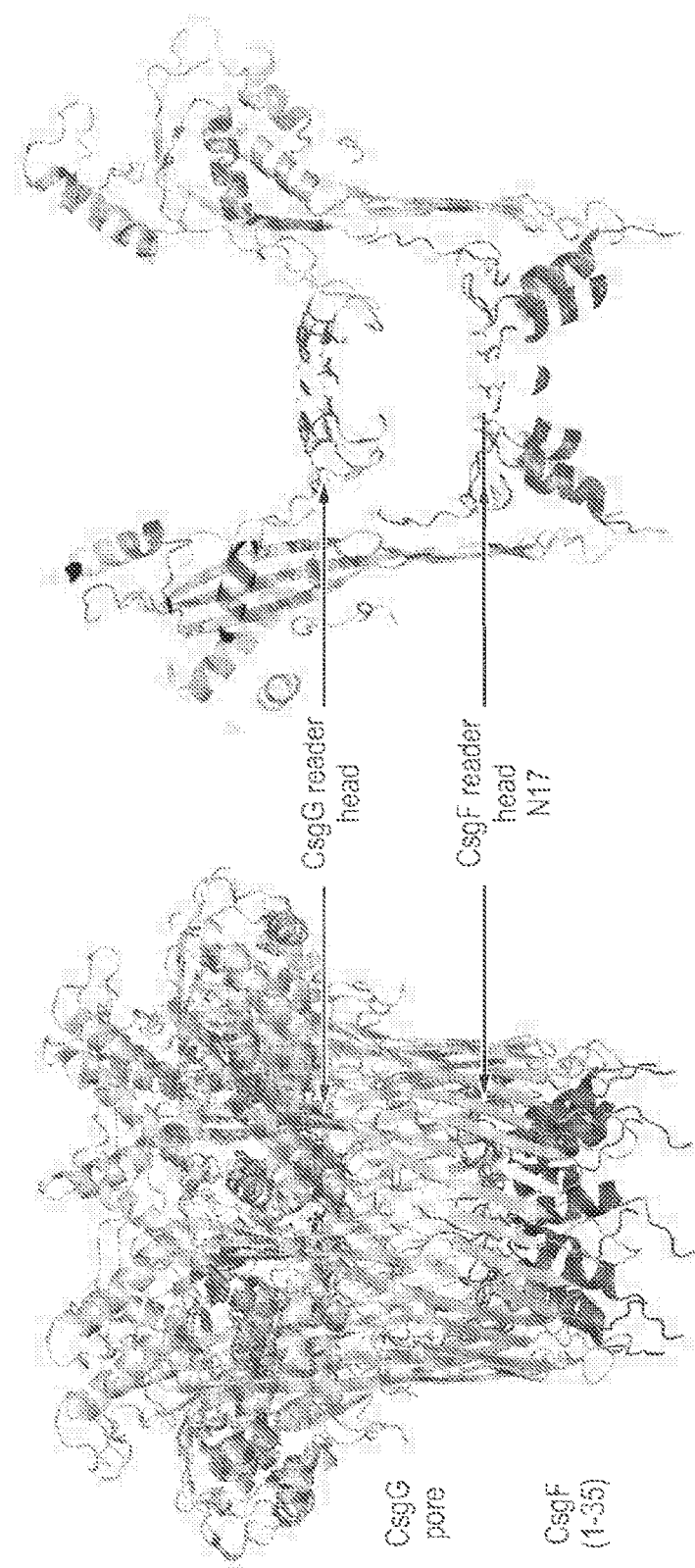
FIG. 12 Two reader heads of the CsgG:CsgF complex. CsgG is shown in light grey and reader head of the CsgG pore is shown in dark grey. CsgF is shown in black and the reader head of the CsgF is labelled.

The signal observed when a DNA strand translocates through CsgG is well characterised when the pore is inserted in the copolymer membrane and experiments are carried out using the MinION of Oxford Nanopore Technologies (FIG. 31). Y51, N55 and F56 of each subunit of CsgG form the constriction of the CsgG pore (FIG. 12). This sharp constriction serves as the reader head of the CsgG pore (FIG. 31A) and is able to accurately discriminate a mixed sequence of A, C, G and T as it passes through the pore. This is because the measured signal contains characteristic current deflections from which the identity of the sequence can be derived. However, in homopolymeric regions of DNA, the measured signal may not show current deflections of sufficient magnitude to allow single base identification; such that an accurate determination of the length of a homopolymer cannot be made from the magnitude of the measured signal alone (FIGS. 26B and C). The reduction in accuracy of the CsgG reader head is correlated to the length of the homopolymeric region (FIG. 29C). When CsgF interacts with the CsgG pore to make the CsgG:CsgF complex, CsgF introduces a second reader head within the CsgG barrel. This second reader head primarily consists of the N17 position of Seq. ID No. 6. A static strand experiment as described in the methods section and FIG. 27 was carried out to map the two reader heads of the CsgG:CsgF complex experimentally, and results indicate the presence of the two reader heads that are separated from each other by approximately 5-6 bases (FIGS. 27, B, C and D). Reader head discrimination plot for the CsgG:CsgF complex shows that the second reader head introduced by CsgF contributes less to the base discrimination than that of the CsgG reader head (FIG. 27A). Surprisingly, when a second reader head is introduced by CsgF within the CsgG barrel, the homopolymeric region which was flat previously shows a step wise signal (FIGS. 30B and C). These steps contain information that can be used to identify the sequence accurately resulting in a decrease in errors. Accuracy of the DNA signal of the CsgG:CsgF complex remains relatively constant over a longer homopolymeric length compared to the accuracy profile of the CsgG pore by itself (FIG. 29C).

CsgG:CsgF complexes made in any of the methods described in the methods section can be used to characterise the complex in DNA sequencing experiments. Signals of a lambda DNA strand passing through various CsgG:CsgF complexes made by different methods consisting of different CsgG mutant pores and different CsgF peptides with different lengths are shown in FIGS. 21-24. Reader head discrimination of those pore complexes and their base contribution profiles are shown in FIG. 28(A-H). Surprisingly, different modifications at constrictions of both CsgG pore and the CsgF peptide can alter the signal of the CsgG:CsgF pore complex significantly. For example, when the CsgG:CsgF complexes are made with the same CsgG pore, but with two different CsgF peptides of the same length containing either Asn or Ser at position 17 (of Seq ID No. 6) (made by the same method of co-expression of the full length CsgF protein followed by TEV protease cleavage of CsgF between positions 35 and 36), the signals generated are different from each other (FIG. 21). The CsgG:CsgF complex with Ser at position 17 of the CsgF peptide shows lower noise and higher signal:noise ratio compared to the CsgG:CsgF complex with Asn at position 17 of the CsgF peptide. Similarly, when the same CsgG pore was reconstituted with two different peptides of CsgF of the same length (1-35 of Seq ID No. 6) but with either Ser or Val at positon 17 to make the CsgG:CsgF complexes, the complex with Val at position 17 of CsgF shows a noisier signal than the complex with Ser at position 17 of CsgF (FIG. 22). When the same CsgF peptide of the same length was reconstituted with different CsgG pores containing different mutations at the CsgG reader head (positions 51, 55 and 56), the resulting CsgG:CsgF complexes showed very different signals (FIG. 23, A-F) with different signal to noise ratios (FIG. 25). Surprisingly, when different lengths of CsgF peptides that contained the same constriction region were reconstituted with the same CsgG pore to make CsgG:CsgF complexes, they gave signals with a different range (FIG. 24). CsgG:CsgF complex which contains the shortest CsgF peptide (1-29 of Seq ID No. 6) showed the largest range and the CsgG:CsgF complex which contains the longest CsgF peptide (1-45 of Seq ID No. 6) showed the smallest range (FIG. 24).

Materials and Methods for Characterisation of Analytes:

The proteins produced by the methods described below can be used interchangeably with those produced by the methods described above with respect to structural determination.

Methods

Expression of the CsgG:CsgF or CsgG:FCP Complex by Co-Expression

Genes encoding the CsgG proteins and its mutants are constructed in the pT7 vector which contains ampicillin resistance gene. Genes encoding the CsgF or FCP proteins and its mutants are constructed in the pRham vector which contains Kanamycin resistant gene. 1 μL of both plasmids is mixed with 50 μL of Lemo(DE3)ΔCsgEFG for 10 minutes on ice. The sample is then heated at 42° C. for 45 seconds before being returned to ice for another 5 minutes. 150 μL of NEB SOC outgrowth medium is added and the sample is incubated at 37° C. with shaking at 250 rpm for 1 hour. The entire volume is spread onto an agar plate containing kanamycin (40 μg/mL), ampicillin (100 μg/mL) and chloramphenicol (34 μg/ml) and incubated overnight at 37° C. Single colony is taken from the plate and inoculated into 100 ml of LB media containing kanamycin (40 μg/mL), ampicillin (100 μg/mL) and chloramphenicol (34 μg/ml) and incubated overnight at 37° C. with shaking at 250 rpm. 25 mL of the starter culture is added to 500 mL of LB media containing 3 mM ATP, 15 mM MgSO$_4$, kanamycin (40 μg/mL), ampicillin (100 μg/mL) and chloramphenicol (34 μg/ml) and incubated overnight at 37° C. The culture was allowed to grow for 7 hours, at which point the OD600 was greater than 3.0. Lactose (1.0% final concentration), glucose (0.2% final concentration) and rhamnose (2 mM final concentration) were added and the temperature dropped to 18° C. whist shaking is maintained at 250 rpm for 16 hours. Culture was centrifuged at 6000 rpm for 20 mins at 4° C. The supernatant was discarded and the pellet kept. Cells stored at −80° C. until purification.

Expression of the CsgG Pore with or without a C-Term Strep Tag and CsgF with or without a C Terminal Strep or His Tag All genes encoding all the CsgG proteins and CsgF or FCP proteins are constructed in the pT7 vector which contains ampicillin resistance gene. Expression procedure is same as above except for Kanacmycin is being omitted in all medias and buffers.

Cell Lysis (Co Expressed Complex or Individual CsgG/CsgF/FCP Proteins)

The lysis buffer is made of 50 mM Tris, pH 8.0, 150 mM NaCl, 0.1% DDM, 1× Bugbuster Protein Extraction Reagent (Merck), 2.5 μL Benzonase Nuclease (stock ≥250 units/μL)/100 ml of lysis buffer and 1 tablet Sigma Protease inhibitor cocktail/100 mL of lysis buffer. 5× volume of lysis buffer is used to lyse 1× weight of harvested cells. Cells resuspended and left to spin at room temperature for 4 hours until a homogenous lysate is produced. Lysate is spun at 20,000 rpm for 35 minutes at 4° C. The supernatant is carefully extracted and filtered through a 0.2 uM Acrodisc syringe filter.

Strep Purification of the CsgG or CsgF/FCP Proteins or Co-Expressed Complex if the CsgG Contains a C-Term Strep Tag and CsgF or FCP Contains a C-Term His Tag The filtered sample was then loaded onto a 5 mL Strep Trap column with the following parameters: Loading speed: 0.8 mL/min, Complete sample loading: 10 mL, Wash out unbound: 10CV (5 mL/min), Extra wash: 10CV (5 mL/min), Elution: 3CV (5 ml/min). Affinity buffer: 50 mL Tris, pH 8.0, 150 mM NaCl, 0.1% DDM; Wash buffer: 50 mL Tris, pH 8.0, 2M NaCl, 0.1% DDM; Elution buffer: 50 mL Tris, pH8.0, 150 mM NaCl, 0.1% DDM, 10 mM desthiobiotin. Eluted sample is collected.

His Purification of the CsgG or CsgF/FCP Proteins or Co-Expressed Complex if the CsgG Contains a C-Term Strep Tag and CsgF or FCP Contains a C-Term His Tag Filtered sample or pooled eluted peaks from Strep purification (in case of the complex) loaded onto 5 mL HisTrap column using the same parameters as above, except with the following buffers: Affinity & wash buffer: 50 mL Tris, pH 8.0, 150 mM NaCl, 0.1% DDM, 25 mM imidazole; Elution: 50 mL Tris, pH 8.0, 150 mM NaCl, 0.1% DDM, 350 mM imidazole. Peak eluted, concentrated in 30 kDa MWCO Merck Milipore centrifugal unit to a volume of 500 μL.

Formation of the Complex In Vitro with In Vivo Purified Components.

Both the CsgG and the CsgF/FCP proteins expressed and purified separately are mixed in various ratios to identify the correct ratio. however always in excess CsgF conditions. The complex was then incubated overnight at 25° C. To remove the excess CsgF and remove DTT from the buffer, the mixture was again injected onto the Superdex Increase 200 10/300 equilibrated in 50 mM Tris, pH 8.0, 150 mM NaCl, 0.1% DDM. The complex usually elutes between 9 to 10 mL on this column.

Polishing Step with Gel Filtration for the Complex (Co-Expressed or Made In Vitro)

If necessary, Strep purified or His purified or His followed by Strep purified CsgG:CsgF or CsgG:FCP can be subjected to a further polishing step by gel filtration. 500 μL of the sample was injected into a 1 mL sample loop and onto the Superdex Increase 200 10/300 equilibrated in 50 mM Tris, pH 8.0, 150 mM NaCl, 0.1% DDM. The peak associated to the complex usually elutes between 9 and 10 mL on this column when run 1 mL/min. Sample was heated at 60° C. for 15 minutes and centrifuged at 21,000rcf for 10 mins.

Supernatant was taken for testing. Samples were subjected to SDS-PAGE to confirm and identify fractions eluted with the complex.

Cleavage of CsgF or FCP at the TEV Protease Site

If the CsgF or FCP contains a TEV cleavage site, TEV-protease with a C-term Histidine tag is added to the sample (amount added is identified based on the rough concentration of the protein complex) with 2 mM DTT. Sample incubated overnight at 4° C. on the roller mixer at 25 rpm. The mixture is then run back through a 5 mL His Trap column and the flow through is collected. Anything uncleaved will remain bound to the column and the cleaved protein will elute. Same buffers and parameters and the final heating step are used as in the His purification described above.

Purifying the CsgG:FCP Complex with In Vivo Purified CsgG Pore and Synthetic FCP Lyophilised FCP peptides received from Genscript and Lifetein. 1 mg of peptide dissolved in 1 ml of nuclease free ddH$_2$O to obtain 1 mg/ml sample. Sample was vortexed until no peptide remains visible. Due to differences in expression levels of CsgG pores and mutants, it's difficult to measure the concentration accurately. Intensity of protein bands on SDS-PAGE against known markers can be used to get a rough estimate of the sample. CsgG and FCP are then mixed in approximately 1:50 molar ratio and incubate at 25° C. overnight at 700 rpm. Samples were heated at 60° C. for 15 minutes and centrifuged at 21,000rcf for 10 mins. Supernatant was taken for testing. If needed, the complex can be purified as detailed above in co-expression.

Purifying CsgG:CsgF or CsgG:FCP Containing Cysteine Mutants

Same procedure as above can be used to purify the CsgG:CsgF or CsgG:FCP complexes (with I or II or III below) if either or both components contain cysteines except for the composition of affinity, wash and elution buffers in His and Strep purifications and the buffer used in gel filtration. To purify cysteine mutants, all these buffers should contain 2 mM DTT. 2 mM DTT was also been added when synthetic peptides containing cysteines are dissolved in ddH$_2$O I. co-expression of CsgG and CsgF or FCP
II. Making the CsgG:CsgF or CsgG:FCP complexes in vitro with in vivo purified individual components
III. Making the CsgG:CsgF or CsgG:FCP complexes in vitro with in vivo purified CsgG and synthetic FCP Determination of Cys-Bond Formation Two tubes of 50 μL each from the final elution were separated. In one of the tube, 2 mM DTT was added as a reducing agent and in the other tube 100 μM of Cu(II): 1-10 Phenanthroline (33 mM: 100 mM) was added as an oxidizing agent. Samples were mixed 1:1 with Laemmli buffer containing 4% SDS. Half the sample were heat treated to 100 deg for 10 min (denaturating condition) and half of them were left untreated, before running on a 4-20% TGX gel (Bio-rad Criterion) in TGS buffer.

Coupled In Vitro Transcription and Translation (IVTT)

All proteins were generated by coupled in vitro transcription and translation (IVTT) by using an E. coli T7-S30 extract system for circular DNA (Promega). The complete 1 mM amino acid mixture minus cysteine and the complete 1 mM amino acid mixture minus methionine were mixed in equal volumes to obtain the working amino acid solution required to generate high concentrations of the proteins. The amino acids (10 uL) were mixed with premix solution (40 uL), [35S]L-methionine (2 uL. 1175 Ci/mmol, 10 mCi/mL). plasmid DNA (16 uL. 400 ng/uL) and T7 S30 extract (30 uL) and rifampicin (2 uL, 20 mg/mL) to generate a 100 uL reaction of IVTT proteins. Synthesis was carried out for 4 hours at 30° C. followed by overnight incubation at room temperature. If the CsgG:CsgF of CsgG;FCP complexes were made in co-expression, plasmid DNAs encoding each component were mixed in equal amounts, and a portion of the mixture (16 uL) was used for IVTT. After incubation, the tube was centrifuged for 10 minutes at 22000g. of which the supernatant was discarded. The resulting pellet was resuspended and washed in MBSA (10 mM MOPS, 1 mg/ml BSA pH7.4) and centrifuged again under the same conditions. The protein present in the pellet was re-suspended in 1× Laemmli sample buffer and run in 4-20% TGX gel at 300V for 25 min. The gel was then dried and exposed to Carestream® Kodak® BioMax® MR film overnight. The film was then processed and the protein in the gel visualized.

Samples for Testing in MinIONs

All samples prior to testing are incubated with Brij58 (final concentration of 0.1%) for 10 minutes at room temperature before making up subsequent pore dilutions necessary for pore insertion.

Method for Preparing and Running Static Strands

A set of polyA DNA strands (SS20 to SS38 of FIG. 27) in which one base is missing from the DNA backbone (ISpc3) is obtained by Integrated DNA Technologies (IDT). 3' end of each of these strand also comprise a biotin modification. The static strands are incubated with monovalent streptavidin at room temperature for 20 minutes, resulting in the biotin binding to the streptavidin. The streptavidin-static strand complex was diluted to 500 nM (B. FIG. 27) and 2 uM (C, FIG. 27) in 25 mM HEPES, 430 mM KCl, 30 mM ATP, 30 mM MgCl2, 2.15 mM EDTA, pH8 (known as RBFM). The residual current generated by each static strand is recorded in a MinION set up. MinIOn flow cells were flushed as per standard running protocols, and then the sequencing protocol was started with 1 minute static flicks. Initially 10 minutes of open pore recording was generated before 150 ul of the first streptavidin-static strand complex was added. After 10 minutes. 800 ul of RBFM was flushed through the flow cell before the next streptavidin-static strand complex was added. This process was repeated for all streptavidin-static strands. Once the final streptavidin-static strand complex had been incubated on the flow cell, 800 uL of RBFM was flushed through the flow cell and 10 minutes of open pore recording was generated before finishing the experiment.

Method for Making Discrimination Profile Plots

The reader head discrimination profiles show the average variation in modelled current when the base at each reader head position is varied. To calculate the reader head discrimination at position/for a model of length k with alphabet of length n, we defined the discrimination at reader head position i as the median of the standard deviations in current level for each of the $n^{k-1}$ groups of size n where position i is varied while other positions are held constant.

Aspects of the Disclosure

1. An isolated pore complex comprising a CsgG pore, or a homologue or mutant thereof, and a modified CsgF peptide, or a homologue or mutant thereof.
2. The isolated pore complex according to 1, wherein the modified CsgF peptide, or a homologue or mutant thereof, is inserted into the lumen of the CsgG pore, or a homologue or mutant thereof.

3. The isolated pore complex according to 2, wherein the pore complex has two or more channel constrictions, comprising a CsgG channel constriction and a CsgF channel constriction.
4. The isolated pore complex according to any one of 1 to 3, wherein the CsgG pore, or homologue or mutant thereof, is a mutant CsgG pore.
5. The isolated pore complex according to 3 or 4, wherein the CsgF channel constriction has a diameter in the range from 0.5 nm to 2.0 nm
6. A modified CsgF peptide, or a modified peptide of a CsgF homologue or mutant, wherein the modification comprises a truncation of the CsgF protein SEQ ID NO:6 or of a homologue or mutant thereof.
7. A modified CsgF peptide, or a modified peptide of a CsgF homologue or mutant, according to 6, wherein said modified CsgF peptide comprises SEQ ID NO:39, or SEQ ID NO:40, or a homologue or mutant thereof.
8. A modified CsgF peptide, or a modified peptide of a CsgF homologue or mutant, according to 6, wherein said modified CsgF peptide comprises SEQ ID NO:15, or a homologue or mutant thereof.
9. A modified CsgF peptide according to 8, or a modified peptide of a CsgF homologue or mutant, wherein one or more positions in the region comprising SEQ ID NO:15 are mutated, with a minimal of 35% amino acid identity to SEQ ID NO:15.
10. A polynucleotide which encodes a modified CsgF peptide according to any one of 6 to 9.
11. The isolated pore complex according to any one of 1 to 5, wherein said modified CsgF peptide, or a homologue or mutant thereof, is a peptide according to any one of 6 to 9.
12. The isolated pore complex according to 11, wherein the modified CsgF peptide and the CsgG pore, or homologues or mutants thereof, are covalently coupled.
13. The isolated pore complex according to 12, wherein the covalent coupling is via:
(i) a cysteine residue at a position corresponding to 132, 133, 136, 138, 140, 142, 144, 145, 147, 149, 151, 153, 155, 183, 185, 187, 189, 191, 201, 203, 205, 207 or 209 of SEQ ID NO: 3, or of a homologue thereof;
(ii) a non-native reactive or photoreactive amino acid at a position corresponding to 132, 133, 136, 138, 140, 142, 144, 145, 147, 149, 151, 153, 155, 183, 185, 187, 189, 191, 201, 203, 205, 207 or 209 of SEQ ID NO: 3, or of a homologue thereof.
14. An isolated transmembrane pore complex comprising the isolated pore complex according to any one of 1 to 5 or 11 to 13, and the components of a membrane.
15. A method for producing a transmembrane pore complex, wherein the pore complex is formed by a CsgG pore and a modified CsgF peptide, or homologues or mutants thereof, comprising co-expressing CsgG as depicted in SEQ ID NO:2, or a homologue or mutant thereof, and a modified CsgF peptide, or a homologue or mutant thereof, in a suitable host cell, thereby allowing in vivo transmembrane pore complex formation.
16. The method according to 15, wherein the modified CsgF peptide, or homologue or mutant thereof, comprises SEQ ID NO:12 or SEQ ID NO:14, or a homologue or mutant thereof.
17. A method for producing an isolated pore complex, wherein the isolated pore is formed by a CsgG pore, or a homologue or mutant thereof, and a modified CsgF peptide, or a homologue or mutant thereof, comprising contacting the CsgG monomers of SEQ ID NO:3, or a homologue or mutant thereof, with modified CsgF peptide, or a homologue or mutant thereof, thereby allowing in vitro reconstitution of the isolated pore complex.
18. The method according to 17, wherein the modified CsgF peptide, or a homologue or mutant thereof, comprises SEQ ID NO:15 or SEQ ID NO:16, or a homologue or mutant thereof.
19. A method for determining the presence, absence or one or more characteristics of a target analyte, comprising the steps of:
(i) contacting the target analyte with a pore complex according to any one of 1 to 5 or 11 to 13 or with a transmembrane pore complex according to 14, such that the target analyte moves into the pore complex; and
(ii) taking one or more measurements as the analyte moves through the pore complex and thereby determining the presence, absence or one or more characteristics of the analyte.
20. A method according to 19, wherein the analyte is a polynucleotide.
21. A method according to 19, wherein the analyte is a (poly)peptide
22. A method according to 19, wherein the analyte is a polysaccharide
23. A method according to 19, wherein the analyte is a small organic or inorganic compound, such as pharmacologically active compounds, toxic compounds and pollutants.
24. A method according to 20, comprising determining one or more characteristics selected from (i) the length of the polynucleotide, (ii) the identity of the polynucleotide, (iii) the sequence of the polynucleotide, (iv) the secondary structure of the polynucleotide and (v) whether or not the polynucleotide is modified.
25. A method of characterising a polynucleotide or a (poly)peptide using an isolated transmembrane pore complex, wherein the pore complex is a complex comprising a CsgG pore, or a homologue or mutant thereof, and a modified CsgF peptide, or a homologue or mutant thereof.
26. A method according to 25, wherein the CsgG pore, or homologue or mutant thereof, comprises six to ten monomers.
27. Use of the isolated pore complex according to any one of 1 to 5 or 11 to 13 or of the transmembrane pore complex according to 14 to determine the presence, absence or one or more characteristics of a target analyte.
28. A kit for characterising a target analyte comprising (a) an isolated pore complex according to any one of 1 to 5 or 11 to 13 and (b) the components of a membrane.

Sequences

Description of the Sequences:

SEQ ID NO:1 shows polynucleotide sequence of wild-type E. coli CsgG from strain K12, including signal sequence (Gene ID: 945619).

SEQ ID NO:2 shows amino acid sequence of wild-type E. coli CsgG including signal sequence (Uniprot accession number POAEA2).

SEQ ID NO:3 shows amino acid sequence of wild-type E. coli CsgG as mature protein (Uniprot accession number POAEA2).

SEQ ID NO:4 shows polynucleotide sequence of wild-type E. coli CsgF from strain K12, including signal sequence (Gene ID: 945622).

SEQ ID NO:5 shows amino acid sequence of wild-type E. coli CsgF including signal sequence (Uniprot accession number P0AE98).

SEQ ID NO:6 shows amino acid sequence of wild-type E. coli CsgF as mature protein (Uniprot accession number P0AE98).

SEQ ID NO:7 shows polynucleotide sequence of a fragment of wild-type E. coli CsgF encoding amino acids 1 to 27 and a C-terminal 6 His tag.

SEQ ID NO:8 shows amino acid sequence of a fragment of wild-type E. coli CsgF encompassing amino acids 1 to 27 and a C-terminal 6 His tag.

SEQ ID NO:9 shows polynucleotide sequence of a fragment of wild-type E. coli CsgF encoding amino acids 1 to 38 and a C-terminal 6 His tag.

SEQ ID NO:10 shows amino acid sequence of a fragment of wild-type E. coli CsgF encompassing amino acids 1 to 38 and a C-terminal 6 His tag.

SEQ ID NO:11 shows polynucleotide sequence of a fragment of wild-type E. coli CsgF encoding amino acids 1 to 48 and a C-terminal 6 His tag.

SEQ ID NO:12 shows amino acid sequence of a fragment of wild-type E. coli CsgF encompassing amino acids 1 to 48 and a C-terminal 6 His tag.

SEQ ID NO:13 shows polynucleotide sequence of a fragment of wild-type E. coli CsgF encoding amino acids 1 to 64 and a C-terminal 6 His tag.

SEQ ID NO:14 shows amino acid sequence of a fragment of wild-type E. coli CsgF encompassing amino acids 1 to 64 and a C-terminal 6 His tag.

SEQ ID NO:15 shows amino acid sequence of a peptide corresponding to residues 20 to 53 of E. coli CsgF SEQ ID NO:16 shows amino acid sequence of a peptide corresponding to residues 20 to 42 of E. coli CsgF, including KD at its C-terminus SEQ ID NO:17 shows amino acid sequence of a peptide corresponding to residues 23 to 55 of CsgF homologue Q88H88

SEQ ID NO:18 shows amino acid sequence of a peptide corresponding to residues 25 to 57 of CsgF homologue A0A143HJA0

SEQ ID NO:19 shows amino acid sequence of a peptide corresponding to residues 21 to 53 of CsgF homologue Q5E245

SEQ ID NO:20 shows amino acid sequence of a peptide corresponding to residues 19 to 51 of CsgF homologue Q084E5

SEQ ID NO:21 shows amino acid sequence of a peptide corresponding to residues 15 to 47 of CsgF homologue F0LZU2

SEQ ID NO:22 shows amino acid sequence of a peptide corresponding to residues 26 to 58 of CsgF homologue A0A136HQR0

SEQ ID NO:23 shows amino acid sequence of a peptide corresponding to residues 21 to 53 of CsgF homologue A0A0W1SRL3

SEQ ID NO:24 shows amino acid sequence of a peptide corresponding to residues 26 to 59 of CsgF homologue B0UH01

SEQ ID NO:25 shows amino acid sequence of a peptide corresponding to residues 22 to 53 of CsgF homologue Q6NAU5

SEQ ID NO:26 shows amino acid sequence of a peptide corresponding to residues 7 to 38 of CsgF homologue G8PUY5

SEQ ID NO:27 shows amino acid sequence of a peptide corresponding to residues 25 to 57 of CsgF homologue A0AOS2ETP7

SEQ ID NO:28 shows amino acid sequence of a peptide corresponding to residues 19 to 51 of CsgF homologue E311Z1

SEQ ID NO:29 shows amino acid sequence of a peptide corresponding to residues 24 to 55 of CsgF homologue F3Z094

SEQ ID NO:30 shows amino acid sequence of a peptide corresponding to residues 21 to 53 of CsgF homologue A0A176T7M2

SEQ ID NO:31 shows amino acid sequence of a peptide corresponding to residues 14 to 45 of CsgF homologue D2QPP8

SEQ ID NO:32 shows amino acid sequence of a peptide corresponding to residues 28 to 58 of CsgF homologue N21YT1

SEQ ID NO:33 shows amino acid sequence of a peptide corresponding to residues 26 to 58 of CsgF homologue W7QHV5

SEQ ID NO:34 shows amino acid sequence of a peptide corresponding to residues 23 to 55 of CsgF homologue D4ZLW2

SEQ ID NO:35 shows amino acid sequence of a peptide corresponding to residues 21 to 53 of CsgF homologue D2QT92

SEQ ID NO:36 shows amino acid sequence of a peptide corresponding to residues 20 to 51 of CsgF homologue A0A167UJA2

SEQ ID NO:37 shows amino acid sequence of a fragment of wild-type E. coli CsgF encompassing amino acids 20 to 27.

SEQ ID NO:38 shows amino acid sequence of a fragment of wild-type E. coli CsgF encompassing amino acids 20 to 38.

SEQ ID NO:39: shows amino acid sequence of a fragment of wild-type E. coli CsgF encompassing amino acids 20 to 48.

SEQ ID NO:40 shows amino acid sequence of a fragment of wild-type E. coli CsgF encompassing amino acids 20 to 64.

SEQ ID NO:41 shows the nucleotide sequence of primer CsgF_d27_end

SEQ ID NO:42 shows the nucleotide sequence of primer CsgF_d38_end

SEQ ID NO:43 shows the nucleotide sequence of primer CsgF_d48_end

SEQ ID NO:44 shows the nucleotide sequence of primer CsgF_d64_end

SEQ ID NO:45 shows the nucleotide sequence of primer pNa62_CsgF_histag_Fw

SEQ ID NO:46 shows the nucleotide sequence of primer CsgF-His_pET22b_FW

SEQ ID NO:47 shows the nucleotide sequence of primer CsgF-His_pET22b_Rev

SEQ ID NO:48 shows the nucleotide sequence of primer csgEFG_pDONR221_FW

SEQ ID NO:49 shows the nucleotide sequence of primer csgEFG_pDONR221_Rev

SEQ ID NO:50 shows the nucleotide sequence of primer Mut_csgF_His_FW

SEQ ID NO:51 shows the nucleotide sequence of primer Mut_csgF_His_Rev

SEQ ID NO:52 shows the nucleotide sequence of primer DelCsgE_Rev

SEQ ID NO:53 shows the nucleotide sequence of primer DelCsgE FW

SEQ ID NO: 54 shows the amino acid sequence of residues 1 to 30 of mature E. coli CsgF SEQ ID NO: 55 shows the amino acid sequence of residues 1 to 35 of mature E. coli CsgF SEQ ID NO: 56 shows the amino acid sequence of a mutated (T4C/N17S) CsgF sequence with a signal sequence, and a TEV protease cleavage site (ENLYFQS) inserted between residues 35 and 36 of sequence of the mature protein.

SEQ ID NO: 57 shows the amino acid sequence of a mutated (N17S-Del) CsgF sequence with a signal sequence, and a TEV protease cleavage site (ENLYFQS) inserted between residues 35 and 36 of sequence of the mature protein.

SEQ ID NO: 58 shows the amino acid sequence of a mutated (G1C/N17S) CsgF sequence with a signal sequence, and a TEV protease cleavage site (ENLYFQS) inserted between residues 35 and 36 of sequence of the mature protein.

SEQ ID NO: 59 shows the amino acid sequence of a mutated (G1C) CsgF sequence with a signal sequence, and a TEV protease cleavage site (ENLYFQS) inserted between residues 35 and 36 of sequence of the mature protein.

SEQ ID NO: 60 shows the amino acid sequence of a CsgF sequence with a signal sequence, a TEV protease cleavage site (ENLYFQS) inserted between residues 45 and 46 of sequence of the mature protein, and a Histo tag at the C-terminus.

SEQ ID NO: 61 shows the amino acid sequence of a CsgF sequence with a signal sequence, a TEV protease cleavage site (ENLYFQS) inserted between residues 35 and 36 of sequence of the mature protein, and a His10 tag at the C-terminus.

SEQ ID NO: 62 shows the amino acid sequence of a CsgF sequence with a signal sequence, a TEV protease cleavage site (ENLYFQS) inserted between residues 30 and 31 of sequence of the mature protein, and a His10 tag at the C-terminus.

SEQ ID NO: 63 shows the amino acid sequence of a CsgF sequence with a signal sequence, a TEV protease cleavage site (ENLYFQS) inserted between residues 45 and 51 of sequence of the mature protein, and a His10 tag at the C-terminus.

SEQ ID NO: 64 shows the amino acid sequence of a CsgF sequence with a signal sequence, a TEV protease cleavage site (ENLYFQS) inserted between residues 30 and 37 of sequence of the mature protein, and a His10 tag at the C-terminus.

SEQ ID NO: 65 shows the amino acid sequence of a CsgF sequence with a signal sequence, a HCV C3 protease cleavage site (LEVLFQGP) inserted between residues 34 and 36 of sequence of the mature protein, and a Histo tag at the C-terminus.

SEQ ID NO: 66 shows the amino acid sequence of a CsgF sequence with a signal sequence, a HCV C3 protease cleavage site (LEVLFQGP) inserted between residues 42 and 43 of sequence of the mature protein, and a Histo tag at the C-terminus.

SEQ ID NO: 67 shows the amino acid sequence of a CsgF sequence with a signal sequence, a HCV C3 protease cleavage site (LEVLFQGP) inserted between residues 38 and 47 of sequence of the mature protein, and a His10 tag at the C-terminus.

SEQ ID NO: 68 shows the amino acid sequence of YP_001453594.1: 1-248 of hypothetical protein CKO_02032 [Citrobacter koseri ATCC BAA-895], which is 99% identical to SEQ ID NO: 3.

SEQ ID NO: 69 shows the amino acid sequence of WP_001787128.1: 16-238 of curli production assembly/transport component CsgG, partial [Salmonella enterica], which is 98% to SEQ ID NO: 3.

SEQ ID NO: 70 shows the amino acid sequence of KEY44978.1|: 16-277 of curli production assembly/transport protein CsgG [Citrobacter amalonaticus], which is 98% identical to SEQ ID NO: 3.

SEQ ID NO: 71 shows the amino acid sequence of YP_003364699.1: 16-277 of curli production assembly/transport component [Citrobacter rodentium ICC168], which is 97% identical to SEQ ID NO: 3.

SEQ ID NO: 72 shows the amino acid sequence of YP_004828099.1: 16-277 of curli production assembly/transport component CsgG [Enterobacter asburiae LF7a], which is 94% identical to SEQ ID NO: 3.

SEQ ID NO: 73 shows the amino acid sequence of WP_006819418.1: 19-280 of transporter [Yokenella regensburgei], which is 91% identical to SEQ ID NO: 3.

SEQ ID NO: 74 shows the amino acid sequence of WP_024556654.1: 16-277 of curli production assembly/transport protein CsgG [Cronobacter pulveris], which is 89% identical to SEQ ID NO: 3.

SEQ ID NO: 75 shows the amino acid sequence of YP_005400916.1:16-277 of curli production assembly/transport protein CsgG [Rahnella aquatilis HX2], which is 84% identical to SEQ ID NO: 3.

SEQ ID NO: 76 shows the amino acid sequence of KFC99297.1: 20-278 of CsgG family curli production assembly/transport component [Kluyvera ascorbata ATCC 33433], which is 82% identical to SEQ ID NO: 3.

SEQ ID NO: 77 shows the amino acid sequence of KFC86716.1|: 16-274 of CsgG family curli production assembly/transport component [Hafnia alvei ATCC 13337], which is 81% identical to SEQ ID NO: 3.

SEQ ID NO: 78 shows the amino acid sequence of YP_007340845.1|:16-270 of uncharacterised protein involved in formation of curli polymers [Enterobacteriaceae bacterium strain FGI 57], which is 76% identical to SEQ ID NO: 3.

SEQ ID NO: 79 shows the amino acid sequence of WP_010861740.1: 17-274 of curli production assembly/transport protein CsgG [Plesiomonas shigelloides], which is 70% identical to SEQ ID NO: 3.

SEQ ID NO: 80 shows the amino acid sequence of YP_205788.1: 23-270 of curli production assembly/transport outer membrane lipoprotein component CsgG [Vibrio fischeri ES114], which is 60% identical to SEQ ID NO: 3.

SEQ ID NO: 81 shows the amino acid sequence of WP_017023479.1: 23-270 of curli production assembly protein CsgG [Aliivibrio logei], which is 59% identical to SEQ ID NO: 3.

SEQ ID NO: 82 shows the amino acid sequence of WP_007470398.1: 22-275 of Curli production assembly/transport component CsgG [Photobacterium sp. AK15], which is 57% identical to SEQ ID NO: 3.

SEQ ID NO: 83 shows the amino acid sequence of WP_021231638.1: 17-277 of curli production assembly protein CsgG [Aeromonas veronii], which is 56% identical to SEQ ID NO: 3.

SEQ ID NO: 84 shows the amino acid sequence of WP_033538267.1: 27-265 of curli production assembly/transport protein CsgG [Shewanella sp. ECSMB14101], which is 56% identical to SEQ ID NO: 3.

SEQ ID NO: 85 shows the amino acid sequence of WP_003247972.1: 30-262 of curli production assembly protein CsgG [Pseudomonas putida], which is 54% identical to SEQ ID NO: 3.

SEQ ID NO: 86 shows the amino acid sequence of YP_003557438.1: 1-234 of curli production assembly/transport component CsgG [Shewanella violacea DSS12], which is 53% identical to SEQ ID NO: 3.

SEQ ID NO: 87 shows the amino acid sequence of WP_027859066.1: 36-280 of curli production assembly/transport protein CsgG [Marinobacterium jannaschii], which is 53% identical to SEQ ID NO: 3.

SEQ ID NO: 88 shows the amino acid sequence of CEJ70222.1: 29-262 of Curli production assembly/transport component CsgG [Chryseobacterium oranimense G311], which is 50% identical to SEQ ID NO: 3.

```
SEQ ID NO: 1 (>P0AEA2; coding sequence for WT CsgG from E. coli K12)
ATGCAGCGCTTATTTCTTTTGGTTGCCGTCATGTTACTGAGCGGATGCTTAACCGCCCCGCCTAAA

GAAGCCGCCAGACCGACATTAATGCCTCGTGCTCAGAGCTACAAAGATTTGACCCATCTGCCAGCG

CCGACGGGTAAAATCTTTGTTTCGGTATACAACATTCAGGACGAAACCGGGCAATTTAAACCCTACC

CGGCAAGTAACTTCTCCACTGCTGTTCCGCAAAGCGCCACGGCAATGCTGGTCACGGCACTGAAA

GATTCTCGCTGGTTTATACCGCTGGAGCGCCAGGGCTTACAAAACCTGCTTAACGAGCGCAAGATT

ATTCGTGCGGCACAAGAAAACGGCACGGTTGCCATTAATAACCGAATCCCGCTGCAATCTTTAACG

GCGGCAAATATCATGGTTGAAGGTTCGATTATCGGTTATGAAAGCAACGTCAAATCTGGCGGGGTT

GGGGCAAGATATTTTGGCATCGGTGCCGACACGCAATACCAGCTCGATCAGATTGCCGTGAACCT

GCGCGTCGTCAATGTGAGTACCGGCGAGATCCTTTCTTCGGTGAACACCAGTAAGACGATACTTTC

CTATGAAGTTCAGGCCGGGGTTTTCCGCTTTATTGACTACCAGCGCTTGCTTGAAGGGGAAGTGGG

TTACACCTCGAACGAACCTGTTATGCTGTGCCTGATGTCGGCTATCGAAACAGGGGTCATTTTCCT

GATTAATGATGGTATCGACCGTGGTCTGTGGGATTTGCAAAATAAAGCAGAACGGCAGAATGACAT

TCTGGTGAAATACCGCCATATGTCGGTTCCACCGGAATCCTGA

SEQ ID NO: 2 (>P0AEA2 (1:277); WT prepro CsgG from E. coli K12)
MQRLFLLVAVMLLSGCLTAPPKEAARPTLMPRAQSYKDLTHLPAPTGKIFVSVYNIQDETGQFKPYPAS

NFSTAVPQSATAMLVTALKDSRWFIPLERQGLQNLLNERKIIRAAQENGTVAINNRIPLQSLTAANIMVEG

SIIGYESNVKSGGVGARYFGIGADTQYQLDQIAVNLRVVNVSTGEILSSVNTSKTILSYEVQAGVFRFIDY

QRLLEGEVGYTSNEPVMLCLMSAIETGVIFLINDGIDRGLWDLQNKAERQNDILVKYRHMSVPPES

SEQ ID NO: 3 (>P0AEA2 (16:277); mature CsgG from E. coli K12)
CLTAPPKEAARPTLMPRAQSYKDLTHLPAPTGKIFVSVYNIQDETGQFKPYPASNFSTAVPQSATAMLVT

ALKDSRWFIPLERQGLQNLLNERKIIRAAQENGTVAINNRIPLQSLTAANIMVEGSIIGYESNVKSGGVGA

RYFGIGADTQYQLDQIAVNLRVVNVSTGEILSSVNTSKTILSYEVQAGVFRFIDYQRLLEGEVGYTSNEPV

MLCLMSAIETGVIFLINDGIDRGLWDLQNKAERQNDILVKYRHMSVPPES

SEQ ID NO: 4 (>P0AE98; coding sequence for WT CsgF from E. coli K12)
ATGCGTGTCAAACATGCAGTAGTTCTACTCATGCTTATTTCGCCATTAAGTTGGGCTGGAACCATGA

CTTTCCAGTTCCGTAATCCAAACTTTGGTGGTAACCCAAATAATGGCGCTTTTTTATTAAATAGCGCT

CAGGCCCAAAACTCTTATAAAGATCCGAGCTATAACGATGACTTTGGTATTGAAACACCCTCAGCGT

TAGATAACTTTACTCAGGCCATCCAGTCACAAATTTTAGGTGGGCTACTGTCGAATATTAATACCGG

TAAACCGGGCCGCATGGTGACCAACGATTATATTGTCGATATTGCCAACCGCGATGGTCAATTGCA

GTTGAACGTGACAGATCGTAAAACCGGACAAACCTCGACCATCCAGGTTTCGGGTTTACAAAATAA

CTCAACCGATTTT

SEQ ID NO: 5 (>P0AE98 (1:138); WT pre CsgF from E. coli K12)
MRVKHAVVLLMLISPLSWAGTMTFQFRNPNFGGNPNNGAFLLNSAQAQNSYKDPSYNDDFGIETPSAL

DNFTQAIQSQILGGLLSNINTGKPGRMVTNDYIVDIANRDGQLQLNVTDRKTGQTSTIQVSGLQNNSTDF
```

-continued

SEQ ID NO: 6 (>P0AE98 (20:138); WT mature CsgF from *E. coli* K12)
GTMTFQFRNPNFGGNPNNGAFLLNSAQAQNSYKDPSYNDDFGIETPSALDNFTQAIQSQILGGLLSNIN

TGKPGRMVTNDYIVDIANRDGQLQLNVTDRKTGQTSTIQVSGLQNNSTDF

SEQ ID NO: 7 (>P0AE98; coding sequence for CsgF 1:27_6His)
ATGCGTGTCAAACATGCAGTAGTTCTACTCATGCTTATTTCGCCATTAAGTTGGGCTGGAACCATGA

CTTTCCAGTTCCGTCATCACCATCACCATCACTAAGCCC

SEQ ID NO: 8 (>P0AE98 (1:28); preprotein of CsgF 20:27_6His)
MRVKHAVVLLMLISPLSWAGTMTFQFRHHHHHH SEQ ID NO: 9 (>P0AE98; coding sequence for CsgF 1:38_6His)
ATGCGTGTCAAACATGCAGTAGTTCTACTCATGCTTATTTCGCCATTAAGTTGGGCTGGAACCATGA

CTTTCCAGTTCCGTAATCCAAACTTTGGTGGTAACCCAAATAATGGCCATCACCATCACCATCACTA

AGCCC

SEQ ID NO: 10 (>P0AE98 (1:39); preprotein of CsgF 20:38_6His)
MRVKHAVVLLMLISPLSWAGTMTFQFRNPNFGGNPNNGHHHHHH SEQ ID NO: 11 (>P0AE98; coding sequence for CsgF 1:48_6His)
ATGCGTGTCAAACATGCAGTAGTTCTACTCATGCTTATTTCGCCATTAAGTTGGGCTGGAACCATGA

CTTTCCAGTTCCGTAATCCAAACTTTGGTGGTAACCCAAATAATGGCGCTTTTTTATTAAATAGCGCT

CAGGCCCAACATCACCATCACCATCACTAAGCCC

SEQ ID NO: 12 (>P0AE98 (1:49); preprotein of CsgF 20:48_6His)
MRVKHAVVLLMLISPLSWAGTMTFQFRNPNFGGNPNNGAFLLNSAQAQHHHHHH SEQ ID NO: 13 (>P0AE98; coding sequence for CsgF 1:64_6His)
ATGCGTGTCAAACATGCAGTAGTTCTACTCATGCTTATTTCGCCATTAAGTTGGGCTGGAACCATGA

CTTTCCAGTTCCGTAATCCAAACTTTGGTGGTAACCCAAATAATGGCGCTTTTTTATTAAATAGCGCT

CAGGCCCAAAACTCTTATAAAGATCCGAGCTATAACGATGACTTTGGTATTGAAACA

CATCACCATCACCATCACTAAGCCC

SEQ ID NO: 14 (>P0AE98 (1:65); preprotein of CsgF 20:64_6His)
MRVKHAVVLLMLISPLSWAGTMTFQFRNPNFGGNPNNGAFLLNSAQAQNSYKDPSYNDDFGIETHHHH

HH

SEQ ID NO: 15 (>P0AE98 (20:53); mature peptide of CsgF 20:53)
GTMTFQFRNPNFGGNPNNGAFLLNSAQAQNSYKD SEQ ID NO: 16 (>P0AE98 (20:42); mature peptide of CsgF 20:42 + KD)
GTMTFQFRNPNFGGNPNNGAFLLKD

SEQ ID NO: 17 (>Q88H88_PSEPK (23:55))
TELVYTPVNPAFGGNPLNGTWLLNNAQAQNDY

SEQ ID NO: 18 (>A0A143HJA0_9GAMM (25:57))
TELIYEPVNPNFGGNPLNGSYLLNNAQAQDRH

SEQ ID NO: 19 (>Q5E245_VIBF1 (21:53))
SELVYTPVNPNFGGNPLNTSHLFGGANAINDY

SEQ ID NO: 20 (>Q084E5_SHEFN (19:51))
TQLVYTPVNPAFGGSYLNGSYLLANASAQNEH

SEQ ID NO: 21 (>F0LZU2_VIBFN (15:47))
SSLVYEPVNPTFGGNPLNTTHLFSRAEAINDY

SEQ ID NO: 22 (>A0A136HQR0_9ALTE (26:58))
TELVYEPINPSFGGNPLNGSFLLSKANSQNAH

SEQ ID NO: 23 (>A0A0W1SRL3_9GAMM (21:53))
TEIVYQPINPSFGGNPMNGSFLLQKAQSQNAH

SEQ ID NO: 24 (>B0UH01_METS4 (26:59))
SSLVYQPVNPAFGGPQLNGSWLQAEANAQNIPQ

SEQ ID NO: 25 (>Q6NAU5_RHOPA (22:53))
GSLVYTPTNPAFGGSPLNGSWQMQQATAGNH

-continued

SEQ ID NO: 26 (>G8PUY5_PSEUV (7:38))
QQLIYQPTNPSFGGYAANTTHLFATANAQKTA

SEQ ID NO: 27 (>A0A0S2ETP7_9RHIZ (25:57))
GDLVYTPVNPSFGGSPLNSAHLLSIAGAQKNA

SEQ ID NO: 28 (>E3I1Z1_RHOVT (19:51))
AELGYTPVNPSFGGSPLNGSTLLSEASAQKPN

SEQ ID NO: 29 (>F3Z094_DESAF (24:55))
TELVFSFTNPSFGGDPMIGNFLLNKADSQKR

SEQ ID NO: 30 (>A0A176T7M2_9FLAO (21:53))
QQLVYKSINPFFGGGDSFAYQQLLASANAQND

SEQ ID NO: 31 (>D2QPP8_SPILD (14:45))
QALVYHPNNPAFGGNTFNYQWMLSSAQAQDR

SEQ ID NO: 32 (>N2IYT1_9PSED (26:58))
TELVYTPKNPAFGGSPLNGSYLLGNAQAQNDY

SEQ ID NO: 33 (>W7QHV5_9GAMM (26:58))
GQLIYQPINPSFGGDPLLGNHLLNKAQAQDTK

SEQ ID NO: 34 (>D4ZLW2_SHEVD (23:55))
TQLIYTPVNPNFGGSYLNGSYLLANASVQNDH

SEQ ID NO: 35 (>D2QT92_SPILD (21:53))
QAFVYHPNNPNFGGNTFNYSWMLSSAQAQDRT

SEQ ID NO: 36 (>A0A167UJA2_9FLAO (20:51))
QGLIYKPKNPAFGGDTFNYQWLASSAESQNK

SEQ ID NO: 37 (>P0AE98 (20:28); mature peptide of CsgF 20:27)
GTMTFQFR

SEQ ID NO: 38 (>P0AE98 (20:39); mature peptide of CsgF 20:38)
GTMTFQFRNPNFGGNPNNG SEQ ID NO: 39 (>P0AE98 (20:49); mature peptide of CsgF 20:48)
GTMTFQFRNPNFGGNPNNGAFLLNSAQAQ SEQ ID NO: 40 (>P0AE98 (20:65); mature peptide of CsgF 20:64)
GTMTFQFRNPNFGGNPNNGAFLLNSAQAQNSYKDPSYNDDFGIET SEQ ID NO: 41 (CsgF_d27_end)
ACGGAACTGGAAAGTCATGGTTCC SEQ ID NO: 42 (CsgF_d38_end)
GCCATTATTTGGGTTACCACCAAAGTTTGG SEQ ID NO: 43 (CsgF_d48_end)
TTGGGCCTGAGCGCTATTTAATAAAAAAGC SEQ ID NO: 44 (CsgF_d64_end)
TGTTTCAATACCAAAGTCATCGTTATAGCTCGG SEQ ID NO: 45 (pNa62_CsgF_histag_Fw)
CATCACCATCACCATCACTAAGCCC SEQ ID NO: 46 (CsgF-His_pET22b_FW)
CCCCCATATGGGAACCATGACTTTCCAGTTCC SEQ ID NO: 47: (CsgF-His_pET22b_Rev)
CCCCGAATTCCTAATGGTGATGGTGATGGTGAAAATCGGTTGAGTTATTTTG SEQ ID NO: 48: (csgEFG_pDONR221_FW)
GGGGACAAGTTTGTACAAAAAAGCAGGCTACCTCAGGCGATAAAGCCATGAAACGTTA SEQ ID NO: 49: (csgEFG_pDONR221_Rev)
GGGGACCACTTTGTACAAGAAAGCTGGGTGTTTAAACTCATTTTTCGAACTGCGGGTGGCTCCAAG
CGCTGG SEQ ID NO: 50: (Mut_csgF_His_FW)
CAAAATAACTCAACCGATTTTCATCACCATCACCATCACTAAGCCCCAGCTTCAIAAGG SEQ ID NO: 51: (Mut_csgF_His_Rev)
CCTTATGAAGCTGGGGCTTAGTGATGGTGATGGTGATGAAAATCGGTTGAGTTATTTTG -continued SEQ ID NO: 52: (DelCsgE_Rev)
AGCCTGCTTTTTTGTACAAAC SEQ ID NO: 53: (DelCsgE FW)
ATAAAAAATTGTTCGGAGGCTGC SEQ ID NO: 54 (>P0AE98 (20:50); mature peptide of CsgF 1:30)
GTMTFQFRNPNFGGNPNNGAFLLNSAQAQN SEQ ID NO: 55 (>P0AE98 (20:54); mature peptide of CsgF 1:35)
GTMTFQFRNPNFGGNPNNGAFLLNSAQAQNSYKDP Examples of CsgF sequences with protease cleavage sites made into proteins. Signal peptide is shown in bold TEV protease cleavage site in bold and underline and HCV C3 protease cleavage site in underline. StrepII indicate the Strep tag at the C terminus, H10 indicates the 10×Histidine tag at the C terminus and ** indicates STOP codons.

Pro-CsgF-Eco-(WT-T4C/N17S/P35-TEV-S36)-StrepII
SEQ ID NO: 56
MRVKHAVVLLMLISPLSWAGTMCFQFRNPNFGGNPSNGAFLLNSAQAQNSYKDPENLYFQSYNDDF
GIETPSALDNFTQAIQSQILGGLLSNINTGKPGRMVTNDYIVDIANRDGQLQLNVTDRKTGQTSTIQVSGL
QNNSTDFSAWSHPQFEK**

Pro-CsgF-Eco-(WT-N17S-Del(P35-[TEV]-S36)-StrepII
SEQ ID NO: 57
MRVKHAVVLLMLISPLSWAGTMTFQFRNPNFGGNPSNGAFLLNSAQAQNSYKDPENLYFQSYNDDF
GIETPSALDNFTQAIQSQILGGLLSNINTGKPGRMVTNDYIVDIANRDGQLQLNVTDRKTGQTSTIQVSGL
QNNSTDFSAWSHPQFEK**

Pro-CsgF-Eco-(WT-G1C/N17S/P35-[TEV]-S36)-StrepII
SEQ ID NO: 58
MRVKHAVVLLMLISPLSWACTMTFQFRNPNFGGNPSNGAFLLNSAQAQNSYKDPENLYFQSYNDDF
GIETPSALDNFTQAIQSQILGGLLSNINTGKPGRMVTNDYIVDIANRDGQLQLNVTDRKTGQTSTIQVSGL
QNNSTDFSAWSHPQFEK**

Pro-CsgF-Eco-(WT-G1C/P35-[TEV]-S36)-StrepII
SEQ ID NO: 59
MRVKHAVVLLMLISPLSWACTMTFQFRNPNFGGNPNNGAFLLNSAQAQNSYKDPENLYFQSYNDDF
GIETPSALDNFTQAIQSQILGGLLSNINTGKPGRMVTNDYIVDIANRDGQLQLNVTDRKTGQTSTIQVSGL
QNNSTDFSAWSHPQFEK**

Pro-CsgF-Eco-(WT-T45-TEV-P46)-H10
SEQ ID NO: 60
MRVKHAVVLLMLISPLSWAGTMTFQFRNPNFGGNPNNGAFLLNSAQAQNSYKDPSYNDDFGIET**ENL
YFQS**PSALDNFTQAIQSQILGGLLSNINTGKPGRMVTNDYIVDIANRDGQLQLNVTDRKTGQTSTIQVSG
LQNNSTDFHHHHHHHHHH**

Pro-CsgF-Eco-(WT-P35-TEV-S36)-H10
SEQ ID NO: 61
MRVKHAVVLLMLISPLSWAGTMTFQFRNPNFGGNPNNGAFLLNSAQAQNSYKDPENLYFQSYNDDF
GIETPSALDNFTQAIQSQILGGLLSNINTGKPGRMVTNDYIVDIANRDGQLQLNVTDRKTGQTSTIQVSGL
QNNSTDFHHHHHHHHHH**

Pro-CsgF-Eco-(WT-N30-TEV-S31)-H10
SEQ ID NO: 62
MRVKHAVVLLMLISPLSWAGTMTFQFRNPNFGGNPNNGAFLLNSAQAQNENLYFQSSYKDPSYNDDF
GIETPSALDNFTQAIQSQILGGLLSNINTGKPGRMVTNDYIVDIANRDGQLQLNVTDRKTGQTSTIQVSGL
QNNSTDFHHHHHHHHHH**

Pro-CsgF-Eco-(WT-T45-TEV-F51)-H10

SEQ ID NO: 63

MRVKHAVVLLMLISPLSWAGTMTFQFRNPNFGGNPNNGAFLLNSAQAQNSYKDPSYNDDFGIET**ENL
YFQS**FTQAIQSQILGGLLSNINTGKPGRMVTNDYIVDIANRDGQLQLNVTDRKTGQTSTIQVSGLQNNST
DFHHHHHHHHHH\*\*

Pro-CsgF-Eco-(WT-N30-TEV-Y37)-H10

SEQ ID NO: 64

MRVKHAVVLLMLISPLSWAGTMTFQFRNPNFGGNPNNGAFLLNSAQAQNENLYFQSYNDDFGIETPS
ALDNFTQAIQSQILGGLLSNINTGKPGRMVTNDYIVDIANRDGQLQLNVTDRKTGQTSTIQVSGLQNNST
DFHHHHHHHHHH\*\*

Pro-CsgF-Eco-(WT-D34-[C3]-S36)

SEQ ID NO: 65

MRVKHAVVLLMLISPLSWACTMTFQFRNPNFGGNPNNGAFLLNSAQAQNSYKDLEVLFQGPSYNDDF
GIETPSALDNFTQAIQSQILGGLLSNINTGKPGRMVTNDYIVDIANRDGQLQLNVTDRKTGQTSTIQVSGL
QNNSTDFSAWSHPQFEK\*\*

Pro-CsgF-Eco-(WT-I42-[C3]-E43)

SEQ ID NO: 66

MRVKHAVVLLMLISPLSWACTMTFQFRNPNFGGNPNNGAFLLNSAQAQNSYKDPSYNDDFGILEVLFQ
GPETPSALDNFTQAIQSQILGGLLSNINTGKPGRMVTNDYIVDIANRDGQLQLNVTDRKTGQTSTIQVSG
LQNNSTDFSAWSHPQFEK\*\*

Pro-CsgF-Eco-(WT-N38-[C3]-S47)

SEQ ID NO: 67

MRVKHAVVLLMLISPLSWACTMTFQFRNPNFGGNPNNGAFLLNSAQAQNSYKDPSYNLEVLFQGPSA
LDNFTQAIQSQILGGLLSNINTGKPGRMVTNDYIVDIANRDGQLQLNVTDRKTGQTSTIQVSGLQNNSTD
FSAWSHPQFEK\*\*

SEQ ID NO: 68
MPRAQSYKDLTHLPMPTGKIFVSVYNIQDETGQFKPYPASNFSTAVPQSATAMLVTALKDSRWFIPLER
QGLQNLLNERKIIRAAQENGTVAINNRIPLQSLTAANIMVEGSIIGYESNVKSGGVGARYFGIGADTQY
QLDQIAVNLRVVNVSTGEILSSVNTSKTILSYEVQAGVFRFIDYQRLLEGEIGYTSNEPVMLCLMSAIE
TGVIFLINDGIDRGLWDLQNKAERQNDILVKYRHMSVPPES

SEQ ID NO: 69
CLTAPPKQAAKPTLMPRAQSYKDLTHLPAPTGKIFVSVYNIQDETGQFKPYPASNFSTAVPQSATAMLV
TALKDSRWFIPLERQGLQNLLNERKIIRAAQENGTVAMNNRIPLQSLTAANIMVEGSIIGYESNVKSGG
VGARYFGIGADTQYQLDQIAVNLRVVNVSTGEILSSVNTSKTILSYEVQAGVFRFIDYQRLLEGEIGYT
SNEPVMLCLMSAIETG

SEQ ID NO: 70
CLTAPPKEAAKPTLMPRAQSYKDLTHLPIPTGKIFVSVYNIQDETGQFKPYPASNFSTAVPQSATAMLV
TALKDSRWFVPLERQGLQNLLNERKIIRAAQENGTVAINNRIPLQSLTAANIMVEGSIIGYESNVKSGG
VGARYFGIGADTQYQLDQIAVNLRVVNVSTGEILSSVNTSKTILSYEVQAGVFRFIDYQRLLEGEIGYT
SNEPVMLCLMSAIETGVIFLINDGIDRGLWDLQNKADRQNDILVKYRHMSVPPES

SEQ ID NO: 71
CLTTPPKEAAKPTLMPRAQSYKDLTHLPVPTGKIFVSVYNIQDETGQFKPYPASNFSTAVPQSATAMLV
TALKDSRWFIPLERQGLQNLLNERKIIRAAQENGTVAINNRIPLPSLTAANIMVEGSIIGYESNVKSGG
AGARYFGIGADTQYQLDQIAVNLRVVNVSTGEILSSVNTSKTILSYEVQAGVFRFIDYQRLLEGEIGYT
SNEPVMLCLMSAIETGVIFLINDGIDRGLWDLQNKADRQNDILVKYRQMSVPPES

SEQ ID NO: 72
CLTAPPKEAAKPTLMPRAQSYRDLTHLPAPTGKIFVSVYNIQDETGQFKPYPASNFSTAVPQSATAMLV
TALKDSRWFIPLERQGLQNLLNERKIIRAAQENGTVANNNRMPLQSLAAANVMIEGSIIGYESNVKSGG

```
VGARYFGIGADTQYQLDQIAVNLRVVNVSTGEVLSSVNTSKTILSYEVQAGVFRFIDYQRLLEGEIGYT

SNEPVMMCLMSAIETGVIFLINDGIDRGLWDLQNKADAQNPVLVKYRDMSVPPES
```

SEQ ID NO: 73
```
CLTAPPKEAAKPTLMPRAQSYRDLTHLPLPSGKVFVSVYNIQDETGQFKPYPASNFSTAVPQSATAMLVTALKDSR

WFVPLERQGLQNLLNERKIIRAAQENGTVADNNRIPLQSLTAANVMIEGSIIGYESNVKSGGVGARYFGIGADTQY

QLDQIAVNLRVVNVSTGEVLSSVNTSKTILSYEVQAGVFRFVDYQRLLEGEIGYTSNEPVMLCLMSAIETGVIYLI

NDGIERGLWDLQQKADVDNPILARYRNMSAPPES
```

SEQ ID NO: 74
```
CLTAPPKEAAKPTLMPRAQSYRDLTNLPDPKGKLFVSVYNIQDETGQFKPYPASNFSTAVPQSATSMLVTALKDSR

WFIPLERQGLQNLLNERKIIRAAQENGTVAENNRMPLQSLVAANVMIEGSIIGYESNVKSGGVGARYFGIGGDTQY

QLDQIAVNLRVVNVSTGEVLSSVNTSKTILSYEVQAGVFRFIDYQRLLEGEIGYTANEPVMLCLMSAIETGVIHLI

NDGINRGLWELKNKGDAKNT1LAKYRSMAVPPES
```

SEQ ID NO: 75
```
CLTAAPKEAARPTLLPRAPSYTDLTHLPSPQGRIFVSVYNIQDETGQFKPYPACNFSTAVPQSATAMLVSALKDSK

WFIPLERQGLQNLLNERKIIRAAQENGSVAINNQRPLSSLVAANILIEGSIIGYESNVKSGGVGARYFGIGASTQY

QLDQIAVNLRAVDVNTGEVLSSVNTSKTILSYEVQAGVFRFIDYQRLLEGELGYTTNEPVMLCLMSAIESGVIYLV

NDGIERNLWQLQNPSEINSPILQRYKNNIVPAES
```

SEQ ID NO: 76
```
CITSPPKQAAKPTLLPRSQSYQDLTHLPEPQGRLFVSVYNISDETGQFKPYPASNFSTSVPQSATAMLVSALKDSN

WFIPLERQGLQNLLNERKIIRAAQENGTVAVNNRTQLPSLVAANILIEGSIIGYESNVKSGGAGARYFGIGASTQY

QLDQIAVNLRVVNVSTGEVLSSVNTSKTILSYEFQAGVFRYIDYQRLLEGEVGYTVNEPVMLCLMSAIETGVIYLV

NDGISRNLWQLKNASDINSPVLEKYKSIIVP
```

SEQ ID NO: 77
```
CLTAPPKQAAKPTLMPRAQSYQDLTHLPEPAGKLFVSVYNIQDETGQFKPYPASNFSTAVPQSATAMLVSALKDSG

WFIPLERQGLQNLLNERKIIRAAQENGTAAVNNQHQLSSLVAANVLVEGSIIGYESNVKSGGAGARFFGIGASTQY

QLDQIAVNLRVVDVNTGQVLSSVNTSKTILSYEVQAGVFRYIDYQRLLEGEIGYTTNEPVMLCVMSAIETGVIYLV

NDGINRNLWTLKNPQDAKSSVLERYKSTIVP
```

SEQ ID NO: 78
```
CITTPPQEAAKPTLLPRDATYKDLVSLPQPRGKIYVAVYNIQDETGQFQPYPASNFSTSVPQSATAMLV

SSLKDSRWFVPLERQGLNNLLNERKIIRAAQQNGTVGDNNASPLPSLYSANVIVEGSIIGYASNVKTGG

FGARYFGIGGSTQYQLDQVAVNLRIVNVHTGEVLSSVNTSKTILSYEIQAGVFRFIDYQRLLEGEAGFT

TNEPVMTCLMSAIEEGVIHLINDGINKKLWALSNAADINSEVLTRYRK
```

SEQ ID NO: 79
```
ITEVPKEAAKPTLMPRASTYKDLVALPKPNGKIIVSVYSVQDETGQFKPLPASNFSTAVPQSGNAMLTSALKDSGW

FVPLEREGLQNLLNERKIIRAAQENGTVAANNQQPLPSLLSANVVIEGAIIGYDSDIKTGGAGARYFGIGADGKYR

VDQVAVNLRAVDVRTGEVLLSVNTSKTILSSELSAGVFRFIEYQRLLELEAGYTTNEPVMMCMMSALEAGVAHLIV

EGIRQNLWSLQNPSDINNPIIQRYMKEDVP
```

SEQ ID NO: 80
```
PETSESPTLMQRGANYIDLISLPKPQGKIFVSVYDFRDQTGQYKPQPNSNFSTAVPQGGTALLTMALLDSEWFYPL

ERQGLQNLLTERKIIRAAQKKQESISNHGSTLPSLLSANVMIEGGIVAYDSNIKTGGAGARYLGIGGSGQYRADQV

TVNIRAVDVRSGKILTSVTTSKTILSYEVSAGAFRFVDYKELLEVELGYTNNEPVNIALMSAIDSAVIHLIVKGVQ

QGLWRPANLDTRNNPIFKKY
```

SEQ ID NO: 81
```
PDASESPTLMQRGATYLDLISLPKPQGKIYVSVYDFRDQTGQYKPQPNSNFSTAVPQGGTALLTMALLDSEWFYPL

ERQGLQNLLTERKIIRAAQKKQESISNHGSTLPSLLSANVMIEGGIVAYDSNIKTGGAGARYLGIGGSGQYRADQV
```

-continued

TVNIRAVDVRSGKILTSVTTSKTILSYELSAGAFRFVDYKELLEVELGYTNNEPVNIALMSAIDSAVIHLIVKGIE

EGLWRPENQNGKENPIFRKY

SEQ ID NO: 82

PETSKEPTLMARGTAYQDLVSLPLPKGKVYVSVYDFRDQTGQYKPQPNSNFSTAVPQGGAALLTTALLDSRWFMPL

EREGLQNLLTERKIIRAAQKKDEIPTNHGVHLPSLASANIMVEGGIVAYDTNIQTGGAGARYLGVGASGQYRTDQV

TVNIRAVDVRTGRILLSVTTSKTILSKELQTGVFKFVDYKDLLEAELGYTTNEPVNLAVMSAIDAAVVHVIVDGIK

TGLWEPLRGEDLQHPIIQEYMNRSKP

SEQ ID NO: 83

CATHIGSPVADEKATLMPRSVSYKELISLPKPKGKIVAAVYDFRDQTGQYLPAPASNFSTAVTQGGVAMLSTALWD

SQWFVPLEREGLQNLLTERKIVRAAQNKPNVPGNNANQLPSLVAANILIEGGIVAYDSNVRTGGAGAKYFGIGASG

EYRVDQVTVNLRAVDIRSGRILNSVTTSKTVMSQQVQAGVFRFVEYKRLLEAEAGFSTNEPVQMCVMSAIESGVIR

LIANGVRDNLWQLADQRDIDNPILQEYLQDNAP

SEQ ID NO: 84

ASSSLMPKGESYYDLINLPAPQGVMLAAVYDFRDQTGQYKPIPSSNFSTAVPQSGTAFLAQALNDSSWFIPVEREG

LQNLLTERKIVRAGLKGDANKLPQLNSAQILMEGGIVAYDTNVRTGGAGARYLGIGAATQFRVDTVTVNLRAVDIR

TGRLLSSVTTTKSILSKEITAGVFKFIDAQELLESELGYTSNEPVSLCVASAIESAVVHMIADGIWKGAWNLADQA

SGLRSPVLQKY

SEQ ID NO: 85

QDSETPTLTPRASTYYDLINMPRPKGRLMAVVYGFRDQTGQYKPTPASSFSTSVTQGAASMLMDALSASGWEVVLE

REGLQNLLTERKIIRASQKKPDVAENIMGELPPLQAANLMLEGGIIAYDTNVRSGGEGARYLGIDISREYRVDQVT

VNLRAVDVRTGQVLANVMTSKTIYSVGRSAGVFKFIEFKKLLEAEVGYTTNEPAQLCVLSAIESAVGHLLAQGIEQ

RLWQV

SEQ ID NO: 86

MPKSDTYYDLIGLPHPQGSMLAAVYDFRDQTGQYKAIPSSNFSTAVPQSGTAFLAQALNDSSWFVPVER

EGLQNLLTERKIVRAGLKGEANQLPQLSSAQILMEGGIVAYDTNIKTGGAGARYLGIGVNSKFRVDTVT

VNLRAVDIRTGRLLSSVTTTKSILSKEVSAGVFKFIDAQDLLESELGYTSNEPVSLCVAQAIESAVVHM

IADGIWKRAWNLADTASGLNNPVLQKY

SEQ ID NO: 87

LTRRMSTYQDLIDMPAPRGKIVTAVYSFRDQSGQYKPAPSSSFSTAVTQGAAAMLVNVLNDSGWFIPLEREGLQNI

LTERKIIRAALKKDNVPVNNSAGLPSLLAANIMLEGGIVGYDSNIHTGGAGARYFGIGASEKYRVDEVTVNLRAID

IRTGRILHSVLTSKKILSREIRSDVYRFIEFKHLLEMEAGITTNDPAQLCVLSAIESAVAHLIVDGVIKKSWSLAD

PNELNSPVIQAYQQQRI

SEQ ID NO: 88

PSDPERSTMGELTPSTAELRNLPLPNEKIVIGVYKFRDQTGQYKPSENGNNWSTAVPQGTTTILIKALEDSRWFIP

IERENIANLLNERQIIRSTRQEYMKDADKNSQSLPPLLYAGILLEGGVISYDSNTMTGGFGARYFGIGASTQYRQD

RITIYLRAVSTLNGEILKTVYTSKTILSTSVNGSFFRYIDTERLLEAEVGLTQNEPVQLAVTEAIEKAVRSLIIEG

TRDKIW

REFERENCES

Chin J W., Martin A B., King D S., Wang L., Schultz P G. (2002) Addition of a photocrosslinking amino acid to the genetic code of Escherichia coli. Proc Nat Acad Sci USA 99(17): 11020-11024.

Goyal P, Van Gerven N, Jonckheere W, Remaut H. (2013) Crystallization and preliminary X-ray crystallographic analysis of the curli transporter CsgG. Acta Crystallogr Sect F Struct Biol Cryst Commun. 69 (Pt 12):1349-53.

Goyal P, Krasteva P V, Van Gerven N, Gubellini F, Van den Broeck I, Troupiotis-Tsaïlaki A, Jonckheere W, Péhau-Arnaudet G, Pinkner J S, Chapman M R, Hultgren S J, Howorka S, Fronzes R, Remaut H. (2014) Structural and mechanistic insights into the bacterial amyloid secretion channel CsgG. Nature 516(7530):250-3.

Hammar M, Arnqvist A, Bian Z, Olsen A, Normark S. (1995) Expression of two csg operons is required for production of fibronectin- and congo red-binding curli polymers in Escherichia coli K-12. Mol Microbiol. 18(4): 661-70.

Juncker A S, Willenbrock H, Von Heijne G, Brunak S, Nielsen H, Krogh A. (2003) Prediction of lipoprotein signal peptides in Gram-negative bacteria. Protein Sci. 12(8):1652-62.

Ludtke S J. 2016, Single-particle refinement and variability analysis in EMAN2.1. Methods Enzymol. 579:159-89.

Rohou A and Grigorieff N 2015, CTFFIND4: Fast and accurate defocus estimation from electron micrographs. J Struct Biol. 192(2):216-21.

Robinson L S, Ashman E M, Hultgren S J, Chapman M R. (2006) Secretion of curli fibre subunits is mediated by the outer membrane-localized CsgG protein. Molecular Microbiology 59, 870-881.

Scheres 2012, RELION: implementation of a Bayesian approach to cryo-EM structure determination. J. Struct. Biol. 180(3):519-30.

Wang A., Winblade Nairn N., Marelli M., Grabstein K. (2012). Protein Engineering with Non-Natural Amino Acids. Protein Engineering, Prof. Pravin Kaumaya (Ed.), InTech, DOI: 10.5772/28719.

Zheng S Q., Palovcak E., Armache J-P., Verba K A., Cheng Y., Agard D A. (2017) MotionCor2: anisotropic correction of beam-induced

---

The invention claimed is:

1. A pore comprising a CsgG pore and a CsgF peptide, wherein the CsgF peptide is bound to CsgG and forms a constriction in the pore, wherein the CsgF peptide is a truncated CsgF peptide lacking the C-terminal head domain of CsgF and at least part of the neck domain of CsgF, wherein the CsgF peptide is a homologue of SEQ ID NO: 6, and wherein the CsgF peptide comprises one or more amino acid substitutions relative to SEQ ID NO: 6.

2. The pore according to claim 1, wherein the CsgF peptide comprises an amino acid sequence that is at least 50% identical to the amino acid sequence of SEQ ID NO: 6 from residue 1 up to any one of residues 28 to 45 of SEQ ID NO: 6.

3. The pore according to claim 1, wherein the CsgF peptide comprises an amino acid sequence that is at least 70% identical to the amino acid sequence of SEQ ID NO: 6 from residue 1 up to any one of residues 28 to 45 of SEQ ID NO: 6.

4. The pore according to claim 1, wherein the CsgF peptide; (i) has a length of from 25 to 45 amino acids; (ii) comprises an amino acid sequence that is at least 50% identical to the amino acid sequence of SEQ ID NO: 39 (residues 1 to 29 of SEQ ID NO: 6); (iii) comprises an amino acid sequence that is at least 50% identical to the amino acid sequence of SEQ ID NO: 15 (residues 1 to 34 of SEQ ID NO: 6); (iv) comprises an amino acid sequence that is at least 50% identical to the amino acid sequence of SEQ ID NO: 40 (residues 1 to 45 of SEQ ID NO: 6); (v) comprises an amino acid sequence that is at least 50% identical to the amino acid sequence of SEQ ID NO: 54 (residues 1 to 30 of SEQ ID NO: 6); or (vi) comprises an amino acid sequence that is at least 50% identical to the amino acid sequence of SEQ ID NO: 55 (residues 1 to 35 of SEQ ID NO: 6).

5. The pore according to claim 1, wherein the CsgG pore comprises from 6 to 10 CsgG monomers.

6. The pore according to claim 1, wherein the CsgF peptide and the CsgG pore are covalently coupled and the covalent coupling is via: (i) a cysteine residue at a position corresponding to 132, 133, 136, 138, 140, 142, 144, 145, 147, 149, 151, 153, 155, 183, 185, 187, 189, 191, 201, 203, 205, 207 or 209 of SEQ ID NO: 3, (ii) a non-native reactive or photoreactive amino acid at a position corresponding to 132, 133, 136, 138, 140, 142, 144, 145, 147, 149, 151, 153, 155, 183, 185, 187, 189, 191, 201, 203, 205, 207 or 209 of SEQ ID NO: 3, (iii) residues at a position corresponding to one or more of the following pairs of positions of the homologue of SEQ ID NO: 6 and SEQ ID NO: 3, respectively: 1 and 153, 4 and 133, 5 and 136, 8 and 187, 8 and 203, 9 and 203, 11 and 142, 11 and 201, 12 and 149, 12 and 203, 26 and 191, and 29 and 144, or (iv) a disulphide bond or click chemistry.

7. The pore according to claim 1, wherein the CsgG pore comprises at least one monomer comprising one or more modification corresponding to the following modifications in SEQ ID NO: 3: (i) a modification at one or more positions Y51, N55 and F56; (ii) at least one substitution selected from R97W or R97Y and R93W or R93Y; (iii) deletion of V105, A106 and 1107 of SEQ ID NO:3; (iv) deletion of one or more of positions R192, F193, 1194, D105, Y196, Q197, R198, L199 and E201 of SEQ ID NO:3; (v) at least one substitution selected from K94N/Q/R/F/Y/W/L/S, D43S, E44S, F48S/N/Q/Y/W/I/V/H/R/K, Q87N/R/K, N91K/R, R97F/Y/W/V/I/K/S/Q/H, E101I/L/A/H, N102K/Q/L/I/V/S/H, R110F/G/N, Q114R/K, R142Q/S, T150Y/A/V/L/S/Q/N; (vi) a modification at one or more of positions 141, R93, A98, Q100, G103, T104, A106, 1107, N108, L113, S115, T117, Y130, K135, E170, S208, D233, D238, E244, Q42, E44, L90, N91, 195, A99, E101 and Q114; (vii) at least one substitution selected from Y51A/I/V/S/T, N55A/I/V/S/T and F56/A/I/V/S/T/Q; (viii) the substitution R97W; (ix) deletion of F193, 1194, D195, Y196, Q197, R198 and L199 or deletion of D195, Y196, Q197, R198 and L199; (x) deletion of V105, A106 and 1107; (xi) a substitution selected from K94Q and K94N; (xii) at least one substitution selected from Q42K or Q42R; E44N or E44Q; L90R or L90K; N91R or N91K; 195R or 195K; A99R or A99K; E101H, E101K, E101N, E101Q or E101T; and/or Q114K; (xiii) the substitution N55V; and/or (xiv) R or K at a position corresponding to R192.

8. The pore according to claim 1, which is a double pore comprising two CsgG pores, wherein the CsgF peptide is inserted into the lumen of at least one of the CsgG pores.

9. The pore according to claim 4, wherein one or more of the residues in SEQ ID NO: 15, SEQ ID NO: 39, SEQ ID NO: 40, SEQ ID NO: 54, or SEQ ID NO: 55 are modified.

10. A pore comprising a CsgG pore and a CsgF peptide, wherein the CsgF peptide is bound to CsgG and forms a constriction in the pore, wherein the CsgF peptide is a truncated CsgF peptide lacking the C-terminal head domain of CsgF and at least part of the neck domain of CsgF, wherein the CsgF peptide is a homologue of SEQ ID NO: 6, and wherein the CsgF peptide comprises a modification at a position corresponding to one or more of the following positions in SEQ ID NO: 6: G1, T4, F5, R8, N9, N11, F12, A26, Q29, N15, N17, A20, N24, A28 and D34.

11. The pore according to claim 10, wherein the modification is the introduction of a cysteine, a hydrophobic amino acid, a charged amino acid, a non-native reactive amino acid, or a photoreactive amino acid.

12. The pore according to claim 10, wherein the CsgF peptide comprises an amino acid sequence that is at least 50% identical to the amino acid sequence of SEQ ID NO: 6 from residue 1 up to any one of residues 28 to 45 of SEQ ID NO: 6.

13. The pore according to claim 10, wherein the CsgF peptide; (i) has a length of from 25 to 45 amino acids; (ii) comprises an amino acid sequence that is at least 50% identical to the amino acid sequence of SEQ ID NO: 39 (residues 1 to 29 of SEQ ID NO: 6); (iii) comprises an amino acid sequence that is at least 50% identical to the amino acid sequence of SEQ ID NO: 15 (residues 1 to 34 of SEQ ID NO: 6); (iv) comprises an amino acid sequence that is at least 50% identical to the amino acid sequence of SEQ ID NO: 40 (residues 1 to 45 of SEQ ID NO: 6); (v) comprises an amino acid sequence that is at least 50% identical to the amino acid sequence of SEQ ID NO: 54 (residues 1 to 30 of SEQ ID NO: 6); or (vi) comprises an amino acid sequence that is at least 50% identical to the amino acid sequence of SEQ ID NO: 55 (residues 1 to 35 of SEQ ID NO: 6).

14. The pore according to claim 10, wherein the CsgG pore comprises from 6 to 10 CsgG monomers.

15. The pore according to claim 10, wherein the CsgF peptide and the CsgG pore are covalently coupled and the covalent coupling is via: (i) a cysteine residue at a position corresponding to 132, 133, 136, 138, 140, 142, 144, 145, 147, 149, 151, 153, 155, 183, 185, 187, 189, 191, 201, 203, 205, 207 or 209 of SEQ ID NO: 3, (ii) a non-native reactive or photoreactive amino acid at a position corresponding to 132, 133, 136, 138, 140, 142, 144, 145, 147, 149, 151, 153, 155, 183, 185, 187, 189, 191, 201, 203, 205, 207 or 209 of SEQ ID NO: 3, (iii) residues at a position corresponding to one or more of the following pairs of positions of the homologue of SEQ ID NO: 6 and SEQ ID NO: 3, respectively: 1 and 153, 4 and 133, 5 and 136, 8 and 187, 8 and 203, 9 and 203, 11 and 142, 11 and 201, 12 and 149, 12 and 203, 26 and 191, and 29 and 144, or (iv) a disulphide bond or click chemistry.

16. The pore according to claim 10, wherein the CsgG pore comprises at least one monomer comprising one or more modification corresponding to the following modifications in SEQ ID NO: 3: (i) a modification at one or more positions Y51, N55 and F56; (ii) at least one substitution selected from R97W or R97Y and R93W or R93Y; (iii) deletion of V105, A106 and 1107 of SEQ ID NO:3; (iv) deletion of one or more of positions R192, F193, 1194, D105, Y196, Q197, R198, L199 and E201 of SEQ ID NO:3; (v) at least one substitution selected from K94N/Q/R/F/Y/W/L/S, D43S, E44S, F48S/N/Q/Y/W/I/V/H/R/K, Q87N/R/K, N91K/R, R97F/Y/W/V/I/K/S/Q/H, E101I/L/A/H, N102K/Q/L/I/V/S/H, R110F/G/N, Q114R/K, R142Q/S, T150Y/A/V/L/S/Q/N; (vi) a modification at one or more of positions I41, R93, A98, Q100, G103, T104, A106, 1107, N108, L113, S115, T117, Y130, K135, E170, S208, D233, D238, E244, Q42, E44, L90, N91, 195, A99, E101 and Q114; (vii) at least one substitution selected from Y51A/I/V/S/T, N55A/I/V/S/T and F56/A/I/V/S/T/Q; (viii) the substitution R97W; (ix) deletion of F193, 1194, D195, Y196, Q197, R198 and L199 or deletion of D195, Y196, Q197, R198 and L199; (x) deletion of V105, A106 and 1107; (xi) a substitution selected from K94Q and K94N; (xii) at least one substitution selected from Q42K or Q42R; E44N or E44Q; L90R or L90K; N91R or N91K; 195R or 195K; A99R or A99K; E101H, E101K, E101N, E101Q or E101T; and/or Q114K; (xiii) the substitution N55V; and/or (xiv) R or K at a position corresponding to R192.

17. A pore comprising a CsgG pore and a CsgF peptide, wherein the CsgF peptide is bound to CsgG and forms a constriction in the pore, wherein the CsgF peptide is a truncated CsgF peptide lacking the C-terminal head domain of CsgF and at least part of the neck domain of CsgF, wherein the CsgF peptide is a homologue of SEQ ID NO: 6, and wherein the CsgF peptide comprises an amino acid substitution corresponding to one or more of the following substitutions in SEQ ID NO: 6: N15S/A/T/Q/G/L/V/I/F/Y/W/R/K/D/C, N17S/A/T/Q/G/L/V/I/F/Y/W/R/K/D/C, A20S/

T/Q/N/G/L/V/I/F/Y/W/R/K/D/C, N24S/T/Q/A/G/L/V/I/F/Y/W/R/K/D/C, A28S/T/Q/N/G/L/V/I/F/Y/W/R/K/D/C, D34F/Y/W/R/K/N/Q/C, G1C, T4C, N17S, and D34Y or D34N.

18. The pore according to claim 17, wherein the CsgF peptide comprises an amino acid sequence that is at least 50% identical to the amino acid sequence of SEQ ID NO: 6 from residue 1 up to any one of residues 28 to 45 of SEQ ID NO: 6.

19. The pore according to claim 17, wherein the CsgF peptide; (i) has a length of from 25 to 45 amino acids; (ii) comprises an amino acid sequence that is at least 50% identical to the amino acid sequence of SEQ ID NO: 39 (residues 1 to 29 of SEQ ID NO: 6); (iii) comprises an amino acid sequence that is at least 50% identical to the amino acid sequence of SEQ ID NO: 15 (residues 1 to 34 of SEQ ID NO: 6); (iv) comprises an amino acid sequence that is at least 50% identical to the amino acid sequence of SEQ ID NO: 40 (residues 1 to 45 of SEQ ID NO: 6); (v) comprises an amino acid sequence that is at least 50% identical to the amino acid sequence of SEQ ID NO: 54 (residues 1 to 30 of SEQ ID NO: 6); or (vi) comprises an amino acid sequence that is at least 50% identical to the amino acid sequence of SEQ ID NO: 55 (residues 1 to 35 of SEQ ID NO: 6).

20. The pore according to claim 17, wherein the CsgG pore comprises from 6 to 10 CsgG monomers.

21. The pore according to claim 17, wherein the CsgF peptide and the CsgG pore are covalently coupled and the covalent coupling is via: (i) a cysteine residue at a position corresponding to 132, 133, 136, 138, 140, 142, 144, 145, 147, 149, 151, 153, 155, 183, 185, 187, 189, 191, 201, 203, 205, 207 or 209 of SEQ ID NO: 3, (ii) a non-native reactive or photoreactive amino acid at a position corresponding to 132, 133, 136, 138, 140, 142, 144, 145, 147, 149, 151, 153, 155, 183, 185, 187, 189, 191, 201, 203, 205, 207 or 209 of SEQ ID NO: 3, (iii) residues at a position corresponding to one or more of the following pairs of positions of the homologue of SEQ ID NO: 6 and SEQ ID NO: 3, respectively: 1 and 153, 4 and 133, 5 and 136, 8 and 187, 8 and 203, 9 and 203, 11 and 142, 11 and 201, 12 and 149, 12 and 203, 26 and 191, and 29 and 144, or (iv) a disulphide bond or click chemistry.

22. The pore according to claim 17, wherein the CsgG pore comprises at least one monomer comprising one or more modification corresponding to the following modifications in SEQ ID NO: 3: (i) a modification at one or more positions Y51, N55 and F56; (ii) at least one substitution selected from R97W or R97Y and R93W or R93Y; (iii) deletion of V105, A106 and 1107 of SEQ ID NO:3; (iv) deletion of one or more of positions R192, F193, 1194, D105, Y196, Q197, R198, L199 and E201 of SEQ ID NO:3; (v) at least one substitution selected from K94N/Q/R/F/Y/W/L/S, D43S, E44S, F48S/N/Q/Y/W/I/V/H/R/K, Q87N/R/K, N91K/R, R97F/Y/W/V/I/K/S/Q/H, E101I/L/A/H, N102K/Q/L/I/V/S/H, R110F/G/N, Q114R/K, R142Q/S, T150Y/A/V/L/S/Q/N; (vi) a modification at one or more of positions 141, R93, A98, Q100, G103, T104, A106, 1107, N108, L113, S115, T117, Y130, K135, E170, S208, D233, D238, E244, Q42, E44, L90, N91, 195, A99, E101 and Q114; (vii) at least one substitution selected from Y51A/I/V/S/T, N55A/I/V/S/T and F56/A/I/V/S/T/Q; (viii) the substitution R97W; (ix) deletion of F193, 1194, D195, Y196, Q197, R198 and L199 or deletion of D195, Y196, Q197, R198 and L199; (x) deletion of V105, A106 and 1107; (xi) a substitution selected from K94Q and K94N; (xii) at least one substitution selected from Q42K or Q42R; E44N or E44Q; L90R or L90K; N91R or N91K; 195R or 195K; A99R or A99K; E101H, E101K, E101N, E101Q or E101T; and/or Q114K; (xiii) the substitution N55V; and/or (xiv) R or K at a position corresponding to R192.

23. A pore comprising a CsgG pore and a CsgF peptide, wherein the CsgF peptide is bound to CsgG and forms a constriction in the pore, wherein the CsgF peptide is a truncated CsgF peptide lacking the C-terminal head domain of CsgF and at least part of the neck domain of CsgF, wherein the CsgF peptide is a homologue of SEQ ID NO: 6, and wherein CsgF peptide is bound to the CsgG pore by hydrophobic interactions, electrostatic or covalent interactions at a position corresponding to one or more of the following pairs of positions of the homologue of SEQ ID NO: 6 and SEQ ID NO: 3, respectively: 1 and 153, 4 and 133, 5 and 136, 8 and 187, 8 and 203, 9 and 203, 11 and 142, 11 and 201, 12 and 149, 12 and 203, 26 and 191, and 29 and 144.

24. The pore according to claim 23, wherein the CsgF peptide comprises an amino acid sequence that is at least 50% identical to the amino acid sequence of SEQ ID NO: 6 from residue 1 up to any one of residues 28 to 45 of SEQ ID NO: 6.

25. The pore according to claim 23, wherein the CsgF peptide comprises one or more amino acid substitutions relative to SEQ ID NO: 6.

26. The pore according to claim 23, wherein the CsgF peptide; (i) has a length of from 25 to 45 amino acids; (ii) comprises an amino acid sequence that is at least 50% identical to the amino acid sequence of SEQ ID NO: 39 (residues 1 to 29 of SEQ ID NO: 6); (iii) comprises an amino acid sequence that is at least 50% identical to the amino acid sequence of SEQ ID NO: 15 (residues 1 to 34 of SEQ ID NO: 6); (iv) comprises an amino acid sequence that is at least 50% identical to the amino acid sequence of SEQ ID NO: 40 (residues 1 to 45 of SEQ ID NO: 6); (v) comprises an amino acid sequence that is at least 50% identical to the amino acid sequence of SEQ ID NO: 54 (residues 1 to 30 of SEQ ID NO: 6); or (vi) comprises an amino acid sequence that is at least 50% identical to the amino acid sequence of SEQ ID NO: 55 (residues 1 to 35 of SEQ ID NO: 6).

27. The pore according to claim 23, wherein the CsgG pore comprises from 6 to 10 CsgG monomers.

28. The pore according to claim 23, wherein the CsgG pore comprises at least one monomer comprising one or more modification corresponding to the following modifications in SEQ ID NO: 3: (i) a modification at one or more positions Y51, N55 and F56; (ii) at least one substitution selected from R97W or R97Y and R93W or R93Y; (iii) deletion of V105, A106 and 1107 of SEQ ID NO:3; (iv) deletion of one or more of positions R192, F193, 1194, D105, Y196, Q197, R198, L199 and E201 of SEQ ID NO:3; (v) at least one substitution selected from K94N/Q/R/F/Y/W/L/S, D43S, E44S, F48S/N/Q/Y/W/I/V/H/R/K, Q87N/R/K, N91K/R, R97F/Y/W/V/I/K/S/Q/H, E101IL/A/H, N102K/Q/L/I/V/S/H, R110F/G/N, Q114R/K, R142Q/S, T150Y/A/V/L/S/Q/N; (vi) a modification at one or more of positions 141, R93, A98, Q100, G103, T104, A106, 1107, N108, L113, S115, T117, Y130, K135, E170, S208, D233, D238, E244, Q42, E44, L90, N91, 195, A99, E101 and Q114; (vii) at least one substitution selected from Y51A/I/V/S/T, N55A/I/V/S/T and F56/A/I/V/S/T/Q; (viii) the substitution R97W; (ix) deletion of F193, 1194, D195, Y196, Q197, R198 and L199 or deletion of D195, Y196, Q197, R198 and L199; (x) deletion of V105, A106 and 1107; (xi) a substitution selected from K94Q and K94N; (xii) at least one substitution selected from Q42K or Q42R; E44N or E44Q; L90R or L90K; N91R or N91K; 195R or 195K;

A99R or A99K; E101H, E101K, E101N, E101Q or E101T; and/or Q114K; (xiii) the substitution N55V; and/or (xiv) R or K at a position corresponding to R192.

\* \* \* \* \*

UNITED STATES PATENT AND TRADEMARK OFFICE
CERTIFICATE OF CORRECTION

PATENT NO. : 12,084,477 B2
APPLICATION NO. : 17/933061
DATED : September 10, 2024
INVENTOR(S) : Han Remaut et al.

It is certified that error appears in the above-identified patent and that said Letters Patent is hereby corrected as shown below:

In the Claims

At Column 187, Claim 7, Lines 11-38:
7.The pore according to claim 1, wherein the CsgG pore comprises at least one monomer comprising one or more modification corresponding to the following modifications in SEQ ID NO: 3: (i) a modification at one or more positions Y51, N55 and F56; (ii) at least one substitution selected from R97W or R97Y and R93W or R93Y; (iii) deletion of V105, A106 and I107 of SEQ ID NO:3; (iv) deletion of one or more of positions R192, F193, I194, D105, Y196, Q197, R198, L199 and E201 of SEQ ID NO:3; (v) at least one substitution selected from K94N/Q/R/F/Y/W/L/S, D43S, E44S, F48S/N/Q/Y/W/I/V/H/R/K, Q87N/R/K, N91K/R, R97F/Y/W/V/I/K/S/Q/H, E101I/L/A/H, N102K/Q/L/I/V/S/H, R110F/G/N, Q114R/K, R142Q/S, T150Y/A/V/L/S/Q/N; (vi) a modification at one or more of positions 141, R93, A98, Q100, G103, T104, A106, I107, N108, L113, S115, T117, Y130, K135, E170, S208, D233, D238, E244, Q42, E44, L90, N91, 195, A99, E101 and Q114; (vii) at least one substitution selected from Y51A/I/V/S/T, N55A/I/V/S/T and F56/A/I/V/S/T/Q; (viii) the substitution R97W; (ix) deletion of F193, I194, D195, Y196, Q197, R198 and L199 or deletion of D195, Y196, Q197, R198 and L199; (x) deletion of V105, A106 and I107; (xi) a substitution selected from K94Q and K94N; (xii) at least one substitution selected from Q42K or Q42R; E44N or E44Q; L90R or L90K; N91R or N91K; 195R or 195K; A99R or A99K; E101H, E101K, E101N, E101Q or E101T; and/or Q114K; (xiii) the substitution N55V; and/or (xiv) R or K at a position corresponding to R192.

Should be:
7. The pore according to claim 1, wherein the CsgG pore comprises at least one monomer comprising one or more modification corresponding to the following modifications in SEQ ID NO: 3: (i) a modification at one or more positions Y51, N55 and F56; (ii) at least one substitution selected from R97W or R97Y and R93W or R93Y; (iii) deletion of V105, A106 and I107 of SEQ ID NO:3; (iv) deletion of one or more of positions R192, F193, I194, D105, Y196, Q197, R198, L199 and E201 of SEQ ID NO:3; (v) at least one substitution selected from K94N/Q/R/F/Y/W/L/S, D43S, E44S, F48S/N/Q/Y/W/I/V/H/R/K, Q87N/R/K, N91K/R, R97F/Y/W/V/I/K/S/Q/H, E101I/L/A/H, N102K/Q/L/I/V/S/H, R110F/G/N, Q114R/K, R142Q/S, T150Y/A/V/L/S/Q/N; (vi) a modification at Signed and Sealed this
Twenty-fourth Day of December, 2024

Derrick Brent
*Acting Director of the United States Patent and Trademark Office* one or more of positions I41, R93, A98, Q100, G103, T104, A106, I107, N108, L113, S115, T117, Y130, K135, E170, S208, D233, D238, E244, Q42, E44, L90, N91, I95, A99, E101 and Q114; (vii) at least one substitution selected from Y51A/I/V/S/T, N55A/I/V/S/T and F56/A/I/V/S/T/Q; (viii) the substitution R97W; (ix) deletion of F193, I194, D195, Y196, Q197, R198 and L199 or deletion of D195, Y196, Q197, R198 and L199; (x) deletion of V105, A106 and I107; (xi) a substitution selected from K94Q and K94N; (xii) at least one substitution selected from Q42K or Q42R; E44N or E44Q; L90R or L90K; N91R or N91K; I95R or I95K; A99R or A99K; E101H, E101K, E101N, E101Q or E101T; and/or Q114K; (xiii) the substitution N55V; and/or (xiv) R or K at a position corresponding to R192.